United States Patent
Okada et al.

(10) Patent No.: US 10,710,967 B2
(45) Date of Patent: Jul. 14, 2020

(54) PYRIMIDINE DERIVATIVE

(71) Applicant: ASKA PHARMACEUTICAL CO., LTD., Tokyo (JP)

(72) Inventors: Makoto Okada, Kanagawa (JP);
Youichi Nakano, Kanagawa (JP);
Takashi Nose, Kanagawa (JP);
Takahiro Nishimoto, Kanagawa (JP);
Satoshi Maeda, Kanagawa (JP)

(73) Assignee: ASKA PHARMACEUTICAL CO., LTD., Tokyo (JP)

( * ) Notice: Subject to any disclaimer, the term of this patent is extended or adjusted under 35 U.S.C. 154(b) by 267 days.

(21) Appl. No.: 15/770,002

(22) PCT Filed: Oct. 28, 2016

(86) PCT No.: PCT/JP2016/081993
§ 371 (c)(1),
(2) Date: Apr. 20, 2018

(87) PCT Pub. No.: WO2017/073709
PCT Pub. Date: May 4, 2017

(65) Prior Publication Data
US 2020/0071280 A1   Mar. 5, 2020

(30) Foreign Application Priority Data

Oct. 29, 2015  (JP) .................... 2015-212920
Apr. 11, 2016  (JP) .................... 2016-078697

(51) Int. Cl.
| | | |
|---|---|---|
| C07D 239/36 | (2006.01) |
| C07D 401/04 | (2006.01) |
| C07D 401/10 | (2006.01) |
| C07D 401/12 | (2006.01) |
| C07D 401/14 | (2006.01) |
| C07D 403/04 | (2006.01) |
| C07D 405/14 | (2006.01) |
| C07D 409/04 | (2006.01) |
| C07D 417/04 | (2006.01) |
| A61K 31/506 | (2006.01) |

(52) U.S. Cl.
CPC ......... *C07D 239/36* (2013.01); *C07D 401/04* (2013.01); *C07D 401/10* (2013.01); *C07D 401/12* (2013.01); *C07D 401/14* (2013.01); *C07D 403/04* (2013.01); *C07D 405/14* (2013.01); *C07D 409/04* (2013.01); *C07D 417/04* (2013.01)

(58) Field of Classification Search
CPC combination set(s) only.
See application file for complete search history.

(56) References Cited

U.S. PATENT DOCUMENTS

| | | | |
|---|---|---|---|
| 6,096,753 A | 8/2000 | Spohr et al. | |
| 6,410,729 B1 | 6/2002 | Spohr et al. | |
| 6,420,385 B1 | 7/2002 | Spohr et al. | |
| 2003/0069425 A1 | 4/2003 | Spohr et al. | |
| 2003/0073704 A1 | 4/2003 | Spohr et al. | |
| 2011/0301109 A1* | 12/2011 | Liu ................ | A61K 31/505 514/35 |
| 2015/0087646 A1 | 3/2015 | Gharat et al. | |
| 2015/0266834 A1 | 9/2015 | Nagamori et al. | |
| 2015/0283117 A1 | 10/2015 | Gharat et al. | |

(Continued)

FOREIGN PATENT DOCUMENTS

| | | |
|---|---|---|
| JP | 2002-514195 A | 5/2002 |
| JP | 2012-511517 A | 5/2012 |
| JP | 5601422 B2 | 10/2014 |

(Continued)

OTHER PUBLICATIONS

Extended European search report, European Patent Office, Application No. No. 16859937.1, dated Mar. 21, 2019.

(Continued)

*Primary Examiner* — Amanda L. Aguirre
(74) *Attorney, Agent, or Firm* — Greenblum & Bernstein, P.L.C.

(57) ABSTRACT

A compound represented by the formula (1), or a salt thereof (X represents carbonyl group, or sulfonyl group; $R^1$ represents hydrogen atom, a halogen atom, an alkyl group, an alkanoyl group, cyano group, or carboxyl group; $R^2$ represents an alkyl group, a cyclic carbon group, or a heterocyclic group; $R^3$ represents hydrogen atom, or 1 to 3 substituents; $R^4$ and $R^5$ represents hydrogen atom, a halogen atom, or an alkyl group; and $R^6$ represents an alkyl group, or an alkoxy group), which has an mPGES-1 inhibitory action, and is useful as an active ingredient of a medicament for prophylactic and/or therapeutic treatment of inflammation, pain, rheumatism, and the like.

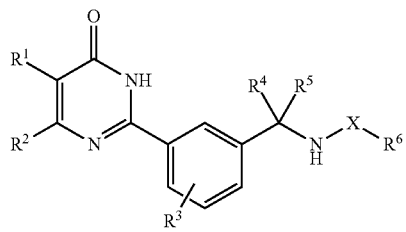

13 Claims, No Drawings

(56) References Cited

U.S. PATENT DOCUMENTS

2016/0339000 A1 11/2016 Gharat et al.

FOREIGN PATENT DOCUMENTS

| JP | 2015-523353 A | 8/2015 | |
|---|---|---|---|
| WO | WO-0170726 A1 * | 9/2001 | ........... C07D 401/14 |
| WO | 2013/186692 A1 | 12/2013 | |
| WO | 2015/059618 A1 | 4/2015 | |
| WO | 2015/125842 A1 | 8/2015 | |

OTHER PUBLICATIONS

India Office Action, India Patent Office, Application No. 201837017785, dated Feb. 13, 2020.

Jakobsson et al., "Identification of human prostaglandin E synthase: A microsomal, glutathione-dependent, inducible enzyme, constituting a potential novel drug target", Proc. Natl. Acad. Sci. USA, vol. 96, pp. 7220-7225, 1999.

Kamei et al., "Reduced Pain Hypersensitivity and Inflammation in Mice Lacking Microsomal Prostaglandin E Synthase-1", J. Biol Chem., vol. 279, No. 32, pp. 33684-33695, 2004.

Samuelsson et al., "Membrane Prostaglandin E Synthase-1: A Novel Therapeutic Target", Pharmacol. Rev., vol. 59, No. 3, pp. 207-224, 2007.

Trebino et al., "Redirection of Eicosanoid Metabolism in mPGES-1-deficient Macrophages", J. Biol. Chem., vol. 280, No. 17, pp. 16579-16585, 2005.

International Search Report issued in International Bureau of WIPO Patent Application No. PCT/JP2016/081993, dated Jan. 24, 2017.

International Preliminary Report on Patentability issued in International Bureau of WIPO Patent Application No. PCT/JP2016/081993, dated May 1, 2018.

Australian Office Action issued in Australian patent application No. 2016346557, dated Apr. 22, 2020.

* cited by examiner

PYRIMIDINE DERIVATIVE

TECHNICAL FIELD

The present invention relates to a novel pyrimidine derivative. More specifically, the present invention relates to a pyrimidine derivative having an mPGES-1 inhibitory action, and useful as an active ingredient of a medicament for prophylactic and/or therapeutic treatment of such diseases as inflammation, pain, and rheumatism.

BACKGROUND ART

Prostaglandin E2 (PGE2) is involved in inflammation, pain, pyrexia, and the like by means of PGE receptors, and can suppress the PGE2 production to suppress inflammation. Non-steroidal anti-inflammatory drugs (NSAIDs) inhibit cyclooxygenase (COX) in the upstream of the prostaglandin biosynthesis pathway, and thereby exhibit anti-inflammatory activity. However, they totally suppress the prostaglandin biosynthesis pathway downstream from the prostanoid production in which COX is involved, and therefore they cause gastric mucosal injury as side effects due to suppression of secretion of gastric mucus or blood flow in gastric mucosa.

There are two types of isozymes of COX, COX-1 and COX-2. Among them, COX-2 is expressed and induced in inflammatory tissues by various inflammation-promoting stimuli (for example, those of cytokines such as interleukin-1β). Medicaments that selectively inhibit this COX-2 suppress the production of PGI2, which has vasodilatation and platelet aggregation actions; however, since they do not inhibit the production of thromboxane A2 (TXA2) catalyzed by COX-1 (TXA2 causes vasoconstriction and platelet coagulation), they are considered to increase risk of thrombosis, and increase cardiovascular events, either.

In the downstream of the biosynthesis pathway of PGE2, PGE2 is biosynthesized from PGH2 by the prostaglandin E synthase (PGE synthase, PGES). As PGES, there are three kinds of enzymes, mPGES-1 (microsomal prostaglandin E2 synthase-1), mPGES-2 (microsomal prostaglandin E2 synthase-2), and cPGES (cytosolic PGE synthase). Among them, mPGES-1 is an inducible trimer enzyme, of which expression is increased by inflammatory stimuli (Proc. Natl. Acad. Sci. USA, 96, pp. 7220-7225, 1999), and it is known to participate in cancer, inflammation, pain, pyrexia, tissue repair, and the like.

Since mPGES-1 inhibitors can selectively inhibit the final step of the PGE2 biosynthesis pathway in inflammation lesions (Pharmacol. Rev., 59, pp. 207-224, 2007; J. Biol. Chem., 279, pp. 33684-33695, 2004), they are expected as anti-inflammatory agents that do not cause gastric mucosal injuries, unlike the non-steroidal anti-inflammatory agents. There are also expected efficacies of mPGES-1 inhibitors for prophylactic and/or therapeutic treatment of pain, rheumatism, osteoarthritis, pyrexia, Alzheimer's disease, multiple sclerosis, arteriosclerosis, ocular hypertension such as glaucoma, ischemic retinopathy, systemic scleroderma, malignant tumors such as large intestine tumor, and diseases for which suppression of the PGE2 production exhibits efficacy (refer to International Patent Publication WO2015/125842 for PGE2, PGES, and mPGES-1, as well as uses of mPGES-1 inhibitors, and the like). In addition, it is also known that mPGES-1 inhibitors increase productions of other prostanoids in connection with the suppression of the PGE2 production (J. Biol. Chem., 280, pp. 16579-16585, 2005).

As such mPGES-1 inhibitors, there are known the heterocyclic derivatives disclosed in Japanese Patent No. 5601422, the substituted pyrimidine compounds disclosed in International Patent Publication WO2015/59618, the triazine compounds disclosed in International Patent Publication WO2015/125842, and the like. International Patent Publication WO2015/59618 discloses a pyrimidine compound substituted with p-trifluoromethylphenyl group and 2-chloro-5-isobutyramidobenzyl group (Example 2), and International Patent Publication WO2015/125842 discloses triazine compounds substituted with p-trifluoromethylphenyl group and 2-chloro-5-isobutyramidobenzyl group (Examples 1 to 28).

PRIOR ART REFERENCES

Patent Documents

Patent document 1: Japanese Patent No. 5601422
Patent document 2: International Patent Publication WO2015/59618
Patent document 3: International Patent Publication WO2015/125842

Non-Patent Documents

Non-patent document 1: Proc. Natl. Acad. Sci. USA, 96, pp. 7220-7225, 1999
Non-patent document 2: Pharmacol. Rev., 59, pp. 207-224, 2007
Non-patent document 3: J. Biol. Chem., 279, pp. 33684-33695, 2004
Non-patent document 4: J. Biol. Chem., 280, pp. 16579-16585, 2005

SUMMARY OF THE INVENTION

Object to be Achieved by the Invention

An object of the present invention is to provide a novel compound having an mPGES-1 inhibitory action, and useful as an active ingredient of a medicament for prophylactic and/or therapeutic treatment of such diseases as inflammation, pain, and rheumatism.

Means for Achieving the Object

The inventors of the present invention conducted various researches in order to achieve the aforementioned object. As a result, they found that pyrimidine derivatives represented by the following general formula (1) have a potent mPGES-1 inhibitory action, and are useful as active ingredients of medicaments for prophylactic and/or therapeutic treatment of such diseases as inflammation, pain, and rheumatism, and accomplished the present invention.

The present invention thus provides a compound represented by the following general formula (1):

[Formula 1]

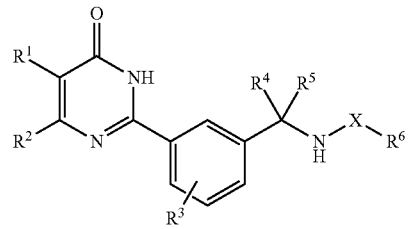

(in the formula, X represents carbonyl group, or sulfonyl group; $R^1$ represents hydrogen atom, a halogen atom, an alkyl group, an alkanoyl group, cyano group, or carboxyl group; $R^2$ represents an alkyl group, a cyclic carbon group which may have a substituent, or a heterocyclic group which may have a substituent; $R^3$ represents hydrogen atom, or 1 to 3 substituents substituting on the benzene ring (these substituents are selected from the group consisting of a halogen atom, an alkyl group (this alkyl group may be substituted with a halogen atom), and an alkoxy group (this alkoxy group may be substituted with a halogen atom)); $R^4$ and $R^5$ independently represent hydrogen atom, a halogen atom, or an alkyl group; and $R^6$ represents an alkyl group (this alkyl group may be substituted with hydroxy group, a halogen atom, or an alkoxy group), or an alkoxy group), or a salt thereof.

According to preferred embodiments of the aforementioned invention, there are provided the compound represented by the aforementioned general formula (1), or a salt thereof, wherein X is carbonyl group; the compound represented by the aforementioned general formula (1), or a salt thereof, wherein $R^6$ is a branched $C_{1-6}$ alkyl group (this alkyl group may be substituted with a $C_{1-6}$ alkoxy group); the compound represented by the aforementioned general formula (1), or a salt thereof, wherein both $R^4$ and $R^5$ are hydrogen atoms; the compound represented by the aforementioned general formula (1), or a salt thereof, wherein $R^6$ consists of one halogen atom; the compound represented by the aforementioned general formula (1), or a salt thereof, wherein $R^1$ is hydrogen atom, an alkyl group, or cyano group; and the compound represented by the aforementioned general formula (1), or a salt thereof, wherein $R^2$ is a saturated or partially saturated 3- to 7-membered monocyclic hydrocarbon group which may have a substituent, a phenyl group which may have a substituent, a saturated or partially saturated 3- to 7-membered monocyclic heterocyclic group which may have a substituent (this heterocyclic group contains 1 to 3 ring-constituting heteroatoms), or a monocyclic aromatic heterocyclic group which may have a substituent (this heterocyclic group contains 1 to 3 ring-constituting heteroatoms).

As other aspects, the present invention provides an mPGES-1 inhibitor containing a compound represented by the aforementioned general formula (1), or a salt thereof; and a PGE2 biosynthesis inhibitor containing a compound represented by the aforementioned general formula (1), or a salt thereof.

As still another aspect, the present invention provides a medicament containing a compound represented by the aforementioned general formula (1) or a physiologically acceptable salt thereof as an active ingredient. This medicament can be used for prophylactic and/or therapeutic treatment of, for example, inflammation, pain, rheumatism, osteoarthritis, pyrexia, Alzheimer's disease, multiple sclerosis, arteriosclerosis, ocular hypertension such as glaucoma, ischemic retinopathy, systemic scleroderma, malignant tumors such as large intestine tumor, and diseases for which suppression of the PGE2 production exhibits efficacy.

The present invention also provides use of a compound represented by the aforementioned general formula (1) or a salt thereof for manufacture of the aforementioned mPGES-1 inhibitor, the aforementioned PGE2 biosynthesis inhibitor, or the aforementioned medicament; a method for inhibiting mPGES-1 in a living body of a mammal including human, which comprises the step of administrating an effective amount of a compound represented by the aforementioned general formula (1) or a physiologically acceptable salt thereof to the mammal including human; a method for inhibiting biosynthesis of PGE2 in a living body of a mammal including human, which comprises the step of administrating an effective amount of a compound represented by the aforementioned general formula (1) or a physiologically acceptable salt thereof to the mammal including human; and a method for promoting production of a prostanoid other than PGE2 by inhibiting biosynthesis of PGE2 in a living body of a mammal including human, which comprises the step of administrating an effective amount of a compound represented by the aforementioned general formula (1) or a physiologically acceptable salt thereof to the mammal including human.

Effect of the Invention

The compounds represented by the aforementioned general formula (1) and salts thereof provided by the present invention can exhibit a potent inhibitory action against mPGES-1 to inhibit the biosynthesis of PGE2. Therefore, they are useful as an active ingredient of a medicament for prophylactic and/or therapeutic treatment of, for example, pain, rheumatism, osteoarthritis, pyrexia, Alzheimer's disease, multiple sclerosis, arteriosclerosis, ocular hypertension such as glaucoma, ischemic retinopathy, systemic scleroderma, malignant tumors such as large intestine tumor, and diseases for which suppression of the PGE2 production exhibits efficacy.

MODES FOR CARRYING OUT THE INVENTION

In the aforementioned general formula (1), X represents carbonyl group, or sulfonyl group. It is preferred that X is carbonyl group.

$R^1$ represents hydrogen atom, a halogen atom, an alkyl group, an alkanoyl group, cyano group, or carboxyl group. In this specification, the term halogen atom may mean fluorine atom, chlorine atom, bromine atom, or iodine atom. As the halogen atom, fluorine atom or chlorine atom is preferred.

In this specification, the term alkyl group may mean a straight, branched, or cyclic alkyl group, or an alkyl group consisting of a combination of the foregoing alkyl groups. Although carbon number of the alkyl group is not particularly limited, it is, for example, 1 to 12, preferably 1 to 6, particularly preferably 1 to 4. The same shall apply to alkyl moieties of other substituents having an alkyl moiety (for example, alkoxy group). As $R^1$, hydrogen atom, an alkyl group, or cyano group is preferred, hydrogen atom, methyl group, or cyano group is more preferred, and hydrogen atom is particularly preferred.

$R^2$ represents an alkyl group, a cyclic carbon group which may have a substituent, or a heterocyclic group which may have a substituent. As the cyclic carbon group, for example, an aromatic hydrocarbon group, or a saturated or partially saturated cyclic hydrocarbon group can be used. As the aromatic hydrocarbon group, for example, phenyl group, naphthyl group, and the like can be used, and as the saturated or partially saturated cyclic hydrocarbon group, for example, a saturated, or partially saturated 3- to 12-membered monocyclic or bicyclic cyclic hydrocarbon group can be used. As the aromatic hydrocarbon group, phenyl group can be preferably used. As the cyclic hydrocarbon group, a saturated 3- to 7-membered monocyclic cyclic hydrocarbon group can be preferably used, and cyclopropyl group, cyclobutyl group, cyclopentyl group, cyclohexyl group, cycloheptyl group, and the like are more preferred.

As the heterocyclic group, a saturated or partially saturated heterocyclic group having 1 or 2 or more ring-constituting heteroatoms, or an aromatic heterocyclic group having 1 or 2 or more ring-constituting heteroatoms can be used. As the ring-constituting heteroatoms, nitrogen atom, oxygen atom, sulfur atom, and the like can be used. As the saturated or partially saturated heterocyclic group having 1 or 2 or more ring-constituting heteroatoms, for example, a saturated or partially saturated 3- to 7-membered monocyclic heterocyclic group, or 8- to 12-membered bicyclic heterocyclic group can be used. Examples of the saturated or partially saturated 3- to 7-membered monocyclic heterocyclic group include, for example, 1-aziridinyl group, 1-azetidinyl group, 1-pyrrolidinyl group, 2-pyrrolidinyl group, 3-pyrrolidinyl group, 2-tetrahydrofuryl group, 3-tetrahydrofuryl group, thiolanyl group, 1-imidazolidinyl group, 2-imidazolidinyl group, 4-imidazolidinyl group, 1-pyrazolidinyl group, 3-pyrazolidinyl group, 4-pyrazolidinyl group, 1-(2-pyrrolinyl) group, 1-(2-imidazolinyl) group, 2-(2-imidazolinyl) group, 1-(2-pyrazolinyl) group, 3-(2-pyrazolinyl) group, piperidino group, 2-piperidinyl group, 3-piperidinyl group, 4-piperidinyl group, 1-homopiperidinyl group, 2-tetrahydropyranyl group, morpholino group, (thiomorpholin)-4-yl group, 1-piperazinyl group, 1-homopiperazinyl group, and the like, and examples of the saturated or partially saturated 8- to 12-membered bicyclic heterocyclic group include, for example, 2-quinuclidinyl group, 2-cromanyl group, 3-cromanyl group, 4-cromanyl group, 5-cromanyl group, 6-cromanyl group, 7-cromanyl group, 8-cromanyl group, 1-isocromanyl group, 3-isocromanyl group, 4-isocromanyl group, 5-isocromanyl group, 6-isocromanyl group, 7-isocromanyl group, 8-isocromanyl group, 2-thiocromanyl group, 3-thiocromanyl group, 4-thiocromanyl group, 5-thiocromanyl group, 6-thiocromanyl group, 7-thiocromanyl group, 8-thiocromanyl group, 1-isothiocromanyl group, 3-isothiocromanyl group, 4-isothiocromanyl group, 5-isothiocromanyl group, 6-isothiocromanyl group, 7-isothiocromanyl group, 8-isothiocromanyl group, 1-indolinyl group, 2-indolinyl group, 3-indolinyl group, 4-indolinyl group, 5-indolinyl group, 6-indolinyl group, 7-indolinyl group, 1-isoindolinyl group, 2-isoindolinyl group, 4-isoindolinyl group, 5-isoindolinyl group, 2-(4H-chromenyl) group, 3-(4H-chromenyl) group, 4-(4H-chromenyl) group, 5-(4H-chromenyl) group, 6-(4H-chromenyl) group, 7-(4H-chromenyl) group, 8-(4H-chromenyl) group, 1-isochromenyl group, 3-isochromenyl group, 4-isochromenyl group, 5-isochromenyl group, 6-isochromenyl group, 7-isochromenyl group, 8-isochromenyl group, 1-(1H-pyrrolidinyl) group, 2-(1H-pyrrolidinyl) group, 3-(1H-pyrrolidinyl) group, 5-(1H-pyrrolidinyl) group, 6-(1H-pyrrolidinyl) group, 7-(1H-pyrrolidinyl) group, and the like, but the examples are not limited to these.

As for the aromatic heterocyclic group having 1 or 2 or more ring-constituting heteroatoms, examples of monocyclic aromatic heterocyclic group include, for example, 2-furyl group, 3-furyl group, 2-thienyl group, 3-thienyl group, 1-pyrrolyl group, 2-pyrrolyl group, 3-pyrrolyl group, 2-oxazolyl group, 4-oxazolyl group, 5-oxazolyl group, 3-isoxazolyl group, 4-isoxazolyl group, 5-isoxazolyl group, 2-thiazolyl group, 4-thiazolyl group, 5-thiazolyl group, 3-isothiazolyl group, 4-isothiazolyl group, 5-isothiazolyl group, 1-imidazolyl group, 2-imidazolyl group, 4-imidazolyl group, 5-imidazolyl group, 1-pyrazolyl group, 3-pyrazolyl group, 4-pyrazolyl group, 5-pyrazolyl group, (1,2,3-oxadiazol)-4-yl group, (1,2,3-oxadiazol)-5-yl group, (1,2,4-oxadiazol)-3-yl group, (1,2,4-oxadiazol)-5-yl group, (1,2,5-oxadiazol)-3-yl group, (1,2,5-oxadiazol)-4-yl group, (1,3,4-oxadiazol)-2-yl group, (1,3,4-oxadiazol)-5-yl group, furazanyl group, (1,2,3-thiadiazol)-4-yl group, (1,2,3-thiadiazol)-5-yl group, (1,2,4-thiadiazol)-3-yl group, (1,2,4-thiadiazol)-5-yl group, (1,2,5-thiadiazol)-3-yl group, (1,2,5-thiadiazol)-4-yl group, (1,3,4-thiadiazolyl)-2-yl group, (1,3,4-thiadiazolyl)-5-yl group. (1H-1,2,3-triazol)-1-yl group, (1H-1,2,3-triazol)-4-yl group, (1H-1,2,3-triazol)-5-yl group, (2H-1,2,3-triazol)-2-yl group, (2H-1,2,3-triazol)-4-yl group, (1H-1,2,4-triazol)-1-yl group, (1H-1,2,4-triazol)-3-yl group, (1H-1,2,4-triazol)-5-yl group, (4H-1,2,4-triazol)-3-yl group, (4H-1,2,4-triazol)-4-yl group, (1H-tetrazol)-1-yl group, (1H-tetrazol)-5-yl group, (2H-tetrazol)-2-yl group. (2H-tetrazol)-5-yl group, 2-pyridyl group, 3-pyridyl group, 4-pyridyl group, 3-pyridazinyl group, 4-pyridazinyl group, 2-pyrimidinyl group, 4-pyrimidinyl group, 5-pyrimidinyl group, 2-pyrazinyl group, (1,2,3-triazin)-4-yl group, (1,2,3-triazin)-5-yl group, (1,2,4-triazin)-3-yl group, (1,2,4-triazin)-5-yl group. (1,2,4-triazin)-6-yl group, (1,3,5-triazin)-2-yl group, 1-azepinyl group, 2-azepinyl group, 3-azepinyl group, 4-azepinyl group, (1,4-oxazepin)-2-yl group, (1,4-oxazepin)-3-yl group, (1,4-oxazepin)-5-yl group, (1,4-oxazepin)-6-yl group, (1,4-oxazepin)-7-yl group, (1,4-thiazepin)-2-yl group, (1,4-thiazepin)-3-yl group, (1,4-thiazepin)-5-yl group, (1,4-thiazepin)-6-yl group, (1,4-thiazepin)-7-yl group, and the like, but the examples are not limited to these.

Examples of condensed polycyclic aromatic heterocyclic group include, for example, 8- to 14-membered condensed polycyclic aromatic heterocyclic groups such as 2-benzofuranyl group, 3-benzofuranyl group, 4-benzofuranyl group, 5-benzofuranyl group, 6-benzofuranyl group, 7-benzofuranyl group, 1-isobenzofuranyl group, 4-isobenzofuranyl group, 5-isobenzofuranyl group, 2-benzo[b]thienyl group, 3-benzo[b]thienyl group, 4-benzo[b]thienyl group, 5-benzo[b]thienyl group, 6-benzo[b]thienyl group, 7-benzo[b]thienyl group, 1-benzo[c]thienyl group, 4-benzo[c]thienyl group, 5-benzo[c]thienyl group, 1-indolyl group, 2-indolyl group, 3-indolyl group, 4-indolyl group, 5-indolyl group, 6-indolyl group, 7-indolyl group, (2H-isoindol)-1-yl group, (2H-isoindol)-2-yl group, (2H-isoindol)-4-yl group, (2H-isoindol)-5-yl group, (1H-indazol)-1-yl group, (1H-indazol)-3-yl group, (1H-indazol)-4-yl group, (1H-indazol)-5-yl group, (1H-indazol)-6-yl group. (1H-indazol)-7-yl group, (2H-indazol)-1-yl group, (2H-indazol)-2-yl group, (2H-indazol)-4-yl group, (2H-indazol)-5-yl group, 2-benzoxazolyl group, 4-benzoxazolyl group, 5-benzoxazolyl group, 6-benzoxazolyl group, 7-benzoxazolyl group, (1,2-benzisoxazol)-3-yl group, (1,2-benzisoxazol)-4-yl group, (1,2-benzisoxazol)-5-yl group, (1,2-benzisoxazol)-6-yl group, (1,2-benzisoxazol)-7-yl group, (2,1-benzisoxazol)-3-yl group, (2,1-benzisoxazol)-4-yl group, (2,1-benzisoxazol)-5-yl group, (2,1-benzisoxazol)-6-yl group, (2,1-benzisoxazol)-7-yl group, 2-benzothiazolyl group, 4-benzothiazolyl group, 5-benzothiazolyl group, 6-benzothiazolyl group, 7-benzothiazolyl group, (1,2-benzisothiazol)-3-yl group, (1,2-benzisothiazol)-4-yl group, (1,2-benzisothiazol)-5-yl group, (1,2-benzisothiazol)-6-yl group, (1,2-benzisothiazol)-7-yl group, (2,1-benzisothiazol)-3-yl group, (2,1-benzisothiazol)-4-yl group, (2,1-benzisothiazol)-5-yl group, (2,1-benzisothiazol)-6-yl group, (2,1-benzisothiazol)-7-yl group, (1,2,3-benzoxadiazol)-4-yl group, (1,2,3-benzoxadiazol)-5-yl group, (1,2,3-benzoxadiazol)-6-yl group, (1,2,3-benzoxadiazol)-7-yl group, (2,1,3-benzoxadiazol)-4-yl group. (2,1,3-benzoxadiazol)-5-yl group, (1,2,3-benzothiadiazol)-4-yl group, (1,2,3-benzothiadiazol)-5-yl group, (1,2,3-benzothiadiazol)-6-yl group, (1,2,3-benzothiadiazol)-7-yl group, (2,1,3-benzothiadiazol)-4-yl group, (2,1,3-benzothiadiazol)-5-yl group, (1H-benzotriazol)-1-yl group, (1H-benzotriazol)-4-yl group, (1H-benzotriazol)-5-yl group, (1H-benzotriazol)-6-yl group, (1H-benzotriazol)-7-yl group, (2H-benzotriazol)-2-yl group, (2H-benzotriazol)-4-yl group, (2H-benzotriazol)-5-yl group, 2-quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 3-cinnolinyl group, 4-cinnolinyl group, 5-cinnolinyl group, 6-cinnolinyl group, 7-cinnolinyl group, 8-cinnolinyl group, 2-quinazolinyl group, 4-quinazolinyl group, 5-quinazolinyl group, 6-quinazolinyl group, 7-quinazolinyl group, 8-quinazolinyl group, 2-quinoxalinyl group, 5-quinoxalinyl group, 6-quinoxalinyl group, 1-phthalazinyl group, 5-phthalazinyl group, 6-phthalazinyl group, 2-naphthyridinyl group, 3-naphthyridinyl group, 4-naphthyridinyl group, 2-purinyl group, 6-purinyl group, 7-purinyl group, 8-purinyl group, 2-pteridinyl group, 4-pteridinyl group, 6-pteridinyl group, 7-pteridinyl group, 1-carbazolyl group, 2-carbazolyl group, 3-carbazolyl group, 4-carbazolyl group, 9-carbazolyl group, 2-($\alpha$-carbolinyl) group, 3-($\alpha$-carbolinyl) group, 4-($\alpha$-carbolinyl) group, 5-($\alpha$-carbolinyl) group, 6-($\alpha$-carbolinyl) group, 7-($\alpha$-carbolinyl) group, 8-($\alpha$-carbolinyl) group, 9-($\alpha$-carbolinyl) group, 1-($\beta$-carbonylyl) group, 3-($\beta$-carbonylyl) group, 4-($\beta$-carbonylyl) group, 5-($\beta$-carbonylyl) group, 6-($\beta$-carbonylyl) group, 7-($\beta$-carbonylyl) group, 8-($\beta$-carbonylyl) group, 9-($\beta$-carbonylyl) group, 1-($\gamma$-carbolinyl) group, 2-($\gamma$-carbolinyl) group, 4-($\gamma$-carbolinyl) group, 5-($\gamma$-carbolinyl) group, 6-($\gamma$-carbolinyl) group, 7-($\gamma$-carbolinyl) group, 8-($\gamma$-carbolinyl) group, 9-($\gamma$-carbolinyl) group, 1-acridinyl group, 2-acridinyl group, 3-acridinyl group, 4-acridinyl group, 9-acridinyl group, 1-phenoxazinyl group, 2-phenoxazinyl group, 3-phenoxazinyl group, 4-phenoxazinyl group, 10-phenoxazinyl group, 1-phenothiazinyl group, 2-phenothiazinyl group, 3-phenothiazinyl group, 4-phenothiazinyl group, 10-phenothiazinyl group, 1-phenazinyl group, 2-phenazinyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 2-phenanthrolinyl group, 3-phenanthrolinyl group, 4-phenanthrolinyl group, 5-phenanthrolinyl group, 6-phenanthrolinyl group, 7-phenanthrolinyl group, 8-phenanthrolinyl group, 9-phenanthrolinyl group, 10-phenanthrolinyl group, 1-thianthrenyl group, 2-thianthrenyl group, 1-indolizinyl group, 2-indolizinyl group, 3-indolizinyl group, 5-indolizinyl group, 6-indolizinyl group, 7-indolizinyl group, 8-indolizinyl group, 1-phenoxathiinyl group, 2-phenoxathiinyl group, 3-phenoxathiinyl group, 4-phenoxathiinyl group, thieno[2,3-b]furyl group, pyrrolo[1,2-b]pyridazinyl group, pyrazolo[1,5-a]pyridyl group, imidazo[11,2-a]pyridyl group, imidazo[1,5-a]pyridyl group, imidazo[1,2-b]pyridazinyl group, imidazo[1,2-a]pyrimidinyl group, 1,2,4-triazolo[4,3-a]pyridyl group, and 1,2,4-triazolo[4,3-a]pyridazinyl group, but the examples are not limited to these.

When the expression "which may have a substituent" is used for a certain functional group in this specification, it means that the functional group is unsubstituted, or the functional group has one or two or more substituents at chemically substitutable positions, unless otherwise indicated. Type, number, and substitution position of substituent existing on a functional group are not particularly limited, and when there are two or more substituents, they may be the same or different. Examples of the substituent existing on a functional group include, for example, an alkyl group, a halogen atom, oxo group, thioxo group, nitro group, nitroso group, cyano group, isocyano group, cyanato group, tiocyanato group, isocyanato group, isotiocyanato group, hydroxy group, sulfanyl group, carboxy group, sulfanylcarbonyl group, oxalo group, mesoxalo group, thiocarboxy group, dithiocarboxy group, carbamoyl group, thiocarbamoyl group, sulfo group, sulfamoyl group, sulfino group, sulfinamoyl group, sulfeno group, sulfenamoyl group, phosphono group, hydroxyphosphonyl group, a hydrocarbon group, a heterocyclic group, a hydrocarbon-oxy group, a (heterocyclic ring)-oxy group, a hydrocarbon-sulfanyl group, a (heterocyclic ring)-sulfanyl group, an acyl group, amino group, hydrazino group, hydrazono group, diazenyl group, ureido group, thioureido group, guanidino group, carbamoimidoyl group (amidino group), azido group, imino group, hydroxyamino group, hydroxyimino group, aminoxy group, diazo group, semicarbazino group, semicarbazono group, allophanyl group, hydantoyl group, phosphano group, phosphoroso group, phospho group, boryl group, silyl group, stanyl group, selanyl group, oxido group, and the like, but the examples are not limited to these examples.

The substituent in the aforementioned definitions may be substituted with another substituent at a chemically substitutable position on the substituent. Type, number, and substitution position of the substituent are not particularly limited, and when the substituent is substituted with two or more substituents, they may be the same or different. Examples of such a substituent include, for example, a halogenated alkyl group (for example, trifluoromethyl group and the like), a hydroxyalkyl group (for example, hydroxymethyl group and the like), a halogenated alkyl-carbonyl group (for example, trifluoroacetyl and the like), a halogenated alkyl-sulfonyl group (for example, trifluoromethanesulfonyl and the like), an acyl-oxy group, an acyl-sulfanyl group, an N-hydrocarbon-amino group, an N,N-di(hydrocarbon)-amino group, an N-(heterocyclic ring)-amino group, an N-hydrocarbon-N-(heterocyclic ring)-amino group, an acyl-amino group, a di(acyl)-amino group, and the like, but the examples are not limited to these examples.

As $R^2$, a saturated or partially saturated 3- to 7-membered monocyclic cyclic hydrocarbon group which may have a substituent, a phenyl group which may have a substituent, a saturated or partially saturated 3- to 7-membered monocyclic heterocyclic group which may have a substituent (this heterocyclic group contains 1 to 3 ring-constituting heteroatoms), or a aromatic monocyclic heterocyclic group which may have a substituent (this heterocyclic group contains 1 to 3 ring-constituting heteroatoms) is preferred. As $R^2$, a saturated cyclic hydrocarbon group such as cyclopentyl group, and cyclohexyl group, phenyl group, thienyl group, pyridyl group, pyrimidyl group, thiazolyl group, pyrazolyl group, oxodihydropyridyl group, benzothiophene group, and the like are preferred, and examples of substituents substituting on the rings of these cyclic groups include, for example, one or two or more substituents selected from methyl group, isobutyl group, chlorine atom, fluorine atom, cyano group, trifluoromethyl group, difluoromethyl group, methoxy group, difluoromethoxy group, trifluoromethoxy group, ethoxy group, methoxyethoxy group, ethoxyethoxy group, trifluoroethoxy group, isopropoxy group, methoxypropoxy group, methylsulfanyl group, cyclopropyl group, cyclopropylethynyl group, propynyl group, tetrahydropyran-4-yl-methoxy group, and the like, but the examples are not limited to these.

$R^3$ represents hydrogen atom, or 1 to 3 substituents substituting on the benzene ring, and these substituents are selected from the group consisting of a halogen atom, an alkyl group (this alkyl group may be substituted with a halogen atom), and an alkoxy group (this alkoxy group may be substituted with a halogen atom). $R^3$ preferably represents one or two substituents substituting on the benzene ring, and it is preferred that these substituents are chlorine atom, fluorine atom, trifluoromethyl group, or difluoromethoxy group. When there are two substituents, chlorine atom, fluorine atom, or trifluoromethyl group is preferred. Although substitution position of $R^3$ is not particularly limited, when $R^3$ consists of one substituent substituting on the benzene ring, it is preferred that it substitutes at the ortho-position of the pyrimidinyl group substituting on the benzene ring, and it is more preferred that this substituent substitutes at the ortho-position of the pyrimidinyl group substituting on the benzene ring, and the para-position of the aminomethyl group substituting on the benzene ring. Although substitution position of $R^3$ is not particularly limited, when $R^3$ consists of two substituents substituting on the benzene ring, it is preferred that they substitute at the ortho-positions of the pyrimidinyl group substituting on the benzene ring, and it is more preferred that these substituents substitute at the ortho-positions of the pyrimidinyl group substituting on the benzene ring, and the ortho-position and the para-position of the aminomethyl group substituting on the benzene ring.

$R^4$ and $R^5$ independently represent hydrogen atom, a halogen atom, or an alkyl group. It is preferred that both $R^4$ and $R^5$ are hydrogen atoms.

$R^6$ represents an alkyl group (this alkyl group may be substituted with hydroxy group, a halogen atom, or an alkoxy group), or an alkoxy group. $R^6$ is preferably a straight, branched, or cyclic $C_{1-6}$ alkyl group, and the branched $C_{1-6}$ alkyl group may be substituted with a $C_{1-6}$ alkoxy group. As $R^6$, ethyl group, propyl group, isopropyl group, 1-methyl-1-methoxyethyl group, cyclopropyl group, t-butyl group, and the like can be preferably used, and ethyl group, propyl group, and isopropyl group can be particularly preferably used.

According to the present invention, the compounds represented by the formula (1) can be prepared by, for example, one of the methods of (a) to (d) mentioned below.
Method (a):
A pyrimidine derivative represented by the formula (1) wherein $R^1$ is cyano group can be prepared by reacting an amidine derivative represented by the following formula (2):

[Formula 2]

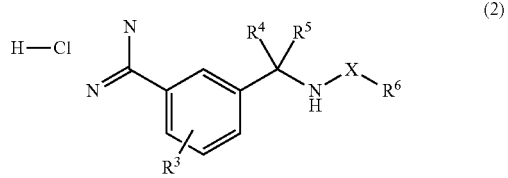

(2)

(in the formula, $R^3$, $R^4$, $R^5$, $R^6$, and X have the same meanings as those defined above), an ester represented by the following formula (3)

[Formula 3]

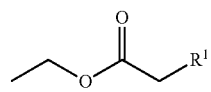

Formula (3)

(in the formula, $R^1$ is cyano group), and an aldehyde represented by the following formula (4)

[Formula 4]

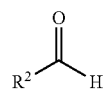

Formula (4)

(in the formula, $R^2$ has the same meaning as that defined above).

Examples of base used for this reaction include organic bases (amines, for example, mono- to trialkylamines such as methylamine, ethylamine, diethylamine, triethylamine, propylamine, isopropylamine, and diisopropylethylamine; alkanolamines such as ethanolamine; alkylenepolyamines such as ethylenediamine, and diethylenetriamine, and the like), inorganic bases [metal hydroxides (alkali metal or alkaline earth metal hydroxides, and the like) such as sodium hydroxide, potassium hydroxide, calcium hydroxide, iron hydroxide, and aluminum hydroxide; alkali metal carbonates such as sodium carbonate, sodium hydrogencarbonate, potassium carbonate, rubidium carbonate, and cesium carbonate; ammonia, and the like], and the like. Preferred examples include alkali metal bases and organic bases, and particularly preferred examples include potassium carbonate, sodium ethoxide, and diisopropylethylamine. A salt may be formed with one or two or more kinds of these bases.

Reaction time, reaction temperature, and the like may be selected from conventionally used ranges. Reaction temperature is preferably 0 to 140° C., particularly preferably 20 to 80° C. Reaction time is preferably 0.25 to 48 hours, particularly preferably 0.5 to 24 hours.

Solvent used for this reaction may be selected from conventionally used solvents. Water, N,N-dimethylacetamide, methanol, ethanol, 1-propanol, 2-propanol, 1-butanol, 1-pentanol, and the like are preferred.

The ester represented by the formula (3) used in this reaction may be an ester represented by the following formula (3)-1 or (3)-2.

[Formula 5]

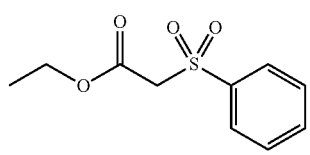

(3)-1

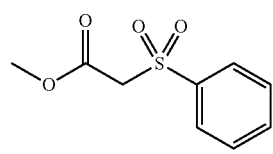

(3)-2

If the pyrimidine derivative is prepared by using an ester represented by the formula (3)-1 or (3)-2, the compound represented by the formula (1) wherein $R^1$ is hydrogen atom can be prepared.

Method (b):

A pyrimidine derivative represented by the formula (1) can be prepared by reacting an amidine derivative represented by the formula (2) (in the formula, $R^3$, $R^4$, $R^5$, $R^6$, and X have the same meanings as those defined above), and a 6-ketoester represented by the following formula (5):

[Formula 6]

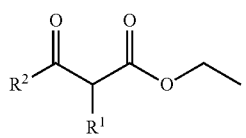

Formula (5)

(in the formula, $R^1$ and $R^2$ have the same meanings as those defined above).

Solvent used for this reaction may be selected from conventionally used solvents. Methanol, ethanol, 1-propanol, and 2-propanol are preferred.

Reaction time, reaction temperature, and the like may be selected from conventionally used ranges. Reaction temperature is preferably 25 to 120° C., particularly preferably 60 to 80° C. Reaction time is preferably 2 to 48 hours, particularly preferably 10 to 24 hours.

The ester represented by the formula (3) used in this reaction may be an ester represented by the aforementioned formula (3)-1.

Method (c):

A pyrimidine derivative represented by the formula (1) can be prepared by reacting a pyrimidine derivative represented by the following formula (1):

[Formula 7]

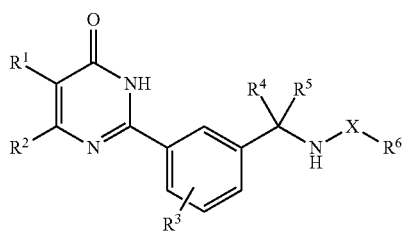

Formula (1)

(in the formula, $R^1$, $R^2$, $R^3$, $R^4$, $R^5$, $R^6$, and X have the same meanings as those defined above) with a deprotecting agent, and reacting the resultant with a compound represented by the following formula (7):

[Formula 8]

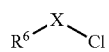

Formula (7)

(in the formula, $R^6$ and X have the same meanings as those defined above).

Examples of the deprotecting agent include, for example, inorganic acids (hydrochloric acid, sulfuric acid, nitric acid, and the like), organic acids [sulfonic acids (aliphatic sulfonic acids such as methanesulfonic acid, halogenated aliphatic sulfonic acids such as trifluoromethanesulfonic acid, aromatic sulfonic acid such as benzenesulfonic acid, and toluenesulfonic acid, and the like), carboxylic acids (halogenated carboxylic acids such as trifluoroacetic acid, and mono-, di-, or trichloroacetic acid), and the like]. Among these strong acids, inorganic acids such as hydrochloric acid, carboxylic acids such as trifluoroacetic acid, and sulfonic acids such as trifluoromethanesulfonic acid are preferred.

Solvent used for the deprotection reaction may be selected from conventionally used solvents. Dichloromethane, and the like are preferred, and it is also preferable to perform the reaction without solvent.

Reaction time, reaction temperature, and the like of the deprotection reaction may be selected from conventionally used ranges. Reaction temperature is preferably 0 to 50° C., particularly preferably 10 to 30° C. Reaction time is preferably 1 to 48 hours, particularly preferably 3 to 24 hours.

Solvent used for the amidation reaction may be selected from conventionally used solvents. N,N-Dimethylformamide, dichloromethane, and the like are preferred. Reaction time, reaction temperature, and the like of the amidation reaction may be selected from conventionally used ranges. Reaction temperature is preferably −10 to 60° C., particularly preferably 0 to 30° C. Reaction time is preferably 1 to 48 hours, particularly preferably 3 to 24 hours.

Method (d):

By reacting an amidine derivative represented by the following formula (7):

[Formula 9]

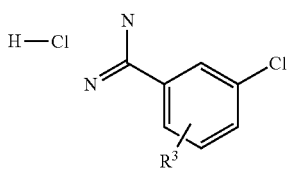

Formula (7)

(in the formula, $R^3$ has the same meaning as that defined above), a compound represented by the following formula (3)-1:

[Formula 10]

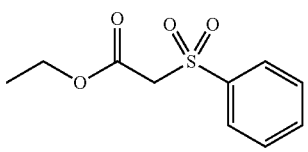

(in the formula, $R^3$ has the same meaning as that defined above), and an aldehyde represented by the following formula (4):

[Formula 11]

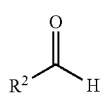

Formula (4)

(in the formula, $R^2$ has the same meaning as that defined above), a pyrimidine derivative represented by the formula (8) can be prepared.

[Formula 12]

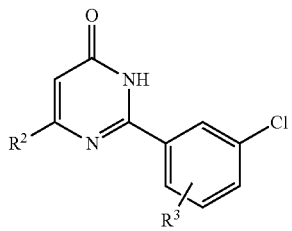

Formula (8)

Examples of base used for this reaction include organic bases (amines, for example, mono- to trialkylamines such as methylamine, ethylamine, diethylamine, triethylamine, propylamine, isopropylamine, and diisopropylethylamine; alkanolamines such as ethanolamine; alkylenepolyamines such as ethylenediamine, and diethylenetriamine, and the like), inorganic bases [metal hydroxides (alkali metal or alkaline earth metal hydroxides, and the like) such as sodium hydroxide, potassium hydroxide, calcium hydroxide, iron hydroxide, and aluminum hydroxide; alkali metal carbonates such as sodium carbonate, sodium hydrogencarbonate, potassium carbonate, rubidium carbonate, and cesium carbonate; ammonia, and the like], and the like. Preferred examples include alkali metal bases and organic bases, and particularly preferred examples include potassium carbonate, sodium ethoxide, and diisopropylethylamine. A salt may be formed with one or two or more kinds of these bases.

Reaction time, reaction temperature, and the like may be selected from conventionally used ranges. Reaction temperature is preferably 0 to 140° C., particularly preferably 20 to 80° C. Reaction time is preferably 0.25 to 48 hours, particularly preferably 0.5 to 24 hours.

Solvent used for this reaction may be selected from conventionally used solvents. Water, N,N-dimethylacetamide, methanol, ethanol, 1-propanol, 2-propanol, 1-butanol, 1-pentanol, and the like are preferred.

Then, a pyrimidine derivative represented by the formula (1) wherein $R^1$, $R^4$, and $R^5$ are hydrogen atoms, X is C=O, and $R^6$ is isopropyl group can be prepared by reacting the pyrimidine derivative represented by the formula (8) with a compound represented by the following formula:

[Formula 13]

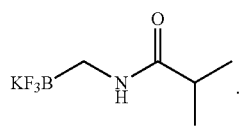

Examples of base used for this reaction include inorganic bases [alkali metal carbonates such as sodium carbonate, sodium hydrogencarbonate, potassium carbonate, rubidium carbonate, and cesium carbonate, alkali metal phosphates such as tripotassium phosphate], organic bases (amines, for example, trialkylamines such as triethylamine, and diisopropylethylamine), and the like. Preferred examples include sodium carbonate, potassium carbonate, and cesium carbonate.

Examples of metal catalyst used for this reaction include, Pd(OAc)$_2$, Pd(dba)$_2$, Pd$_2$(dba)$_3$, Pd(PPh$_3$)$_4$, PdCl$_2$(dppf)-CH$_2$Cl$_2$, and the like. Preferred examples include Pd(OAc)$_2$, and Pd(dba)$_2$.

Examples of ligand used for this reaction include XPhos, SPhos, RuPhos, and the like.

Reaction time, reaction temperature, and the like may be selected from conventionally used ranges. Reaction temperature is preferably 30 to 180° C., particularly preferably 60 to 140° C. Reaction time is preferably 0.5 to 48 hours, particularly preferably 1 to 24 hours.

Solvent used for this reaction may be selected from conventionally used solvents. 1,4-Dioxane/water, CPME/water, toluene/water, THF/water, i-PrOH/water, EtOH/water, MeOH, THF, CPME, DME, 1,4-dioxane, and the like are preferred.

Examples of the compounds of the present invention falling within the scope of the general formula (1) include, for example;

N-{4-chloro-3-[4-(4-chloro-2-fluorophenyl)-5-cyano-6-oxo-1,6-dihydropyrimidin-2-yl]benzyl}-2,2-dimethylpropionamide;
N-[4-chloro-3-(5-cyano-6-oxo-4-thiophen-3-yl-1,6-dihydropyrimidin-2-yl)benzyl]-2,2-dimethylpropionamide;
N-[4-chloro-3-(5-cyano-6-oxo-4-thiophen-3-yl-1,6-dihydropyrimidin-2-yl)benzyl]isobutyramide;
N-[4-chloro-3-(6-oxo-4-thiophen-3-yl-1,6-dihydropyrimidin-2-yl)benzyl]isobutyramide;
N-{4-chloro-3-[4-(4-chloro-2-fluorophenyl)-6-oxo-1,6-dihydropyrimidin-2-yl]benzyl}isobutyramide;
N-{4-chloro-3-[4-(4-chlorophenyl)-6-oxo-1,6-dihydropyrimidin-2-yl]benzyl}isobutyramide;
N-{4-chloro-3-[4-(5-chloropyridin-2-yl)-6-oxo-1,6-dihydropyrimidin-2-yl]benzyl}isobutyramide;
N-[4-chloro-3-(6-oxo-4-phenyl-1,6-dihydropyrimidin-2-yl)benzyl]isobutyramide;
N-{4-chloro-3-[6-oxo-4-(6-trifluoromethylpyridin-3-yl)-1,6-dihydropyrimidin-2-yl]benzyl}isobutyramide;
N-{4-chloro-3-[4-(4-chloro-3-fluorophenyl)-6-oxo-1,6-dihydropyrimidin-2-yl]benzyl}isobutyramide;
N-[4-chloro-3-(6-oxo-4-thiophen-3-yl-1,6-dihydropyrimidin-2-yl)benzyl]-2-methoxy-2-methylpropionamide;
N-{4-chloro-3-[6-oxo-4-(5-trifluoromethylpyridin-2-yl)-1,6-dihydropyrimidin-2-yl]benzyl}isobutyramide;
N-{4-chloro-3-[4-(5-chloropyridin-2-yl)-6-oxo-1,6-dihydropyrimidin-2-yl]benzyl}-2-methoxy-2-methylpropionamide;
N-{4-chloro-3-[4-(3-chloro-2-fluorophenyl)-6-oxo-1,6-dihydropyrimidin-2-yl]benzyl}isobutyramide;
N-{4-chloro-3-[4-(2-chloro-4-fluorophenyl)-6-oxo-1,6-dihydropyrimidin-2-yl]benzyl}isobutyramide;
N-{4-chloro-3-[4-(4-difluoromethoxy-2-fluorophenyl)-6-oxo 1,6-dihydropyrimidin-2-yl]benzyl}isobutyramide;
N-{4-chloro-3-[4-(2-fluoro-4-trifluoromethoxyphenyl)-6-oxo-1,6-dihydropyrimidin-2-yl]benzyl}isobutyramide;
N-{4-chloro-3-[4-(2-fluoro-4-methoxyphenyl)-6-oxo-1,6-dihydropyrimidin-2-yl]benzyl}isobutyramide;
N-{4-chloro-3-[4-(4-methoxyphenyl)-6-oxo-1,6-dihydropyrimidin-2-yl]benzyl}isobutyramide;
N-{4-chloro-3-[4-(4-difluoromethoxyphenyl)-6-oxo-1,6-dihydropyrimidin-2-yl]benzyl}isobutyramide;
N-{4-chloro-3-[6-oxo-4-(4-trifluoromethylphenyl)-1,6-dihydropyrimidin-2-yl]benzyl}isobutyramide;
N-{4-chloro-3-[4-(3-fluorothiophen-2-yl)-6-oxo-1,6-dihydropyrimidin-2-yl]benzyl}isobutyramide;
N-[4-chloro-3-(4-cyclopentyl-6-oxo-1,6-dihydropyrimidin-2-yl)benzyl]isobutyramide;
N-{4-chloro-3-[6-oxo-4-(4-trifluoromethoxyphenyl)-1,6-dihydropyrimidin-2-yl]benzyl}isobutyramide;
N-{4-chloro-3-[4-(2,4-difluorophenyl)-6-oxo-1,6-dihydropyrimidin-2-yl]benzyl}isobutyramide;

N-{4-chloro-3-[4-(2-chlorothiophen-3-yl)-6-oxo-1,6-dihydropyrimidin-2-yl]benzyl}isobutyramide;
N-[4-chloro-3-(4-cyclohexyl-6-oxo-1,6-dihydropyrimidin-2-y)benzyl]isobutyramide;
N-{4-chloro-3-[4-(2-fluoro-5-methoxyphenyl)-6-oxo-1,6-dihydropyrimidin-2-yl]benzyl}isobutyramide;
N-{4-chloro-3-[4-(5-chloro-2-fluorophenyl)-6-oxo-1,6-dihydropyrimidin-2-yl]benzyl}isobutyramide;
N-{4-chloro-3-[6-oxo-4-(6-trifluoromethylpyrimidin-2-yl)-1,6-dihydropyrimidin-2-yl]benzyl}isobutyramide;
N-{4-chloro-3-[4-(2-fluorophenyl)-6-oxo-1,6-dihydropyrimidin-2-yl]benzyl}isobutyramide;
N-{3-[4-(5-chloropyridin-2-yl)-6-oxo-1,6-dihydropyrimidin-2-yl]benzyl}isobutyramide;
N-[4-chloro-3-(6-oxo-4-thiophen-2-yl-1,6-dihydropyrimidin-2-yl)benzyl]isobutyramide;
N-[4-chloro-3-(5-methyl-6-oxo-4-phenyl-1,6-dihydropyrimidin-2-yl)benzyl]isobutyramide;
N-{4-chloro-3-[4-(6-methoxypyridin-3-yl)-6-oxo-1,6-dihydropyrimidin-2-yl]benzyl}isobutyramide;
N-{4-chloro-3-[4-(6-ethoxypyridin-3-yl)-6-oxo-1,6-dihydropyrimidin-2-yl]benzyl}isobutyramide;
N-{4-chloro-3-[4-(3-fluoro-4-methylphenyl)-6-oxo-1,6-dihydropyrimidin-2-yl]benzyl}isobutyramide;
N-(4-chloro-3-{4-[4-(2-methoxyethoxy)phenyl]-6-oxo-1,6-dihydropyrimidin-2-yl}benzyl)isobutyramide;
N-{4-chloro-3-[4-(5-methylpyridin-2-yl)-6-oxo-1,6-dihydropyrimidin-2-yl]benzyl}isobutyramide;
N-(4-chloro-3-{6-oxo-4-[6-(trifluoromethyl)pyridin-3-yl]-1,6-dihydropyrimidin-2-yl}benzyl)cyclopropanecarboxamide;
N-(4-chloro-3-{4-[4-(difluoromethyl)phenyl]-6-oxo-1,6-dihydropyrimidin-2-yl}benzyl)isobutyramide;
N-(4-chloro-3-{6-oxo-4-[5-(trifluoromethyl)thiophen-2-yl]-1,6-dihydropyrimidin-2-yl}benzyl)isobutyramide;
N-(4-chloro-3-{6-oxo-4-[2-(trifluoromethyl)thiazol-5-yl]-1,6-dihydropyrimidin-2-yl}benzyl)isobutyramide;
N-{4-chloro-3-[4-(2-fluoro-4-methylphenyl)-6-oxo-1,6-dihydropyrimidin-2-yl]benzyl}isobutyramide;
N-(4-chloro-3-{4-[6-(difluoromethoxy)pyridin-3-y]-6-oxo-1,6-dihydropyrimidin-2-yl}benzyl)isobutyramide;
N-(4-chloro-3-{4-[4-(2-ethoxyethoxy)-3-fluorophenyl]-6-oxo-1,6-dihydropyrimidin-2-yl}benzyl)isobutyramide;
N-(4-chloro-3-{4-[4-(2-ethoxyethoxy)-2-fluorophenyl]-6-oxo-1,6-dihydropyrimidin-2-yl}benzyl)isobutyramide;
N-{4-chloro-3-[4-(6-isopropoxypyridin-3-yl)-6-oxo-1,6-dihydropyrimidin-2-yl]benzyl}isobutyramide;
N-(4-chloro-3-{6-oxo-4-[6-(2,2,2-trifluoroethoxy)pyridin-3-yl]-1,6-dihydropyrimidin-2-yl}benzyl)isobutyramide;
N-{3-[4-(1-tert-butyl-1H-pyrazol-4-yl)-6-oxo-1,6-dihydropyrimidin-2-yl]-4-chlorobenzyl}isobutyramide;
N-{4-chloro-3-[4-(1-isobutyl-1H-pyrazol-4-yl)-6-oxo-1,6-dihydropyrimidin-2-yl]benzyl}isobutyramide;
N-{4-chloro-3-[4-(2-methoxythiazol-5-yl)-6-oxo-1,6-dihydropyrimidin-2-yl]benzyl}isobutyramide;
N-(4-chloro-3-{6-oxo-4-[6-(trifluoromethyl)pyridin-3-yl]-1,6-dihydropyrimidin-2-yl}benzyl)-3,3,3-trifluoro-2,2-dimethylpropioniamide;
N-{4-chloro-3-[4-(6-methoxypyridin-3-yl)-6-oxo-1,6-dihydropyrimidin-2-yl]benzyl}-3,3,3-trifluoro-2,2-dimethylpropionamide;
N-(4-chloro-3-{4-[6-(difluoromethoxy)pyridin-3-yl]-6-oxo-1,6-dihydropyrimidin-2-yl}benzyl)-3,3,3-trifluoro-2,2-dimethylpropionamide;
N-(4-fluoro-3-{6-oxo-4-[6-(trifluoromethyl)pyridin-3-yl]-1,6-dihydropyrimidin-2-yl}benzyl)-2,2-dimethylpropionamide;
N-(3-{4-[6-(difluoromethoxy)pyridin-3-yl]-6-oxo-1,6-dihydropyrimidin-2-yl}-4-fluorobenzyl)-2,2-dimethylpropionamide;
N-(4-difluoromethoxy-3-{6-oxo-4-[6-(trifluoromethyl)pyridin-3-yl]-1,6-dihydropyrimidin-2-yl}benzyl)isobutyramide;
N-(4-chloro-3-{4-[6-(2-ethoxyethoxy)pyridin-3-yl]-6-oxo-1,6-dihydropyrimidin-2-yl}benzyl)isobutyramide;
N-(4-chloro-3-{4-[6-(3-methoxypropoxy)pyridin-3-yl]-6-oxo-1,6-dihydropyrimidin-2-yl}benzyl)isobutyramide;
N-(4-chloro-3-{4-[6-(2-methoxyethoxy)pyridin-3-yl]-6-oxo-1,6-dihydropyrimidin-2-yl}benzyl)isobutyramide;
N-{4-chloro-3-[4-(3-fluorophenyl)-6-oxo-1,6-dihydropyrimidin-2-yl]benzyl}isobutyramide;
N-(4-chloro-3-{6-oxo-4-[4-(pyridin-2-ylethynyl)phenyl]-1,6-dihydropyrimidin-2-yl}benzyl)isobutyramide;
N-[4-chloro-3-(5-fluoro-6-oxo-4-phenyl-1,6-dihydropyrimidin-2-yl)benzyl]isobutyramide;
N-{4-chloro-3-[5-fluoro-4-(4-methoxyphenyl)-6-oxo-1,6-dihydropyrimidin-2-yl]benzyl}isobutyramide;
N-{4-chloro-3-[5-fluoro-6-oxo-4-(thiophen-2-yl)-1,6-dihydropyrimidin-2-yl]benzyl}isobutyramide;
N-{4-chloro-3-[5-fluoro-6-oxo-4-(thiophen-3-yl)-1,6-dihydropyrimidin-2-yl]benzyl}isobutyramide;
N-{3-[4-(benzo[b]thiophen-7-yl)-6-oxo-1,6-dihydropyrimidin-2-yl]-4-chloro-benzyl}isobutyramide;
N-{4-chloro-3-[4-(4-cyanophenyl)-6-oxo-1,6-dihydropyrimidin-2-yl]benzyl}isobutyramide;
N-(4-chloro-3-{4-[4-(methylsulfanyl)phenyl]-6-oxo-1,6-dihydropyrimidin-2-yl}benzyl)isobutyramide;
N-{4-chloro-3-[6-oxo-4-(p-toluyl)-1,6-dihydropyrimidin-2-yl]benzyl}isobutyramide;
N-(4-chloro-3-{4-[4-(diethylsulfamoyl)phenyl]-6-oxo-1,6-dihydropyrimidin-2-yl}benzyl)isobutyramide;
N-(4-chloro-3-{6-oxo-4-[4-(piperidine-1-sulfonyl)phenyl]-1,6-dihydropyrimidin-2-yl}benzyl)isobutyramide;
N-{4-chloro-3-[4-(4-cyclopropylphenyl)-6-oxo-1,6-dihydropyrimidin-2-yl]benzyl}isobutyramide
N-(3-(6-oxo-4-[6-(trifluoromethyl)pyridin-3-yl]-1,6-dihydropyrimidin-2-yl)-4-(trifluoromethyl)benzyl)isobutyramide;
N-{3-[4-(6-methoxypyridin-3-yl)-6-oxo-1,6-dihydropyrimidin-2-yl]-4-(trifluoromethyl)benzyl}isobutyramide;
N-(3-{4-[6-(difluoromethoxy)pyridin-3-yl]-6-oxo-1,6-dihydropyrimidin-2-yl}-4-(trifluoromethyl)benzyl)isobutyramide;
N-(3-[4-{6-ethoxypyrimidin-3-yl)-6-oxo-1,6-dihydropyrimidin-2-yl]-4-(trifluoromethyl)benzyl}isobutyramide;
N-(4-methyl-3-{6-oxo-4-[6-(trifluoromethyl)pyridin-3-yl]-1,6-dihydropyrimidin-2-yl}benzyl)isobutyramide;
N-(3-{4-[6-(difluoromethoxy)pyridin-3-yl]-6-oxo-1,6-dihydropyrimidin-2-yl}-4-methylbenzyl)isobutyramide;
N-{3-[4-(6-ethoxypyridin-3-y)-6-oxo-1,6-dihydropyrimidin-2-yl]-4-methylbenzyl}isobutyramide;
N-[4-(difluoromethyl)-3-{6-oxo-4-[6-(trifluoromethyl)pyridin-3-yl]-1,6-dihydropyrimidin-2-yl}benzyl]isobutyramide;
N-(3-{4-[6-(difluoromethoxy)pyridin-3-yl]-6-oxo-1,6-dihydropyrimidin-2-yl}-4-(difluoromethyl)benzyl)isobutyramide;
N-(4-chloro-3-{6-oxo-4-[2-(trifluoromethyl)pyridin-4-yl]-1,6-dihydropyrimidin-2-yl}benzyl) isobutyramide;
N-(4-chloro-3-{4-[2-(difluoromethoxy)pyridin-4-yl]-6-oxo-1,6-dihydropyrimidin-2-yl}benzyl)isobutyramide;
N-{4-chloro-3-[4-(3-fluoro-4-methoxyphenyl)-6-oxo-1,6-dihydropyrimidin-2-yl]benzyl}isobutyramide;

4-{2-[2-chloro-5-(isobutyrylaminomethyl)phenyl]-6-oxo-1,6-dihydropyrimidin-4-yl}-N,N-dimethylbenzamide;
N-{4-chloro-3-[4-(4-fluorophenyl)-6-oxo-1,6-dihydropyrimidin-2-yl]benzyl}isobutyramide;
N-{4-chloro-3-[4-(6-methoxypyridin-2-yl)-6-oxo-1,6-dihydropyrimidin-2-yl]benzyl}isobutyramide;
N-(4-fluoro-3-{6-oxo-4-[6-(trifluoromethyl)pyridin-3-yl]-1,6-dihydropyrimidin-2-yl}benzyl)isobutyramide;
N-{4-chloro-3-[4-(6-cyclopropylpyrimidin-3-yl)-6-oxo-1,6-dihydropyrimidin-2-yl]benzyl}isobutyramide;
N-{3-[4-(6-ethoxypyridin-3-yl)-6-oxo-1,6-dihydropyrimidin-2-yl]-4-fluorobenzyl}isobutyramide;
N-[4-chloro-3-(2'-methoxy-6-oxo-1,6-dihydro[4,5']bipyrimidinyl-2-yl)benzyl]isobutyramide;
N-(3-{4-[6-(difluoromethoxy)pyridin-3-yl]-6-oxo-1,6-dihydropyrimidin-2-yl}-4-fluorobenzyl)isobutyramide;
N-(4-chloro-2-fluoro-3-{6-oxo-4-[6-(trifluoromethyl)pyridin-3-yl]-1,6-dihydropyrimidin-2-yl}benzyl)isobutyramide;
N-(4-chloro-3-{4-[6-(difluoromethoxy)pyridin-3-yl]-6-oxo-1,6-dihydropyrimidin-2-y}-2-fluorobenzyl)isobutyramide;
N-(4-fluoro-3-{6-oxo-4-[6-(trifluoromethyl)pyridin-3-yl]-1,6-dihydropyrimidin-2-yl}benzyl)-1-(trifluoromethyl)cyclopropane-1-carboxamide;
methyl 4-{2-[2-chloro-5-(isobutyrylaminomethyl)phenyl]-6-oxo-1,6-dihydropyrimidin-4-yl}benzoate;
N-(3-{4-[6-(difluoromethoxy)pyridin-3-y]-6-oxo-1,6-dihydropyrimidin-2-yl}-4-fluorobenzyl)-1-(trifluoromethyl)cyclopropane-1-carboxamide;
N-(2,4-difluoro-3-{6-oxo-4-[6-(trifluoromethyl)pyridin-3-y]-1,6-dihydropyrimidin-2-yl}benzyl)isobutyramide;
N-(4-chloro-3-{6-oxo-4-[6-(2-propoxyethoxy)pyridin-3-yl]-1,6-dihydropyrimidin-2-yl}benzyl)isobutyramide;
N-(3-{4-[6-(2-butoxyethoxy)pyridin-3-yl]-6-oxo-1,6-dihydropyrimidin-2-yl}-4-chlorobenzyl)isobutyramide;
N-{4-chloro-3-[6-oxo-2'-(trifluoromethyl)-1,6-dihydro[4,5']-bipyrimidin-2-yl]benzyl}isobutyramide;
N-(4-chloro-3-{4-[6-(3-ethoxypropoxy)pyridin-3-yl]-6-oxo 1,6-dihydropyrimidin-2-yl}benzyl)isobutyramide;
N-(4-chloro-3-{4-[6-(cyclopropylmethoxy)pyrimidin-3-yl]-6-oxo-1,6-dihydropyrimidin-2-yl}benzyl)isobutyramide;
N-[3-(4-{6-[2-(2-butoxyethoxy)ethoxy]pyridin-3-yl}-6-oxo-1,6-dihydropyrimidin-2-yl)-4-chlorobenzyl]isobutyramide;
N-(4-chloro-3-{6-oxo-4-[6-(pyridin-2-ylmethoxy)pyridin-3-yl]-1,6-dihydropyrimidin-2-yl}benzyl)isobutyramide;
N-(3-{6-oxo-4-[6-(pyridin-2-ylmethoxy)pyridin-3-yl]-1,6-dihydropyrimidin-2-yl}-4-(trifluoromethyl)benzyl)isobutyramide;
N-(4-chloro-3-{4-[6-(6-methylpyridin-3-ylmethoxy)pyridin-3-yl]-6-oxo-1,6-dihydropyrimidin-2-yl}benzyl)isobutyramide;
N-{4-chloro-3-[6-oxo-4-(2-oxo-1-pentyl-1,2-dihydropyridin-4-yl)-1,6-dihydropyrimidin-2-yl]benzyl}isobutyramide;
N-{3-[4-(1-butyl-2-oxo-1,2-dihydropyridin-4-yl)-6-oxo-1,6-dihydropyrimidin-2-yl]-4-chlorobenzyl}isobutyramide;
N-(4-chloro-3-{4-[6-(difluoromethoxy)pyridin-3-yl]-6-oxo-1,6-dihydropyrimidin-2-yl}benzyl)propionamide;
N-(4-chloro-3-{4-[6-(cyclopropylmethoxy)pyridin-3-yl]-6-oxo-1,6-dihydropyrimidin-2-yl}benzyl)propionamide;
N-(4-chloro-3-{4-[6-(difluoromethoxy)pyridin-3-y]-6-oxo-1,6-dihydropyrimidin-2-yl}benzyl)butyramide;
N-(4-chloro-3-{6-oxo-4-[6-(2-propoxyethoxy)pyridin-3-yl]-1,6-dihydropyrimidin-2-yl}benzyl)butyramide;

N-{4-chloro-3-[4-(5-fluoropyridin-3-yl)-6-oxo-1,6-dihydropyrimidin-2-yl]benzyl}isobutyramide;
N-(4-chloro-3-{6-oxo-4-[6-(2,2,2-trifluoroethoxy)pyridin-3-yl]-1,6-dihydropyrimidin-2-yl}benzyl)propionamide;
N-(4-chloro-3-{4-[5-(difluoromethoxy)pyridin-2-yl]-6-oxo-1,6-dihydropyrimidin-2-yl}benzyl)butyramide;
N-{3-[4-(5-chloropyridin-3-yl)-6-oxo-1,6-dihydropyrimidin-2-yl]-4-(trifluoromethyl)benzyl}isobutyramide;
N-{3-[4-(5-fluoropyridin-3-yl)-6-oxo-1,6-dihydropyrimidin-2-yl]-4-(trifluoromethyl)benzyl}isobutyramide;
N-(4-chloro-3-{4-[5-(difluoromethoxy)pyridin-2-yl]-6-oxo-1,6-dihydropyrimidin-2-yl}benzyl)propionamide;
N-{4-chloro-3-[4-(5-methoxypyridin-3-yl)-6-oxo-1,6-dihydropyrimidin-2-yl]benzyl}isobutyramide;
N-{3-[4-(5-methoxypyridin-3-yl)-6-oxo-1,6-dihydropyrimidin-2-yl]-4-(trifluoromethyl)benzyl}isobutyramide;
N-(4-chloro-3-{6-oxo-4-[6-propoxy pyridin-3-yl]-1,6-dihydropyrimidin-2-yl}benzyl)propionamide;
N-(4-chloro-3-{4-[6-(2,2-difluoroethoxy)pyridin-3-yl]-6-oxo-1,6-dihydropyrimidin-2-yl}benzyl)propionamide;
N-{4-chloro-3-[4-(5-methylpyridin-3-yl)-6-oxo-1,6-dihydropyrimidin-2-yl]benzyl}isobutyramide;
N-{3-[4-(5-methylpyridin-3-yl)-6-oxo-1,6-dihydropyrimidin-2-yl]-4-(trifluoromethyl)benzyl}isobutyramide;
N-{4-chloro-2-fluoro-3-[4-(5-methylpyridin-3-yl)-6-oxo-1,6-dihydropyrimidin-2-yl]benzyl}isobutyramide;
N-{4-chloro-3-[4-(5-methoxypyridin-2-yl)-6-oxo-1,6-dihydropyrimidin-2-yl]benzyl}isobutyramide;
N-{4-chloro-3-[4-(1-isopropyl-1H-pyrazol-4-yl)-6-oxo-1,6-dihydropyrimidin-2-yl]benzyl}isobutyramide;
N-{4-chloro-3-[6-oxo-4-(1-propyl-1H-pyrazol-4-yl)-1,6-dihydropyrimidin-2-yl]benzyl}isobutyramide;
N-(4-difluoromethoxy-3-{4-[6-(difluoromethoxy)pyridin-3-yl]-6-oxo-1,6-dihydropyrimidin-2-yl}benzyl)isobutyramide;
N-[4-chloro-3-(4-{6-[2-(2-methoxyethoxy)ethoxy]pyridin-3-y}-6-oxo-1,6-dihydropyrimidin-2-yl)benzyl]isobutyramide;
N-(4-chloro-3-[4-(6-{2-[2-(2-ethoxyethoxy)ethoxy]ethoxy}pyridin-3-yl)-6-oxo-1,6-dihydropyrimidin-2-yl]benzyl}isobutyramide;
N-(4-chloro-3-{4-[6-(6-methylpyridin-2-ylmethoxy)pyridin-3-yl]-6-oxo-1,6-dihydropyrimidin-2-yl}benzyl)isobutyramide;
N-(4-chloro-3-{6-oxo-4-[6-(2-propoxyethoxy)pyridin-3-yl]-1,6-dihydropyrimidin-2-yl}benzyl)propionamide;
N-(4-chloro-3-{4-[6-(2-ethoxyethoxy)pyridin-3-yl]-6-oxo-1,6-dihydropyrimidin-2-yl}benzyl)butyramide;
N-(4-chloro-3-{4-[6-(2-fluoroethoxy)pyridin-3-yl]-6-oxo-1,6-dihydropyrimidin-2-yl}benzyl)butyramide;
N-(4-chloro-3-{4-[6-(3-fluoropropoxy)pyridin-3-yl]-6-oxo-1,6-dihydropyrimidin-2-yl}benzyl)propionamide;
N-(3-{4-[6-(2-ethoxyethoxy)pyridin-3-yl]-6-oxo-1,6-dihydropyrimidin-2-yl}-4-(trifluoromethyl)benzyl)isobutyramide;
N-(3-{6-oxo-4-[6-(2-propoxyethoxy)pyridin-3-yl]-1,6-dihydropyrimidin-2-yl}-4-(trifluoromethyl)benzyl)isobutyramide;
N-{3-[4-(6-cyclopropylpyrimidin-3-yl)-6-oxo-1,6-dihydropyrimidin-2-yl]-4-(trifluoromethyl)benzyl}isobutyramide;
N-(3-{4-[6-(2-butoxyethoxy)pyridin-3-yl]-6-oxo-1,6-dihydropyrimidin-2-yl}-4-(trifluoromethyl)benzyl)isobutyramide;
N-(3-{4-[6-(3-methoxypropoxy)pyrimidin-3-yl]-6-oxo-1,6-dihydropyrimidin-2-yl}-4-(trifluoromethyl)benzyl)isobutyramide;

N-[4-chloro-3-(6-oxo-4-pyridin-3-yl-1,6-dihydropyrimidin-2-yl)benzyl]isobutyramide;

N-{3-[4-(6-methoxypyridin-3-yl)-6-oxo-1,6-dihydropyrimidin-2-yl]-4-methylbenzyl}isobutyramide;

N-(4-chloro-3-{6-oxo-4-[2-(trifluoromethyl)pyridin-4-yl]-1,6-dihydropyrimidin-2-yl}benzyl)isobutyramide;

N-[4-(difluoromethyl)-3-{6-oxo-4-[6-(trifluoromethyl)pyridin-3-yl]-1,6-dihydropyrimidin-2-yl}benzyl]isobutyramide;

N-(3-{4-[2-(cyclopropylmethoxy)pyridin-4-yl]-6-oxo-1,6-dihydropyrimidin-2-yl}-4-(trifluoromethyl)benzyl)isobutyramide;

N-(3-{4-[6-(cyclopropylmethoxy)pyridazin-3-yl]-6-oxo-1,6-dihydropyrimidin-2-yl}-4-(trifluoromethyl)benzyl)isobutyramide;

4-(2-{2-chloro-5-[(3,3,3-trifluoro-2,2-dimethylpropionylamino)methyl]phenyl}-6-oxo-1,6-dihydropyrimidin-4-yl)-N,N-dimethylbenzamide;

N-(3-{4-[6-(difluoromethoxy)pyridin-3-yl]-6-oxo-1,6-dihydropyrimidin-2-yl}-2,4-difluorobenzyl)isobutyramide;

N-[3-(2'-methoxy-6-oxo-1,6-dihydro-[4,5'-bipyrimidin]-2-yl)-4-(trifluoromethyl)benzyl]isobutyramide;

N-{4-chloro-3-[4-(5-chloropyridin-3-yl)-6-oxo-1,6-dihydropyrimidin-2-yl]benzyl}isobutyramide;

N-{4-chloro-3-[4-(6-cyclopropylpyridin-3-yl)-6-oxo-1,6-dihydropyrimidin-2-yl]-2-fluorobenzyl}isobutyramide;

N-[4-chloro-3-(2'-cyclopropyl-6-oxo-1,6-dihydro-[4,5'-bipyrimidin]-2-yl)benzyl]isobutyramide;

N-(4-chloro-3-{4-[6-(cyclopropylmethoxy)pyridin-3-yl]-6-oxo-1,6-dihydropyrimidin-2-yl}-2-fluorobenzyl)isobutyramide;

N-(4-chloro-3-{4-[6-(2-ethoxyethoxy)pyridin-3-yl]-6-oxo-1,6-dihydropyrimidin-2-yl}-2-fluorobenzyl)isobutyramide;

N-(3-{4-[6-(cyclopropylmethoxy)pyrimidin-3-yl]-6-oxo-1,6-dihydropyrimidin-2-yl}-4-(trifluoromethyl)benzyl)isobutyramide;

N-(4-chloro 2-fluoro-3-{6-oxo-4-[6-(2-propoxyethoxy)pyridin-3-yl]-1,6-dihydropyrimidin-2-yl}benzyl)isobutyramide;

N-{4-chloro-3-[4-(6-ethoxypyridin-3-yl)-6-oxo-1,6-dihydropyrimidin-2-yl]-2-fluorobenzyl}isobutyramide;

N-(4-chloro-2-fluoro-3-{6-oxo-4-[5-(trifluoromethyl)pyridin-2-yl]-1,6-dihydropyrimidin-2-yl}benzyl)isobutyramide;

N-(3-{4-[6-(2-ethoxyethoxy)pyridin-3-yl]-6-oxo-1,6-dihydropyrimidin-2-yl}-2,4-difluorobenzyl)isobutyramide;

N-(3-{4-[6-(cyclopropylmethoxy)pyridin-3-yl]-6-oxo-1,6-dihydropyrimidin-2-yl}-2,4-difluorobenzyl)isobutyramide;

N-(2-chloro-3-{4-[6-(difluoromethoxy)pyridin-3-yl]-6-oxo-1,6-dihydropyrimidin-2-yl}-4-fluorobenzyl)isobutyramide;

N-(2-chloro-3-{4-[6-(cyclopropylmethoxy)pyridin-3-yl]-6-oxo-1,6-dihydropyrimidin-2-yl}-4-fluorobenzyl)isobutyramide;

N-(4-chloro-2-fluoro-3-{6-oxo-4-[6-(2,2,2-trifluoroethoxy)pyridin-3-yl]-1,6-dihydropyrimidin-2-yl}benzyl)isobutyramide;

N-{4-chloro-3-[4-(5-chloropyridin-3-yl)-6-oxo-1,6-dihydropyrimidin-2-yl]-2-fluorobenzyl}isobutyramide;

N-(2-fluoro-3-{6-oxo-4-[6-(trifluoromethyl)pyridin-3-yl]-1,6-dihydropyrimidin-2-yl}-4-(trifluoromethyl)benzyl)isobutyramide;

N-(2-chloro-4-fluoro-3-{6-oxo-4-[6-(2,2,2-trifluoroethoxy)pyridin-3-yl]-1,6-dihydropyrimidin-2-yl}benzyl)isobutyramide;

N-{4-chloro-3-[4-(5-chloropyridin-2-yl)-6-oxo-1,6-dihydropyrimidin-2-yl]-2-fluorobenzyl}isobutyramide;

N-(4-chloro-2-fluoro-3-{6-oxo-4-[6-(3,3,3-trifluoropropoxy)pyridin-3-yl]-1,6-dihydropyrimidin-2-yl}benzyl)isobutyramide;

N-(2-chloro-4-fluoro-3-{6-oxo-4-[5-(trifluoromethyl)pyridin-2-yl]-1,6-dihydropyrimidin-2-yl}benzyl)isobutyramide;

N-(3-{4-[6-(difluoromethoxy)pyridin-3-yl]-6-oxo-1,6-dihydropyrimidin-2-yl}-2-fluoro-4-(trifluoromethyl)benzyl)isobutyramide;

N-(4-chloro-2-fluoro-3-{6-oxo-4-[5-(2-propoxyethoxy)pyridin-2-yl]-1,6-dihydropyrimidin-2-yl}benzyl)isobutyramide;

N-(3-{4-[6-(2-ethoxyethoxy)pyridin-3-yl]-6-oxo-1,6-dihydropyrimidin-2-yl}-2-fluoro-4-(trifluoromethyl)benzyl)isobutyramide;

N-(4-chloro-3-{4-[6-(2,2-difluoroethoxy)pyridin-3-yl]-6-oxo-1,6-dihydropyrimidin-2-yl}-2-fluorobenzyl)isobutyramide;

N-(2-chloro-3-{4-[6-(2,2-difluoroethoxy)pyridin-3-yl]-6-oxo-1,6-dihydropyrimidin-2-yl}-4-fluorobenzyl)isobutyramide;

N-(4-chloro-3-{4-[5-(difluoromethoxy)pyridin-2-yl]-6-oxo-1,6-dihydropyrimidin-2-yl}-2-fluorobenzyl)isobutyramide;

N-(4-chloro-3-{4-[5-(2-ethoxyethoxy)pyridin-2-yl]-6-oxo-1,6-dihydropyrimidin-2-yl}-2-fluorobenzyl)isobutyramide;

N-{3-[4-(5-chloropyridin-3-yl)-6-oxo-1,6-dihydropyrimidin-2-y]-4-fluorobenzyl}isobutyramide;

N-(2-fluoro-3-{6-oxo-4-[5-(trifluoromethyl)pyridin-2-yl]-1,6-dihydropyrimidin-2-yl}-4-(trifluoromethyl)benzyl)isobutyramide;

N-(4-chloro-3-{4-[5-(cyclopropylmethoxy)pyrimidin-2-yl]-6-oxo-1,6-dihydropyrimidin-2-yl}-2-fluorobenzyl)isobutyramide;

N-{4-chloro-2-fluoro-3-[4-(5-fluoropyridin-3-yl)-6-oxo-1,6-dihydropyrimidin-2-yl]benzyl}isobutyramide;

N-(2-chloro-3-{4-[6-(2-ethoxyethoxy)pyridin-3-yl]-6-oxo-1,6-dihydropyrimidin-2-yl}-4-fluorobenzyl)isobutyramide;

N-(2-chloro-3-{4-[5-(cyclopropylmethoxy)pyridin-2-yl]-6-oxo-1,6-dihydropyrimidin-2-yl}-4-fluorobenzyl)isobutyramide;

N-(2-chloro-4-fluoro-3-{6-oxo-4-[6-(3,3,3-trifluoropropoxy)pyridin-3-yl]-1,6-dihydropyrimidin-2-yl}benzyl)isobutyramide;

N-(4-chloro-3-{6-oxo-4-[6-(tetrahydropyran-4-ylmethoxy)pyridin-3-yl]-1,6-dihydropyrimidin-2-yl}benzyl)isobutyramide;

N-(3-{6-oxo-4-[6-(tetrahydropyran-4-ylmethoxy)pyridin-3-yl]-1,6-dihydropyrimidin-2-yl}-4-(trifluoromethyl)benzyl)isobutyramide;

N-(4-chloro-3-{6-oxo-4-[6-(tetrahydropyran-4-ylmethoxy)pyridin-3-yl]-1,6-dihydropyrimidin-2-yl}benzyl)butyramide:

N-{4-chloro-2-fluoro-3-[6-oxo-4-(4-trifluoromethylthiazol-2-yl)-1,6-dihydropyrimidin-2-yl]benzyl}isobutyramide;

N-{4-chloro-3-[4-(5-ethynylpyrimidin-3-yl)-6-oxo-1,6-dihydropyrimidin-2-yl]benzyl}isobutyramide;

N-(4-chloro-3-{6-oxo-4-[5-(1-propynyl)pyridin-3-yl]-1,6-dihydropyrimidin-2-yl}benzyl)isobutyramide;

N-(3-{4-[6-(3-methyloxetan-3-ylmethoxy)pyridin-3-yl]-6-oxo-1,6-dihydropyrimidin-2-yl}-4-(trifluoromethyl)benzyl)isobutyramide;

N-{3-[4-(5-ethynylpyrimidin-3-yl)-6-oxo-1,6-dihydropyrimidin-2-yl]-4-(trifluoromethyl)benzyl}isobutyramide;
N-(4-chloro-3-{4-[6-(3-methyloxetan-3-ylmethoxy)pyridin-3-yl]-6-oxo-1,6-dihydropyrimidin-2-ylbenzyl)isobutyramide;
N-(3-{6-oxo-4-[5-(1-propynyl)pyridin-3-yl]-1,6-dihydropyrimidin-2-yl}-4-(trifluoromethyl)benzyl)isobutyramide;
N-(4-chloro-3-{6-oxo-4-[5-(trifluoromethyl)pyridin-3-y]-1,6-dihydropyrimidin-2-yl}benzyl)isobutyramide;
N-(3-{4-[6-(3-ethoxypropoxy)pyridin-3-yl]-6-oxo-1,6-dihydropyrimidin-2-yl}-4-(trifluoromethyl)benzyl)isobutyramide;
N-(4-chloro-3-{4-[6-(2,2-difluoroethoxy)pyrimidin-3-yl]-6-oxo-1,6-dihydropyrimidin-2-yl}benzyl)isobutyramide;
N-(3-{4-[6-(2,2-difluoroethoxy)pyridin-3-yl]-6-oxo-1,6-dihydropyrimidin-2-yl}-4-(trifluoromethyl)benzyl)isobutyramide;
N-(3-{6-oxo-4-[6-(2,2,2-trifluoroethoxy)pyridin-3-yl]-1,6-dihydropyrimidin-2-yl}-4-(trifluoromethyl)benzyl)isobutyramide;
N-(3-{6-oxo-4-[6-(3,3,3-trifluoropropoxy)pyridin-3-yl]-1,6-dihydropyrimidin-2-yl}-4-(trifluoromethyl)benzyl)isobutyramide;
N-(3-{4-[6-(2-fluoroethoxy)pyridin-3-yl]-6-oxo-1,6-dihydropyrimidin-2-yl}-4-(trifluoromethyl)benzyl)isobutyramide;
N-(3-{4-[6-(3-fluoropropoxy)pyridin-3-y]-6-oxo-1,6-dihydropyrimidin-2-yl}-4-(trifluoromethyl)benzyl)isobutyramide;
N-(3-{4-[2-(difluoromethoxy)pyridin-4-yl]-6-oxo-1,6-dihydropyrimidin-2-yl}-4-(trifluoromethyl)benzyl)isobutyramide;
N-(3-{6-oxo-4-[5-(trifluoromethyl)pyridin-2-yl]-1,6-dihydropyrimidin-2-yl}-4-(trifluoromethyl)benzyl)isobutyramide;
N-{3-[4-(5-chloropyridin-2-yl)-6-oxo-1,6-dihydropyrimidin-2-yl]-4-(trifluoromethyl)benzyl}isobutyramide;
N-(3-{6-oxo-4-[5-(2-propoxyethoxy)pyridin-2-yl]-1,6-dihydropyrimidin-2-yl}-4-(trifluoromethyl)benzyl)isobutyramide;
N-(3-{4-[5-(difluoromethoxy)pyridin-2-yl]-6-oxo-1,6-dihydropyrimidin-2-yl}-4-(trifluoromethyl)benzyl)isobutyramide;
N-(4-chloro-3-{4-[5-(cyclopropylmethoxy)pyrimidin-2-yl]-6-oxo-1,6-dihydropyrimidin-2-yl}benzyl)isobutyramide;
N-(3-{4-[5-(cyclopropylmethoxy)pyrimidin-2-yl]-6-oxo-1,6-dihydropyrimidin-2-yl}-4-(trifluoromethyl)benzyl)isobutyramide;
N-(4-chloro-2-fluoro-3-{6-oxo-4-[6-(trifluoromethyl)pyrimidin-3-yl]-1,6-dihydropyrimidin-2-yl}benzyl)butyramide;
N-(4-chloro-3-{4-[6-(difluoromethoxy)pyridin-3-yl]-6-oxo-1,6-dihydropyrimidin-2-yl}-2-fluorobenzyl)butyramide;
N-[3-(2'-cyclopropylmethoxy-6-oxo-1,6-dihydro-[4,5'-bipyrimidin]-2-yl)-4-(trifluoromethyl)benzyl]isobutyramide;
N-{3-[4-(6-butoxypyridazin-3-y)-6-oxo-1,6-dihydropyrimidin-2-yl]-4-(trifluoromethyl)benzyl}isobutyramide;
N-{4-chloro-3-[6-oxo-2'-(trifluoromethyl)-1,6-dihydro-[4,5'-bipyrimidin]-2-yl]benzyl}isobutyramide;
N-(4-chloro-3-{4-[(2-cyclopropylmethoxy)pyridin-4-y]-6-oxo-1,6-dihydropyrimidin-2-yl}benzyl)isobutyramide;
N-{4-chloro-2-fluoro-3-[4-(5-fluoropyridin-2-y)-6-oxo-1,6-dihydropyrimidin-2-yl]benzyl}isobutyramide;
N-{2-fluoro-3-[4-(6-methoxypyridin-3-y)-6-oxo-1,6-dihydropyrimidin-2-yl]-4-(trifluoromethyl)benzyl}isobutyramide;
N-(4-chloro-3-{4-[6-(cyclopropylethynyl)pyridin-3-yl]-6-oxo-1,6-dihydropyrimidin-2-yl}-2-fluorobenzyl)isobutyramide;
N-{2-chloro-3-[4-(5-chloropyrimidin-2-yl)-6-oxo-1,6-dihydropyrimidin-2-yl]-4-fluorobenzyl}isobutyramide;
N-{4-chloro-3-[4-(4-cyanophenyl)-6-oxo-1,6-dihydropyrimidin-2-yl]-2-fluorobenzyl}isobutyramide;
N-{4-chloro-2-fluoro-3-[6-oxo-4-(6-phenylpyridin-3-yl)-1,6-dihydropyrimidin-2-yl]benzyl}isobutyramide;
N-(2,4-difluoro-3-{6-oxo-4-[5-(trifluoromethyl)pyridin-2-yl]-1,6-dihydropyrimidin-2-yl}benzyl)isobutyramide;
N-(3-[4-(5-chloropyridin-3-yl)-6-oxo-1,6-dihydropyrimidin-2-yl]-2,4-difluorobenzyl)isobutyramide;
N-(4-chloro-3-{4-[6-(difluoromethyl)pyridin-3-yl]-6-oxo-1,6-dihydropyrimidin-2-yl}-2-fluorobenzyl)isobutyramide;
N-(2-chloro-3-{4-[6-(cyclopropylethynyl)pyrimidin-3-yl]-6-oxo-1,6-dihydropyrimidin-2-yl}-4-fluorobenzyl)isobutyramide;
N-(4-chloro-3-{4-[5-(difluoromethyl)pyridin-2-yl]-6-oxo-1,6-dihydropyrimidin-2-yl}-2-fluorobenzyl)isobutyramide;
N-{3-[4-(5-chloropyridin-2-yl)-6-oxo-1,6-dihydropyrimidin-2-yl]-2,4-difluorobenzyl}isobutyramide;
N-(4-chloro-2-fluoro-3-{6-oxo-4-[6-(trifluoromethyl)pyridin-2-y]-1,6-dihydropyrimidin-2-yl}benzyl)isobutyramide;
N-(2-chloro-4-fluoro-3-{6-oxo-4-[4-(trifluoromethyl)thiazol-2-yl]-1,6-dihydropyrimidin-2-yl}benzyl)isobutyramide;
N-(4-chloro-3-{4-[2-(cyclopropylethynyl)thiazol-5-y]-6-oxo-1,6-dihydropyrimidin-2-yl}-2-fluorobenzyl)isobutyramide;
N-(2-chloro-3-{4-[5-(cyclopropylethynyl)pyridin-2-yl]-6-oxo-1,6-dihydropyrimidin-2-y}-4-fluorobenzyl)isobutyramide;
N-(4-chloro-3-{4-[6-(3-ethyloxetan-3-ylmethoxy)pyridin-3-yl]-6-oxo-1,6-dihydropyrimidin-2-yl}benzyl)isobutyramide;
N-(3-{4-[6-(3-ethyloxetan-3-ylmethoxy)pyridin-3-yl]-6-oxo-1,6-dihydropyrimidin-2-yl}-4-(trifluoromethyl)benzyl)isobutyramide:
N-{4-chloro-2-fluoro-3-[4-(4-methylthiazol-2-yl)-6-oxo-1,6-dihydropyrimidin-2-yl]benzyl}isobutyramide;
N-(4-chloro-2-fluoro-3-{6-oxo-4-[4-(1-propynyl)thiazol-2-yl]-1,6-dihydropyrimidin-2-yl}benzyl)isobutyramide;
N-(4-chloro-3-{4-[5-(cyclopropylethynyl)thiazol-2-y]-6-oxo-1,6-dihydropyrimidin-2-yl}-2-fluorobenzyl)isobutyramide;
N-(4-chloro-3-{4-[4-(cyclopropylethynyl)thiazol-2-yl]-6-oxo-1,6-dihydropyrimidin-2-yl}-2-fluorobenzyl)isobutyramide;
N-(3-{4-[5-(cyclopropylethynyl)thiazol-2-yl]-6-oxo-1,6-dihydropyrimidin-2-yl}-4-(trifluoromethyl)benzyl)isobutyramide;
N-(3-(4-[6-(cyclopropylethynyl)pyridin-2-yl]-6-oxo-1,6-dihydropyrimidin-2-yl)-4-(trifluoromethyl)benzyl)isobutyramide;
N-(4-chloro-3-{4-[5-(cyclopropylethynyl)pyridin-3-yl]-6-oxo-1,6-dihydropyrimidin-2-yl}benzyl)isobutyramide;
N-(3-(4-[5-(cyclopropylethynyl)pyridin-3-yl]-6-oxo-1,6-dihydropyrimidin-2-yl)-4-(trifluoromethyl)benzyl)isobutyramide;
N-(3-{4-[6-(3-morpholin-4-ylpropoxy)pyridin-3-yl]-6-oxo-1,6-dihydropyrimidin-2-yl}-4-(trifluoromethyl)benzyl)isobutyramide;
N-(3-{6-oxo-4-[5-(trifluoromethyl)pyridin-3-y]-1,6-dihydropyrimidin-2-yl}-4-(trifluoromethyl)benzyl)isobutyramide;

N-(4-chloro-2-fluoro-3-{6-oxo-4-[5-(trifluoromethyl)pyridin-3-yl]-1,6-dihydropyrimidin-2-yl}benzyl)isobutyramide;

N-{3-(2'-butyl-6-oxo-1,6-dihydro-[4,5'-bipyrimidin]-2-yl)-4-(trifluoromethyl)benzyl}isobutyramide;

N-(3-{6-oxo-4-[5-(trifluoromethyl)pyridin-2-yl]-1,6-dihydropyrimidin-2-yl}-4-(trifluoromethyl)benzyl)butyramide;

N-(4-chloro-2-fluoro-3-{6-oxo-4-[5-(trifluoromethyl)pyridin-2-yl]-1,6-dihydropyrimidin-2-yl}benzyl)butyramide;

N-{4-chloro-2-fluoro-3-[6-oxo-4-(6-propylpyrimidin-3-yl)-1,6-dihydropyrimidin-2-yl]benzyl}isobutyramide;

N-{3-[6-oxo-4-(6-propylpyrimidin-3-yl)-1,6-dihydropyrimidin-2-yl]-4-(trifluoromethyl)benzyl}isobutyramide;

N-{3-[2'-(3,3-dimethyl-1-butynyl)-6-oxo-1,6-dihydro-[4,5'-bipyrimidin]-2-yl]-4-(trifluoromethyl)benzyl}isobutyramide;

N-{4-chloro-3-[2'-(3,3-dimethyl-1-butynyl)-6-oxo-1,6-dihydro-[4,5'-bipyrimidin]-2-yl]-2-fluorobenzyl}isobutyramide;

N-(4-chloro-3-{4-[5-(cyclopropylethynyl)pyrimidin-2-yl]-6-oxo-1,6-dihydropyrimidin-2-yl}-2-fluorobenzyl)isobutyramide;

N-(4-chloro-2-fluoro-3-{6-oxo-4-[6-(1-propynyl)pyridin-3-yl]-1,6-dihydropyrimidin-2-yl}benzyl)isobutyramide;

N-(2,4-difluoro-3-{6-oxo-4-[6-(2-propoxyethoxy)pyridin-3-yl]-1,6-dihydropyrimidin-2-yl}benzyl)isobutyramide;

N-{4-chloro-2-fluoro-3-[4-(6-methoxypyridin-2-yl)-6-oxo-1,6-dihydropyrimidin-2-yl]benzyl}isobutyramide;

N-{2-fluoro-3-[4-(5-fluoropyridin-3-yl)-6-oxo-1,6-dihydropyrimidin-2-yl]-4-(trifluoromethyl)benzyl}isobutyramide;

N-[4-chloro-2-fluoro-3-(4-{6-[(1-hydroxycyclohexyl)ethynyl]pyridin-3-yl}-6-oxo-1,6-dihydropyrimidin-2-yl)benzyl]isobutyramide;

N-(4-chloro-2-fluoro-3-{6-oxo-4-[5-(1-propynyl)pyridin-2-yl]-1,6-dihydropyrimidin-2-yl}benzyl)isobutyramide;

N-{3-[4-(6-ethoxypyridin-3-yl)-6-oxo-1,6-dihydropyrimidin-2-yl]-2-fluoro-4-(trifluoromethyl)benzyl}isobutyramide;

N-{3-[4-(benzothiazol-2-yl)-6-oxo-1,6-dihydropyrimidin-2-yl]-4-chloro-2-fluorobenzyl}isobutyramide;

N-(3-{4-[6-(2-isopropoxyethoxy)pyridin-3-yl]-6-oxo-1,6-dihydropyrimidin-2-yl}-4-(trifluoromethyl)benzyl)isobutyramide;

N-(4-chloro-2-fluoro-3-{4-[6-(2-isopropoxyethoxy)pyridin-3-yl]-6-oxo-1,6-dihydropyrimidin-2-yl}benzyl)isobutyramide;

N-(2,4-difluoro-3-{4-[6-(2-isopropoxyethoxy)pyridin-3-yl]-6-oxo-1,6-dihydropyrimidin-2-yl}benzyl)isobutyramide;

N-(2-chloro-4-fluoro-3-{4-[6-(2-isopropoxyethoxy)pyridin-3-yl]-6-oxo-1,6-dihydropyrimidin-2-yl}benzyl)isobutyramide;

N-(3-{6-oxo-4-[6-(tetrahydropyran-4-ylmethoxy)pyridin-3-yl]-1,6-dihydropyrimidin-2-yl}-4-(trifluoromethyl)benzyl)butyramide;

N-(3-{4-[6-(2-isopropoxyethoxy)pyridin-3-yl]-6-oxo-1,6-dihydropyrimidin-2-yl}-4-(trifluoromethyl)benzyl)butyramide;

N-(3-{4-[6-(2-ethoxyethoxy)pyridin-3-yl]-6-oxo-1,6-dihydropyrimidin-2-yl}-4-(trifluoromethyl)benzyl)butyramide;

N-(3-{6-oxo-4-[6-(2-propoxyethoxy)pyridin-3-yl]-1,6-dihydropyrimidin-2-yl}-4-(trifluoromethyl)benzyl)butyramide;

N-{3-[4-(benzothiazol-2-yl)-6-oxo-1,6-dihydropyrimidin-2-yl]-2,4-difluorobenzyl}isobutyramide;

N-{3-[4-(benzothiazol-2-yl)-6-oxo-1,6-dihydropyrimidin-2-yl]-4-(trifluoromethyl)benzyl}isobutyramide;

N-(2-chloro-4-fluoro-3-{6-oxo-4-[6-(2-propoxyethoxy)pyridin-3-yl]-1,6-dihydropyrimidin-2-yl}benzyl)isobutyramide;

N-(3-{6-oxo-4-[4-(trifluoromethyl)thiazol-2-yl]-1,6-dihydropyrimidin-2-yl}-4-(trifluoromethyl)benzyl)isobutyramide;

N-{4-chloro-3-[4-(5-ethynylpyridin-3-yl)-6-oxo-1,6-dihydropyrimidin-2-yl]-2-fluorobenzyl}isobutyramide;

N-[3-(6-oxo-4-{6-[2-(2,2,2-trifluoroethoxy)ethoxy]pyridin-3-yl}-1,6-dihydropyrimidin-2-yl)-4-(trifluoromethyl)benzyl]isobutyramide;

N-[4-chloro-2-fluoro-3-(6-oxo-4-{6-[2-(2,2,2-trifluoroethoxy)ethoxy]pyridin-3-yl}-1,6-dihydropyrimidin-2-yl)benzyl]isobutyramide;

N-[2,4-difluoro-3-(6-oxo-4-{6-[2-(2,2,2-trifluoroethoxy)ethoxy]pyridin-3 yl}-1,6-dihydropyrimidin-2-yl)benzyl]isobutyramide;

N-[2-chloro-4-fluoro-3-(6-oxo-4-{6-[2-(2,2,2-trifluoroethoxy)ethoxy]pyridin-3-yl}-1,6-dihydropyrimidin-2-yl)benzyl]isobutyramide;

N-(3-{4-[5-(cyclopropylethynyl)pyridin-2-yl]-6-oxo-1,6-dihydropyrimidin-2-y}-4-(trifluoromethyl)benzyl)butyramide;

N-(4-chloro-3-{4-[5-(cyclopropylethynyl)pyridin-2-yl]-6-oxo-1,6-dihydropyrimidin-2-yl}-2-fluorobenzyl)butyramide;

N-(3-{4-[5-(3,3-dimethyl-1-butynyl)pyrazin-2-yl]-6-oxo-1,6-dihydropyrimidin-2-yl}-4-(trifluoromethyl)benzyl)isobutyramide;

N-(3-(4-[5-(cyclopropylethynyl)pyrazin-2-yl]-6-oxo-1,6-dihydropyrimidin-2-yl)-4-(trifluoromethyl)benzyl)isobutyramide;

N-{3-[2'-(4-methyl-1-pentynyl)-6-oxo-1,6-dihydro-[4,5'-bipyrimidin]-2-yl]-4-(trifluoromethyl)benzyl}isobutyramide;

N-{3-[6-oxo-4-(5-propylpyridin-2-yl)-1,6-dihydropyrimidin-2-yl]-4-(trifluoromethyl)benzyl}isobutyramide;

N-{4-chloro-2-fluoro-3-[6-oxo-4-(5-propylpyridin-2-yl)-1,6-dihydropyrimidin-2-yl]benzyl}isobutyramide;

N-{4-chloro-3-[2'-(cyclopropylmethoxy)-6-oxo-1,6-dihydro-[4,5'-bipyrimidin]-2-yl]-2-fluorobenzyl}isobutyramide;

N-{3-[2'-(cyclopropylmethoxy)-6-oxo-1,6-dihydro-[4,5'-bipyrimidin]-2-yl]-4-(trifluoromethyl)benzyl}butyramide;

N-{4-chloro-3-[2'-(cyclopropylmethoxy)-6-oxo-1,6-dihydro-[4,5'-bipyrimidin]-2-yl]-2-fluorobenzyl}butyramide;

N-(3-(4-[5-(cyclopropylmethoxy)pyrazin-2-yl]-6-oxo-1,6-dihydropyrimidin-2-yl)-4-(trifluoromethyl)benzyl)isobutyramide;

N-(4-chloro-2-fluoro-3-{6-oxo-4-[2-(1-propynyl)thiazol-5-yl]-1,6-dihydropyrimidin-2-yl}benzyl)isobutyramide;

N-(2-chloro-3-{4-[2-(cyclopropylethynyl)thiazol-5-yl]-6-oxo 1,6-dihydropyrimidin-2-yl}-4-fluorobenzyl)isobutyramide;

N-(3-{4-[5-(cyclopropylethynyl)pyridin-2-yl]-6-oxo-1,6-dihydropyrimidin-2-yl}-2,4-difluorobenzyl)isobutyramide;

N-(3-{4-[6-(cyclopropylethynyl)pyridin-3-yl]-6-oxo-1,6-dihydropyrimidin-2-yl}-2,4-difluorobenzyl)isobutyramide;

N-(2-fluoro-3-{4-[5-(isobutyrylaminomethyl)pyridin-2-yl]-6-oxo-1,6-dihydropyrimidin-2-yl}-4-(trifluoromethyl)benzyl)isobutyramide;

N-(2-fluoro-3-{6-oxo-4-[5-(1-propynyl)pyridin-2-yl]-1,6-dihydropyrimidin-2-yl}-4-(trifluoromethyl)benzyl}isobutyramide;
N-(3-{4-[6-(cyclopropylethynyl)pyridin-3-yl]-6-oxo-1,6-dihydropyrimidin-2-yl}-2-fluoro-4-(trifluoromethyl)benzyl)isobutyramide;
N-(3-{4-[6-(cyclopropylethynyl)pyridin-3-yl]-6-oxo-1,6-dihydropyrimidin-2-yl}-4-(trifluoromethyl)benzyl)isobutyramide;
N-(2-fluoro-3-{6-oxo-4-[6-(2-propoxyethoxy)pyridin-3-yl]-1,6-dihydropyrimidin-2-yl}-4-(trifluoromethyl)benzyl)isobutyramide;
N-(2-fluoro-3-{4-[6-(2-isopropoxyethoxy)pyridin-3-yl]-6-oxo-1,6-dihydropyrimidin-2-yl}-4-(trifluoromethyl)benzyl)isobutyramide;
N-(3-{4-[2-(cyclopropylethynyl)thiazol-5-yl]-6-oxo-1,6-dihydropyrimidin-2-yl}-2-fluoro-4-(trifluoromethyl)benzyl)isobutyramide;
N-[2-fluoro-3-(6-oxo-4-{(6-[2-(2,2,2-trifluoroethoxy)ethoxy]pyridin-3-yl}-1,6-dihydropyrimidin-2-yl)-4-(trifluoromethyl)benzyl]isobutyramide;
N-(4-chloro-2-fluoro-3-{6-oxo-4-[5-(2,2,2-trifluoroethyl)pyridin-2-yl]-1,6-dihydropyrimidin-2-yl}benzyl)isobutyramide;
N-(3-{4-[5-(cyclopropylethynyl)pyridin-2-yl]-6-oxo-1,6-dihydropyrimidin-2-yl}-2-fluoro-4-(trifluoromethyl)benzyl)isobutyramide, and the like, but the examples are not limited to these.

The compounds represented by the general formula (1) may be in the form of salt. The salt is not particularly limited, and appropriately selected depending on the purpose. Examples include, for example, salts with alkali metals such as sodium and potassium; salts with alkaline earth metals such as calcium and magnesium; salts with organic amines such as methylamine, ethylamine, and diethanolamine, mineral acid salts such as hydrochlorides, sulfates, and nitrates, organic acid salts such as p-toluenesulfonates, maleates, and tartrates, and the like.

The compounds represented by the general formula (1) and salts thereof may exist in the form of hydrate or solvate. Type of solvent that forms the solvate is not particularly limited, and examples include, for example, ethanol, ethyl acetate, acetone, and the like. The compounds represented by the general formula (1) may exist as an enantiomer, diastereoisomer, or geometrical isomer depending on type of substituent, and besides arbitrary isomers in a pure form, mixtures of arbitrary isomers also fall within the scope of the present invention.

The compounds represented by the general formula (1) and salts thereof can be easily synthesized by performing common chemical reactions widely used by those skilled in the art with starting compounds easily obtainable for those skilled in the art. Specific preparation methods of the compounds of the present invention are shown in the examples mentioned in this specification. By referring to those synthesis methods, those skilled in the art can easily prepare the compounds of the present invention falling within the scope of the general formula (1).

The compounds of the present invention represented by the general formula (1) have an mPGES-1 inhibitory action, and can inhibit the PGE2 biosynthesis on the basis of the inhibitory action. Therefore, on the basis of the mPGES-1 inhibitory action, the medicament of the present invention containing a compound represented by the general formula (1) or a physiologically acceptable salt thereof of the present invention as an active ingredient can be used for prophylactic and/or therapeutic treatment of, for example, inflammation, pain, rheumatism, osteoarthritis, pyrexia, Alzheimer's disease, multiple sclerosis, arteriosclerosis, ocular hypertension such as glaucoma, ischemic retinopathy, systemic scleroderma, malignant tumors such as large intestine tumor, and diseases for which suppression of the PGE2 production exhibits efficacy.

More specifically, the medicament of the present invention can be used as a medicament for prophylactic and/or therapeutic treatment of, for example, inflammatory colitis, irritable bowel syndrome, migraine, headache, low back pain, lumbar spinal canal stenosis, intervertebral disc herniation, temporomandibular arthrosis, neck-shoulder-arm syndrome, cervical spondylosis, endometriosis, adenomyosis uteri, premature delivery, threatened premature delivery, dysmenorrhea, overactive bladder, bladder outlet obstruction associated with benign prostatic hyperplasia, nocturia, urinary incontinence, neurogenic bladder, interstitial cystitis, bladder pain syndrome, urinary calculus, benign prostatic hyperplasia, chronic prostatitis, intrapelvic pain syndrome, erectile dysfunction, cognitive disorder, neurodegenerative disease, Alzheimer's disease, pulmonary hypertension, psoriasis, rheumatoid arthritis, rheumatic fever, fibromyalgia, neuralgia, complex regional pain syndrome, fascia dyscrasia, ischemic heart disease, hypertension, angina pectoris, viral infectious disorders, bacterial infection, fungal infectious disorders, burn, inflammation and pain after operation, trauma, or extraction of a tooth, malignant tumor, myocardial infarction, atherosclerosis, thrombosis, embolism, type I diabetes mellitus, type II diabetes mellitus, cerebral apoplexy, gout, arthritis, osteoarthritis, juvenile arthritis, ankylosing spondilitis, tenosynovitis, ligamentum osteosis, systemic erythematodes, vasculitis, pancreatitis, nephritis, conjunctivitis, iritis, scleritis, uveitis, wound treatment, dermatitis, eczema, osteoporosis, asthma, chronic obstructive pulmonary disease, fibroid lung, allergic conditions, familial adenomatous polyposis, pachydermia, bursitis, hysteromyoma, or pain in cancer. As for the relation of mPGES-1 inhibitory action and use as medicament, for example, International Patent Publication WO2015/125842 can be referred to. The entire disclosures of this international patent publication and all the references cited therein are incorporated into the disclosure of this specification by reference.

Although a compound represented by the aforementioned general formula (1) or a physiologically acceptable salt thereof as the active ingredient of the medicament of the present invention may be administered as the medicament of the present invention, a pharmaceutical composition for oral or parenteral administration can be preferably prepared by a method well known to those skilled in the art, and administered. Examples of pharmaceutical composition suitable for oral administration include, for example, tablets, powders, capsules, subtilized granules, solutions, granules, syrups, and the like, and pharmaceutical composition suitable for parenteral administration include, for example, injections such as injections for intravenous injection and intramuscular injection, fusion drips, inhalants, eye drops, nose drops, suppositories, transdermal preparations, transmucosal preparations, and the like, but the pharmaceutical composition is not limited to these.

The aforementioned pharmaceutical composition can be produced by a method well known to those skilled in the art using pharmaceutical additives commonly used for preparation of pharmaceutical compositions in this industry. Such pharmaceutical additives are not particularly limited, and can be appropriately chosen depending on form of the pharmaceutical composition, purpose thereof such as impartation of properties for sustained release, and the like. Examples of the pharmaceutical additives include, for example, excipients, binders, fillers, disintegrating agents, surfactants, lubricants, dispersing agents, buffering agents, preservatives, corrigents, perfumes, coating agents, diluents, and the like, but the pharmaceutical additives are not limited to these.

Dose of the medicament of the present invention is not particularly limited, and can be appropriately chosen depending on type of disease to be prevented or treated, purpose of administration such as prevention or treatment, type of active ingredient, weight, age, conditions of patient, administration route, and the like. In the case of oral administration, for example, it can be used at a dose in the range of about 0.01 to 500 mg in terms of weight of the active ingredient as the daily dose for adults. However, the dose can be appropriately chosen by those skilled in the art, and is not limited to the aforementioned range.

EXAMPLES

Hereafter, the present invention will be explained in more detail with reference to examples. However, the present invention is not limited by these examples. The chemical formulas of the compounds of the examples are shown in Tables 1-1 to 1-18.

Reference Example 1: N-(4-Chloro-3-cyanobenzyl)-2,2-dimethylpropionamide

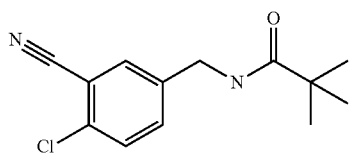

[Formula 14]

To a solution of 5-aminomethyl-2-chlorobenzonitrile (2.44 g) in methylene chloride (50 mL), N,N-diisopropylethylamine (11 mL) was added. Under ice cooling, pivaloyl chloride was added to the resulting mixture. The mixture was returned to room temperature, and stirred for 3 hours. The reaction mixture was poured into water, chloroform was added to the mixture, and the organic layer was separated. The organic layer was washed with saturated brine. The organic layer was dried over sodium sulfate, and then the solvent was evaporated. Silica gel column chromatography was performed to obtain the title compound (3.28 g).

$^1$H-NMR (CDCl$_3$, δ): 1.24 (9H, s), 4.43 (2H, d, J=5.9 Hz), 6.11 (1H, brs), 7.4-7.6 (3H, m)

MS (m/z): 250 (M$^+$)

Reference Example 2: N-(3-Carbamimidoyl-4-chlorobenzyl)-2,2-dimethylpropanoic Acid Amide Hydrochloride

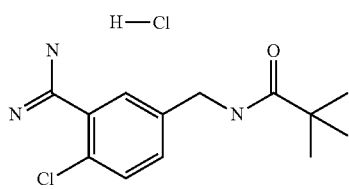

[Formula 15]

A suspension of ammonium chloride (2.09 g) in toluene (49 mL) was cooled on ice under nitrogen substitution, and a solution of trimethylaluminum in toluene (1.8 M, 22 mL) was added to the suspension. The resulting mixture was returned to room temperature, and stirred for 1 hour. N-(4-Chloro-3-cyanobenzyl)-2,2-dimethylpropionamide (3.26 g) was added to the mixture, and the residues were washed off into the mixture with toluene (5 mL). At an external temperature of 80° C., the mixture was stirred overnight. The reaction mixture was cooled on ice, and methanol (105 mL) was added to the mixture. The reaction mixture was warmed to 80° C., and stirred for 30 minutes. The reaction mixture was returned to room temperature, stirred for 18 minutes, and then stirred for 27 minutes under ice cooling. The insoluble matter was removed by filtration, and the solvent of the filtrate was evaporated to obtain the title compound (3.91 g). The obtained compound was used for the following reaction without purification.

Reference Example 3: N-(4-Chloro-3-cyanobenzyl)isobutyramide

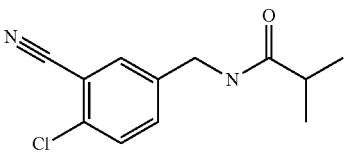

[Formula 16]

By performing operations similar to those of Reference Example 1 using isobutyryl chloride, the title compound was obtained.

$^1$H-NMR (CDCl$_3$, δ): 1.19 (6H, d, J=6.8 Hz), 2.3-2.5 (1H, m), 4.43 (2H, d, J=6.4 Hz), 5.96 (1H, brs), 7.4-7.6 (3H, m)

MS (m/z): 236 (M$^+$)

Reference Example 4: N-(3-Carbamimidoyl-4-chlorobenzyl)isobutyramide Hydrochloride

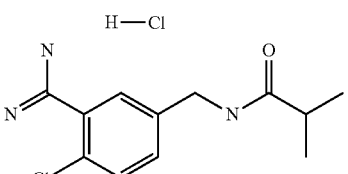

[Formula 17]

By performing operations similar to those of Reference Example 2 using N-(4-chloro-3-cyanobenzyl)isobutyramide, the title compound was obtained. The obtained compound was used for the following reaction without purification.

Reference Example 5: N-(4-Chloro-3-cyanobenzyl)-2-methoxy-2-methylpropionamide

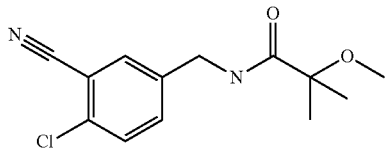

[Formula 18]

A mixture of 5-aminomethyl-2-chlorobenzonitrile (1.53 g), 2-methoxy-2-methylpropionic acid (876 mg), 1-ethyl-3-(3-dimethylaminopropyl)carbodiimide hydrochloride (2.13 g), 1-hydroxybenzotriazol monohydrate (1.50 g), N,N-diisopropylethylamine (3.9 mL), and acetonitrile (18 mL) was stirred overnight. The reaction mixture was poured into saturated aqueous sodium hydrogencarbonate, and extracted with ethyl acetate. The organic layer was washed with saturated brine. The organic layer was dried over sodium sulfate, and then the solvent was evaporated. Silica gel column chromatography was performed to obtain the title compound (1.20 g).

$^1$H-NMR (CDCl$_3$, δ): 1.41 (6H, s), 3.29 (3H, s), 4.43 (2H, d, J=6.4 Hz), 7.18 (1H, brs), 7.4-7.7 (3H, m)

MS (m/z): 266 (M$^+$)

Reference Example 6: N-(3-Carbamimidoyl-4-chlorobenzyl)-2-methoxy-2-methylpropionamide Hydrochloride

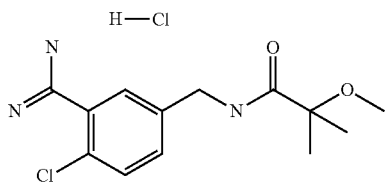

[Formula 19]

By performing operations similar to those of Reference Example 2 using N-(4-chloro-3-cyanobenzyl)-2-methoxy-2-methylpropionamide, the title compound was obtained. The obtained compound was used for the following reaction without purification.

Reference Example 7: tert-Butyl {3-[4-(5-chloropyridin-2-yl)-6-oxo-1,6-dihydropyrimidin-2-yl]benzyl}carbamate

[Formula 20]

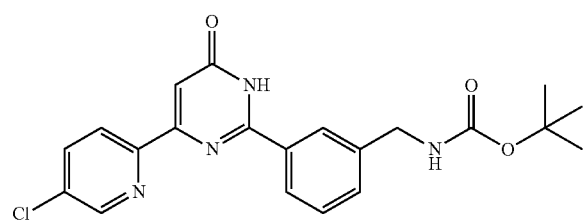

By performing operations similar to those of Example 4 using 5-chloropyridine-2-carbaldehyde, and tert-butyl (3-carbamimidoylbenzyl)carbamate, the title compound was obtained.

$^1$H-NMR (DMSO-d$_6$, δ): 1.41 (9H, m), 4.24 (2H, d, J=6.4 Hz), 7.17 (1H, brs), 7.4-7.5 (4H, m), 8.0-8.1 (2H, m), 8.19 (1H, brs), 8.48 (1H, d, J=8.8 Hz), 8.78 (1H, d, J=2.0 Hz)

MS (m/z): 412 (M$^+$)

Reference Example 8: 2-(3-Aminomethylphenyl)-6-(5-chloropyridin-2-yl)-3H-pyrimidin-4-one

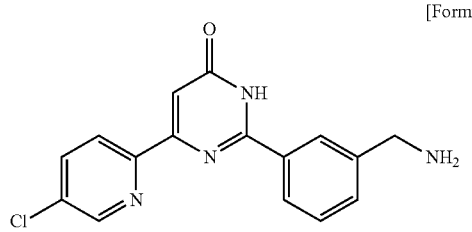

[Formula 21]

To tert-butyl {3-[4-(5-chloropyridin-2-yl)-6-oxo-1,6-dihydropyrimidin-2-yl]benzyl}carbamate (125 mg), trifluoroacetic acid (0.5 mL) was added, and the resulting mixture was stirred at room temperature for 3 hours. The reaction mixture was neutralized with a saturated sodium hydrogencarbonate solution, and then the produced solid was taken by filtration using a filter, and dried under reduced pressure to obtain the title compound (92 mg). The obtained compound was used for the following reaction without purification.

Example 1: N-{4-Chloro-3-[4-(4-chloro-2-fluorophenyl)-5-cyano-6-oxo-1,6-dihydropyrimidin-2-yl]benzyl}-2,2-dimethylpropionamide To N-(3-carbamimidoyl-4-chlorobenzyl)-2,2-dimethylpropanoic acid amide hydrochloride (807 mg), potassium carbonate (611 mg), and water (15 mL) were added, and the resulting mixture was stirred for 10 minutes. Ethyl cyanoacetate (0.47 mL), and 4-chloro-2-fluorobenzaldehyde (350 mg) were added to the reaction mixture, and the resulting mixture was heated to 100° C. for 40 minutes by applying microwaves. After the reaction, the reaction mixture was extracted with ethyl acetate, and the solvent was evaporated. Silica gel column chromatography was performed to obtain the title compound (48 mg).

$^1$H-NMR (DMSO-d$_6$, δ): 1.12 (9H, s), 4.28 (2H, d, J=5.8 Hz), 7.3-7.8 (6H, m), 8.0-8.2 (1H, m)

MS (m/z): 472 (M$^+$)

Example 2: N-[4-Chloro-3-(5-cyano-6-oxo-4-thiophen-3-yl-1,6-dihydropyrimidin-2-yl)benzyl]-2,2-dimethylpropionamide By performing operations similar to those of Example 1 using thiophene-3-carbaldehyde, the title compound was obtained.

$^1$H-NMR (DMSO-d$_6$, δ): 1.13 (9H, s), 4.30 (2H, d, J=5.8 Hz), 7.3-7.9 (5H, m), 8.0-8.2 (1H, m), 8.5-8.6 (1H, m), 13.78 (1H, brs)

MS (m/z): 426 (M$^+$)

Example 3: N-[4-Chloro-3-(5-cyano-6-oxo-4-thiophen-3-yl-1,6-dihydropyrimidin-2-yl)benzyl]isobutyramide By performing operations similar to those of Example 1 using thiophene-3-carbaldehyde, and N-(3-carbamimidoyl-4-chlorobenzyl)isobutyramide hydrochloride, the title compound was obtained.

$^1$H-NMR (DMSO-$d_6$, δ): 1.03 (6H, d, J=6.8 Hz), 2.3-2.5 (1H, m), 4.31 (2H, d, J=5.9 Hz), 7.3-7.9 (5H, m), 8.3-8.4 (1H, m), 8.5-8.6 (1H, m)

MS (m/z): 412 (M$^+$)

Example 4: N-[4-Chloro-3-(6-oxo-4-thiophen-3-yl-1,6-dihydropyrimidin-2-yl)benzyl]isobutyramide To N-(3-carbamimidoyl-4-chlorobenzyl)isobutyramide hydrochloride (1.039 g), potassium carbonate (990 mg), and water (15 mL) were added, and the resulting mixture was stirred for 10 minutes. Ethyl phenylsulfonylacetate (1.634 g), and thiophene-3-carbaldehyde (0.31 mL) were added to the mixture, and the resulting mixture was heated to 100° C. for 40 minutes by applying microwaves. After the reaction, the reaction mixture was extracted with ethyl acetate, and the solvent was evaporated. Purification was performed by silica gel column chromatography to obtain the title compound (89 mg).

$^1$H-NMR (DMSO-$d_6$, δ): 1.03 (6H, d, J=6.8 Hz), 2.3-2.5 (1H, m), 4.31 (2H, d, J=5.9 Hz), 6.84 (1H, s), 7.3-7.8 (5H, m), 8.2-8.4 (2H, m), 12.45 (1H, brs)

MS (m/z): 387 (M$^+$)

Example 5: N-{4-Chloro-3-[4-(4-chloro-2-fluorophenyl)-6-oxo-1,6-dihydropyrimidin-2-yl]benzyl}isobutyramide By performing operations similar to those of Example 4 using 4-chloro-2-fluorobenzaldehyde, the title compound was obtained.

$^1$H-NMR (DMSO-$d_6$, δ): 1.03 (6H, d, J=6.8 Hz), 2.3-2.5 (1H, m), 4.30 (2H, d, J=5.9 Hz), 6.78 (1H, s), 7.3-7.7 (5H, m), 7.9-8.1 (1H, m), 8.2-8.4 (1H, m), 12.95 (1H, brs)

MS (m/z): 433 (M$^+$)

Example 6: N-{4-Chloro-3-[4-(4-chlorophenyl)-6-oxo-1,6-dihydropyrimidin-2-yl]benzyl}isobutyramide By performing operations similar to those of Example 4 using 4-chlorobenzaldehyde, the title compound was obtained.

$^1$H-NMR (DMSO-$d_6$, δ): 1.03 (6H, d, J=6.8 Hz), 2.3-2.5 (1H, m), 4.31 (2H, d, J=5.8 Hz), 6.98 (1H, s), 7.3-7.6 (5H, m), 8.0-8.4 (3H, m), 12.89 (1H, brs)

MS (m/z): 415 (M$^+$)

Example 7: N-{4-Chloro-3-[4-(5-chloropyridin-2-yl)-6-oxo-1,6-dihydropyrimidin-2-yl]benzyl}isobutyramide By performing operations similar to those of Example 4 using 5-chloropyridine-2-carbaldehyde, the title compound was obtained.

$^1$H-NMR (DMSO-$d_6$, δ): 1.04 (6H, d, J=6.8 Hz), 2.3-2.5 (1H, m), 4.32 (2H, d, J=5.9 Hz), 7.21 (1H, s), 7.4-7.7 (3H, m), 8.0-8.4 (3H, m), 8.78 (1H, d, J=1.9 Hz), 13.04 (1H, brs)

MS (m/z): 416 (M$^+$)

Example 8: N-[4-Chloro-3-(6-oxo-4-phenyl-1,6-dihydropyrimidin-2-yl)benzyl]isobutyramide By performing operations similar to those of Example 4 using benzaldehyde, the title compound was obtained.

$^1$H-NMR (DMSO-$d_6$, δ): 1.03 (6H, d, J=6.8 Hz), 2.3-2.5 (1H, m), 4.31 (2H, d, J=5.9 Hz), 6.94 (1H, s), 7.3-7.6 (6H, m), 8.0-8.2 (2H, m), 8.3-8.4 (1H, m), 12.85 (1H, brs)

MS (m/z): 381 (M$^+$)

Example 9: N-{4-Chloro-3-[6-oxo-4-(6-trifluoromethylpyridin-3-yl)-1,6-dihydropyrimidin-2-yl]benzyl}isobutyramide By performing operations similar to those of Example 4 using 6-trifluoromethylpyridine-3-carbaldehyde, the title compound was obtained.

$^1$H-NMR (DMSO-$d_6$, δ): 1.03 (6H, d, J=6.8 Hz), 2.3-2.5 (1H, m), 4.32 (2H, d, J=6.4 Hz), 7.25 (1H, s), 7.4-7.7 (3H, m), 8.03 (1H, d, J=8.3 Hz), 8.2-8.4 (1H, m), 8.69 (1H, dd, J=1.4 Hz, 8.3 Hz), 9.40 (1H, s), 13.13 (1H, brs)

MS (m/z): 450 (M$^+$)

Example 10: N-{4-Chloro-3-[4-(4-chloro-3-fluorophenyl)-6-oxo-1,6-dihydropyrimidin-2-yl]benzyl}isobutyramide By performing operations similar to those of Example 4 using 4-chloro-3-fluorobenzaldehyde, the title compound was obtained.

$^1$H-NMR (DMSO-$d_6$, δ): 1.04 (6H, d, J=6.8 Hz), 2.3-2.5 (1H, m), 4.31 (2H, d, J=6.3 Hz), 7.08 (1H, s), 7.3-7.8 (4H, m), 7.97 (1H, dd, J=1.4 Hz, 8.3 Hz), 8.09 (1H, dd, J=1.9 Hz, 9.3 Hz), 8.2-8.4 (1H, m), 12.90 (1H, brs)

MS (m/z): 433 (M$^+$)

Example 11: N-[4-Chloro-3-(6-oxo-4-thiophen-3-yl-1,6-dihydropyrimidin-2-yl)benzyl]-2-methoxy-2-methylpropionamide By performing operations similar to those of Example 4 using thiophene-3-carbaldehyde, and N-(3-carbamimidoyl-4-chlorobenzyl)-2-methoxy-2-methylpropionamide hydrochloride, the title compound was obtained.

$^1$H-NMR (DMSO-$d_6$, δ): 1.27 (6H, s), 3.16 (3H, s), 4.32 (2H, d, J=6.3 Hz), 6.83 (1H, s), 7.3-7.8 (5H, m), 8.2-8.5 (2H, m), 12.75 (1H, brs)

MS (m/z): 417 (M$^+$)

Example 12: N-{4-Chloro-3-[6-oxo-4-(5-trifluoromethylpyridin-2-yl)-1,6-dihydropyrimidin-2-yl]benzyl}isobutyramide By performing operations similar to those of Example 4 using 5-trifluoromethylpyridine-2-carbaldehyde, the title compound was obtained.

$^1$H-NMR (DMSO-$d_6$, δ): 1.04 (6H, d, J=7.3 Hz), 2.3-2.5 (1H, m), 4.32 (2H, d, J=5.8 Hz), 7.31 (1H, as), 7.4-7.7 (3H, m), 8.2-8.5 (3H, m), 9.12 (1H, d, J=0.9 Hz), 13.14 (1H, brs)

MS (m/z): 450 (M$^+$)

Example 13: N-{4-Chloro-3-[4-(5-chloropyridin-2-yl)-6-oxo-1,6-dihydropyrimidin-2-yl]benzyl}-2-methoxy-2-methylpropionamide By performing operations similar to those of Example 4 using 5-chloropyridine-2-carbaldehyde, and N-(3-carbamimidoyl-4-chlorobenzyl)-2-methoxy-2-methylpropionamide hydrochloride, the title compound was obtained.

$^1$H-NMR (DMSO-d$_6$, δ): 1.28 (6H, s), 3.17 (3H, s), 4.33 (2H, d, J=5.8 Hz), 7.21 (1H, s), 7.4-7.7 (3H, m), 8.0-8.5 (3H, m), 8.78 (1H, d, J=1.9 Hz), 13.06 (1H, brs)

MS (m/z): 446 (M$^+$)

Example 14: N-{4-Chloro-3-[4-(3-chloro-2-fluorophenyl)-6-oxo-1,6-dihydropyrimidin-2-yl]benzyl}isobutyramide By performing operations similar to those of Example 4 using 3-chloro-2-fluorobenzaldehyde, the title compound was obtained.

$^1$H-NMR (DMSO-d$_6$, δ): 1.03 (6H, d, J=7.2 Hz), 2.43 (1H, sept, J=6.8 Hz), 4.30 (2H, d, J=6.4 Hz), 6.78 (1H, brs), 7.35 (1H, t, J=7.2 Hz), 7.42 (1H, dd, J=2.0 Hz, 8.0 Hz), 7.5-7.6 (2H, m), 7.7-7.8 (1H, m), 7.91 (1H, t, J=6.8 Hz), 8.33 (1H, t, J=6.0 Hz), 13.08 (1H, s)

MS (m/z): 433 (M$^+$)

Example 15: N-{4-Chloro-3-[4-(2-chloro-4-fluorophenyl)-6-oxo 1,6-dihydropyrimidin-2-yl]benzyl}isobutyramide By performing operations similar to those of Example 4 using 2-chloro-4-fluorobenzaldehyde, the title compound was obtained.

$^1$H-NMR (DMSO-d$_6$, δ): 1.02 (6H, d, J=6.8 Hz), 2.3-2.5 (1H, m), 4.29 (2H, d, J=5.6 Hz), 6.62 (1H, brs), 7.3-7.5 (2H, m), 7.51 (1H, d, J=2.0 Hz), 7.5-7.6 (2H, m), 7.72 (1H, dd, J=6.0 Hz, 8.8 Hz), 8.2-8.3 (1H, m), 13.03 (1H, brs)

MS (m/z): 433 (M$^+$)

Example 16: N-{4-Chloro-3-[4-(4-difluoromethoxy-2-fluorophenyl)-6-oxo-1,6-dihydropyrimidin-2-yl]benzyl}isobutyramide By performing operations similar to those of Example 4 using 4-difluoromethoxy-2-fluorobenzaldehyde, the title compound was obtained.

$^1$H-NMR (DMSO-d$_6$, δ): 1.03 (6H, d, J=6.8 Hz), 2.3-2.6 (1H, m), 4.30 (2H, d, J=5.6 Hz), 6.74 (1H, brs), 7.16 (1H, dd, J=2.8 Hz, 8.8 Hz), 7.29 (1H, dd, J=2.4 Hz, 12.8 Hz), 7.40 (1H, t, J=73.2 Hz), 7.41 (1H, dd, J=2.4 Hz, 8.4 Hz), 7.5-7.6 (2H, m), 8.07 (1H, t, J=8.8 Hz), 8.33 (1H, t, J=6.0 Hz), 13.01 (1H, brs)

MS (m/z): 465 (M$^+$)

Example 17: N-{4-Chloro-3-[4-(2-fluoro-4-trifluoromethoxyphenyl)-6-oxo-1,6-dihydropyrimidin-2-yl]benzyl}isobutyramide By performing operations similar to those of Example 4 using 2-fluoro-4-trifluoromethoxybenzaldehyde, the title compound was obtained.

$^1$H-NMR (DMSO-d$_6$, δ): 1.03 (6H, d, J=6.8 Hz), 2.3-2.6 (1H, m), 4.30 (2H, d, J=6.0 Hz), 6.79 (1H, brs), 7.37 (1H, d, J=8.8 Hz), 7.41 (1H, dd, J=2.0 Hz, 8.4 Hz), 7.5-7.6 (3H, m), 8.12 (1H, L, J=8.8 Hz), 8.33 (1H, t, J=6.0 Hz), 13.04 (1H, brs)

MS (m/z): 483 (M$^+$)

Example 18: N-{4-Chloro-3-[4-(2-fluoro-4-methoxyphenyl)-6-oxo-1,6-dihydropyrimidin-2-yl]benzyl}isobutyramide By performing operations similar to those of Example 4 using 2-fluoro-4-methoxybenzaldehyde, the title compound was obtained.

$^1$H-NMR (DMSO-d$_6$, δ): 1.03 (6H, d, J=6.8 Hz), 2.43 (1H, sept, J=6.8 Hz), 3.84 (3H, s), 4.31 (2H, d, J=6.0 Hz), 6.68 (1H, brs), 6.90 (1H, dd, J=2.4 Hz, 8.8 Hz), 6.98 (1H, dd, J=2.4 Hz, 13.6 Hz), 7.41 (1H, dd, J=2.0 Hz, 8.4 Hz), 7.5-7.6 (2H, m), 8.00 (1H, t, J=8.8 Hz), 8.33 (1H, t, J=6.4 Hz), 12.89 (1H, brs)

MS (m/z): 429 (M$^+$)

Example 19: N-{4-Chloro-3-[4-(4-methoxyphenyl)-6-oxo 1,6-dihydropyrimidin-2-yl]benzyl}isobutyramide By performing operations similar to those of Example 4 using 4-methoxybenzaldehyde, the title compound was obtained.

$^1$H-NMR (DMSO-d$_6$, δ): 1.03 (6H, d, J=6.8 Hz), 2.4-2.6 (1H, m), 3.82 (3H, s), 4.31 (2H, d, J=6.0 Hz), 6.84 (1H, brs), 7.0-7.1 (2H, m), 7.41 (1H, dd, J=2.0 Hz, 8.4 Hz), 7.5-7.6 (2H, m), 8.04 (2H, d, J=8.8 Hz), 8.34 (1H, t, J=6.0 Hz), 12.75 (1H, brs)

MS (m/z): 411 (M$^+$)

Example 20: N-{4-Chloro-3-[4-(4-difluoromethoxyphenyl)-6-oxo-1,6-dihydropyrimidin-2-yl]benzyl}isobutyramide By performing operations similar to those of Example 4 using 4-difluoromethoxybenzaldehyde, the title compound was obtained.

$^1$H-NMR (DMSO-d$_6$, δ): 1.03 (6H, d, J=6.8 Hz), 2.3-2.5 (1H, m), 4.31 (2H, d, J=5.6 Hz), 6.95 (1H, brs), 7.27 (2H, d, J=8.8 Hz), 7.34 (1H, t, J=73.6 Hz), 7.42 (1H, d, J=8.4 Hz), 7.5-7.6 (2H, m), 8.14 (2H, d, J=8.4 Hz), 8.3-8.4 (1H, m), 12.90 (1H, brs)

MS (m/z): 447 (M$^+$)

Example 21: N-{4-Chloro-3-[6-oxo-4-(4-trifluoromethylphenyl)-1,6-dihydropyrimidin-2-yl]benzyl}isobutyramide By performing operations similar to those of Example 4 using 4-trifluoromethylbenzaldehyde, the title compound was obtained.

$^1$H-NMR (DMSO-d$_6$, δ): 1.03 (6H, d, J=6.8 Hz), 2.43 (1H, sept, J=6.8 Hz), 4.31 (2H, d, J=5.6 Hz), 7.08 (1H, brs), 7.42 (1H, dd, J=2.0 Hz, 8.4 Hz), 7.5-7.6 (2H, m), 7.84 (2H, d, J=8.0 Hz), 8.2-8.4 (3H, m), 13.04 (1H, brs)

MS (m/z): 449 (M$^+$)

Example 22: N-{4-Chloro-3-[4-(3-fluorothiophen-2-yl)-6-oxo-1,6-dihydropyrimidin-2-yl]benzyl}isobutyramide By performing operations similar to those of Example 4 using 3-fluorothiophene-2-carbaldehyde, the title compound was obtained.

$^1$H-NMR (DMSO-d$_6$, δ): 1.04 (6H, d, J=7.2 Hz), 2.3-2.6 (1H, m), 4.31 (2H, d, J=6.0 Hz), 6.61 (1H, brs), 7.18 (1H, d, J=5.6 Hz), 7.42 (1H, d, J=8.4 Hz), 7.49 (1H, s), 7.57 (1H, d, J=8.0 Hz), 7.81 (1H, t, J=5.6 Hz), 8.34 (1H, t, J=6.0 Hz), 12.91 (1H, brs)

MS (m/z): 405 (M$^+$)

Example 23: N-[4-Chloro-3-(4-cyclopentyl-6-oxo-1,6-dihydropyrimidin-2-yl)benzyl]isobutyramide Under a nitrogen atmosphere, N-(3-carbamimidoyl-4-chlorobenzyl)isobutyramide hydrochloride (580 mg) was dissolved in ethanol (8 mL), and ethyl 3-cyclopentyl-3-oxopropanoate (405 mg) was added to the solution. Under ice cooling, a 20% solution of sodium ethoxide in ethanol (1.5 mL) was slowly added dropwise to the solution, and the resulting mixture was refluxed overnight by heating. Ethanol was removed under reduced pressure, the residue was dissolved in ethyl acetate, and the solution was successively washed with 2 N hydrochloric acid, water, and saturated brine. The solvent was removed under reduced pressure, and then the obtained residue was purified by silica gel column chromatography, and dried under reduced pressure to obtain the title compound (88 mg).

$^1$H-NMR (DMSO-d$_6$, δ): 1.03 (6H, d, J=6.8 Hz), 1.5-2.0 (8H, m), 2.42 (1H, sept, J=6.8 Hz), 2.8-3.0 (1H, m), 4.29 (2H, d, J=5.6 Hz), 6.19 (1H, brs), 7.38 (1H, dd, J=2.0 Hz, 8.4 Hz), 7.41 (1H, d, J=1.6 Hz), 7.53 (1H, d, J=8.4 Hz), 8.3-8.4 (1H, m), 12.62 (1H, brs)

MS (m/z): 373 (M$^+$)

Example 24: N-{4-Chloro-3-[6-oxo-4-(4-trifluoromethoxyphenyl)-1,6-dihydropyrimidin-2-yl]benzyl}isobutyramide By performing operations similar to those of Example 4 using 4-trifluoromethoxybenzaldehyde, the title compound was obtained.

$^1$H-NMR (DMSO-d$_6$, δ): 1.03 (6H, d, J=6.8 Hz), 2.43 (1H, sept, J=6.8 Hz), 4.31 (2H, d, J=6.4 Hz), 7.01 (1H, brs), 7.4-7.6 (5H, m), 8.21 (2H, d, J=8.8 Hz), 8.34 (1H, t, J=6.4 Hz), 12.96 (1H, brs)

MS (m/z): 465 (M$^+$)

Example 25: N-{4-Chloro-3-[4-(2,4-difluorophenyl)-6-oxo-1,6-dihydropyrimidin-2-yl]benzyl}isobutyramide By performing operations similar to those of Example 4 using 2,4-difluorobenzaldehyde, the title compound was obtained.

$^1$H-NMR (DMSO-d$_6$, δ): 1.03 (6H, d, J=6.8 Hz), 2.43 (1H, sept, J=6.8 Hz), 4.30 (2H, d, J=6.0 Hz), 6.73 (1H, brs), 7.2-7.3 (1H, m), 7.4-7.6 (4H, m), 8.07 (1H, ddd, J=2.4 Hz, 6.8 Hz, 8.8 Hz), 8.32 (1H, t, J=6.4 Hz), 12.96 (1H, brs)

MS (m/z): 417 (M$^+$)

Example 26: N-{4-Chloro-3-[4-(2-chlorothiophen-3-yl)-6-oxo-1,6-dihydropyrimidin-2-yl]benzyl}isobutyramide By performing operations similar to those of Example 4 using 2-chlorothiophene-3-carbaldehyde, the title compound was obtained.

$^1$H-NMR (DMSO-d$_6$, δ): 1.03 (6H, d, J=6.8 Hz), 2.42 (1H, sept, J=6.8 Hz), 4.30 (2H, d, J=5.6 Hz), 6.83 (1H, brs), 7.41 (1H, dd, J=2.0 Hz, 8.0 Hz), 7.45 (1H, d, J=6.0 Hz), 7.5-7.6 (3H, m), 8.3-8.4 (1H, m), 12.96 (1H, brs)

MS (m/z): 422 (M$^+$)

Example 27: N-[4-Chloro-3-(4-cyclohexyl-6-oxo-1,6-dihydropyrimidin-2-yl)benzyl]isobutyramide By performing operations similar to those of Example 23 using ethyl 3-cyclohexyl-3-oxopropanoate, the title compound was obtained.

$^1$H-NMR (DMSO-d$_6$, δ): 1.03 (6H, d, J=6.8 Hz), 1.2-1.4 (5H, m), 1.7-1.9 (5H, m), 2.3-2.6 (2H, m), 4.29 (2H, d, J=5.6 Hz), 6.13 (1H, brs), 7.4-7.5 (2H, m), 7.52 (1H, d, J=8.0 Hz), 8.3-8.4 (1H, m), 12.63 (1H, brs)

MS (m/z): 387 (M$^+$)

Example 28: N-{4-Chloro-3-[4-(2-fluoro-5-methoxyphenyl)-6-oxo-1,6-dihydropyrimidin-2-yl]benzyl}isobutyramide By performing operations similar to those of Example 4 using 2-fluoro-5-methoxybenzaldehyde, the title compound was obtained.

$^1$H-NMR (DMSO-d$_6$, δ): 1.03 (6H, d, J=6.8 Hz), 2.3-2.6 (1H, m), 3.77 (3H, s), 4.31 (2H, d, J=6.0 Hz), 6.76 (1H, brs), 7.0-7.1 (1H, m), 7.2-7.3 (1H, m), 7.41 (1H, dd, J=2.0 Hz, 8.4 Hz), 7.4-7.5 (1H, m), 7.5-7.6 (2H, m), 8.33 (1H, t, J=6.0 Hz), 13.00 (1H, brs)

MS (m/z): 429 (M$^+$)

Example 29: N-{4-Chloro-3-[4-(5-chloro-2-fluorophenyl)-6-oxo-1,6-dihydropyrimidin-2-yl]benzyl}isobutyramide By performing operations similar to those of Example 4 using 5-chloro-2-fluorobenzaldehyde, the title compound was obtained.

$^1$H-NMR (DMSO-d$_6$, δ): 1.04 (6H, d, J=6.8 Hz), 2.43 (1H, sept, J=6.8 Hz), 4.31 (2H, d, J=6.0 Hz), 6.79 (1H, brs), 7.4-7.6 (5H, m), 7.98 (1H, dd, J=2.8 Hz, 6.8 Hz), 8.34 (1H, t, J=6.4 Hz), 13.06 (1H, brs)

MS (m/z): 433 (M$^+$)

Example 30: N-{4-Chloro-3-[6-oxo-4-(6-trifluoromethylpyridin-2-yl)-1,6-dihydropyrimidin-2-yl]benzyl}isobutyramide By performing operations similar to those of Example 4 using 6-trifluoromethylpyridine-2-carbaldehyde, the title compound was obtained.

$^1$H-NMR (DMSO-d$_6$, δ): 1.03 (6H, d, J=6.8 Hz), 2.43 (1H, sept, J=6.8 Hz), 4.31 (2H, d, J=6.4 Hz), 7.18 (1H, brs), 7.41 (1H, dd, J=1.9 Hz, 8.3 Hz), 7.5-7.6 (2H, m), 8.03 (1H, dd, J=0.8 Hz, 8.0 Hz), 8.25 (1H, t, J=8.0 Hz), 8.34 (1H, t, J=6.4 Hz), 8.49 (1H, d, J=8.0 Hz), 13.13 (1H, brs)

MS (m/z): 450 (M$^+$)

Example 31: N-{4-Chloro-3-[4-(2-fluorophenyl)-6-oxo-1,6-dihydropyrimidin-2-yl]benzyl}isobutyramide By performing operations similar to those of Example 4 using 2-fluorobenzaldehyde, the title compound was obtained.

$^1$H-NMR (DMSO-d$_6$, δ): 1.03 (6H, d, J=6.8 Hz), 2.43 (1H, sept, J=6.8 Hz), 4.30 (2H, d, J=6.0 Hz), 6.75 (1H, brs), 7.3-7.4 (3H, m), 7.5-7.6 (3H, m), 8.00 (1H, dt, J=2.0 Hz, 8.0 Hz), 8.33 (1H, t, J=6.0 Hz), 12.98 (1H, brs)
MS (m/z): 399 (M+)

Example 32: N-{3-[4-(5-Chloropyridin-2-yl)-6-oxo-1,6-dihydropyrimidin-2-yl]benzyl}isobutyramide To a solution of 2-(3-aminomethylphenyl)-6-(5-chloropyridin-2-yl)-3H-pyrimidin-4-one (92 mg) in N,N-dimethylformamide (4 mL), diisopropylethylamine (178 µL) was added. Under ice cooling, isobutyryl chloride (46 µL) was added dropwise to the mixture, and the resulting mixture was stirred overnight at room temperature. Ethyl acetate was added to the reaction mixture, the resulting mixture was washed twice with water, and the organic layer was concentrated under reduced pressure. The obtained residue was purified by silica gel column chromatography to obtain the title compound (10 mg).

$^1$H-NMR (DMSO-$d_6$, δ): 1.07 (6H, d, J=6.8 Hz), 2.4-2.6 (1H, m), 4.37 (2H, d, J=5.6 Hz), 7.19 (1H, brs), 7.4-7.6 (2H, m), 8.0-8.3 (4H, m), 8.47 (1H, d, J=8.4 Hz), 8.7-8.8 (1H, m), 12.94 (1H, brs)
MS (m/z): 382 (M+)

Example 33: N-[4-Chloro-3-(6-oxo-4-thiophen-2-yl-1,6-dihydropyrimidin-2-yl)benzyl]isobutyramide By performing operations similar to those of Example 4 using thiophene-2-carbaldehyde, the title compound was obtained.

$^1$H-NMR (DMSO-$d_6$, δ): 1.04 (6H, d, J=7.2 Hz), 2.43 (1H, sept, J=6.8 Hz), 4.31 (2H, d, J=5.6 Hz), 6.86 (1H, brs), 7.1-7.2 (1H, m), 7.42 (1H, dd, J=2.0 Hz, 8.4 Hz), 7.50 (1H, d, J=2.0 Hz), 7.57 (1H, d, J=8.4 Hz), 7.77 (1H, dd, J=0.8 Hz, 4.8 Hz), 7.92 (1H, d, J=3.2 Hz), 8.34 (1H, t, J=5.6 Hz), 12.82 (1H, brs)
MS (m/z): 387 (M+)

Example 34: N-[4-Chloro-3-(5-methyl-6-oxo-4-phenyl-1,6-dihydropyrimidin-2-yl)benzyl]isobutyramide By performing operations similar to those of Example 23 using ethyl 2-methyl-3-oxo-3-phenylpropanoate, the title compound was obtained.

$^1$H-NMR (DMSO-$d_6$, δ): 1.02 (6H, d, J=6.8 Hz), 2.07 (3H, s), 2.3-2.6 (1H, m), 4.28 (2H, d, J=6.0 Hz), 7.18 (1H, brs), 7.3-7.6 (7H, m), 8.3-8.4 (1H, m), 12.38 (1H, brs)
MS (m/z): 395 (M+)

Reference Example 9: N-(4-Chloro-3-cyanobenzyl)cyclopropanecarboxamide

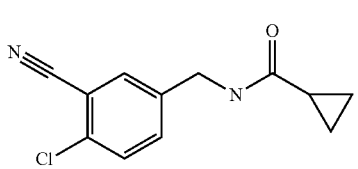

[Formula 22]

By performing operations similar to those of Reference Example 1 using cyclopropanecarbonyl chloride, the title compound was obtained.

$^1$H-NMR (CDCl$_3$, δ): 0.7-1.1 (4H, m), 1.3-1.5 (1H, m), 4.44 (2H, d, J=5.8 Hz), 6.16 (1H, brs), 7.4-7.5 (2H, m), 7.58 (1H, brs)
MS (m/z): 234 (M+)

Reference Example 10: N-(3-Carbamimidoyl-4-chlorobenzyl)cyclopropanecarboxamide Hydrochloride

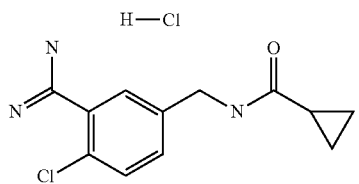

[Formula 23]

By performing operations similar to those of Reference Example 2 using N-(4-chloro-3-cyanobenzyl)cyclopropanecarboxamide, the title compound was obtained. The obtained compound was used for the following reaction without purification.

Reference Example 11: 4-(2-Ethoxyethoxy)-2-fluorobenzaldehyde

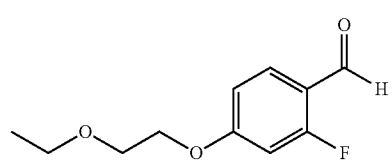

[Formula 24]

2-Fluoro-4-hydroxybenzaldehyde (560 mg), 1-bromo-2-ethoxyethane (1.84 g), potassium carbonate (1.11 g), and acetonitrile (10 mL) were mixed, and the mixture was heated to 85° C. under a nitrogen atmosphere. After 16 hours, the reaction mixture was left to cool. The reaction mixture was poured into brine, the resulting mixture was extracted with ethyl acetate, and then the solvent was evaporated. Silica gel column chromatography was performed to obtain the title compound (670 mg).

$^1$H-NMR (CDCl$_3$, δ): 1.25 (3H, t, J=7.1 Hz), 3.60 (2H, q, J=7.0 Hz), 3.7-3.9 (2H, m), 4.1-4.3 (2H, m), 6.68 (1H, dd, J=2.4 Hz, 12.7 Hz), 6.81 (1H, dd, J=2.4 Hz, 8.8 Hz), 7.81 (1H, t. J=8.3 Hz), 10.21 (1H, s)
MS (m/z): 212 (M+)

Reference Example 12: N-(4-Chloro-3-cyanobenzyl)-3,3,3-trifluoro-2,2-dimethylpropionamide

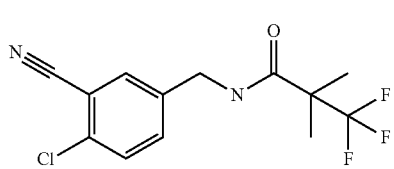

[Formula 25]

By performing operations similar to those of Reference Example 5 using 3,3,3-trifluoro-2,2-dimethylpropionic acid, the title compound was obtained.

¹H-NMR (CDCl₃, δ): 1.44 (6H, s), 4.48 (2H, d, J=6.4 Hz), 6.33 (1H, brs), 7.43 (1H, dd, J=1.9 Hz, 8.3 Hz), 7.48 (1H, d, J=8.3 Hz), 7.54 (1H, d, J=2.5 Hz)
MS (m/z): 304 (M⁺)

Reference Example 13: N-(3-Carbamimidoyl-4-chlorobenzyl)-3,3,3-trifluoro-2,2-dimethylpropionamide Hydrochloride

[Formula 26]

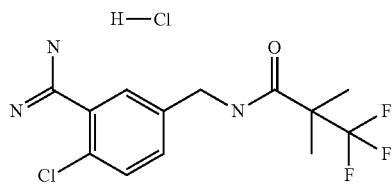

By performing operations similar to those of Reference Example 2 using N-(4-chloro-3-cyanobenzyl)-3,3,3-trifluoro-2,2-dimethylpropionamide, the title compound was obtained. The obtained compound was used for the following reaction without purification.

Reference Example 14: N-(3-Cyano-4-fluorobenzyl)-2,2-dimethylpropionamide

[Formula 27]

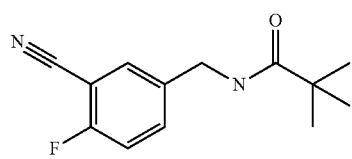

By performing operations similar to those of Reference Example 1 using 5-aminomethyl-2-fluorobenzonitrile, the title compound was obtained.
¹H-NMR (CDCl₃, δ): 1.23 (9H, s), 4.42 (2H, d, J=6.4 Hz), 6.10 (1H, brs), 7.18 (1H, t, J=8.6 Hz), 8.4-8.6 (2H, m)
MS (m/z): 234 (M⁺)

Reference Example 15: N-(3-Carbamimidoyl-4-fluorobenzyl)-2,2-dimethylpropionamide Hydrochloride

[Formula 28]

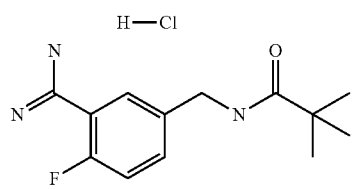

By performing operations similar to those of Reference Example 2 using N-(3-cyano-4-fluorobenzyl)-2,2-dimethylpropionamide, the title compound was obtained. The obtained compound was used for the following reaction without purification.

Reference Example 16: [3-Cyano-4-(difluoromethoxy)benzyl]carbamic Acid Tert-Butyl Ester

[Formula 29]

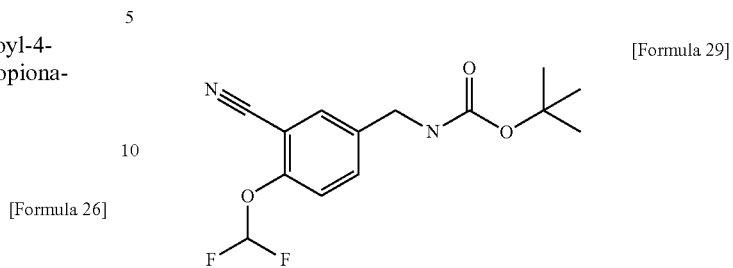

5-Bromo-2-(difluoromethoxy)benzonitrile (4.48 g), potassium N—BOC-aminomethyltrifluoroborate (4.50 g), palladium acetate (205 mg), 2-dicyclohexylphosphino-2',6'-dimethoxybiphenyl (745 mg), potassium carbonate (7.51 g), toluene (60 mL), and water (15 mL) were mixed, and the mixture was heated to 85° C. under a nitrogen atmosphere. After 17 hours, the reaction mixture was left to cool. The reaction mixture was poured into water, the resulting mixture was extracted with ethyl acetate, and then the organic layer was dried over sodium sulfate. The solvent was evaporated, and then silica gel column chromatography was performed to obtain the title compound (6.38 g).

Reference Example 17: 5-Aminomethyl-2-(difluoromethoxy)benzonitrile

[Formula 30]

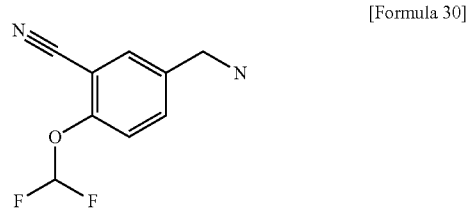 [SMILES: N#Cc1cc(CN)ccc1OC(F)F]

To [3-cyano-4-(difluoromethoxy)benzyl]carbamic acid tert-butyl ester (6.38 g), dichloromethane (25 mL), and trifluoroacetic acid (12.4 mL) were added, and the resulting mixture was stirred at room temperature for 1.2 hours. The reaction mixture was poured into water, and the aqueous layer was washed twice with chloroform. To the aqueous layer, 2 N aqueous sodium hydroxide (100 mL) was added, and the resulting mixture was extracted twice with chloroform. The organic layer was dried over sodium sulfate, and then the solvent was evaporated to obtain the title compound (2.73 g).

¹H-NMR (CDCl₃, δ): 1.41 (2H, brs), 3.92 (2H, s), 6.63 (1H, t, J=71.8 Hz), 7.2-7.4 (1H, m), 7.58 (1H, dd, J=1.9 Hz, 8.3 Hz), 7.68 (1H, d, J=1.9 Hz)
MS (m/z): 197 (M⁺−1)

Reference Example 18: N-[3-Cyano-4-(difluoromethoxy)benzyl]isobutyramide

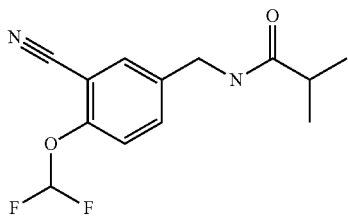

[Formula 31]

By performing operations similar to those of Reference Example 1 using 5-aminomethyl-2-(difluoromethoxy)benzonitrile, and isobutyryl chloride, the title compound was obtained.

$^1$H-NMR (CDCl$_3$, δ): 1.19 (6H, d, J=6.8 Hz), 2.42 (1H, sept, J=6.8 Hz), 4.44 (2H, d, J=6.31 Hz), 5.97 (1H, brs), 6.63 (1H, t, J=71.6 Hz), 7.2-7.4 (1H, m), 7.53 (1H, dd, J=2.4 Hz, 8.8 Hz), 7.57 (1H, d, J=2.0 Hz)

MS (m/z): 268 (M$^+$)

Reference Example 19: N-[3-Carbamimidoyl-4-(difluoromethoxy)benzyl]isobutyramide Hydrochloride

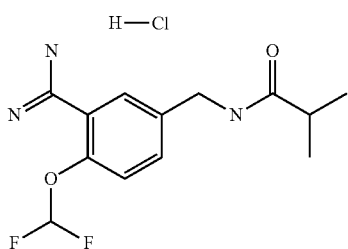

[Formula 32]

By performing operations similar to those of Reference Example 2 using N-[3-cyano-4-(difluoromethoxy)benzyl]isobutyramide, the title compound was obtained. The obtained compound was used for the following reaction without purification.

Reference Example 20: 6-(3-Methoxypropoxy)pyridine-3-carbaldehyde

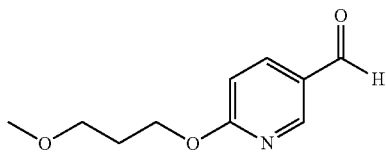

[Formula 33]

To 3-methoxypropan-1-ol (25 g), 60% sodium hydride (1.12 g) was added portionwise under ice cooling. Then, 6-chloropyridine-3-carbaldehyde (2.48 g) was added portionwise to the mixture. The resulting mixture was returned to room temperature, and stirred for 14 hours under a nitrogen atmosphere. The reaction mixture was poured into saturated aqueous ammonium chloride, and the resulting mixture was extracted with t-butyl methyl ether. The organic layer was washed with saturated brine, and the solvent was evaporated. Silica gel column chromatography was performed to obtain the title compound (866 mg).

$^1$H-NMR (CDCl$_3$, δ): 2.0-2.2 (2H, m), 3.36 (3H, s), 3.55 (2H, t, J=6.4 Hz), 4.50 (2H, t, J=6.6 Hz), 6.83 (1H, d, J=8.8 Hz), 8.06 (1H, dd, J=2.5 Hz, 8.8 Hz), 8.62 (1H, d, J=1.9 Hz), 9.95 (1H, s)

MS (m/z): 196 (M++1)

Reference Example 21: 4-(Pyridin-2-ylethynyl)benzaldehyde

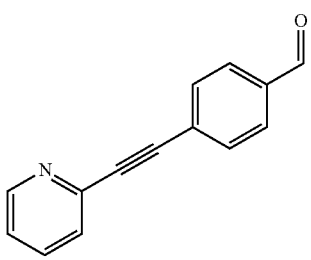

[Formula 34]

To a solution of 4-ethynylbenzaldehyde (1.24 g) in triethylamine (20 mL), 2-bromopyridine (975 μL), bis(triphenylphosphine)palladium chloride (133 mg), and copper iodide (46 mg) were added under a nitrogen atmosphere, and the resulting mixture was refluxed by heating for 2 hours. After cooling, triethylamine was removed under reduced pressure, chloroform was added to the obtained residue, and the resulting mixture was filtered through a Celite layer. The filtrate was washed successively with 15% potassium carbonate, water, and saturated brine, dried over magnesium sulfate, and filtered, and the solvent was evaporated under reduced pressure. To the obtained residue, ethanol was added, and the resulting mixture was heated, cooled, filtered, and dried to obtain the title compound (953 mg).

$^1$H-NMR (d$_6$-DMSO, δ): 7.4-7.5 (1H, m), 7.7-7.8 (1H, m), 7.8-7.9 (3H, m), 7.9-8.0 (2H, m), 8.6-8.7 (1H, m), 10.06 (1H, s)

MS (m/z): 207 (M$^+$)

Reference Example 22: Ethyl 2-fluoro-3-oxo-3-phenylpropanoate

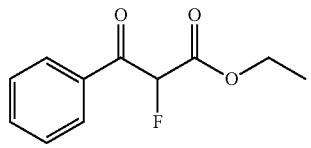

[Formula 35]

To a solution of ethyl 3-oxo-3-phenylpropanoate (961 mg) in acetonitrile (20 mL), Selectfluor (registered trade mark, 1.95 g) was added under a nitrogen atmosphere, and the resulting mixture was stirred at 80° C. for 6 hours. After cooling, acetonitrile was removed under reduced pressure. To the obtained residue, ethyl acetate was added, and the organic layer was washed successively with water, and saturated brine, and dried over magnesium sulfate. The organic layer was filtered, and the solvent was evaporated under reduced pressure. The obtained residue was purified by silica gel column chromatography to obtain the title compound (858 mg).

$^1$H-NMR (d$_6$-DMSO, δ): 1.26 (3H, t, J=7.2 Hz), 4.2-4.3 (2H, m), 5.86 (1H, d, J=48.8 Hz), 7.4-7.5 (2H, m), 7.6-7.7 (1H, m), 8.0-8.1 (2H, m)

MS (m/z): 210 (M$^+$)

Reference Example 23: Ethyl 2-fluoro-3-(4-methoxyphenyl)-3-oxopropanoate

[Formula 36]

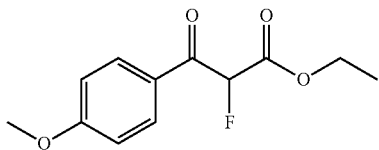

By performing operations similar to those of Reference Example 22 using ethyl 4-methoxybenzoylacetate, the title compound was obtained.

$^1$H-NMR (CDCl$_3$, δ): 1.27 (3H, t, J=7.2 Hz), 3.89 (3H, s), 4.2-4.3 (2H, m), 5.81 (1H, d, J=48.8 Hz), 6.9-7.0 (2H, m), 8.0-8.1 (2H, m)

MS (m/z): 240 (M$^+$)

Reference Example 24: Ethyl 2-fluoro-3-oxo-3-(thiophen-2-yl)propanoate

[Formula 37]

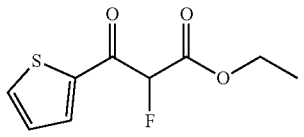

By performing operations similar to those of Reference Example 22 using ethyl 3-oxo-3-(thiophen-2-yl)propanoate, the title compound was obtained.

$^1$H-NMR (d$_6$-DMSO, δ): 1.16 (3H, t, J=6.8 Hz), 4.22 (2H, q, J=6.8 Hz), 6.53 (1H, d, J=46.8 Hz), 7.35 (1H, dd, J=4.8 Hz), 8.1-8.2 (1H, m), 8.22 (1H, dd, J=0.8 Hz, 4.8 Hz)

MS (m/z): 216 (M$^+$)

Reference Example 25: Ethyl 3-oxo-3-(thiophen-3-yl)propanoate

[Formula 38]

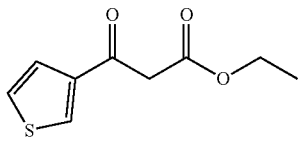

Under a nitrogen atmosphere, a solution of diethyl carbonate (2.3 g) in toluene (10 mL) was warmed to 65° C., t-butoxy potassium (875 mg) was added to the solution, and the resulting mixture was stirred at 65° C. for 30 minutes. The reaction mixture was warmed to 80° C., and then a solution of 3-acetylthiophene (618 mg) dissolved in toluene (5 mL) was added dropwise, and the resulting mixture was stirred at 80° C. for 1.5 hours. The reaction mixture was left to cool to room temperature, then ethyl acetate was added to the reaction mixture, and the organic layer was washed successively with water, and saturated brine, and dried over magnesium sulfate. The obtained residue was purified by silica gel column chromatography to obtain the title compound (765 mg).

$^1$H-NMR (CDCl$_3$, δ): 1.26 (3H, t, J=7.2 Hz), 3.89 (2H, s), 4.21 (2H, q, J=7.2 Hz), 7.3-7.4 (1H, m), 7.56 (1H, dd, J=1.6 Hz, 5.6 Hz), 8.11 (1H, dd, J=1.6 Hz, 2.8 Hz)

MS (m/z): 198 (M$^+$)

Reference Example 26: Ethyl 2-fluoro-3-oxo-3-(thiophen-3-yl)propanoate

[Formula 39]

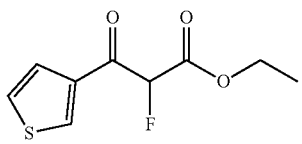

By performing operations similar to those of Reference Example 22 using ethyl 3-oxo-3-(thiophen-3-yl)propanoate, the title compound was obtained.

$^1$H-NMR (CDCl$_3$, δ): 1.28 (3H, t, J=6.8 Hz), 4.2-4.4 (2H, m), 5.65 (1H, d, J=49.2 Hz), 7.36 (1H, dd, J=2.8 Hz, 4.8 Hz), 7.65 (1H, dd, J=0.8 Hz, 6.4 Hz), 8.40 (1H, quin, J=1.6 Hz)

MS (m/z): 216 (M$^+$)

Reference Example 27: N,N-Diethyl-4-formylbenzenesulfonamide

[Formula 40]

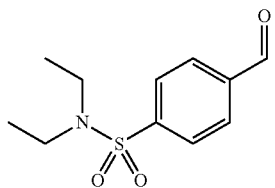

To a solution of 4-formylbenzenesulfonyl chloride (1.0 g) in chloroform (10 mL), diethylamine (731 mg), and then saturated aqueous sodium hydrogencarbonate (11 mL) were added, and the resulting mixture was vigorously stirred at room temperature for 2 hours. The chloroform layer was separated, washed with saturated brine, dried over magnesium sulfate, and filtered, and the solvent was evaporated under reduced pressure. To the obtained residue, a mixture of hexane and ethyl acetate (3:1) was added, and the resulting mixture was heated, cooled, filtered, and dried to obtain the title compound (946 mg).

¹H-NMR (d₆-DMSO, δ): 1.05 (6H, t, J=7.2 Hz), 3.21 (4H, q, J=7.2 Hz)), 7.9-8.0 (2H, m), 8.0-8.1 (2H, m), 10.11 (1H, s)

MS (m/z): 241 (M⁺)

Reference Example 28:
4-(Piperidine-1-sulfonyl)benzaldehyde

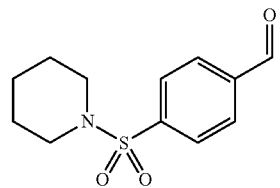

[Formula 41]

To a solution of 4-formylbenzenesulfonyl chloride (818 mg) in chloroform (20 mL), diisopropylethylamine (1.4 mL), and then piperidine (394 µL) were added, and the resulting mixture was stirred overnight at room temperature. Water was added to the reaction mixture, and the chloroform layer was washed twice with water. The chloroform layer was further washed with saturated brine, dried over magnesium sulfate, and filtered, and the solvent was evaporated under reduced pressure to obtain the title compound (988 mg).

¹H-NMR (d₆-DMSO, δ): 1.4-1.5 (2H, m), 1.65 (4H, quin, J=5.6 Hz), 3.04 (4H, t, J=5.6 Hz), 7.93 (2H, dd, J=2.0 Hz, 6.8 Hz), 8.04 (2H, dd, J=2.0 Hz, 6.4 Hz), 10.12 (1H, s)

MS (m/z): 253 (M⁺)

Reference Example 29: N-[3-Cyano-4-(trifluoromethyl)benzyl]isobutyramide

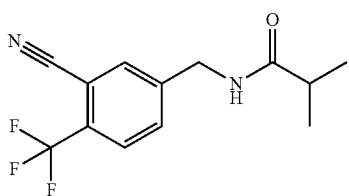

[Formula 42]

By performing operations similar to those of Reference Example 1 using 5-aminomethyl-2-(trifluoromethyl)benzonitrile, and isobutyryl chloride, the title compound was obtained.

¹H-NMR (d₆-DMSO, δ): 1.05 (6H, d, J=7.6 Hz), 2.45 (1H, sept, J=6.8 Hz), 4.38 (2H, d, J=6.0 Hz), 7.76 (1H, d, J=8.8 Hz), 7.9-8.0 (2H, m), 8.40 (1H, t, J=6.0 Hz)

MS (m/z): 270 (M⁺)

Reference Example 30: N-[3-Carbamimidoyl-4-(trifluoromethyl)benzyl]isobutyramide Hydrochloride

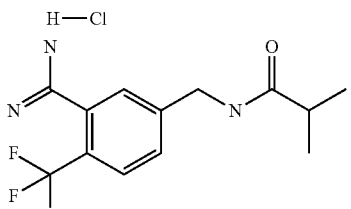

[Formula 43]

By performing operations similar to those of Reference Example 2 using N-[3-cyano-4-(trifluoromethyl)benzyl]isobutyramide, the title compound was obtained. The obtained compound was used for the following reaction without purification.

Reference Example 31:
N-(3-Bromo-4-methylbenzyl)isobutyramide

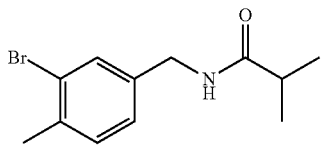

[Formula 44]

By performing operations similar to those of Reference Example 1 using 4-aminomethyl-2-bromo-1-methylbenzene, and isobutyryl chloride, the title compound was obtained.

¹H-NMR (d₆-DMSO, δ): 1.02 (6H, d, J=6.8 Hz), 2.2-2.5 (4H, m), 4.20 (2H, d, J=6.0 Hz), 7.14 (1H, dd, J=2.0 Hz, 7.6 Hz), 7.29 (1H, d, J=7.6 Hz), 7.42 (1H, d, J=1.2 Hz), 8.23 (1H, t, J=5.2 Hz)

MS (m/z): 269 (M⁺-1)

Reference Example 32:
N-(3-Cyano-4-methylbenzyl)isobutyramide

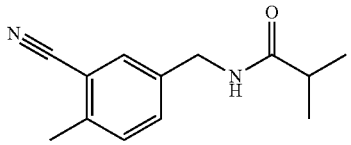

[Formula 45]

To a solution of N-(3-bromo-4-methylbenzyl)isobutyramide (2.1 g) in N-methylpyrrolidinone (15 mL), potassium ferrocyanide trihydrate (1.7 g), palladium acetate (37 mg), diphenylphosphinoferrocene (172 mg), and potassium carbonate (1.6 g) were added under a nitrogen atmosphere, and the resulting mixture was stirred overnight at 160° C. The reaction mixture was left to cool to room temperature, and then filtered through a Celite layer, ethyl acetate and water were added to the filtrate, and the organic layer was washed with a saturated sodium hydrogencarbonate solution, and saturated brine, and dried over magnesium sulfate. The organic layer was filtered, the solvent was evaporated under reduced pressure, and the obtained residue was purified by silica gel column chromatography to obtain the title compound (1.1 g).

$^1$H-NMR (d$_6$-DMSO, δ): 1.03 (6H, d, J=6.8 Hz), 2.3-2.6 (4H, m), 4.24 (2H, d, J=5.6 Hz), 7.4-7.5 (2H, m), 7.58 (1H, s), 8.30 (1H, t, J=6.0 Hz)

MS (m/z): 216 (M$^+$)

Reference Example 33:
N-(3-Carbamimidoyl-4-methylbenzyl)isobutyramide Hydrochloride

[Formula 46]

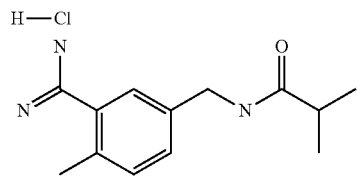

By performing operations similar to those of Reference Example 2 using N-(3-cyano-4-methylbenzyl)isobutyramide, the title compound was obtained. The obtained compound was used for the following reaction without purification.

Reference Example 34: N-[3-Cyano-4-(difluoromethyl)benzyl]isobutyramide

[Formula 47]

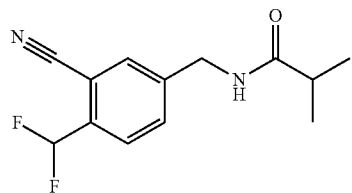

By performing operations similar to those of Reference Example 1 using 5-aminomethyl-2-(difluoromethyl)benzonitrile and isobutyryl chloride, the title compound was obtained.

$^1$H-NMR (d$_6$-DMSO, δ): 1.04 (6H, d, J=6.8 Hz), 2.44 (1H, sept, J=6.8 Hz), 4.34 (2H, d, J=5.6 Hz), 7.23 (1H, t, J=54 Hz), 7.69 (1H, d, J=8.0 Hz), 7.78 (1H, d, J=8.0 Hz), 7.85 (1H, s), 8.36 (1H, t, J=5.6 Hz)

MS (m/z): 252 (M$^+$)

Reference Example 35: N-[3-Carbamimidoyl-4-(difluoromethyl)benzyl]isobutyramide Hydrochloride

[Formula 48]

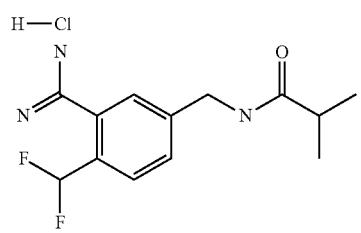

By performing operations similar to those of Reference Example 2 using N-[3-cyano-4-(difluoromethyl)benzyl]isobutyramide, the title compound was obtained. The obtained compound was used for the following reaction without purification.

Reference Example 36:
N-(3-Cyano-4-fluorobenzyl)isobutyramide

[Formula 49]

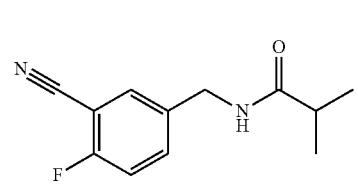

By performing operations similar to those of Reference Example 1 using 5-aminomethyl-2-fluorobenzonitrile, and isobutyryl chloride, the title compound was obtained.

$^1$H-NMR (d$_6$-DMSO, δ): 1.03 (6H, d, J=7.2 Hz), 2.42 (1H, sept, J=6.8 Hz), 4.26 (2H, d, J=5.6 Hz), 7.49 (1H, t, J=8.8 Hz), 7.6-7.7 (1H, m), 7.7-7.8 (1H, m), 8.30 (1H, t, J=5.6 Hz)

MS (m/z): 220 (M$^+$)

Reference Example 37:
N-(3-Carbamimidoyl-4-fluorobenzyl)isobutyramide Hydrochloride

[Formula 50]

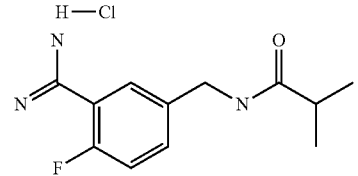

By performing operations similar to those of Reference Example 2 using N-(3-cyano-4-fluorobenzyl)isobutyramide, the title compound was obtained. The obtained compound was used for the following reaction without purification.

Reference Example 38: 3-Bromomethyl-6-chloro-2-fluorobenzonitrile

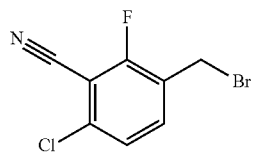

[Formula 51]

Under a nitrogen atmosphere, 6-chloro-2-fluoro-3-methylbenzonitrile (2.29 g) was dissolved in acetonitrile (54 mL), 1,3-dibromo-5,5-dimethylhydantoin (1.93 g), and 2,2'-azobis(isobutyronitrile) (222 mg) were added to the solution, and the resulting mixture was refluxed for 3 hours by heating. 1 N Hydrochloric acid was added to the reaction mixture, the resulting mixture was extracted with ethyl acetate, and the solvent was removed under reduced pressure. The obtained residue was purified by silica gel column chromatography, and dried under reduced pressure to obtain the title compound (2.40 g).

$^1$H-NMR (d$_6$-DMSO, δ): 4.74 (2H, d, J=1.2 Hz), 7.66 (1H, dd, J=1.2 Hz, 8.8 Hz), 7.95 (1H, t, J=8.8 Hz)

MS (m/z): 249 (M$^+$+1)

Reference Example 39: 3-Aminomethyl-6-chloro-2-fluorobenzonitrile

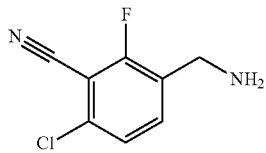

[Formula 52]

3-Bromomethyl-6-chloro-2-fluorobenzonitrile (2.34 g) was dissolved in N,N-dimethylformamide (24 mL), sodium azide (613 mg) was added to the solution under ice cooling, and the resulting mixture was stirred for 35 minutes. Saturated brine was added to the reaction mixture, the resulting mixture was extracted with ethyl acetate, and then the organic layer was washed with saturated brine. The solvent was removed under reduced pressure, and the obtained compound was used for the following reaction without purification.

The obtained compound was dissolved in tetrahydrofuran (24 mL), and water (1 mL), triphenylphosphine (2.97 g) was added to the solution under ice cooling, and the resulting mixture was stirred overnight at room temperature. 1 N Hydrochloric acid was added to the reaction mixture, and the resulting mixture was washed with diethyl ether. The aqueous layer was made alkaline by adding 1 N sodium hydroxide. The aqueous layer was extracted with dichloromethane, then the organic layer was dried over magnesium sulfate, and the obtained organic layer was used as it was for the following reaction.

Reference Example 40: N-(4-Chloro-3-cyano-2-fluorobenzyl)isobutyramide

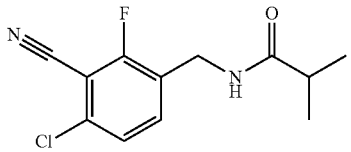

[Formula 53]

By performing operations similar to those of Reference Example 1 using 3-aminomethyl-6-chloro-2-fluorobenzonitrile, and isobutyryl chloride, the title compound was obtained.

$^1$H-NMR (d$_6$-DMSO, δ): 1.02 (6H, d, J=6.8 Hz), 2.41 (1H, sept, J=6.8 Hz), 4.29 (2H, d, J=5.6 Hz), 7.5-7.7 (2H, m), 8.33 (1H, t, J=5.6 Hz)

MS (m/z): 254 (M$^+$)

Reference Example 41: N-(3-Carbamimidoyl-4-chloro-2-fluorobenzyl)isobutyramide Hydrochloride

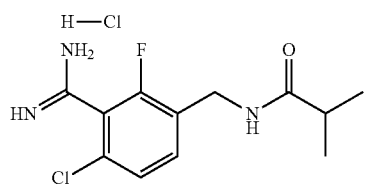

[Formula 54]

By performing operations similar to those of Reference Example 2 using N-(4-chloro-3-cyano-2-fluorobenzyl)isobutyramide, the title compound was obtained. The obtained compound was used for the following reaction without purification.

Reference Example 42: N-(3-Cyano-4-fluorobenzyl)-1-(trifluoromethyl)cyclopropane-1-carboxamide

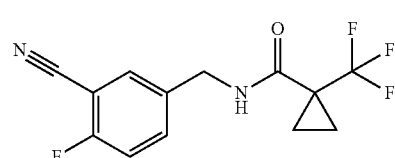

[Formula 55]

By performing operations similar to those of Reference Example 1 using 5-aminomethyl-2-fluorobenzonitrile, and 1-(trifluoromethyl)cyclopropane-1-carbonylchloride, the title compound was obtained.

$^1$H-NMR (d$_6$-DMSO, δ): 1.2-1.4 (4H, m), 4.29 (2H, d, J=6.0 Hz), 7.49 (1H, t, J=8.8 Hz), 7.5-7.7 (1H, m), 7.7-7.8 (1H, m), 8.41 (1H, t, J=5.6 Hz)

MS (m/z): 286 (M$^+$)

Reference Example 43: N-(3-Carbamimidoyl-4-fluorobenzyl)-1-(trifluoromethyl)cyclopropane-1-carboxamide Hydrochloride

[Formula 56]

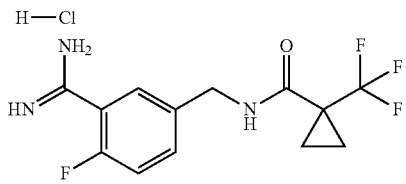

By performing operations similar to those of Reference Example 2 using N-(3-cyano-4-fluorobenzyl)-1-(trifluoromethyl)cyclopropane-1-carboxamide, the title compound was obtained. The obtained compound was used for the following reaction without purification.

Reference Example 44: N-(3-Cyano-2,4-difluorobenzyl)isobutyramide

[Formula 57]

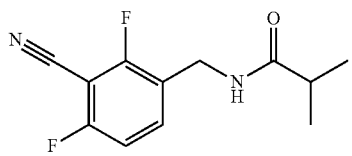

By performing operations similar to those of Reference Example 1 using 3-aminomethyl-2,6-difluorobenzonitrile, and isobutyryl chloride, the title compound was obtained.

$^1$H-NMR (d$_6$-DMSO, δ): 1.02 (6H, d, J=6.8 Hz), 2.41 (1H, sept, J=6.8 Hz), 4.28 (2H, d, J=6.0 Hz), 7.3-7.5 (1H, m), 7.6-7.8 (1H, m), 8.32 (1H, t, J=5.6 Hz)

MS (m/z): 238 (M$^+$)

Reference Example 45: N-(3-Carbamimidoyl-2,4-difluorobenzyl)isobutyramide Hydrochloride

[Formula 58]

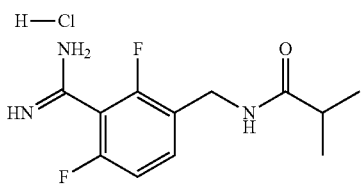

By performing operations similar to those of Reference Example 2 using N-(3-cyano-2,4-difluorobenzyl)isobutyramide, the title compound was obtained. The obtained compound was used for the following reaction without purification.

Reference Example 46: 6-(2-Propoxyethoxy)pyridine-3-carbaldehyde

[Formula 59]

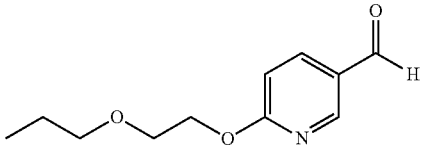

By performing operations similar to those of Reference Example 20 using 2-propoxyethanol, the title compound was obtained.

$^1$H-NMR (CDCl$_3$, δ): 0.93 (3H, t, J=7.3 Hz), 1.5-1.8 (2H, m), 3.49 (2H, t, J=6.8 Hz), 3.7-3.9 (2H, m), 4.5-4.7 (2H, m), 6.90 (1H, d, J=8.3 Hz), 8.06 (1H, dd, J=2.5 Hz, 8.8 Hz), 8.61 (1H, d, J=1.9 Hz), 9.95 (1H, s)

MS (m/z): 210 (M++1)

Example 35: N-{4-Chloro-3-[4-(6-methoxypyridin-3-yl)-6-oxo-1,6-dihydropyrimidin-2-yl]benzyl}isobutyramide By performing operations similar to those of Example 4 using 6-methoxypyridine-3-carbaldehyde, the title compound was obtained.

$^1$H-NMR (d$_6$-DMSO, δ): 1.03 (6H, d, J=6.8 Hz), 2.43 (1H, sept, J=6.8 Hz), 3.92 (3H, s), 4.31 (2H, d, J=5.8 Hz), 6.91 (1H, d, J=8.3 Hz), 6.96 (1H, brs), 7.3-7.6 (3H, m), 8.2-8.4 (2H, m), 8.89 (1H, d, J=2.0 Hz), 12.79 (1H, brs)

MS (m/z): 412 (M$^+$)

Example 36: N-{4-Chloro-3-[4-(6-ethoxypyridin-3-yl)-6-oxo-1,6-dihydropyrimidin-2-yl]benzyl}isobutyramide By performing operations similar to those of Example 4 using 6-ethoxypyridine-3-carbaldehyde, the title compound was obtained.

$^1$H-NMR (d$_6$-DMSO, δ): 1.03 (6H, d, J=6.8 Hz), 1.34 (3H, t, J=6.8 Hz), 2.43 (1H, sept, J=6.8 Hz), 4.31 (2H, d, J=5.8 Hz), 4.37 (2H, q, J=7.0 Hz), 6.88 (1H, d, J=8.8 Hz), 6.95 (1H, brs), 7.3-7.6 (3H, m), 8.2-8.4 (2H, m), 8.87 (1H, d, J=2.4 Hz), 12.81 (1H, brs)

MS (m/z): 426 (M$^+$)

Example 37: N-{4-Chloro-3-[4-(3-fluoro-4-methylphenyl)-6-oxo-1,6-dihydropyrimidin-2-yl]benzyl}isobutyramide By performing operations similar to those of Example 4 using 3-fluoro-4-methylbenzaldehyde, the title compound was obtained.

$^1$H-NMR (d$_6$-DMSO, δ): 1.04 (6H, d, J=6.8 Hz), 2.29 (3H, d, J=1.0 Hz), 2.44 (1H, sept, J=6.8 Hz), 4.32 (2H, d, J=6.4 Hz), 6.98 (1H, brs), 7.3-7.9 (6H, m), 8.2-8.4 (1H, m), 12.91 (1H, brs)

MS (m/z): 413 (M$^+$)

Example 38: N-(4-Chloro-3-{4-[4-(2-methoxyethoxy)phenyl]-6-oxo-1,6-dihydropyrimidin-2-yl}benzyl)isobutyramide By performing operations similar to those of Example 4 using 4-(2-methoxyethoxy)benzaldehyde, the title compound was obtained.

¹H-NMR (d₆-DMSO, δ): 1.04 (6H, d, J=6.8 Hz), 2.43 (1H, sept, J=6.8 Hz), 3.32 (3H, s), 3.6-3.8 (2H, m), 4.1-4.2 (2H, m), 4.31 (2H, d, J=6.3 Hz), 6.84 (1H, brs), 7.03 (2H, d, J=9.3 Hz), 7.41 (1H, dd, J=1.9 Hz, 8.3 Hz), 7.53 (1H, d, J=2.0 Hz), 7.56 (1H, d, J=8.3 Hz), 8.03 (2H, d, J=8.8 Hz), 8.2-8.4 (1H, m), 12.77 (1H, brs)

MS (m/z): 455 (M⁺)

Example 39: N-{4-Chloro-3-[4-(5-methylpyridin-2-yl)-6-oxo-1,6-dihydropyrimidin-2-yl]benzyl}isobutyramide By performing operations similar to those of Example 4 using 5-methylpyridine-2-carbaldehyde, the title compound was obtained.

¹H-NMR (d₆-DMSO, δ): 1.04 (6H, d, J=6.8 Hz), 2.37 (3H, s), 2.3-2.5 (1H, m), 4.32 (2H, d, J=5.9 Hz), 7.20 (1H, brs), 7.42 (1H, dd, J=1.9 Hz, 8.3 Hz), 7.5-7.6 (2H, m), 7.76 (1H, dd, J=2.4 Hz, 8.3 Hz), 8.14 (1H, d, J=8.3 Hz), 8.3-8.4 (1H, m), 8.57 (1H, d, J=2.4 Hz)

MS (m/z): 396 (M⁺)

Example 40: N-(4-Chloro-3-{6-oxo-4-[6-(trifluoromethyl)pyridin-3-yl]-1,6-dihydropyrimidin-2-yl}benzyl)cyclopropanecarboxamide By performing operations similar to those of Example 4 using 6-(trifluoromethyl)pyridine-3-carbaldehyde, and N-(3-carbamimidoyl-4-chlorobenzyl)cyclopropanecarboxamide hydrochloride, the title compound was obtained.

¹H-NMR (d₆-DMSO, δ): 0.6-0.8 (4H, m), 1.5-1.7 (1H, m), 4.35 (2H, d, J=6.4 Hz), 7.25 (1H, brs), 7.4-7.7 (3H, m), 8.03 (1H, d, J=8.3 Hz), 8.5-8.8 (2H, m), 9.41 (1H, s), 13.13 (1H, brs)

MS (m/z): 448 (M⁺)

Example 41: N-(4-Chloro-3-{4-[4-(difluoromethyl)phenyl]-6-oxo-1,6-dihydropyrimidin-2-yl}benzyl)isobutyramide By performing operations similar to those of Example 4 using 4-(difluoromethyl)benzaldehyde, the title compound was obtained.

¹H-NMR (d₆-DMSO, δ): 1.04 (6H, d, J=6.8 Hz), 2.44 (1H, sept, J=6.8 Hz), 4.32 (2H, d, J=6.4 Hz), 7.03 (1H, brs), 7.10 (1H, t, J=56.0 Hz), 7.42 (1H, dd, J=2.4 Hz, 8.3 Hz), 7.56 (1H, d, J=2.0 Hz), 7.58 (1H, d, J=8.3 Hz), 7.68 (2H, d, J=8.3 Hz), 8.21 (2H, d, J=8.3 Hz), 8.3-8.4 (1H, m), 12.96 (1H, brs)

MS (m/z): 431 (M⁺)

Example 42: N-(4-Chloro-3-{6-oxo-4-[5-(trifluoromethyl)thiophen-2-yl]-1,6-dihydropyrimidin-2-yl}benzyl)isobutyramide By performing operations similar to those of Example 4 using 5-(trifluoromethyl)thiophene-2-carbaldehyde, the title compound was obtained.

¹H-NMR (d₆-DMSO, δ): 1.04 (6H, d, J=6.8 Hz), 2.44 (1H, sept, J=6.8 Hz), 4.31 (2H, d, J=6.3 Hz), 7.12 (1H, brs), 7.43 (1H, dd, J=2.4 Hz, 8.3 Hz), 7.52 (1H, d, J=2.0 Hz), 7.58 (1H, d, J=8.3 Hz), 7.68 (1H, dd, J=1.2 Hz, 4.2 Hz), 8.04 (1H, dd, J=1.5 Hz, 3.9 Hz), 8.3-8.4 (1H, m), 13.01 (1H, brs)

MS (m/z): 455 (M⁺)

Example 43: N-(4-Chloro-3-{6-oxo-4-[2-(trifluoromethyl)thiazol-5-yl]-1,6-dihydropyrimidin-2-yl}benzyl)isobutyramide By performing operations similar to those of Example 4 using 2-(trifluoromethyl)thiazole-5-carbaldehyde, the title compound was obtained.

¹H-NMR (d₆-DMSO, δ): 1.04 (6H, d, J=6.8 Hz), 2.43 (1H, sept, J=6.8 Hz), 4.31 (2H, d, J=5.9 Hz), 7.24 (1H, brs), 7.44 (1H, dd, J=1.9 Hz, 8.4 Hz), 7.52 (1H, d, J=1.9 Hz), 7.58 (1H, d, J=8.3 Hz), 8.2-8.4 (1H, m), 8.91 (1Hs), 13.15 (1H, brs)

MS (m/z): 456 (M⁺)

Example 44: N-{4-Chloro-3-[4-(2-fluoro-4-methylphenyl)-6-oxo-1,6-dihydropyrimidin-2-yl]benzyl}isobutyramide By performing operations similar to those of Example 4 using 2-fluoro-4-methylbenzaldehyde, the title compound was obtained.

¹H-NMR (d₆-DMSO, δ): 1.03 (6H, d, J=6.8 Hz), 2.37 (3H, s), 2.3-2.5 (1H, m), 4.31 (2H, d, J=5.9 Hz), 6.74 (1H, brs), 7.14 (1H, d, J=7.8 Hz), 7.19 (1H, d, J=12.7 Hz), 7.41 (1H, dd, J=2.4 Hz, 8.3 Hz), 7.54 (1H, d, J=1.9H), 7.57 (1H, d, J=8.3 Hz), 7.92 (1H, t, J=8.1 Hz), 8.2-8.4 (1H, m), 12.93 (1H, brs)

MS (m/z): 413 (M⁺)

Example 45: N-(4-Chloro-3-{4-[6-(difluoromethoxy)pyridin-3-yl]-6-oxo-1,6-dihydropyrimidin-2-yl}benzyl)isobutyramide By performing operations similar to those of Example 4 using 6-(difluoromethoxy)pyridine-3-carbaldehyde, the title compound was obtained.

¹H-NMR (d₆-DMSO, δ): 1.03 (6H, d, J=6.8 Hz), 2.43 (1H, sept, J=6.8 Hz), 4.31 (2H, d, J=5.8 Hz), 7.08 (1H, brs), 7.20 (1H, d, J=8.8 Hz), 7.42 (1H, dd, J=1.9 Hz, 8.3 Hz), 7.5-7.6 (2H, m), 7.77 (1H, t, J=73.0 Hz), 8.2-8.4 (1H, m), 8.53 (1H, dd, J=2.5 Hz, 8.3 Hz), 8.95 (1H, d, J=2.0 Hz), 12.97 (1H, brs)

MS (m/z): 448 (Mt)

Example 46: N-(4-Chloro-3-{4-[4-(2-ethoxyethoxy)-3-fluorophenyl]-6-oxo-1,6-dihydropyrimidin-2-yl}benzyl)isobutyramide By performing operations similar to those of Example 4 using 4-(2-ethoxyethoxy)-3-fluorobenzaldehyde, the title compound was obtained.

¹H-NMR (d₆-DMSO, δ): 1.04 (6H, d, J=6.8 Hz), 1.13 (3H, t, J=7.1 Hz), 2.44 (1H, sept, J=6.8 Hz), 3.52 (2H, q, J=7.0 Hz), 3.7-3.8 (2H, m), 4.2-4.3 (2H, m), 4.32 (2H, d, J=6.4 Hz), 6.94 (1H, brs), 7.27 (1H, t, J=8.8 Hz), 7.42 (1H, dd, J=2.0 Hz, 8.3 Hz), 7.54 (1H, d, J=2.0 Hz), 7.57 (1H, d, J=8.3 Hz), 7.8-8.0 (2H, m), 8.2-8.4 (1H, m), 12.80 (1H, brs)

MS (m/z): 487 (M⁺)

Example 47: N-(4-Chloro-3-{4-[4-(2-ethoxyethoxy)-2-fluorophenyl]-6-oxo-1,6-dihydropyrimidin-2-yl}benzyl)isobutyramide By performing operations similar to those of Example 4 using 4-(2-ethoxyethoxy)-2-fluorobenzaldehyde, the title compound was obtained.

¹H-NMR (d₆-DMSO, δ): 1.03 (6H, d, J=6.8 Hz), 1.13 (3H, t, J=7.1 Hz), 2.43 (1H, sept, J=6.8 Hz), 3.50 (2H, q, J=7.0 Hz), 3.6-3.8 (2H, m), 4.1-4.3 (2H, m), 4.31 (2H, d, J=5.9 Hz), 6.70 (1H, brs), 6.91 (1H, dd, J=2.5 Hz, 8.8 Hz), 6.99 (1H, dd, J=2.4 Hz, 14.2 Hz), 7.41 (1H, dd, J=2.0 Hz, 8.3 Hz), 7.54 (1H, d, J=2.4 Hz), 7.56 (1H, d, J=8.3 Hz), 8.00 (1H, t, J=9.3 Hz), 8.2-8.4 (1H, m), 12.84 (1H, brs)

MS (m/z): 487 (M⁺)

Example 48: N-{4-Chloro-3-[4-(6-isopropoxypyridin-3-yl)-6-oxo-1,6-dihydropyrimidin-2-yl]benzyl}isobutyramide By performing operations similar to those of Example 4 using 6-isopropoxypyridine-3-carbaldehyde, the title compound was obtained.

¹H-NMR (d₆-DMSO, δ): 1.03 (6H, d, J=6.8 Hz), 1.31 (6H, d, J=5.9 Hz), 2.43 (1H, sept, J=6.8 Hz), 4.31 (2H, d, J=5.8 Hz), 5.32 (1H, quin, J=6.4 Hz), 6.83 (1H, d, J=8.3 Hz), 6.94 (1H, brs), 7.41 (1H, dd, J=1.9 Hz, 8.3 Hz), 7.55 (1H, d, J=1.9 Hz), 7.57 (1H, d, J=8.3 Hz), 8.30 (1H, dd, J=2.5 Hz, 8.8 Hz), 8.34 (1H, d, J=6.3 Hz), 8.86 (1H, d, J=2.5 Hz), 12.84 (1H, brs)

MS (m/z): 440 (M⁺)

Example 49: N-(4-Chloro-3-({6-oxo-4-[6-(2,2,2-trifluoroethoxy)pyridin-3-yl]-1,6-dihydropyrimidin-2-yl}benzyl)isobutyramide By performing operations similar to those of Example 4 using 6-(2,2,2-trifluoroethoxy)pyridine-3-carbaldehyde, the title compound was obtained.

¹H-NMR (d₆-DMSO, δ): 1.03 (6H, d, J=6.8 Hz), 2.43 (1H, sept, J=6.8 Hz), 4.31 (2H, d, J=6.3 Hz), 5.07 (2H, q, J=9.1 Hz), 7.02 (1H, brs), 7.09 (1H, d, J=8.8 Hz), 7.42 (1H, dd, J=2.5 Hz, 8.3 Hz), 7.5-7.6 (2H, m), 8.2-8.4 (1H, m), 8.44 (1H, dd, J=2.4 Hz, 8.3 Hz), 8.91 (1H, d, J=2.5 Hz), 12.91 (1H, brs)

MS (m/z): 480 (M⁺)

Example 50: N-{3-[4-(1-tert-Butyl-1H-pyrazol-4-yl)-6-oxo-1,6-dihydropyrimidin-2-yl]-4-chlorobenzyl}isobutyramide By performing operations similar to those of Example 4 using 1-tert-butyl-1H-pyrazole-4-carbaldehyde, the title compound was obtained.

¹H-NMR (d₆-DMSO, δ): 1.03 (6H, d, J=6.8 Hz), 1.54 (9H, s), 2.43 (1H, sept, J=6.8 Hz), 4.30 (2H, d, J=5.8 Hz), 6.66 (1H, brs), 7.39 (1H, dd, J=2.0 Hz, 8.3 Hz), 7.47 (1H, d, J=2.0 Hz), 7.54 (1H, d, J=8.3 Hz), 8.01 (1H, s), 8.3-8.4 (2H, m), 12.44 (1H, brs)

MS (m/z): 427 (M⁺)

Example 51: N-{4-Chloro-3-[4-(1-isobutyl-1H-pyrazol-4-yl)-6-oxo-1,6-dihydropyrimidin-2-yl]benzyl}isobutyramide By performing operations similar to those of Example 4 using 1-isobutyl-1H-pyrazole-4-carbaldehyde, the title compound was obtained.

¹H-NMR (d₆-DMSO, δ): 0.84 (6H, d, J=6.8 Hz), 1.03 (6H, d, J=6.8 Hz), 2.12 (1H, sept, J=6.8 Hz), 2.43 (1H, sept, J=6.8 Hz), 3.93 (2H, d, J=7.3 Hz), 4.30 (2H, d, J=5.9 Hz), 6.62 (1H, brs), 7.39 (1H, dd, J=1.9 Hz, 8.3 Hz), 7.48 (1H, d, J=2.0 Hz), 7.54 (1H, d, J=8.3 Hz), 8.02 (1H, s), 8.28 (1H, s), 8.3-8.4 (1H, m), 12.61 (1H, brs)

MS (m/z): 427 (M⁺)

Example 52: N-{4-Chloro-3-[4-(2-methoxythiazol-5-yl)-6-oxo-1,6-dihydropyrimidin-2-yl]benzyl}isobutyramide By performing operations similar to those of Example 4 using 2-methoxythiazole-5-carbaldehyde, the title compound was obtained.

¹H-NMR (d₆-DMSO, δ): 1.03 (6H, d, J=6.8 Hz), 2.43 (1H, sept, J=6.8 Hz), 4.06 (3H, s), 4.30 (2H, d, J=5.9 Hz), 6.83 (1H, brs), 7.41 (1H, dd, J=2.0 Hz, 8.3 Hz), 7.47 (1H, d, J=1.9 Hz), 7.57 (1H, d, J=8.3 Hz), 8.05 (1H, s), 8.3-8.4 (1H, m), 12.85 (1H, brs)

MS (m/z): 418 (M⁺)

Example 53: N-(4-Chloro-3-{6-oxo-4-[6-(trifluoromethyl)pyridin-3-yl]-1,6-dihydropyrimidin-2-yl}benzyl)-3,3,3-trifluoro-2,2-dimethylpropionamide By performing operations similar to those of Example 4 using 6-(trifluoromethyl)pyridine-3-carbaldehyde, and N-(3-carbamimidoyl-4-chlorobenzyl)-3,3,3-trifluoro-2,2-dimethylpropionamide hydrochloride, the title compound was obtained.

¹H-NMR (d₆-DMSO, δ): 1.38 (6H, s), 4.37 (2H, d, J=5.9 Hz), 7.25 (1H, s), 7.41 (1H, dd, J=1.9 Hz, 8.3 Hz), 7.57 (1H, d, J=1.9 Hz), 7.60 (1H, d, J=8.3 Hz), 8.03 (1H, d, J=8.3 Hz), 8.5-8.7 (1H, m), 8.69 (1H, dd, J=1.9 Hz, 8.3 Hz), 9.41 (1H, d, J=1.5 Hz), 13.11 (1H, brs)

MS (m/z): 518 (M⁺)

Example 54: N-{4-Chloro-3-[4-(6-methoxypyridin-3-yl)-6-oxo-1,6-dihydropyrimidin-2-yl]benzyl}-3,3,3-trifluoro-2,2-dimethylpropionamide By performing operations similar to those of Example 4 using 6-methoxypyridine-3-carbaldehyde, and N-(3-carbamimidoyl-4-chlorobenzyl)-3,3,3-trifluoro-2,2-dimethylpropionamide hydrochloride, the title compound was obtained.

¹H-NMR (d₆-DMSO, δ): 1.38 (6H, s), 3.92 (3H, s), 4.37 (2H, d, J=5.9 Hz), 6.91 (1H, d, J=8.8 Hz), 6.96 (1H, brs), 7.40 (1H, dd, J=2.0 Hz, 8.3 Hz), 7.5-7.6 (1H, m), 7.58 (1H, d, J=8.3 Hz), 8.34 (1H, dd, J=2.0 Hz, 8.8 Hz), 8.5-8.7 (1H, m), 8.89 (1H, d, J=1.9 Hz), 12.87 (1H, brs)

MS (m/z): 480 (M⁺)

Example 55: N-(4-Chloro-3-{4-[6-(difluoromethoxy)pyridin-3-yl]-6-oxo-1,6-dihydropyrimidin-2-yl}benzyl)-3,3,3-trifluoro-2,2-dimethylpropionamide By performing operations similar to those of Example 4 using 6-(difluoromethoxy)pyridine-3-carbaldehyde, and N-(3-carbamimidoyl-4-chlorobenzyl)-3,3,3-trifluoro-2,2-dimethylpropionamide hydrochloride, the title compound was obtained.

¹H-NMR (d₆-DMSO, δ): 1.38 (6H, s), 4.37 (2H, d, J=6.4 Hz), 7.08 (1H, brs), 7.20 (1H, d, J=8.8 Hz), 7.40 (1H, dd, J=1.9 Hz, 8.3 Hz), 7.5-7.7 (2H, m), 7.77 (1H, t, J=72.5 Hz), 8.54 (1H, dd, J=2.5 Hz, 8.8 Hz), 8.5-8.7 (1H, m), 8.95 (1H, d, J=2.0 Hz), 12.95 (1H, brs)

MS (m/z): 516 (M⁺)

Example 56: N-(4-Fluoro-3-{6-oxo-4-[6-(trifluoromethyl)pyridin-3-yl]-1,6-dihydropyrimidin-2-yl}benzyl)-2,2-dimethylpropionamide By performing operations similar to those of Example 4 using 6-(trifluoromethyl)pyridine-3-carbaldehyde, and N-(3-carbamimidoyl-4-fluorobenzyl)-2,2-dimethylpropionamide hydrochloride, the title compound was obtained.

¹H-NMR (d₆-DMSO, δ): 1.14 (9H, s), 4.32 (2H, d, J=6.3 Hz), 7.23 (1H, s), 7.3-7.5 (2H, m), 7.6-7.8 (1H, m), 8.04 (1H, d, J=8.3 Hz), 8.1-8.2 (1H, m), 8.71 (1H, dd, J=1.4 Hz, 7.8 Hz), 9.43 (1H, d, J=1.5 Hz), 12.95 (1H, brs)

MS (m/z): 448 (M⁺)

Example 57: N-(3-{4-[6-(Difluoromethoxy)pyridin-3-yl]-6-oxo-1,6-dihydropyrimidin-2-yl}-4-fluorobenzyl)-2,2-dimethylpropionamide By performing operations similar to those of Example 4 using 6-(difluoromethoxy)pyridine-3-carbaldehyde, and N-(3-carbamimidoyl-4-fluorobenzyl)-2,2-dimethylpropionamide hydrochloride, the title compound was obtained.

¹H-NMR (d₆-DMSO, δ): 1.14 (9H, s), 4.32 (2H, d, J=5.9 Hz), 7.08 (1H, brs), 7.22 (1H, d, J=9.3 Hz), 7.3-7.5 (2H, m), 7.72 (1H, d, J=5.3 Hz), 7.79 (1H, t, J=72.6 Hz), 8.1-8.3 (1H, m), 8.57 (1H, dd, J=2.4 Hz, 8.8 Hz), 8.99 (1H, d, J=2.5 Hz), 12.85 (1H, brs)

MS (m/z): 446 (M⁺)

Example 58: N-(4-Difluoromethoxy-3-{6-oxo-4-[6-(trifluoromethyl)pyridin-3-yl]-1,6-dihydropyrimidin-2-yl}benzyl)isobutyramide By performing operations similar to those of Example 4 using 6-(trifluoromethyl)pyridine-3-carbaldehyde, and N-[3-carbamimidoyl-4-(difluoromethoxy)benzyl]isobutyramide hydrochloride, the title compound was obtained.

¹H-NMR (d₆-DMSO, δ): 1.04 (6H, d, J=6.8 Hz), 2.43 (1H, sept, J=6.8 Hz), 4.32 (2H, d, J=6.3 Hz), 7.20 (1H, t, J=73.5 Hz), 7.21 (1H, brs), 7.30 (1H, d, J=8.3 Hz), 7.49 (1H, dd, J=2.5 Hz, 8.8 Hz), 7.66 (1H, d, J=1.9 Hz), 8.03 (1H, d, J=8.3 Hz), 8.2-8.4 (1H, m), 8.70 (1H, dd, J=1.9 Hz, 8.3 Hz), 9.40 (1H, d, J=1.4 Hz), 12.92 (1H, brs)

MS (m/z): 482 (M⁺)

Example 59: N-(4-Chloro-3-{4-[6-(2-ethoxyethoxy)pyridin-3-yl]-6-oxo-1,6-dihydropyrimidin-2-yl}benzyl)isobutyramide By performing operations similar to those of Example 4 using 6-(2-ethoxyethoxy)pyridine-3-carbaldehyde, the title compound was obtained.

¹H-NMR (d₆-DMSO, δ): 1.03 (6H, d, J=6.8 Hz), 1.12 (3H, t, J=7.1 Hz), 2.43 (1H, sept, J=6.8 Hz), 3.49 (2H, q, J=7.0 Hz), 3.6-3.8 (2H, m), 4.31 (2H, d, J=5.8 Hz), 4.4-4.5 (2H, m), 6.93 (1H, d, J=8.7 Hz), 6.96 (1H, brs), 7.41 (1H, dd, J=1.9 Hz, 8.3 Hz), 7.55 (1H, d, J=1.9 Hz), 7.57 (1H, d, J=8.3 Hz), 8.2-8.4 (2H, m), 8.87 (1H, d, J=2.4 Hz), 12.86 (1H, brs)

MS (m/z): 470 (M⁺)

Example 60: N-(4-Chloro-3-{4-[6-(3-methoxypropoxy)pyridin-3-yl]-6-oxo-1,6-dihydropyrimidin-2-yl}benzyl)isobutyramide By performing operations similar to those of Example 4 using 6-(3-methoxypropoxy)pyridine-3-carbaldehyde, the title compound was obtained.

¹H-NMR (d₆-DMSO, δ): 1.03 (6H, d, J=6.8 Hz), 1.97 (2H, quin, J=6.5 Hz), 2.43 (1H, sept, J=6.8 Hz), 3.24 (3H, s), 3.47 (2H, q, J=6.4 Hz), 4.31 (2H, d, J=5.8 Hz), 4.37 (2H, t, J=6.6 Hz), 6.89 (1H, d, J=8.7 Hz), 6.95 (1H, brs), 7.41 (1H, dd, J=2.4 Hz, 8.3 Hz), 7.55 (1H, d, J=2.4 Hz), 7.57 (1H, d, J=8.3 Hz), 8.2-8.4 (2H, m), 8.87 (1H, d, J=2.4 Hz), 12.81 (1H, brs)

MS (m/z): 470 (M⁺)

Example 61: N-(4-Chloro-3-{4-[6-(2-methoxyethoxy)pyridin-3-yl]-6-oxo-1,6-dihydropyrimidin-2-yl}benzyl)isobutyramide By performing operations similar to those of Example 4 using 6-(2-methoxyethoxy)pyridine-3-carbaldehyde, the title compound was obtained.

¹H-NMR (d₆-DMSO, δ): 1.03 (6H, d, J=6.8 Hz), 2.43 (1H, sept, J=6.8 Hz), 3.30 (3H, s), 3.6-3.8 (2H, m), 4.31 (2H, d, J=6.3 Hz), 4.4-4.5 (2H, m), 6.92 (1H, d, J=8.3 Hz), 6.96 (1H, brs), 7.41 (1H, dd, J=2.4 Hz, 8.3 Hz), 7.55 (1H, d, J=1.9 Hz), 7.57 (1H, d, J=8.3 Hz), 8.2-8.4 (2H, m), 8.87 (1H, d, J=2.4 Hz), 12.85 (1H, brs)

MS (m/z): 456 (M⁺)

Example 62: N-{4-Chloro-3-[4-(3-fluorophenyl)-6-oxo-1,6-dihydropyrimidin-2-yl]benzyl}isobutyramide By performing operations similar to those of Example 4 using 3-fluorobenzaldehyde, the title compound was obtained.

¹H-NMR (d₆-DMSO, δ): 1.04 (6H, d, J=7.2 Hz), 2.43 (1H, sept, J=6.8 Hz), 4.32 (2H, d, J=6.0 Hz), 7.03 (1H, s), 7.3-7.4 (1H, m), 7.4-7.5 (1H, m), 7.5-7.6 (3H, m), 7.88 (1H, d, J=10.0 Hz), 7.94 (1H, d, J=8.0 Hz), 8.3-8.4 (1H, m), 12.96 (1H, s)

MS (m/z): 399 (M⁺)

Example 63: N-(4-Chloro-3-{6-oxo-4-[4-(pyridin-2-ylethynyl)phenyl]-1,6-dihydropyrimidin-2-yl}benzyl)isobutyramide By performing operations similar to those of Example 4 using 4-(pyridin-2-ylethynyl)benzaldehyde, the title compound was obtained.

¹H-NMR (d₆-DMSO, δ): 1.04 (6H, d, J=6.8 Hz), 2.44 (1H, sept, J=6.8 Hz), 4.32 (2H, d, J=6.0 Hz), 7.03 (1H, s), 7.4-7.5 (2H, m), 7.5-7.6 (2H, m), 7.6-7.8 (3H, m), 7.87 (1H, ddd, J=1.6 Hz, 7.6 Hz, 7.6 Hz), 8.17 (2H, d, J=8.0 Hz), 8.35 (1H, t, J=6.0 Hz), 8.6-8.7 (1H, m), 12.96 (1H, s)

MS (m/z): 482 (M⁺)

Example 64: N-[4-Chloro-3-(5-fluoro-6-oxo-4-phenyl-1,6-dihydropyrimidin-2-yl)benzyl]isobutyramide By performing operations similar to those of Example 23 using ethyl 2-fluoro-3-oxo-3-phenylpropanoate, the title compound was obtained.

¹H-NMR (d₆-DMSO, δ): 1.03 (6H, d, J=6.8 Hz), 2.43 (1H, sept, J=6.8 Hz), 4.30 (2H, d, J=6.0 Hz), 7.42 (1H, dd, J=2.0 Hz, 8.4 Hz), 7.5-7.6 (5H, m), 7.9-8.0 (2H, m), 8.34 (1H, t, J=6.0 Hz), 13.47 (1H, s)
MS (m/z): 399 (M⁺)

Example 65: N-{4-Chloro-3-[5-fluoro-4-(4-methoxyphenyl)-6-oxo-1,6-dihydropyrimidin-2-yl]benzyl}isobutyramide By performing operations similar to those of Example 23 using ethyl 2-fluoro-3-(4-methoxyphenyl)-3-oxopropanoate, the title compound was obtained.
$^1$H-NMR (d$_6$-DMSO, δ): 1.03 (6H, d, J=6.8 Hz), 2.3-2.6 (1H, m), 3.83 (3H, s), 4.30 (2H, d, J=5.6 Hz), 7.0-7.1 (2H, m), 7.41 (1H, dd, J=2.4 Hz, 8.4 Hz), 7.5-7.6 (2H, m), 7.95 (2H, d, J=8.8 Hz), 8.33 (1H, t, J=6.0 Hz), 13.35 (1H, s)
MS (m/z): 429 (M⁺)

Example 66: N-{4-Chloro-3-[5-fluoro-6-oxo-4-(thiophen-2-yl)-1,6-dihydropyrimidin-2-yl]benzyl}isobutyramide By performing operations similar to those of Example 23 using ethyl 2-fluoro-3-oxo-3-(thiophen-2-yl)propanoate, the title compound was obtained.
$^1$H-NMR (d$_6$-DMSO, δ): 1.04 (6H, d, J=6.8 Hz), 2.43 (1H, sept, J=6.8 Hz), 4.31 (2H, d. J=6.4 Hz), 7.28 (1H, dd, J=4.0 Hz, 4.8 Hz), 7.43 (1H, dd, J=2.0 Hz, 8.4 Hz), 7.51 (1H, d, J=2.0 Hz), 7.57 (1H, d, J=8.4 Hz), 7.83 (1H, d, J=4.0 Hz), 7.91 (1H, dd, J=0.8 Hz, 4.8 Hz), 8.34 (1H, t, J=6.0 Hz), 13.38 (1H, s)
MS (m/z): 405 (M⁺)

Example 67: N-{4-Chloro-3-[5-fluoro-6-oxo-4-(thiophen-3-yl)-1,6-dihydropyrimidin-2-yl]benzyl}isobutyramide By performing operations similar to those of Example 23 using ethyl 2-fluoro-3-oxo-3-(thiophen-3-yl)propanoate, the title compound was obtained.
$^1$H-NMR (d$_6$-DMSO, δ): 1.03 (6H, d, J=6.8 Hz), 2.43 (1H, sept, J=6.8 Hz), 4.30 (2H, d, J=5.6 Hz), 7.41 (1H, dd, J=2.4 Hz, 8.4 Hz), 7.53 (1H, d, J=2.0 Hz), 7.57 (1H, d, J=8.4 Hz), 7.65 (1H, d, J=4.8 Hz), 7.72 (1H, dd, J=2.8 Hz, 4.8 Hz), 8.25 (1H, d, J=2.0 Hz), 8.34 (1H, t. J=6.0 Hz), 13.36 (1H, s)
MS (m/z): 405 (M⁺)

Example 68: N-{3-[4-(Benzo[b]thiophen-7-yl)-6-oxo-1,6-dihydropyrimidin-2-yl]-4-chlorobenzyl}isobutyramide By performing operations similar to those of Example 4 using benzo[b]thiophene-7-carbaldehyde, the title compound was obtained.
$^1$H-NMR (d$_6$-DMSO, δ): 1.03 (6H, d, J=6.8 Hz), 2.46 (1H, sept, J=6.8 Hz), 4.35 (2H, d, J=6.4 Hz), 7.11 (1H, s), 7.45 (1H, dd, J=2.0 Hz, 8.4 Hz), 7.5-7.6 (2H, m), 7.60 (1H, d, J=8.4 Hz), 7.65 (1H, d, J=2.0 Hz), 7.74 (1H, d, J=5.6 Hz), 8.0-8.1 (2H, m), 8.36 (1H, t, J=6.0 Hz), 13.03 (1H, s)
MS (m/z): 437 (M⁺)

Example 69: N-{4-Chloro-3-[4-(4-cyanophenyl)-6-oxo-1,6-dihydropyrimidin-2-yl]benzyl}isobutyramide By performing operations similar to those of Example 4 using 4-cyanobenzaldehyde, the title compound was obtained.

$^1$H-NMR (d$_6$-DMSO, δ): 1.03 (6H, d, J=6.8 Hz), 2.43 (1H, sept, J=6.8 Hz), 4.31 (2H, d, J=6.0 Hz), 7.11 (1H, s), 7.4-7.5 (1H, m), 7.5-7.6 (2H, m), 7.95 (2H, d, J=8.0 Hz), 8.30 (2H, d, J=8.4 Hz), 8.34 (1H, t, J=6.0 Hz), 13.05 (1H, s)
MS (m/z): 406 (M⁺)

Example 70: N-(4-Chloro-3-(4-[4-(methylsulfanyl)phenyl]-6-oxo-1,6-dihydropyrimidin-2-yl)benzyl) isobutyramide By performing operations similar to those of Example 4 using 4-(methylsulfanyl)benzaldehyde, the title compound was obtained.
$^1$H-NMR (d$_6$-DMSO, δ): 1.03 (6H, d, J=6.8 Hz), 2.43 (1H, sept, J=6.8 Hz), 2.52 (3H, s), 4.31 (2H, d, J=6.0 Hz), 6.91 (1H, s), 7.34 (2H, d, J=8.8 Hz), 7.42 (1H, dd, J=2.0 Hz, 8.4 Hz), 7.5-7.6 (2H, m), 8.02 (2H, d, J=8.4 Hz), 8.34 (1H, t, J=6.0 Hz), 12.84 (1H, s)
MS (m/z): 427 (M⁺)

Example 71: N-{4-Chloro-3-[6-oxo-4-(p-toluyl)-1,6-dihydropyrimidin-2-yl]benzyl}isobutyramide By performing operations similar to those of Example 4 using 4-methylbenzaldehyde, the title compound was obtained.
$^1$H-NMR (d$_6$-DMSO, δ): 1.03 (6H, d, J=6.8 Hz), 2.36 (3H, s), 2.3-2.6 (1H, m), 4.31 (2H, d, J=6.0 Hz), 6.88 (1H, s), 7.29 (2H, d, J=8.0 Hz), 7.41 (1H, dd, J=2.0 Hz, 8.4 Hz), 7.5-7.6 (2H, m), 7.97 (2H, d, J=8.4 Hz), 8.34 (1H, t, J=6.0 Hz), 12.83 (1H, s)
MS (m/z): 395 (M⁺)

Example 72: N-(4-Chloro-3-{4-[4-(diethylsulfamoyl)phenyl]-6-oxo-1,6-dihydropyrimidin-2-yl}benzyl)isobutyramide By performing operations similar to those of Example 4 using N,N-diethyl-4-formylbenzenesulfonamide, the title compound was obtained.
$^1$H-NMR (d$_6$-DMSO, δ): 1.0-1.1 (12H, m), 2.3-2.6 (1H, m), 3.19 (4H, q, J=7.2 Hz), 4.31 (2H, d, J=6.4 Hz), 7.07 (1H, s), 7.42 (1H, dd, J=2.4 Hz, 8.4 Hz), 7.5-7.6 (2H, m), 7.88 (2H, d, J=8.0 Hz), 8.27 (2H, d, J=8.8 Hz), 8.34 (1H, t, J=6.0 Hz), 13.02 (1H, s)
MS (m/z): 516 (M⁺)

Example 73: N-(4-Chloro-3-{6-oxo-4-[4-(piperidine-1-sulfonyl)phenyl]-1,6-dihydropyrimidin-2-yl}benzyl)isobutyramide By performing operations similar to those of Example 4 using 4-(piperidin-1-ylsulfonyl)benzaldehyde, the title compound was obtained.
$^1$H-NMR (d$_6$-DMSO, δ): 1.03 (6H, d, J=7.211 Hz), 1.3-1.4 (2H, m), 1.5-1.6 (4H, m), 2.3-2.6 (1H, m), 2.9-3.0 (4H, m), 4.31 (2H, d, J=5.6 Hz), 7.09 (1H, s), 7.43 (1H, dd, J=2.8 Hz, 8.4 Hz), 7.5-7.6 (2H, m), 7.81 (2H, d, J=8.8 Hz), 8.3-8.4 (3H, m), 13.05 (1H, s)
MS (m/z): 529 (M++1)

Example 74: N-{4-Chloro-3-[4-(4-cyclopropylphenyl)-6-oxo-1,6-dihydropyrimidin-2-yl]benzyl}isobutyramide By performing operations similar to those of Example 4 using 4-cyclopropylbenzaldehyde, the title compound was obtained.

¹H-NMR (d₆-DMSO, δ): 0.7-0.8 (2H, m), 1.0-1.1 (8H, m), 1.9-2.0 (1H, m), 2.43 (1H, sept, J=6.8 Hz), 4.31 (2H, d, J=5.6 Hz), 6.87 (1H, s), 7.17 (2H, d, J=8.4 Hz), 7.41 (1H, dd, J=2.0 Hz, 8.4 Hz), 7.5-7.6 (2H, m), 7.95 (2H, d, J=8.4 Hz), 8.33 (1H, t, J=6.0 Hz), 12.80 (1H, s)

MS (m/z): 421 (M⁺)

Example 75: N-(3-{6-Oxo-4-[6-(trifluoromethyl)pyridin-3-yl]-1,6-dihydropyrimidin-2-yl}-4-(trifluoromethyl)benzyl)isobutyramide By performing operations similar to those of Example 4 using 6-(trifluoromethyl)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=6.8 Hz), 2.4-2.6 (1H, m), 4.40 (2H, d, J=6.0 Hz), 7.26 (1H, s), 7.6-7.7 (2H, m), 7.90 (1H, d, J=8.4 Hz), 8.03 (1H, d, J=8.0 Hz), 8.40 (1H, t, J=6.0 Hz), 8.66 (1H, d, J=8.0 Hz), 9.39 (1H, s), 13.23 (1H, s)

MS (m/z): 484 (M⁺)

Example 76: N-{3-[4-(6-Methoxypyridin-3-yl)-6-oxo-1,6-dihydropyrimidin-2-yl]-4-(trifluoromethyl)benzyl}isobutyramide By performing operations similar to those of Example 4 using 6-methoxypyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=6.8 Hz), 2.4-2.6 (1H, m), 3.91 (3H, s), 4.40 (2H, d, J=6.0 Hz), 6.91 (1H, d, J=8.8 Hz), 6.98 (1H, s), 7.5-7.6 (2H, m), 7.88 (1H, d, J=8.4 Hz), 8.31 (1H, dd, J=2.0 Hz, 8.4 Hz), 8.39 (1H, t, J=6.0 Hz), 8.87 (1H, s), 12.97 (1H, s)

MS (m/z): 446 (M⁺)

Example 77: N-(3-{4-[6-(Difluoromethoxy)pyridin-3-yl]-6-oxo-1,6-dihydropyrimidin-2-yl}-4-(trifluoromethyl)benzyl)isobutyramide By performing operations similar to those of Example 4 using 6-(difluoromethoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=6.8 Hz), 2.4-2.6 (1H, m), 4.40 (2H, d, J=6.0 Hz), 7.10 (1H, s), 7.20 (1H, d, J=8.8 Hz), 7.61 (2H, dd, J=4.4 Hz, 12.8 Hz), 7.77 (1H, t, J=72.4 Hz), 7.89 (1H, d, J=8.4 Hz), 8.39 (1H, t, J=6.0 Hz), 8.51 (1H, d, J=8.4 Hz), 8.93 (1H, s), 13.09 (1H, s)

MS (m/z): 482 (M⁺)

Example 78: N-{3-[4-(6-Ethoxypyridin-3-yl)-6-oxo-1,6-dihydropyrimidin-2-yl]-4-(trifluoromethyl)benzyl}isobutyramide By performing operations similar to those of Example 4 using 6-ethoxypyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=7.2 Hz), 1.33 (3H, t, J=7.6 Hz), 2.4-2.6 (1H, m), 4.3-4.4 (4H, m), 6.88 (1H, d, J=8.8 Hz), 6.97 (1H, s), 7.6-7.7 (2H, m), 7.88 (1H, d, J=7.6 Hz), 8.30 (1H, dd, J=2.4 Hz, 8.8 Hz), 8.39 (1H, t, J=6.0 Hz), 8.85 (1H, d, J=2.4 Hz), 12.93 (1H, s)

MS (m/z): 460 (M⁺)

Example 79: N-(4-Methyl-3-{6-oxo-4-[6-(trifluoromethyl)pyridin-3-yl]-1,6-dihydropyrimidin-2-yl}benzyl)isobutyramide By performing operations similar to those of Example 4 using 6-(trifluoromethyl)pyridine-3-carbaldehyde, and N-(3-carbamimidoyl-4-methylbenzyl)isobutyramide hydrochloride, the title compound was obtained.

¹H-NMR (d₆-DMSO, δ): 1.03 (6H, d, J=6.8 Hz), 2.3-2.6 (4H, m), 4.29 (2H, d, J=6.0 Hz), 7.19 (1H, s), 7.32 (2H, s), 7.44 (1H, s), 8.03 (1H, d, J=8.4 Hz), 8.24 (1H, t, J=6.0 Hz), 8.70 (1H, dd, J=1.2 Hz, 8.4 Hz), 9.41 (1H, s), 12.90 (1H, s)

MS (m/z): 430 (M⁺)

Example 80: N-(3-{4-[6-(Difluoromethoxy)pyridin-3-yl]-6-oxo-1,6-dihydropyrimidin-2-yl}-4-methylbenzyl)isobutyramide By performing operations similar to those of Example 4 using 6-(difluoromethoxy)pyridine-3-carbaldehyde, and N-(3-carbamimidoyl-4-methylbenzyl)isobutyramide hydrochloride, the title compound was obtained.

¹H-NMR (d₆-DMSO, δ): 1.03 (6H, d, J=6.8 Hz), 2.3-2.6 (4H, m), 4.29 (2H, d, J=5.6 Hz), 7.02 (1H, s), 7.20 (1H, d, J=8.8 Hz), 7.31 (2H, s), 7.43 (1H, s), 7.77 (1H, t, J=72.8 Hz), 8.24 (1H, t, J=5.6 Hz), 8.55 (1H, dd, J=2.4 Hz, 8.8 Hz), 8.95 (1H, d, J=2.0 Hz), 12.77 (1H, s)

MS (m/z): 428 (M⁺)

Example 81: N-{3-[4-(6-Ethoxypyridin-3-yl)-6-oxo-1,6-dihydropyrimidin-2-yl]-4-methylbenzyl}isobutyramide By performing operations similar to those of Example 4 using 6-ethoxypyridine-3-carbaldehyde, and N-(3-carbamimidoyl-4-methylbenzyl)isobutyramide hydrochloride, the title compound was obtained.

¹H-NMR (d₆-DMSO, δ): 1.03 (6H, d, J=6.8 Hz), 1.34 (3H, t, J=6.8 Hz), 2.3-2.6 (4H, m), 4.28 (2H, d, J=6.0 Hz), 4.37 (2H, q, J=6.8 Hz), 6.87 (1H, s), 6.89 (1H, s), 7.30 (2H, s), 7.42 (1H, s), 8.24 (1H, t, J=6.0 Hz), 8.33 (1H, dd, J=2.4 Hz, 8.8 Hz), 8.87 (1H, d, J=2.4 Hz), 12.64 (1H, s)

MS (m/z): 406 (M⁺)

Example 82: N-[4-(Difluoromethyl)-3-{6-oxo-4-[6-(trifluoromethyl)pyridin-3-yl]-1,6-dihydropyrimidin-2-yl)}benzyl]isobutyramide By performing operations similar to those of Example 4 using 6-(trifluoromethyl)pyridine-3-carbaldehyde, and N-[3-carbamimidoyl-4-(difluoromethyl)benzyl]isobutyramide hydrochloride, the title compound was obtained.

¹H-NMR (d₆-DMSO, δ): 1.05 (6H, d, J=6.8 Hz), 2.4-2.6 (1H, m), 4.39 (2H, d, J=6.0 Hz), 7.26 (1H, s), 7.4-7.7 (2H, m), 7.80 (1H, d, J=8.0 Hz), 8.05 (1H, d, J=8.4 Hz), 8.34 (1H, t, J=5.6 Hz), 8.72 (1H, d, J=7.2 Hz), 9.44 (1H, s), 13.17 (1H, s)

MS (m/z): 466 (M⁺)

Example 83: N-(3-{4-[6-(Difluoromethoxy)pyridin-3-yl]-6-oxo-1,6-dihydropyrimidin-2-yl}-4-(difluoromethyl)benzyl)isobutyramide By performing operations similar to those of Example 4 using 6-(difluoromethoxy)pyridine-3-carbaldehyde, and N-[3-carbamimidoyl-4-(difluoromethyl)benzyl]isobutyramide hydrochloride, the title compound was obtained.

$^1$H-NMR (d$_6$-DMSO, δ): 1.05 (6H, d, J=6.8 Hz), 2.45 (1H, sept, J=6.8 Hz), 4.38 (2H, d, J=6.0 Hz), 7.09 (1H, s), 7.22 (2H, d, J=8.0 Hz), 7.4-8.0 (4H, m), 8.33 (1H, t, J=6.0 Hz), 8.58 (1H, d, J=8.4 Hz), 8.99 (1H, s), 13.04 (1H, s)

MS (m/z): 464 (M$^+$)

Example 84: N-(4-Chloro-3.{6-oxo-4-[2-(trifluoromethyl)pyridin-4-yl]-1,6-dihydropyrimidin-2-yl}benzyl)isobutyramide By performing operations similar to those of Example 4 using 2-(trifluoromethyl)pyridine-4-carbaldehyde, the title compound was obtained.

$^1$H-NMR (d$_6$-DMSO, δ): 1.03 (6H, d, J=6.8 Hz), 2.43 (1H, sept, J=6.8 Hz), 4.32 (2H, d, J=6.0 Hz), 7.36 (1H, s), 7.44 (1H, dd, J=2.0 Hz, 8.4 Hz), 7.5-7.6 (2H, m), 8.3-8.4 (2H, m), 8.45 (1H, s), 8.91 (1H, d, J=5.6 Hz), 13.19 (1H, s)

MS (m/z): 450 (M$^+$)

Example 85: N-(4-Chloro-3-{4-[2-(difluoromethoxy)pyridin-4-yl]-6-oxo-1,6-dihydropyrimidin-2-yl}benzyl)isobutyramide By performing operations similar to those of Example 4 using 2-(difluoromethoxy)pyridine-4-carbaldehyde, the title compound was obtained.

$^1$H-NMR (d$_6$-DMSO, δ): 1.04 (6H, d, J=7.6 Hz), 2.44 (1H, sept, J=6.8 Hz), 4.32 (2H, d, J=6.0 Hz), 7.22 (1H, s), 7.43 (1H, dd, J=1.2 Hz, 8.4 Hz), 7.58 (2H, d, J=8.8 Hz), 7.68 (1H, s), 7.75 (1H, t, J=72.8 Hz), 7.90 (1H, d, J=5.6 Hz), 8.34 (1H, t, J=6.0 Hz), 8.39 (1H, d, J=5.2 Hz), 13.14 (1H, s)

MS (m/z): 448 (M$^+$)

Example 86: N-{4-Chloro-3-[4-(3-fluoro-4-methoxyphenyl)-6-oxo-1,6-dihydropyrimidin-2-yl]benzyl}isobutyramide By performing operations similar to those of Example 4 using 3-fluoro-4-methoxybenzaldehyde, the title compound was obtained.

$^1$H-NMR (d$_6$-DMSO, δ): 1.04 (6H, d, J=7.2 Hz), 2.43 (1H, sept, J=6.8 Hz), 3.91 (3H, s), 4.31 (2H, d, J=6.0 Hz), 6.93 (1H, s), 7.26 (1H, t, J=8.8 Hz), 7.42 (1H, dd, J=2.0 Hz, 8.0 Hz), 7.54 (1H, d, J=1.6 Hz), 7.57 (1H, d, J=8.0 Hz), 7.9-8.0 (2H, m), 8.34 (1H, t, J=6.0 Hz), 12.84 (1H, s)

MS (m/z): 429 (M$^+$)

Example 87: 4-{2-[2-Chloro-5-(isobutyrylaminomethyl)phenyl]-6-oxo-1,6-dihydropyrimidin-4-yl}-N,N-dimethylbenzamide By performing operations similar to those of Example 4 using 4-formyl-N,N-dimethylbenzamide, the title compound was obtained.

$^1$H-NMR (d$_6$-DMSO, δ): 1.03 (6H, d, J=6.8 Hz), 2.43 (1H, sept, J=6.8 Hz), 2.92 (3H, s), 3.00 (3H, s), 4.32 (2H, d, J=5.6 Hz), 6.99 (1H, s), 7.42 (1H, dd, J=1.6 Hz, 8.0 Hz), 7.49 (2H, d, J=8.4 Hz), 7.55 (1H, d, J=1.6 Hz), 7.57 (1H, d, J=8.4 Hz), 8.13 (2H, d, J=8.4 Hz), 8.34 (1H, t, J=5.6 Hz), 12.95 (1H, s)

MS (m/z): 452 (M{)

Example 88: N-{4-Chloro-3-[4-(4-fluorophenyl)-6-oxo-1,6-dihydropyrimidin-2-yl]benzyl}isobutyramide By performing operations similar to those of Example 4 using 4-fluorobenzaldehyde, the title compound was obtained.

$^1$H-NMR (d$_6$-DMSO, δ): 1.03 (6H, d, J=6.8 Hz), 2.43 (1H, sept, J=6.8 Hz), 4.31 (2H, d. J=6.0 Hz), 6.95 (1H, s), 7.2-7.4 (2H, m), 7.42 (1H, dd, J=2.0 Hz, 8.0 Hz), 7.54 (1H, d, J=1.6 Hz), 7.57 (1H, d, J=8.4 Hz), 8.1-8.2 (2H, m), 8.34 (1H, t, J=6.0 Hz), 12.91 (1H, s)

MS (m/z): 399 (M$^+$)

Example 89: N-{4-Chloro-3-[4-(6-methoxypyridin-2-yl)-6-oxo-1,6-dihydropyrimidin-2-yl]benzyl}isobutyramide By performing operations similar to those of Example 4 using 6-methoxypyridine-2-carbaldehyde, the title compound was obtained.

$^1$H-NMR (d$_6$-DMSO, δ): 1.04 (6H, d, J=7.2 Hz), 2.44 (1H, sept, J=6.8 Hz), 3.98 (3H, s), 4.32 (2H, d, J=6.4 Hz), 6.9-7.0 (1H, m), 7.24 (1H, s), 7.42 (1H, dd, J=2.0 Hz, 8.4 Hz), 7.55 (1H, d, J=2.0 Hz), 7.58 (1H, d, J=8.0 Hz), 7.8-7.9 (2H, m), 8.34 (1H, t, J=6.4 Hz), 12.96 (1H, s)

MS (m/z): 412 (M$^+$)

Example 90: N-(4-Fluoro-3-{6-oxo-4-[6-(trifluoromethyl)pyridin-3-yl]-1,6-dihydropyrimidin-2-yl}benzyl)isobutyramide By performing operations similar to those of Example 4 using 6-(trifluoromethyl)pyridine-3-carbaldehyde, and N-(3-carbamimidoyl-4-fluorobenzyl)isobutyramide hydrochloride, the title compound was obtained.

$^1$H-NMR (d$_6$-DMSO, δ): 1.04 (6H, d, J=6.8 Hz), 2.44 (1H, sept, J=6.8 Hz), 4.32 (2H, d, J=5.6 Hz), 7.23 (1H, s), 7.3-7.4 (1H, m), 7.4-7.5 (1H, m), 7.74 (1H, d, J=5.6 Hz), 8.04 (1H, d, J=8.0 Hz), 8.34 (1H, t, J=6.0 Hz), 8.72 (1H, dd, J=1.2 Hz, 8.4 Hz), 9.44 (1H, d, J=1.6 Hz), 12.97 (1H, s)

MS (m/z): 434 (M$^+$)

Example 91: N-{4-Chloro-3-[4-(6-cyclopropylpyridin-3-yl)-6-oxo-1,6-dihydropyrimidin-2-yl]benzyl}isobutyramide By performing operations similar to those of Example 4 using 6-cyclopropylpyridine-3-carbaldehyde, the title compound was obtained.

$^1$H-NMR (d$_6$-DMSO, δ): 0.9-1.1 (4H, m), 1.03 (6H, d, J=6.8 Hz), 2.1-2.2 (1H, m), 2.43 (1H, sept, J=6.8 Hz), 4.31 (2H, d, J=6.0 Hz), 6.99 (1H, s), 7.39 (1H, d, J=8.4 Hz), 7.43 (1H, d, J=2.0 Hz), 7.55 (1H, d, J=1.2 Hz), 7.57 (1H, d, J=8.4 Hz), 8.25 (1H, dd, J=2.0 Hz, 8.4 Hz), 8.33 (1H, t, J=6.0 Hz), 9.06 (1H, d, J=1.6 Hz), 12.91 (1H, s)

MS (m/z): 422 (M$^+$)

Example 92: N-{3-[4-(6-Ethoxypyridin-3-yl)-6-oxo-1,6-dihydropyrimidin-2-yl]-4-fluorobenzyl}isobutyramide By performing operations similar to those of Example 4 using 6-ethoxypyridine-3-carbaldehyde, and N-(3-carbamimidoyl-4-fluorobenzyl)isobutyramide hydrochloride, the title compound was obtained.

$^1$H-NMR (d$_6$-DMSO, δ): 1.04 (6H, d, J=7.6 Hz), 1.34 (3H, t, J=7.2 Hz), 2.44 (1H, sept, J=6.8 Hz), 4.32 (2H, d, J=6.0 Hz), 4.38 (2H, q, J=7.2 Hz), 6.89 (1H, d, J=8.8 Hz), 6.94 (1H, s), 7.3-7.4 (1H, m), 7.4-7.5 (1H, m), 7.73 (1H, d, J=5.6 Hz), 8.3-8.4 (2H, m), 8.92 (1H, d, J=2.0 Hz), 12.72 (1H, s)

MS (m/z): 410 (M$^+$)

Example 93: N-[4-Chloro-3-(2'-methoxy-6-oxo-1,6-dihydro[4,5']bipyrimidinyl-2-yl)benzyl]isobutyramide By performing operations similar to those of Example 4 using 2-methoxypyrimidine-5-carbaldehyde, the title compound was obtained.

$^1$H-NMR (d$_6$-DMSO, δ): 1.03 (6H, d, J=6.8 Hz), 2.43 (1H, sept, J=6.8 Hz), 3.99 (3H, s), 4.31 (2H, d, J=6.0 Hz), 7.07 (1H, s), 7.42 (1H, dd, J=1.6 Hz, 8.0 Hz), 7.5-7.6 (2H, m), 8.33 (1H, t, J=6.0 Hz), 9.22 (2H, s), 12.98 (1H, s)

MS (m/z): 413 (M$^+$)

Example 94: N-(3-{4-[6-(Difluoromethoxy)pyridin-3-yl]-6-oxo-1,6-dihydropyrimidin-2-yl}-4-fluorobenzyl)isobutyramide By performing operations similar to those of Example 4 using 6-(difluoromethoxy)pyridine-3-carbaldehyde, and N-(3-carbamimidoyl-4-fluorobenzyl)isobutyramide hydrochloride, the title compound was obtained.

$^1$H-NMR (d$_6$-DMSO, δ): 1.04 (6H, d, J=6.8 Hz), 2.43 (1H, sept, J=6.8 Hz), 4.32 (2H, d, J=6.0 Hz), 7.07 (1H, s), 7.22 (1H, d, J=9.6 Hz), 7.3-7.4 (1H, m), 7.4-7.5 (1H, m), 7.74 (1H, d, J=5.6 Hz), 7.78 (1H, t, J=72.0 Hz), 8.34 (1H, t, J=6.0 Hz), 8.57 (1H, dd, J=2.4 Hz, 8.8 Hz), 8.99 (1H, d, J=2.4 Hz), 12.84 (1H, s)

MS (m/z): 433 (M$^+$+1)

Example 95: N-(4-Chloro-2-fluoro-3-{6-oxo-4-[6-(trifluoromethyl)pyridin-3-yl]-1,6-dihydropyrimidin-2-yl}benzyl)isobutyramide By performing operations similar to those of Example 4 using 6-(trifluoromethyl)pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.45 (1H, sept, J=6.8 Hz), 4.33 (2H, d. J=6.0 Hz), 7.30 (1H, s), 7.4-7.6 (2H, m), 8.02 (1H, d, J=8.4 Hz), 8.36 (1H, t, J=5.6 Hz), 8.67 (1H, d, J=8.4 Hz), 9.39 (1H, s), 13.37 (1H, s)

MS (m/z): 468 (M$^+$)

Example 96: N-(4-Chloro-3-{4-[6-(difluoromethoxy)pyridin-3-yl]-6-oxo-1,6-dihydropyrimidin-2-yl}-2-fluorobenzyl)isobutyramide By performing operations similar to those of Example 4 using 6-(difluoromethoxy)pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.45 (1H, sept, J=6.8 Hz), 4.32 (2H, d, J=6.0 Hz), 7.13 (1H, s), 7.19 (1H, d, J=8.4 Hz), 7.4-7.6 (2H, m), 7.77 (1H, t, J=72.4 Hz), 8.36 (1H, t, J=6.0 Hz), 8.51 (1H, dd, J=2.0 Hz, 8.8 Hz), 8.93 (1H, s), 13.22 (1H, s)

MS (m/z): 466 (M$^+$)

Example 97: N-(4-Fluoro-3-({6-oxo-4-[6-(trifluoromethyl)pyridin-3-yl]-1,6-dihydropyrimidin-2-yl}benzyl)-1-(trifluoromethyl)cyclopropane-1-carboxamide By performing operations similar to those of Example 4 using 6-(trifluoromethyl)pyridine-3-carbaldehyde, and N-(3-carbamimidoyl-4-fluorobenzyl)-1-(trifluoromethyl)cyclopropane-1-carboxamide hydrochloride, the title compound was obtained.

$^1$H-NMR (d$_6$-DMSO, δ): 1.2-1.4 (4H, m), 4.35 (2H, d, J=5.6 Hz), 7.23 (1H, s), 7.3-7.4 (1H, m), 7.4-7.5 (1H, m), 7.75 (1H, d, J=5.6 Hz), 8.04 (1H, d, J=8.0 Hz), 8.46 (1H, t, J=6.0 Hz), 8.72 (1H, d, J=8.4 Hz), 9.44 (1H, s), 12.99 (1H, s)

MS (m/z): 500 (M$^+$)

Example 98: Methyl 4-{2-[2-chloro-5-(isobutyrylaminomethyl)phenyl]-6-oxo-1,6-dihydropyrimidin-4-yl}benzoate By performing operations similar to those of Example 4 using methyl 4-formylbenzoate, the title compound was obtained.

$^1$H-NMR (d$_6$-DMSO, δ): 1.03 (6H, d, J=6.8 Hz), 2.43 (1H, sept, J=6.8 Hz), 3.88 (3H, s), 4.31 (2H, d, J=6.4 Hz), 7.06 (1H, s), 7.42 (1H, dd, J=2.0 Hz, 8.4 Hz), 7.55 (1H, d, J=2.0 Hz), 7.58 (1H, d, J=8.4 Hz), 8.04 (2H, d, J=8.4 Hz), 8.20 (2H, d, J=8.4 Hz), 8.34 (1H, t, J=6.0 Hz), 13.00 (1H, s)

MS (m/z): 439 (M$^+$)

Example 99: N-(3-{4-[6-(Difluoromethoxy)pyridin-3-yl]-6-oxo-1,6-dihydropyrimidin-2-yl}-4-fluorobenzyl)-1-(trifluoromethyl)cyclopropane-1-carboxamide By performing operations similar to those of Example 4 using 6-(difluoromethoxy)pyridine-3-carbaldehyde, and N-(3-carbamimidoyl-4-fluorobenzyl)-1-(trifluoromethyl)cyclopropane-1-carboxamide hydrochloride, the title compound was obtained.

$^1$H-NMR (d$_6$-DMSO, δ): 1.2-1.4 (4H, m), 4.35 (2H, d, J=6.0 Hz), 7.08 (1H, s), 7.22 (1H, d, J=8.8 Hz), 7.3-7.4 (1H, m), 7.4-7.5 (1H, m), 7.75 (1H, d, J=6.4 Hz), 7.78 (1H, t, J=72.0 Hz), 8.46 (1H, t, J=6.0 Hz), 8.58 (1H, dd, J=2.4 Hz, 8.8 Hz), 9.00 (1H, d, J=2.4 Hz), 12.84 (1H, s)

MS (m/z): 498 (M$^+$)

Example 100: N-(2,4-Difluoro-3-{6-oxo-4-[6-(trifluoromethyl)pyridin-3-yl]-1,6-dihydropyrimidin-2-yl}benzyl)isobutyramide By performing operations similar to those of Example 4 using 6-(trifluoromethyl)pyridine-3-carbaldehyde, and N-(3-carbamimidoyl-2,4-difluorobenzyl)isobutyramide hydrochloride, the title compound was obtained.

$^1$H-NMR (d$_6$-DMSO, δ): 1.04 (6H, d, J=6.8 Hz), 2.45 (1H, sept, J=6.8 Hz), 4.32 (2H, d, J=6.0 Hz), 7.2-7.4 (2H, m), 7.4-7.6 (1H, m), 8.03 (1H, d, J=8.4 Hz), 8.33 (1H, t, J=6.0 Hz), 8.67 (1H, d, J=8.4 Hz), 9.39 (1H, s), 13.37 (1H, s)

MS (m/z): 452 (M$^+$)

Example 101: N-(4-Chloro-3-{6-oxo-4-[6-(2-propoxyethoxy)pyridin-3-yl]-1,6-dihydropyrimidin-2-yl}benzyl)isobutyramide By performing operations similar to those of Example 4 using 6-(2-propoxyethoxy)pyridine-3-carbaldehyde, the title compound was obtained.

$^1$H-NMR (d$_6$-DMSO, δ): 0.85 (3H, t, J=7.3 Hz), 1.03 (6H, d, J=6.8 Hz), 1.4-1.6 (2H, m), 2.43 (1H, sept, J=6.8 Hz), 3.40 (2H, t, J=6.6 Hz), 3.6-3.8 (2H, m), 4.31 (2H, d, J=5.8 Hz), 4.4-4.5 (2H, m), 6.92 (1H, d, J=8.8 Hz), 6.96 (1H, brs), 7.41 (1H, dd, J=1.9 Hz, 8.3 Hz), 7.5-7.7 (2H, m), 8.2-8.4 (2H, m), 8.87 (1H, d, J=2.4 Hz), 12.84 (1H, brs)

MS (m/z): 484 (M$^+$)

Example 102: N-(3-{4-[6-(2-Butoxyethoxy)pyridin-3-yl]-6-oxo-1,6-dihydropyrimidin-2-yl}-4-chlorobenzyl)isobutyramide By performing operations similar to those of Example 4 using 6-(2-butoxyethoxy)pyridine-3-carbaldehyde, the title compound was obtained.

$^1$H-NMR (d$_6$-DMSO, δ): 0.85 (3H, t, J=7.3 Hz), 1.03 (6H, d, J=6.8 Hz), 1.2-1.4 (2H, m), 1.4-1.6 (2H, m), 2.43 (1H, sept, J=6.8 Hz), 3.44 (2H, t, J=6.6 Hz), 3.6-3.8 (2H, m), 4.31 (2H, d, J=5.8 Hz), 4.4-4.5 (2H, m), 6.92 (1H, d, J=8.8 Hz), 6.96 (1H, brs), 7.41 (1H, dd, J=1.9 Hz, 8.3 Hz), 7.5-7.7 (2H, m), 8.2-8.4 (2H, m), 8.87 (1H, d, J=2.0 Hz), 12.87 (1H, brs)

MS (m/): 498 (M$^+$)

Example 103: N-{4-Chloro-3-[6-oxo-2'-(trifluoromethyl)-1,6-dihydro[4,5']-bipyrimidin-2-yl]benzyl}isobutyramide By performing operations similar to those of Example 4 using 2-(trifluoromethyl)pyrimidine-5-carboxaldehyde, the title compound was obtained.

$^1$H-NMR (d$_6$-DMSO, δ): 1.03 (6H, d, J=6.8 Hz), 2.43 (1H, sept, J=6.8 Hz), 4.32 (2H, d, J=6.0 Hz), 7.34 (1H, s), 7.44 (1H, dd, J=2.0 Hz, 8.0 Hz), 7.5-7.6 (2H, m), 8.34 (1H, t, J=6.0 Hz), 9.26 (2H, s), 13.21 (1H, s)

MS (m/z): 451 (M$^+$)

Reference Example 47: 6-(3-Ethoxypropoxy)pyridine-3-carbaldehyde

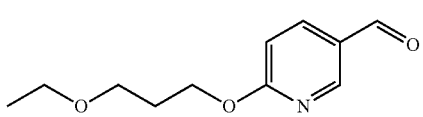

[Formula 60]

By performing operations similar to those of Reference Example 20 using 3-ethoxypropan-1-ol, the title compound was obtained.

$^1$H-NMR (CDCl$_3$, δ): 1.1-1.3 (3H, m), 2.0-2.2 (2H, m), 3.4-3.7 (4H, m), 4.5-4.7 (2H, m), 6.83 (1H, d, J=8.3 Hz), 8.06 (1H, dd, J=2.4 Hz, 8.8 Hz), 8.62 (1H, d, J=1.4 Hz), 9.95 (1H, s)

MS (m/z): 209 (M$^+$)

Reference Example 48: 6-(Cyclopropylmethoxy)pyridine-3-carbaldehyde

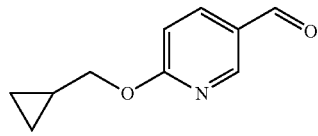

[Formula 61]

By performing operations similar to those of Reference Example 20 using cyclopropylmethanol, the title compound was obtained.

$^1$H-NMR (CDCl$_3$, δ): 0.3-0.7 (4H, m), 1.2-1.4 (1H, m), 4.24 (2H, d, J=7.3 Hz), 6.86 (1H, d, J=8.3 Hz), 8.06 (1H, dd, J=2.5 Hz, 8.8 Hz), 8.60 (1H, d, J=2.5 Hz), 9.95 (1H, s)

Reference Example 49: 6-[2-(2-Butoxyethoxy)ethoxy]pyridine-3-carbaldehyde

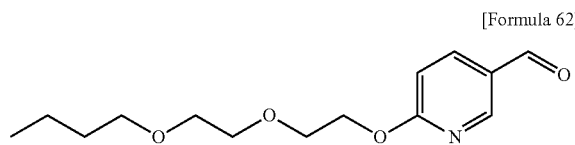

[Formula 62]

By performing operations similar to those of Reference Example 20 using 2-(2-butoxyethoxy)ethanol, the title compound was obtained.

$^1$H-NMR (CDCl$_3$, δ): 0.91 (3H, t, J=7.3 Hz), 1.3-1.7 (4H, m), 3.4-4.0 (8H, m), 4.5-4.7 (2H, m), 6.88 (1H, d, J=8.8 Hz), 8.06 (1H, dd, J=2.0 Hz, 8.3 Hz), 8.60 (1H, d, J=2.4 Hz), 9.95 (1H, s)

MS (m/z): 267 (M$^+$)

Reference Example 50: 6-(Pyridin-2-ylmethoxy)pyridine-3-carbaldehyde

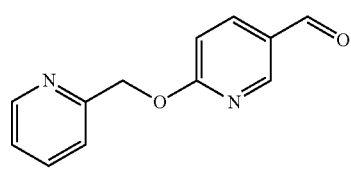

[Formula 63]

By performing operations similar to those of Reference Example 20 using pyridin-2-ylmethanol, the title compound was obtained.

$^1$H-NMR (CDCl$_3$, δ): 5.61 (2H, s), 6.98 (1H, d, J=8.3 Hz), 7.2-7.3 (1H, m), 7.45 (1H, d, J=7.8 Hz), 7.71 (1H, dt, J=2.0 Hz, 7.8 Hz), 8.11 (1H, dd, J=2.4 Hz, 8.8 Hz), 8.6-8.7 (2H, m), 9.97 (1H, s)

MS (m/z): 214 (M$^+$)

Reference Example 51: 6-(6-Methylpyridin-3-yl-methoxy)pyridine-3-carbaldehyde

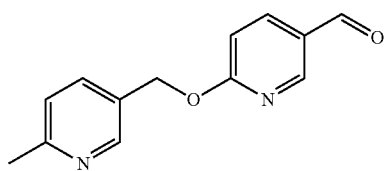

[Formula 64]

By performing operations similar to those of Reference Example 20 using (6-methylpyridin-3-yl)methanol, the title compound was obtained.

$^1$H-NMR (CDCl$_3$, δ): 2.57 (3H, s), 5.47 (2H, s), 6.88 (1H, d, J=8.8 Hz), 7.18 (1H, d, J=8.3 Hz), 7.69 (1H, dd, J=2.5 Hz, 7.9 Hz), 8.09 (1H, dd, J=2.4 Hz, 8.3 Hz), 8.5-8.7 (2H, m), 9.97 (1H, s)

MS (m/z): 228 (M$^+$)

Reference Example 52: 2-Oxo-1-pentyl-1,2-dihydropyridine-4-carbaldehyde

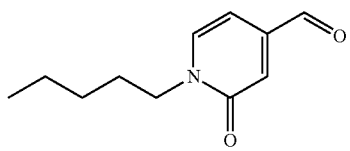

[Formula 65]

To a solution of 2-oxo-1,2-dihydropyridine-4-carbaldehyde (2.46 g) in DMF (50 mL), 60% sodium hydride (960 mg) was added under ice cooling. The resulting mixture was stirred at room temperature for 30 minutes. 1-Bromopentane (3.0 mL) was added to the reaction mixture, and the resulting mixture was stirred at 50° C. for 5 hours. The reaction mixture was poured into saturated aqueous ammonium chloride, and the resulting mixture was extracted with t-butyl methyl ether. The organic layer was washed with water, and dried over sodium sulfate. The organic layer was filtered, and then the solvent was evaporated. Silica gel column chromatography was performed to obtain the title compound (606 mg).

$^1$H-NMR (CDCl$_3$, δ): 0.91 (3H, t, J=7.3 Hz), 1.2-1.5 (4H, m), 1.6-1.9 (2H, m), 3.95 (2H, t, J=7.8 Hz), 6.56 (1H, dd, J=1.5 Hz, 6.8 Hz), 6.99 (1H, d, J=2.0 Hz), 7.37 (1H, d, J=6.8 Hz), 9.88 (1H, d, J=0.9 Hz)

MS (m/z): 193 (M$^+$)

Reference Example 53: 1-Butyl-2-oxo-1,2-dihydropyridine-4-carbaldehyde

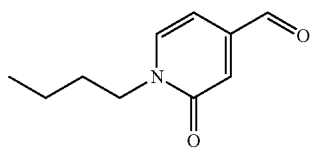

[Formula 66]

By performing operations similar to those of Reference Example 52 using 1-bromobutane, the title compound was obtained.

$^1$H-NMR (CDCl$_3$, δ): 0.97 (3H, t, J=7.3 Hz), 1.3-1.5 (2H, m), 1.6-1.9 (2H, m), 3.96 (2H, t, J=7.3 Hz), 6.56 (1H, dd, J=2.0 Hz, 7.3 Hz), 7.00 (1H, d, J=1.5 Hz), 7.38 (1H, d, J=7.3 Hz), 9.87 (1H, s)

MS (m/z): 179 (M$^+$)

Reference Example 54: N-(4-Chloro-3-cyanobenzyl)propionamide

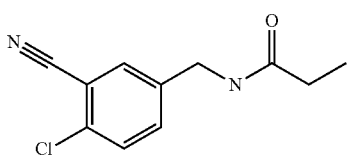

[Formula 67]

By performing operations similar to those of Reference Example 1 using propionyl chloride, the title compound was obtained.

$^1$H-NMR (CDCl$_3$, δ): 1.19 (3H, t, J=7.3 Hz), 2.29 (2H, q, J=7.3 Hz), 4.44 (2H, d, J=5.8 Hz), 5.95 (1H, brs), 7.4-7.6 (2H, m), 7.57 (1H, s)

MS (m/z): 222 (M$^+$)

Reference Example 55: N-(3-Carbamimidoyl-4-chlorobenzyl)propionamide Hydrochloride

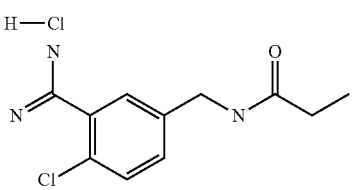

[Formula 68]

By performing operations similar to those of Reference Example 2 using N-(4-chloro-3-cyanobenzyl)propionamide, the title compound was obtained. The obtained compound was used for the following reaction without purification.

Reference Example 56: N-(4-Chloro-3-cyanobenzyl)butyramide

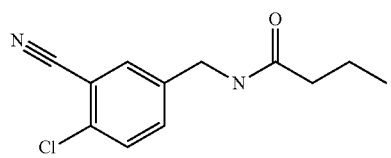

[Formula 69]

By performing operations similar to those of Reference Example 1 using butyryl chloride, the title compound was obtained.

$^1$H-NMR (CDCl$_3$, δ): 0.96 (3H, t, J=7.3 Hz), 1.6-1.8 (2H, m), 2.23 (2H, t, J=7.8 Hz), 4.44 (2H, d, J=5.8 Hz), 5.95 (1H, brs), 7.4-7.6 (2H, m), 7.57 (1H, s)
MS (m/z): 236 (M$^+$)

Reference Example 57:
N-(3-Carbamimidoyl-4-chlorobenzyl)butyramide hydrochloride

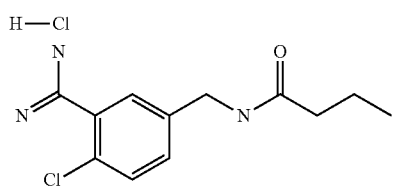

[Formula 70]

By performing operations similar to those of Reference Example 2 using N-(4-chloro-3-cyanobenzyl)butyramide, the title compound was obtained. The obtained compound was used for the following reaction without purification.

Reference Example 58: 6-{2-[2-(2-Ethoxyethoxy)ethoxy]ethoxy}pyridine-3-carbaldehyde

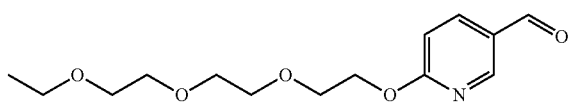

[Formula 71]

By performing operations similar to those of Reference Example 20 using 2-[2-(2-ethoxyethoxy)ethoxy]ethanol, the title compound was obtained. $^1$H-NMR (CDCl$_3$, δ): 1.21 (3H, t, J=7.3 Hz), 3.52 (2H, q, J=6.8 Hz), 3.5-4.0 (10H, m), 4.5-4.7 (2H, m), 6.88 (1H, d, J=8.8 Hz), 8.06 (1H, dd, J=2.5 Hz, 8.8 Hz), 8.60 (1H, d, J=1.9 Hz), 9.95 (1H, s)
MS (m/z): 283 (M$^+$)

Reference Example 59: 6-(6-Methylpyridin-2-yl-methoxy)pyridine-3-carbaldehyde

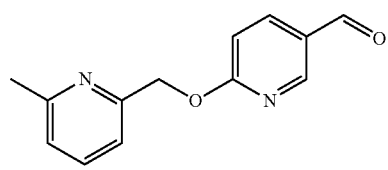

[Formula 72]

By performing operations similar to those of Reference Example 20 using (6-methylpyridin-2-yl)methanol, the title compound was obtained.
$^1$H-NMR (CDCl$_3$, δ): 2.59 (3H, s), 5.57 (2H, s), 6.97 (1H, d, J=8.8 Hz), 7.10 (1H, d, J=7.8 Hz), 7.23 (1H, d, J=7.3 Hz), 7.59 (1H, t, J=7.9 Hz), 8.10 (1H, dd, J=2.4 Hz, 8.8 Hz), 8.63 (1H, d, J=2.4 Hz), 9.96 (1H, s)
MS (m/z): 228 (M$^+$)

Reference Example 60:
6-(3-Fluoropropoxy)pyridine-3-carbaldehyde

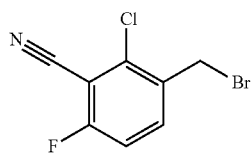

[Formula 73]

By performing operations similar to those of Reference Example 20 using 3-fluoropropan-1-ol, the title compound was obtained.
$^1$H-NMR (CDCl$_3$, δ): 1.1-1.3 (2H, m), 4.4-4.7 (3H, m), 4.70 (1H, t, J=5.4 Hz), 6.84 (1H, d, J=8.8 Hz), 8.08 (1H, dd, J=2.5 Hz, 8.8 Hz), 8.62 (1H, d, J=2.0 Hz), 9.96 (1H, s)
MS (m/z): 183 (M$^+$)

Reference Example 61:
3-(Bromomethyl)-2-chloro-6-fluorobenzonitrile

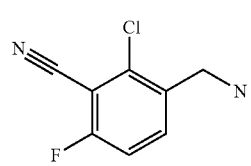

[Formula 74]

Under a nitrogen atmosphere, 2-chloro-6-fluoro-3-methylbenzonitrile (5.18 g) was dissolved in acetonitrile (150 mL), 1,3-dibromo-5,5-dimethylhydantoin (4.37 g), and 2,2'-azobis(isobutyronitrile) (501 mg) were added to the solution, and the resulting mixture was refluxed for 3 hours by heating. 1 N Hydrochloric acid was added to the reaction mixture, the resulting mixture was extracted with ethyl acetate, and then the obtained organic layer was washed with 1 N hydrochloric acid, and saturated brine. The solvent was removed under reduced pressure, and the obtained compound was used for the following reaction without purification.

Reference Example 62:
3-(Aminomethyl)-2-chloro-6-fluorobenzonitrile

[Formula 75]

3-(Bromomethyl)-2-chloro-6-fluorobenzonitrile was dissolved in N,N-dimethylformamide (75 mL), sodium azide (1.99 g) was added to the solution under ice cooling, and the resulting mixture was stirred for 30 minutes. Saturated brine was added to the reaction mixture, the resulting mixture was extracted with ethyl acetate, and then the organic layer was washed with saturated brine. The solvent was removed under reduced pressure, and the obtained compound was used for the following reaction without purification.

The obtained compound was dissolved in tetrahydrofuran (75 mL), and water (3 mL), triphenylphosphine (9.62 g) was added to the solution under ice cooling, and the resulting mixture was stirred overnight at room temperature. 1 N Hydrochloric acid was added to the reaction mixture, and the resulting mixture was washed with diethyl ether. 1 N Aqueous sodium hydroxide was added, the resulting mixture was extracted with dichloromethane, then the organic layer was dried over magnesium sulfate, and the obtained the organic layer was used as it was for the following reaction.

Reference Example 63:
N-(2-Chloro-3-cyano-4-fluorobenzyl)isobutyramide

[Formula 76]

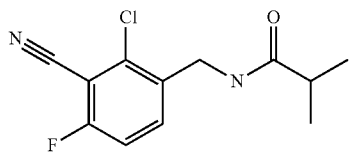

By performing operations similar to those of Reference Example 1 using isobutyryl chloride, the title compound was obtained.
$^1$H-NMR (CDCl$_3$, δ): 1.17 (6H, d, J=6.8 Hz), 2.40 (1H, sept, J=6.8 Hz), 4.50 (2H, d, J=6.4 Hz), 5.98 (1H, s), 7.13 (1H, t, J=8.8 Hz), 7.6-7.7 (1H, m)
MS (m/z): 254 (M$^+$)

Reference Example 64: N-(3-Carbamimidoyl-2-chloro-4-fluorobenzyl)isobutyramide hydrochloride

[Formula 77]

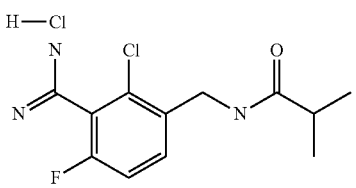

By performing operations similar to those of Reference Example 2 using N-(2-chloro-3-cyano-4-fluorobenzyl) isobutyramide, the title compound was obtained. The obtained compound was used for the following reaction without purification.

Reference Example 65:
3-Chloro-2-fluoro-6-(trifluoromethyl)benzamidine Hydrochloride

[Formula 78]

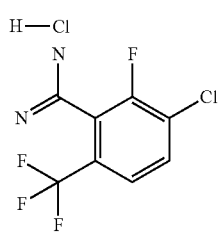

By performing operations similar to those of Reference Example 2 using 3-chloro-2-fluoro-6-(trifluoromethyl)benzonitrile, the title compound was obtained. The obtained compound was used for the following reaction without purification.

Reference Example 66: 2-[3-Chloro-2-fluoro-6-(trifluoromethyl)phenyl]-6-[6-(trifluoromethyl)pyridin-3-yl]pyrimidin-4(3H)-one

[Formula 79]

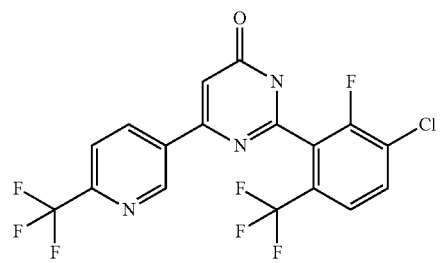

By performing operations similar to those of Example 4 using 6-(trifluoromethyl)pyridine-3-carbaldehyde, and 3-chloro-2-fluoro-6-(trifluoromethyl)benzamidine hydrochloride, the title compound was obtained.
$^1$H-NMR (d$_6$-DMSO, δ): 7.38 (1H, s), 7.87 (1H, d, J=8.4 Hz), 8.04 (1H, d, J=8.4 Hz), 8.10 (1H, t, J=7.6 Hz), 8.65 (1H, d, J=7.6 Hz), 9.38 (1H, s), 13.44 (1H, brs)
MS (m/z): 437 (M$^+$)

Reference Example 67: 2-[3-Chloro-2-fluoro-6-(trifluoromethyl)phenyl]-6-[6-(difluoromethoxy)pyridin-3-yl]pyrimidin-4(3H)-one

[Formula 80]

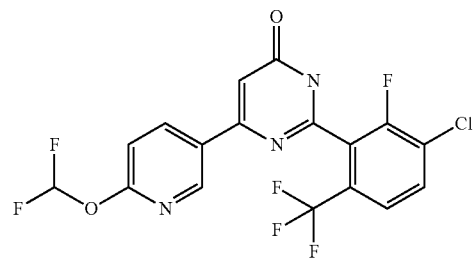

By performing operations similar to those of Example 4 using 6-(difluoromethoxy)pyridine-3-carbaldehyde, and 3-chloro-2-fluoro-6-(trifluoromethyl)benzamidine hydrochloride, the title compound was obtained.
$^1$H-NMR (d$_6$-DMSO, δ): 7.2-7.3 (2H, m), 7.77 (1H, t, J=72.8 Hz), 7.86 (1H, d, J=8.8 Hz), 8.09 (1H, t, J=8.0 Hz), 8.50 (1H, dd, J=2.4 Hz, 8.8 Hz), 8.92 (1H, d, J=2.0 Hz), 13.30 (1H, brs)
MS (m/z): 435 (M$^+$)

Reference Example 68: 2-[3-Chloro-2-fluoro-6-(trifluoromethyl)phenyl]-6-[6-[(2-ethoxyethoxy)pyridin-3-yl]pyrimidin-4(3H)-one

[Formula 81]

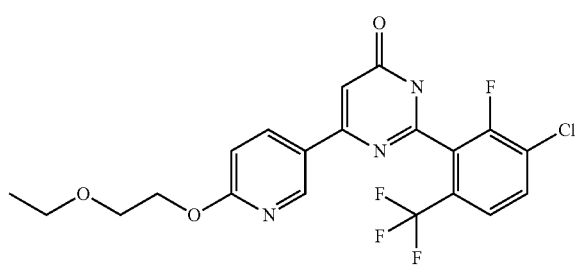

By performing operations similar to those of Example 4 using 6-(2-ethoxyethoxy)pyridine-3-carbaldehyde, and 3-chloro-2-fluoro-6-(trifluoromethyl)benzamidine hydrochloride, the title compound was obtained.

$^1$H-NMR (d$_6$-DMSO, δ): 1.12 (3H, t, J=6.8 Hz), 3.49 (2H, q, J=6.8 Hz), 3.71 (2H, t, J=5.2 Hz), 4.43 (2H, t, J=5.2 Hz), 6.94 (1H, d, J=8.8 Hz), 7.06 (1H, s), 7.85 (1H, d, J=8.0 Hz), 8.08 (1H, t, J=8.0 Hz), 8.30 (1H, d, J=7.2 Hz), 8.84 (1H, s), 13.20 (1H, brs)

MS (m/z): 457 (M$^+$)

Reference Example 69: 2-[3-Chloro-2-fluoro-6-(trifluoromethyl)phenyl]-6-[5-(trifluoromethyl)pyridin-2-yl]pyrimidin-4(3H)-one

[Formula 82]

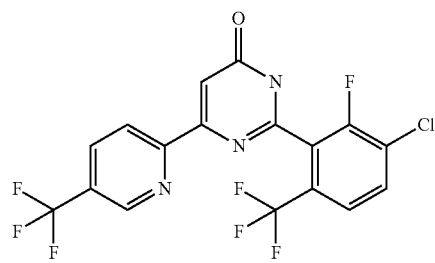

By performing operations similar to those of Example 4 using 5-(trifluoromethyl)pyridine-2-carbaldehyde, and 3-chloro-2-fluoro-6-(trifluoromethyl)benzamidine hydrochloride, the title compound was obtained.

$^1$H-NMR (d$_6$-DMSO, δ): 7.41 (1H, s), 7.88 (1H, d, J=8.8 Hz), 8.11 (1H, t, J=8.4 Hz), 8.34-8.40 (2H, m), 9.13 (1H, s), 13.45 (1H, brs)

MS (m/z): 437 (M$^+$)

Reference Example 70: 6-(Tetrahydropyran-4-yl-methoxy)pyridine-3-carbaldehyde

[Formula 83]

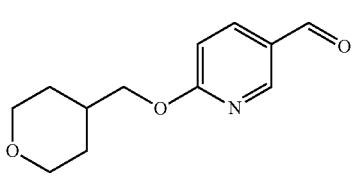

To a solution of (tetrahydropyran-4-yl)methanol (8.36 g) in DMF (150 mL), potassium tert-butoxide (5.84 g) was added, and the resulting mixture was stirred for 30 minutes under a nitrogen atmosphere. 6-Chloropyridine-3-carbaldehyde (4.24 g) was added to the reaction mixture, and the resulting mixture was stirred for 14 hours under a nitrogen atmosphere. The reaction mixture was poured into water, and the resulting mixture was extracted with t-butyl methyl ether. The solvent was evaporated, and then the residue was purified by silica gel column chromatography to obtain the title compound (0.80 g).

$^1$H-NMR (CDCl$_3$, δ): 1.3-1.8 (4H, m), 2.0-2.2 (1H, m), 3.3-3.6 (2H, m), 3.9-4.1 (2H, m), 4.27 (2H, d, J=6.9 Hz), 6.83 (1H, d, J=8.3 Hz), 8.07 (1H, dd, J=2.4 Hz, 8.8 Hz), 8.61 (1H, d, J=2.5 Hz), 9.96 (1H, s)

MS (m/z): 221 (M$^+$)

Reference Example 71: 5-(1-Propynyl)pyridine-3-carbaldehyde

[Formula 84]

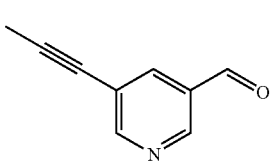

5-Bromopyridine-3-carbaldehyde (595 mg), dichlorobis(triphenylphosphine)palladium(II) (225 mg), copper(I) iodide (120 mg), N,N-diisopropylethylamine (2.2 mL), tetrahydrofuran (10 mL), a 1 M solution of tetrabutylammonium fluoride in tetrahydrofuran (3.4 mL), and 1-(trimethylsilyl)-1-propyne (1.43 mL) were mixed in order. Microwaves were irradiated on the mixture at 50° C. for 30 minutes under a nitrogen atmosphere. The reaction mixture was filtered, then ethyl acetate was added to the filtrate, and the resulting mixture was washed with water. The organic layer was separated, and the solvent was evaporated. The residue was purified by silica gel column chromatography to obtain the title compound (322 mg).

$^1$H-NMR (CDCl$_3$, δ): 2.11 (3H, s), 8.12 (1H, s), 8.83 (1H, s), 8.94 (1H, s), 10.08 (1H, s)

MS (m/z): 145 (M$^+$)

Reference Example 72: 6-(3-Methyloxetan-3-yl-methoxy)pyridine-3-carbaldehyde

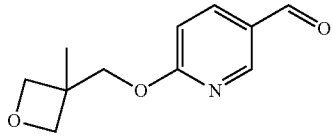

[Formula 85]

By performing operations similar to those of Reference Example 70 using 3-methyl-3-oxetanemethanol, the title compound was obtained.

$^1$H-NMR (CDCl$_3$, δ): 1.44 (3H, s), 4.4-4.8 (6H, m), 6.87 (1H, d, J=8.8 Hz), 8.10 (1H, dd, J=2.5 Hz, 8.8 Hz), 8.63 (1H, d, J=2.0 Hz), 9.97 (1H, s)
MS (m/z): 207 (M$^+$)

Reference Example 73: 6-Butoxypyridazine-3-carbaldehyde

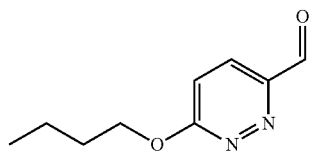

[Formula 86]

To a solution of (6-butoxypyridazin-3-yl)methanol (1.51 g) in chloroform (50 mL), 1,1,1-triacetoxy-1,1-dihydro-1,2-benziodoxol-3-(1H)-one (4.22 g) was slowly added with ice cooling under a nitrogen atmosphere. The resulting mixture was stirred at room temperature for 3 hours, and then saturated aqueous sodium hydrogencarbonate, and aqueous sodium thiosulfate were added to the mixture. The organic layer was separated, dried over magnesium sulfate, and filtered. The solvent was evaporated under reduced pressure, and the obtained residue was purified by silica gel column chromatography to obtain the title compound (790 mg).

$^1$H-NMR (CDCl$_3$, δ): 0.98 (3H, t, J=7.6 Hz), 1.42 (2H, sext, J=7.6 Hz), 1.85 (2H, quin, J=7.6 Hz), 4.26 (2H, t, J=7.6 Hz), 6.96 (1H, d, J=9.2 Hz), 7.74 (1H, d, J=9.6 Hz), 9.74 (1H, d, J=1.2 Hz)
MS (m/z): 180 (M$^+$)

Reference Example 74: N-(4-Chloro-3-cyano-2-fluorobenzyl)butyramide

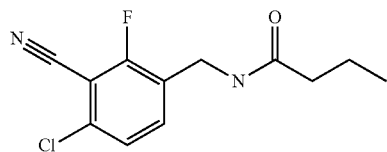

[Formula 87]

By performing operations similar to those of Reference Example 1 using 3-aminomethyl-6-chloro-2-fluorobenzonitrile, and butyryl chloride, the title compound was obtained.

$^1$H-NMR (CDCl$_3$, δ): 0.94 (3H, t, J=7.6 Hz), 1.67 (2H, sext, J=7.6 Hz), 2.19 (2H, t, J=7.6 Hz), 4.46 (2H, t, J=6.4 Hz), 7.29 (1H, dd, J=1.2 Hz, 8.4 Hz), 7.61 (1H, t, J=8.4 Hz)
MS (m/z): 254 (M$^+$)

Reference Example 75: N-(3-Carbamimidoyl-4-chloro-2-fluorobenzyl)butyramide Hydrochloride

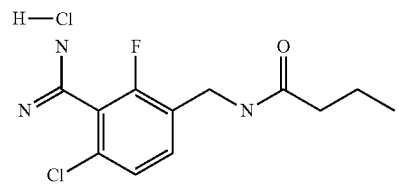

[Formula 88]

By performing operations similar to those of Reference Example 2 using N-(4-chloro-3-cyano-2-fluorobenzyl)butyramide, the title compound was obtained. The obtained compound was used for the following reaction without purification.

Reference Example 76: 2-[3-Chloro-2-fluoro-6-(trifluoromethyl)phenyl]-6-(6-methoxypyridin-3-yl)pyrimidin-4(3H)-one

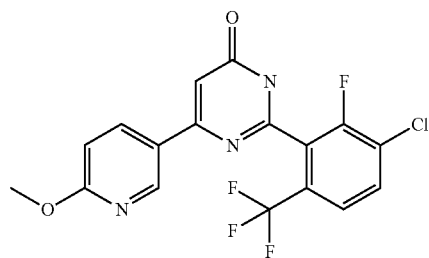

[Formula 89]

By performing operations similar to those of Example 4 using 6-methoxypyridine-3-carbaldehyde, and 3-chloro-2-fluoro-6-(trifluoromethyl)benzamidine hydrochloride, the title compound was obtained.

$^1$H-NMR (d$_6$-DMSO, δ): 3.92 (3H, s), 6.92 (1H, d, J=8.8 Hz), 7.07 (1H, s), 7.85 (1H, d, J=8.4 Hz), 8.08 (1H, t, J=8.4 Hz), 8.30 (1H, dd, J=2.4 Hz, 8.8 Hz), 8.86 (1H, d, J=2.0 Hz), 13.17 (1H, brs)
MS (m/z): 399 (M$^+$)

Reference Example 77: 6-(Cyclopropylethynyl)pyridine-3-carbaldehyde

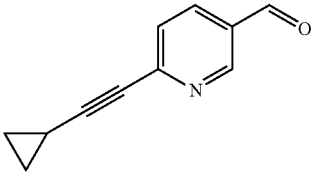

[Formula 90]

To a solution of 6-bromopyridine-3-carbaldehyde (930 mg) in tetrahydrofuran (25 mL), cyclopropylacetylene (0.64 mL), dichlorobis(triphenylphosphine)palladium(II) (70 mg), copper iodide (38 mg), and triethylamine (2.1 mL) were added under a nitrogen atmosphere, and the resulting mixture was stirred overnight at 40° C. After the reaction, the reaction mixture was filtered through a Celite layer, the solvent was evaporated, and then the residue was purified by silica gel column chromatography to obtain the title compound (595 mg).

$^1$H-NMR (CDCl$_3$, δ): 0.9-1.0 (4H, m), 1.5-1.6 (1H, m), 7.48 (1H, d, J=7.6 Hz), 8.08 (1H, dd, J=2.0 Hz, 8.0 Hz), 8.97 (1H, d, J=2.0 Hz), 10.07 (1H, s)

MS (m/z): 171 (M$^+$)

Reference Example 78:
2-(Cyclopropylethynyl)thiazole-5-carbaldehyde

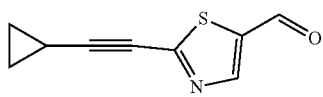

[Formula 91]

To a solution of 2-bromothiazole-5-carbaldehyde (1.92 g) in tetrahydrofuran (40 mL), cyclopropylacetylene (1.27 mL), dichlorobis(triphenylphosphine)palladium(11) (140 mg), copper iodide (76 mg), and triethylamine (4.2 mL) were added under a nitrogen atmosphere, and the resulting mixture was stirred at 40° C. for 3 hours. After the reaction, the reaction mixture was filtered through a Celite layer, the solvent was evaporated, and then the residue was purified by silica gel column chromatography to obtain the title compound (1.42 g).

$^1$H-NMR (CDCl$_3$, δ): 0.9-1.1 (4H, m), 1.5-1.6 (1H, m), 8.32 (1H, s), 9.98 (1H, s)

MS (m/z): 177 (M$^+$)

Reference Example 79:
5-(Cyclopropylethynyl)pyridine-2-carbaldehyde

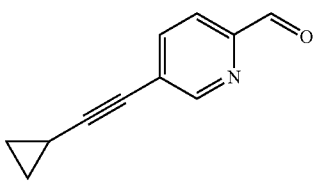

[Formula 92]

To a solution of 5-bromopyridine-2-carbaldehyde (1.86 g) in tetrahydrofuran (40 mL), cyclopropylacetylene (1.27 mL), dichlorobis(triphenylphosphine)palladium(II) (140 mg), copper iodide (76 mg), and triethylamine (4.2 mL) were added under a nitrogen atmosphere, and the resulting mixture was stirred overnight at 40° C. After the reaction, the reaction mixture was filtered through a Celite layer, the solvent was evaporated, and then the residue was purified by silica gel column chromatography to obtain the title compound (1.29 g).

$^1$H-NMR (CDCl$_3$, δ): 0.8-1.0 (4H, m), 1.4-1.6 (1H, m), 7.79 (1H, dd, J=2.0 Hz, 8.0 Hz), 7.87 (1H, d, J=8.0 Hz), 8.72 (1H, d, J=2.0 Hz), 10.05 (1H, s)

MS (m/z): 171 (M$^+$)

Reference Example 80: 6-(3-Ethyloxetan-3-yl-methoxy)pyridine-3-carbaldehyde

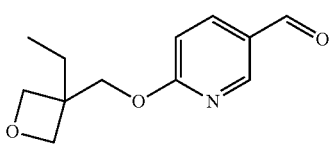

[Formula 93]

Microwaves were irradiated on a mixture of 3-ethyl-3-oxetanemethanol (4.65 g), 6-chloropyridine-3-carbaldehyde (2.83 g), potassium carbonate (5.53 g), and dimethyl sulfoxide (13 mL) at 110° C. for 2 hours, and at 130° C. for further 2 hours. The reaction mixture was poured into water, and the resulting mixture was extracted with t-butyl methyl ether. The insoluble matter was removed by filtration. The solvent was evaporated, and then the residue was purified by silica gel column chromatography to obtain the title compound (0.86 g).

$^1$H-NMR (CDCl$_3$, δ): 0.96 (3H, t, J=7.3 Hz), 1.87 (2H, q, J=7.3 Hz), 4.4-4.7 (6H, m), 6.89 (1H, d, J=8.3 Hz), 8.09 (1H, dd, J=2.5 Hz, 8.8 Hz), 8.63 (1H, d, J=2.5 Hz), 9.97 (1H, s)

MS (m/z): 221 (M$^+$)

Reference Example 81:
4-(1-Propynyl)thiazole-2-carbaldehyde

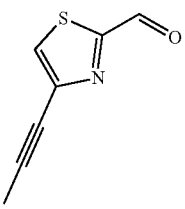

[Formula 94]

By performing operations similar to those of Reference Example 71 using 4-bromothiazole-2-carbaldehyde, the title compound was obtained.

$^1$H-NMR (CDCl$_3$, δ): 2.10 (3H, s), 7.69 (1H, d, J=1.0 Hz), 9.96 (1H, d, J=1.5 Hz)

MS (m/z): 151 (M$^+$)

Reference Example 82:
5-(Cyclopropylethynyl)thiazole-2-carbaldehyde

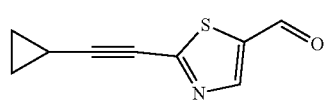

[Formula 95]

By performing operations similar to those of Reference Example 77 using 5-bromothiazole-2-carbaldehyde, the title compound was obtained.

¹H-NMR (CDCl₃, δ): 0.8-1.1 (4H, m), 1.4-1.6 (1H, m), 7.99 (1H, s), 9.90 (1H, s)
MS (m/z): 177 (M⁺)

Reference Example 83:
4-(Cyclopropylethynyl)thiazole-2-carbaldehyde

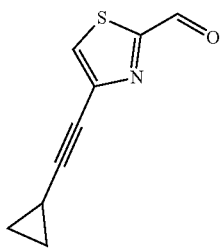

[Formula 96]

By performing operations similar to those of Reference Example 77 using 4-bromothiazole-2-carbaldehyde, the title compound was obtained.
¹H-NMR (CDCl₃, δ): 0.8-1.0 (4H, m), 1.4-1.6 (1H, m), 7.67 (1H, d, J=1.5 Hz), 9.95 (1H, d, J=1.0 Hz)
MS (m/z): 177 (M⁺)

Reference Example 84:
6-(Cyclopropylethynyl)pyridine-2-carbaldehyde

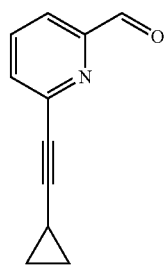

[Formula 97]

By performing operations similar to those of Reference Example 77 using 6-bromopyridine-2-carbaldehyde, the title compound was obtained.
¹H-NMR (CDCl₃, δ): 0.8-1.1 (4H, m), 1.4-1.7 (1H, m), 7.56 (1H, dd, J=1.4 Hz, 7.8 Hz), 7.7-7.9 (2H, m), 10.05 (1H, s)
MS (m/z): 171 (M⁺)

Reference Example 85:
5-(Cyclopropylethynyl)pyridine-3-carbaldehyde

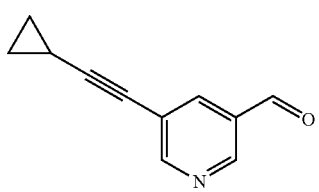

[Formula 98]

By performing operations similar to those of Reference Example 77 using 5-bromopyridine-3-carbaldehyde, the title compound was obtained.

¹H-NMR (CDCl₃, δ): 0.8-1.0 (4H, m), 1.4-1.6 (1H, m), 8.10 (1H, t, J=1.7 Hz), 8.79 (1H, d, J=2.4 Hz), 8.92 (1H, d, J=1.9 Hz), 10.08 (1H, s)
MS (m/z): 171 (M⁺)

Reference Example 86: N-[3-Cyano-4-(trifluoromethyl)benzyl]butyramide

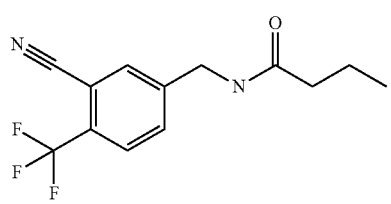

[Formula 99]

By performing operations similar to those of Reference Example 1 using 5-aminomethyl-2-(trifluoromethyl)benzonitrile, and butyryl chloride, the title compound was obtained.
¹H-NMR (CDCl₃, δ): 0.98 (3H, t, J=7.2 Hz), 1.72 (2H, quin, J=7.6 Hz), 2.26 (2H, t, J=7.2 Hz), 4.53 (2H, d, J=5.6 Hz), 6.06 (1H, s), 7.4-7.8 (3H, m)
MS (m/z): 270 (M⁺)

Reference Example 87: N-[3-Carbamimidoyl-4-(trifluoromethyl)benzyl]butyramide Hydrochloride

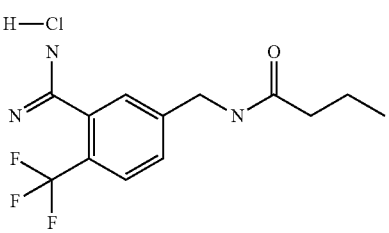

[Formula 100]

By performing operations similar to those of Reference Example 2 using N-[3-cyano-4-(trifluoromethyl)benzyl]butyramide, the title compound was obtained. The obtained compound was used for the following reaction without purification.

Reference Example 88:
6-(3-Morpholin-4-ylpropoxy)pyridine-3-carbaldehyde

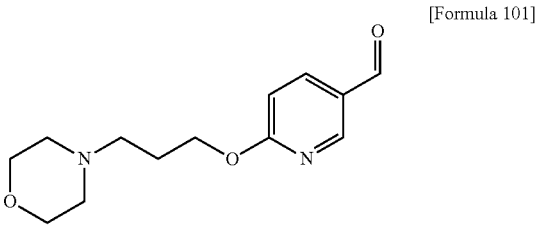 [SMILES: O=Cc1ccc(OCCCN2CCOCC2)nc1]

[Formula 101]

By performing operations similar to those of Reference Example 70 using 4-(3-hydroxypropyl)morpholine, the title compound was obtained.

$^1$H-NMR (CDCl$_3$, δ): 2.0 (2H, sext, J=6.8 Hz), 2.4-2.6 (6H, m), 3.73 (4H, t, J=4.8 Hz), 4.47 (2H, t, J=6.4 Hz), 6.83 (1H, d, J=8.8 Hz), 8.06 (1H, dd, J=2.4 Hz, 8.8 Hz), 8.62 (1H, d, J=2.4 Hz), 9.95 (1H, s)

MS (m/z): 250 (M$^+$)

Reference Example 89: 6-(1-Propynyl)pyridine-3-carbaldehyde

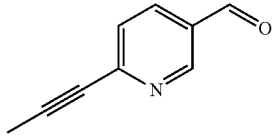

[Formula 102]

6-Bromopyridine-3-carbaldehyde (595 mg), dichlorobis(triphenylphosphine)palladium(II) (225 mg), copper(I) iodide (122 mg), N,N-diisopropylethylamine (2.2 mL), tetrahydrofuran (10 mL), a 1 M solution of tetrabutylammonium fluoride in tetrahydrofuran (3.4 mL), and 1-(trimethylsilyl)-1-propyne (1.42 mL) were mixed in order. Microwaves were irradiated on the mixture at 50° C. for 30 minutes under a nitrogen atmosphere. After the reaction, the reaction mixture was filtered through a Celite layer, the solvent was evaporated, and then the residue was purified by silica gel column chromatography to obtain the title compound (370 mg).

$^1$H-NMR (CDCl$_3$, δ): 2.14 (3H, s), 7.51 (1H, d, J=8.4 Hz), 8.10 (1H, dd, J=2.0 Hz, 8.4 Hz), 8.99 (1H, d, J=1.6 Hz), 10.09 (1H, s)

MS (m/z): 145 (M$^+$)

Reference Example 90: 2-[3-Chloro-2-fluoro-6-(trifluoromethyl)phenyl]-6-(5-fluoropyridin-3-yl)pyrimidin-4(3H)-one

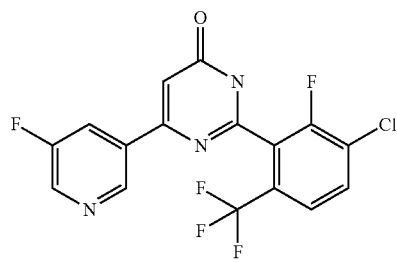

[Formula 103]

By performing operations similar to those of Example 4 using 5-fluoropyridine-3-carbaldehyde, and 3-chloro-2-fluoro-6-(trifluoromethyl)benzamidine hydrochloride, the title compound was obtained.

$^1$H-NMR (d$_6$-DMSO, δ): 7.31 (1H, s), 7.87 (1H, d, J=8.8 Hz), 8.10 (1H, t, J=8.4 Hz), 8.2-8.3 (1H, m), 8.72 (1H, d, J=2.4 Hz), 9.11 (1H, s), 13.37 (1H, brs)

MS (m/z): 387 (M$^+$)

Reference Example 91: 6-[(1-Hydroxycyclohexyl)ethynyl]pyridine-3-carbaldehyde

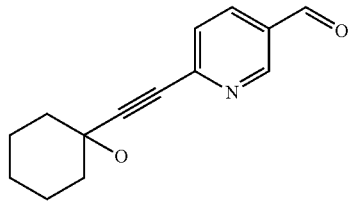

[Formula 104]

To a solution of 6-bromopyridine-3-carbaldehyde (1.86 g) in tetrahydrofuran (40 mL), 1-ethynyl-1-cyclohexanol (1.86 g), dichlorobis(triphenylphosphine)palladium(II) (140 mg), copper(I) iodide (76 mg), and triethylamine (4.2 mL) were added under a nitrogen atmosphere, and the resulting mixture was stirred at 50° C. for 3 hours. After the reaction, the reaction mixture was filtered through a Celite layer, the solvent was evaporated, and then the residue was purified by silica gel column chromatography to obtain the title compound (2.22 g).

$^1$H-NMR (CDCl$_3$, δ): 1.2-1.4 (1H, m), 1.5-1.8 (7H, m), 2.0-2.1 (2H, m), 2.29 (1H, s), 7.58 (1H, d, J=8.0 Hz), 8.13 (1H, dd, J=1.6 Hz, 8.0 Hz), 9.03 (1H, d, J=1.6 Hz), 10.11 (1H, s)

MS (m/z): 229 (M$^+$)

Reference Example 92: 5-(1-Propynyl)pyridine-2-carbaldehyde

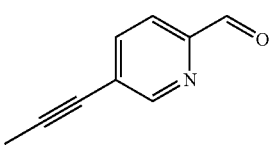

[Formula 105]

5-Bromopyridine-2-carbaldehyde (930 mg), dichlorobis(triphenylphosphine)palladium(II) (351 mg), copper(I) iodide (190 mg), N,N-diisopropylethylamine (3.4 mL), tetrahydrofuran (15 mL), a 1 M solution of tetrabutylammonium fluoride in tetrahydrofuran (5.3 mL), and 1-(trimethylsilyl)-1-propyne (2.22 mL) were mixed in order, and the resulting mixture was stirred at 50° C. for 1 hours under a nitrogen atmosphere. After the reaction, the reaction mixture was filtered through a Celite layer, the solvent was evaporated, and then the residue was purified by silica gel column chromatography to obtain the title compound (454 mg).

$^1$H-NMR (CDCl$_3$, δ): 2.13 (3H, s), 7.8-7.9 (2H, m), 8.75 (1H, d, J=1.2 Hz), 10.06 (1H, s)

MS (m/z): 145 (M$^+$)

Reference Example 93: 2-[3-Chloro-2-fluoro-6-(trifluoromethyl)phenyl]-6-(6-ethoxypyridin-3-yl)pyrimidin-4(3H)-one

[Formula 106]

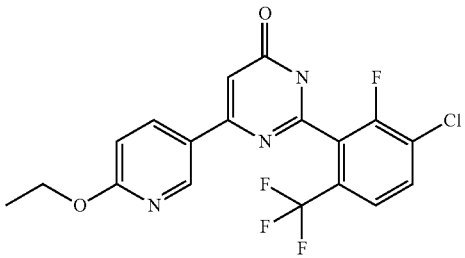

By performing operations similar to those of Example 4 using 6-ethoxypyridine-3-carbaldehyde, and 3-chloro-2-fluoro-6-(trifluoromethyl)benzamidine hydrochloride, the title compound was obtained.

$^1$H-NMR (d$_6$-DMSO, δ): 1.33 (3H, t, J=6.8 Hz), 4.37 (2H, q, J=6.8 Hz), 6.89 (1H, d, J=8.8 Hz), 7.05 (1H, s), 7.85 (1H, d, J=8.8 Hz), 8.08 (1H, t, J=7.6 Hz), 8.29 (1H, dd, J=1.6 Hz, 8.8 Hz), 8.83 (1H, s), 13.19 (1H, brs)

MS (m/z): 413 (M$^+$)

Example 104: N-(4-Chloro-3-{4-[6-(3-ethoxypropoxy)pyridin-3-yl]-6-oxo-1,6-dihydropyrimidin-2-yl}benzyl)isobutyramide By performing operations similar to those of Example 4 using 6-(3-ethoxypropoxy)pyridine-3-carbaldehyde, the title compound was obtained.

$^1$H-NMR (d$_6$-DMSO, δ): 1.03 (6H, d, J=6.8 Hz), 1.10 (3H, t, J=6.8 Hz), 1.96 (2H, quint, J=6.3 Hz), 2.43 (1H, sept, J=6.8 Hz), 3.42 (2H, q, J=6.8 Hz), 3.50 (2H, t, J=5.9 Hz), 4.31 (2H, d, J=6.3 Hz), 4.37 (2H, t, J=6.4 Hz), 6.89 (1H, d, J=8.8 Hz), 6.95 (1H, brs), 7.41 (1H, dd, J=1.9 Hz, 8.3 Hz), 7.5-7.6 (2H, m), 8.2-8.4 (2H, m), 8.87 (1H, d, J=2.4 Hz), 12.80 (1H, brs)

MS (m/z): 484 (M$^+$)

Example 105: N-(4-Chloro-3-{4-[6-(cyclopropylmethoxy)pyridin-3-yl]-6-oxo-1,6-dihydropyrimidin-2-yl}benzyl)isobutyramide By performing operations similar to those of Example 4 using 6-(cyclopropylmethoxy)pyridine-3-carbaldehyde, the title compound was obtained.

$^1$H-NMR (d$_6$-DMSO, δ): 0.3-0.4 (2H, m), 0.5-0.6 (2H, m), 1.03 (6H, d, J=6.811 Hz), 1.1-1.4 (1H, m), 2.43 (1H, sept, J=6.8 Hz), 4.16 (2H, d, J=6.8 Hz), 4.31 (2H, d, J=5.8 Hz), 6.8-7.0 (2H, m), 7.41 (1H, dd, J=1.9 Hz, 8.3 Hz), 7.5-7.6 (2H, m), 8.2-8.4 (2H, m), 8.85 (1H, d, J=1.9 Hz), 12.86 (1H, brs)

MS (m/z): 452 (M$^+$)

Example 106: N-[3-(4-{6-[2-(2-Butoxyethoxy)ethoxy]pyridin-3-yl}-6-oxo-1,6-dihydropyrimidin-2-yl)-4-chlorobenzyl]isobutyramide By performing operations similar to those of Example 4 using 6-[2-(2-butoxyethoxy)ethoxy]pyridine-3-carbaldehyde, the title compound was obtained.

$^1$H-NMR (d$_6$-DMSO, δ): 0.85 (3H, t, J=7.3 Hz), 1.03 (6H, d, J=6.8 Hz), 1.2-1.5 (4H, m), 2.43 (1H, sept, J=7.8 Hz), 3.36 (2H, t, J=6.4 Hz), 3.4-3.6 (4H, m), 3.7-3.8 (2H, m), 4.31 (2H, d, J=5.8 Hz), 4.4-4.5 (2H, m), 6.92 (1H, d, J=8.8 Hz), 6.96 (1H, brs), 7.41 (1H, dd, J=1.9 Hz, 8.3 Hz), 7.5-7.6 (2H, m), 8.2-8.4 (2H, m), 8.87 (1H, d, J=2.4 Hz), 12.77 (1H, brs)

MS (m/z): 542 (M$^+$)

Example 107: N-(4-Chloro-3-{6-oxo-4-[6-(pyridin-2-ylmethoxy)pyridin-3-yl]-1,6-dihydropyrimidin-2-yl}benzyl)isobutyramide By performing operations similar to those of Example 4 using 6-(pyridin-2-ylmethoxy)pyridine-3-carbaldehyde, the title compound was obtained.

$^1$H-NMR (d$_6$-DMSO, δ): 1.03 (6H, d, J=6.8 Hz), 2.43 (1H, sept, J=6.8 Hz), 4.31 (2H, d, J=5.8 Hz), 5.49 (2H, d, J=6.8 Hz), 6.97 (1H, hrs), 7.05 (1H, d, J=8.8 Hz), 7.3-7.4 (1H, m), 7.41 (1H, dd, J=1.9 Hz, 8.3 Hz), 7.46 (1H, d, J=7.8 Hz), 7.5-7.6 (2H, m), 7.81 (1H, dt, J=1.5 Hz, 7.3 Hz), 8.33 (1H, t, J=5.8 Hz), 8.39 (1H, dd, J=2.4 Hz, 8.8 Hz), 8.5-8.6 (1H, m), 8.87 (1H, d, J=2.4 Hz), 12.87 (1H, brs)

MS (m/z): 489 (M$^+$)

Example 108: N-(3-{6-Oxo-4-[6-(pyridin-2-ylmethoxy)pyridin-3-yl]-1,6-dihydropyrimidin-2-yl})-4-(trifluoromethyl)benzyl)isobutyramide By performing operations similar to those of Example 4 using 6-(pyridin-2-ylmethoxy)pyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.04 (6H, d, J=6.8 Hz), 2.45 (1H, sept, J=6.8 Hz), 4.40 (2H, d, J=5.8 Hz), 5.49 (2H, s), 6.98 (1H, brs), 7.04 (1H, d, J=8.8 Hz), 7.2-7.4 (1H, m), 7.46 (1H, d, J=7.8 Hz), 7.5-7.7 (2H, m), 7.80 (1H, dt, J=1.5 Hz, 7.9 Hz), 7.88 (1H, d, J=7.9 Hz), 8.3.8.6 (3H, m), 8.8-8.9 (1H, m), 12.95 (1H, brs)

MS (m/z): 523 (M$^+$)

Example 109: N-(4-Chloro-3-{4-[6-(6-methylpyridin-3-ylmethoxy)pyridin-3-yl]-6-oxo-1,6-dihydropyrimidin-2-yl}benzyl)isobutyramide By performing operations similar to those of Example 4 using 6-(6-methylpyridin-3-ylmethoxy)pyridine-3-carbaldehyde, the title compound was obtained.

$^1$H-NMR (d$_6$-DMSO, δ): 1.03 (6H, d, J=6.8 Hz), 2.43 (1H, sept, J=6.8 Hz), 2.46 (3H, s), 4.31 (2H, d, J=5.8 Hz), 5.42 (2H, s), 6.9-7.1 (2H, m), 7.26 (1H, d, J=1.3 Hz), 7.42 (1H, dd, J=2.0 Hz, 8.3 Hz), 7.5-7.6 (2H, m), 7.77 (1H, dd, J=2.4 Hz, 7.8 Hz), 8.2-8.4 (2H, m), 8.55 (1H, d, J=2.0 Hz), 8.90 (1H, d, J=2.5 Hz)

MS (m/z): 503 (M$^+$)

Example 110: N-{4-Chloro-3-[6-oxo-4-(2-oxo-1-pentyl-1,2-dihydropyridin-4-yl)-1,6-dihydropyrimidin-2-yl]benzyl}isobutyramide By performing operations similar to those of Example 4 using 2-oxo-1-pentyl-1,2-dihydropyridine-4-carbaldehyde, the title compound was obtained.

$^1$H-NMR (d$_6$-DMSO, δ): 0.86 (3H, t, J=7.3 Hz), 1.03 (6H, d, J=6.8 Hz), 1.1-1.4 (2H, m), 1.5-1.7 (2H, m), 2.43 (1H, sept, J=6.8 Hz), 3.89 (2H, t, J=6.9 Hz), 4.31 (2H, d, J=5.8 Hz), 6.80 (1H, dd, J=1.9 Hz, 6.8 Hz), 7.01 (1H, brs), 7.06 (1H, d, J=1.5 Hz), 7.42 (1H, dd, J=2.0 Hz, 8.3 Hz), 7.53 (1H, d, J=2.0 Hz), 7.57 (1H, d, J=8.3 Hz), 7.77 (1H, d, J=7.3 Hz), 8.34 (1H, t, J=6.1 Hz), 13.04 (1H, brs)
MS (m/z): 468 (M$^+$)

Example 111: N-{3-[4-(1-Butyl-2-oxo-1,2-dihydropyridin-4-yl)-6-oxo-1,6-dihydropyrimidin-2-yl]-4-chlorobenzyl}isobutyramide By performing operations similar to those of Example 4 using 1-butyl-2-oxo-1,2-dihydropyridine-4-carbaldehyde, the title compound was obtained.
$^1$H-NMR (d$_6$-DMSO, δ): 0.90 (3H, t, J=7.3 Hz), 1.03 (6H, d, J=6.8 Hz), 1.2-1.4 (2H, m), 1.5-1.7 (2H, m), 2.43 (1H, sept, J=6.8 Hz), 3.90 (2H, t, J=7.0 Hz), 4.31 (2H, d, J=5.8 Hz), 6.80 (1H, dd, J=1.4 Hz, 6.8 Hz), 7.01 (1H, brs), 7.06 (1H, d, J=1.9 Hz), 7.42 (1H, dd, J=2.5 Hz, 8.3 Hz), 7.53 (1H, d, J=2.0 Hz), 7.57 (1H, d, J=8.3 Hz), 7.77 (1H, d, J=7.3 Hz), 8.34 (1H, t, J=5.9 Hz), 13.03 (1H, brs)
MS (m/z): 454 (M$^+$)

Example 112: N-(4-Chloro-3-{4-[6-(difluoromethoxy)pyridin-3-yl]-6-oxo-1,6-dihydropyrimidin-2-yl}benzyl)propionamide By performing operations similar to those of Example 4 using 6-(difluoromethoxy)pyridine-3-carbaldehyde, and N-(3-carbamimidoyl-4-chlorobenzyl)propionamide hydrochloride, the title compound was obtained.
$^1$H-NMR (d$_6$-DMSO, δ): 1.02 (3H, t, J=7.8 Hz), 2.16 (2H, q, J=7.8 Hz), 4.31 (2H, d, J=6.4 Hz), 7.08 (1H, brs), 7.20 (1H, d, J=8.8 Hz), 7.43 (1H, dd, J=1.9 Hz, 8.3 Hz), 7.5-7.7 (2H, m), 7.77 (1H, t, J=72.7 Hz), 8.3-8.4 (1H, m), 8.54 (1H, dd, J=2.5 Hz, 8.8 Hz), 8.95 (1H, d, J=2.0 Hz), 12.95 (1H, brs)
MS (m/z): 434 (M$^+$)

Example 113: N-(4-Chloro-3-{4-[6-(cyclopropylmethoxy)pyridin-3-yl]-6-oxo-1,6-dihydropyrimidin-2-yl}benzyl)propionamide By performing operations similar to those of Example 4 using 6-(cyclopropylmethoxy)pyridine-3-carbaldehyde, and N-(3-carbamimidoyl-4-chlorobenzyl)propionamide hydrochloride, the title compound was obtained.
$^1$H-NMR (d$_6$-DMSO, δ): 0.3-0.4 (2H, m), 0.5-0.6 (2H, m), 1.02 (3H, t, J=7.3 Hz), 1.2-1.4 (1H, m), 2.16 (2H, q, J=7.8 Hz), 4.16 (2H, d, J=7.3 Hz), 4.32 (2H, d, J=5.9 Hz), 6.91 (1H, d, J=8.8 Hz), 6.95 (1H, brs), 7.43 (1H, dd, J=2.0 Hz, 8.8 Hz), 7.5-7.6 (2H, m), 8.2-8.4 (2H, m), 8.85 (1H, d, J=2.0 Hz), 12.80 (1H, brs)
MS (m/z): 438 (M$^+$)

Example 114: N-(4-Chloro-3-{4-[6-(difluoromethoxy)pyridin-3-yl]-6-oxo-1,6-dihydropyrimidin-2-yl}benzyl)butyramide By performing operations similar to those of Example 4 using 6-(difluoromethoxy)pyridine-3-carbaldehyde, and N-(3-carbamimidoyl-4-chlorobenzyl)butyramide hydrochloride, the title compound was obtained.
$^1$H-NMR (d$_6$-DMSO, δ): 0.85 (3H, t, J=7.3 Hz), 1.4-1.6 (2H, m), 2.13 (2H, t, J=7.3 Hz), 4.32 (2H, d, J=5.8 Hz), 7.08 (1H, brs), 7.20 (1H, d, J=8.7 Hz), 7.43 (1H, dd, J=1.9 Hz, 8.3 Hz), 7.5-7.7 (2H, m), 7.77 (1H, t, J=72.2 Hz), 8.3-8.5 (1H, m), 8.54 (1H, dd, J=2.5 Hz, 8.8 Hz), 8.95 (1H, d, J=2.5 Hz), 12.98 (1H, brs)
MS (m/z): 448 (M$^+$)

Example 115: N-(4-Chloro-3-{6-oxo-4-[6-(2-propoxyethoxy)pyridin-3-yl]-1,6-dihydropyrimidin-2-yl}benzyl)butyramide By performing operations similar to those of Example 4 using 6-(2-propoxyethoxy)pyridine-3-carbaldehyde, and N-(3-carbamimidoyl-4-chlorobenzyl)butyramide hydrochloride, the title compound was obtained.
$^1$H-NMR (d$_6$-DMSO, δ): 0.8-0.9 (6H, m), 1.4-1.6 (4H, m), 2.13 (2H, t, J=7.3 Hz), 3.40 (2H, t, J=6.8 Hz), 3.6-3.8 (2H, m), 4.32 (2H, d, J=6.3 Hz), 4.4-4.5 (2H, m), 6.92 (1H, d, J=8.8 Hz), 6.96 (1H, brs), 7.3-7.7 (3H, m), 8.2-8.5 (2H, m), 8.87 (1H, d, J=2.0 Hz), 12.87 (1H, brs)
MS (m/z): 484 (M$^+$)

Example 116: N-{4-Chloro-3-[4-(5-fluoropyridin-3-yl)-6-oxo-1,6-dihydropyrimidin-2-yl]benzyl}isobutyramide By performing operations similar to those of Example 4 using 5-fluoropyridine-3-carbaldehyde, the title compound was obtained.
$^1$H-NMR (d$_6$-DMSO, δ): 1.04 (6H, d, J=6.8 Hz), 2.44 (1H, sept, J=6.8 Hz), 4.32 (2H, d, J=6.4 Hz), 7.19 (1H, brs), 7.43 (1H, dd, J=2.0 Hz, 8.3 Hz), 7.5-7.7 (2H, m), 8.2-8.4 (2H, m), 8.70 (1H, d, J=2.9 Hz), 9.14 (1H, s), 13.05 (1H, brs)
MS (m/z): 400 (M$^+$)

Example 117: N-(4-Chloro-3-{6-oxo-4-[6-(2,2,2-trifluoroethoxy)pyridin-3-yl]-1,6-dihydropyrimidin-2-yl}benzyl)propionamide By performing operations similar to those of Example 4 using 6-(2,2,2-trifluoroethoxy)pyridine-3-carbaldehyde, and N-(3-carbamimidoyl-4-chlorobenzyl)propionamide hydrochloride, the title compound was obtained.
$^1$H-NMR (d$_6$-DMSO, δ): 1.02 (3H, t, J=7.3 Hz), 2.16 (2H, q, J=7.8 Hz), 4.32 (2H, d, J=5.9 Hz), 5.07 (2H, q, J=8.8 Hz), 7.02 (1H, brs), 7.10 (1H, d, J=8.8 Hz), 7.43 (1H, dd, J=1.9 Hz, 8.3 Hz), 7.5-7.6 (2H, m), 8.3-8.4 (1H, m), 8.44 (1H, dd, J=2.4 Hz, 8.8 Hz), 8.91 (1H, d, J=2.5 Hz), 12.83 (1H, brs)
MS (m/z): 466 (M$^+$)

Example 118: N-(4-Chloro-3-{4-[5-(difluoromethoxy)pyridin-2-yl]-6-oxo-1,6-dihydropyrimidin-2-yl}benzyl)butyramide By performing operations similar to those of Example 4 using 5-(difluoromethoxy)pyridine-2-carbaldehyde, and N-(3-carbamimidoyl-4-chlorobenzyl)butyramide hydrochloride, the title compound was obtained.
$^1$H-NMR (d$_6$-DMSO, δ): 0.85 (3H, t, J=7.8 Hz), 1.4-1.6 (2H, m), 2.13 (2H, t, J=7.3 Hz), 4.33 (2H, d, J=5.9 Hz), 7.18 (1H, brs), 7.41 (1H, t, J=72.8 Hz), 7.44 (1H, dd, J=2.0 Hz, 8.3 Hz), 7.5-7.7 (2H, m), 7.80 (1H, dd, J=2.4 Hz, 8.3 Hz), 8.30 (1H, d, J=8.8 Hz), 8.38 (1H, t, J=5.9 Hz), 8.63 (1H, d, J=2.9 Hz), 13.04 (1H, brs)
MS (m/z): 448 (M$^+$)

Example 119: N-{3-[4-(5-Chloropyridin-3-yl)-6-oxo-1,6-dihydropyrimidin-2-yl]-4-(trifluoromethyl)benzyl}isobutyramide By performing operations similar to those of Example 4 using 5-chloropyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=6.8 Hz), 2.46 (1H, sept, J=6.9 Hz), 4.40 (2H, d, J=5.8 Hz), 7.23 (1H, brs), 7.5-7.7 (2H, m), 7.90 (1H, d, J=8.3 Hz), 8.3-8.5 (1H, m), 8.48 (1H, s), 8.74 (1H, d, J=1.9 Hz), 9.19 (1H, s), 13.17 (1H, brs)

MS (m/z): 450 (M$^+$)

Example 120: N-{3-[4-(5-Fluoropyridin-3-yl)-6-oxo-1,6-dihydropyrimidin-2-yl]-4-(trifluoromethyl)benzyl}isobutyramide By performing operations similar to those of Example 4 using 5-fluoropyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=6.8 Hz), 2.46 (1H, sept, J=6.8 Hz), 4.41 (2H, d, J=5.8 Hz), 7.21 (1H, brs), 7.5-7.7 (2H, m), 7.90 (1H, d, J=8.3 Hz), 8.28 (1H, d, J=9.8 Hz), 8.3-8.5 (1H, m), 8.70 (1H, d, J=2.9 Hz), 9.13 (1H, s), 13.16 (1H, brs)

MS (m/z): 434 (M$^+$)

Example 121: N-(4-Chloro-3-{4-[5-(difluoromethoxy)pyridin-2-yl]6-oxo-1,6-dihydropyrimidin-2-yl}benzyl)propionamide By performing operations similar to those of Example 4 using 5-(difluoromethoxy)pyridine-2-carbaldehyde, and N-(3-carbamimidoyl-4-chlorobenzyl)propionamide hydrochloride, the title compound was obtained.

$^1$H-NMR (d$_6$-DMSO, δ): 1.03 (3H, t, J=7.8 Hz), 2.16 (2H, q, J=7.3 Hz), 4.32 (2H, d, J=5.8 Hz), 7.19 (1H, brs), 7.42 (1H, t, J=73.3 Hz), 7.44 (1H, dd, J=2.5 Hz, 8.8 Hz), 7.5-7.7 (2H, m), 7.80 (1H, dd, J=2.4 Hz, 8.3 Hz), 8.31 (1H, d, J=8.8 Hz), 8.35 (1H, t, J=5.8 Hz), 8.63 (1H, d, J=2.4 Hz), 12.96 (1H, brs)

MS (m/z): 434 (M$^+$)

Example 122: N-{4-Chloro-3-[4-(5-methoxypyridin-3-yl)-6-oxo-1,6-dihydropyrimidin-2-yl]benzyl}isobutyramide By performing operations similar to those of Example 4 using 5-methoxypyridine-3-carbaldehyde, the title compound was obtained.

$^1$H-NMR (d$_6$-DMSO, δ): 1.03 (6H, d, J=6.8 Hz), 2.43 (1H, sept, J=6.8 Hz), 3.90 (3H, s), 4.32 (2H, d, J=5.9 Hz), 7.14 (1H, hrs), 7.42 (1H, dd, J=2.4 Hz, 8.3 Hz), 7.5-7.7 (2H, m), 7.94 (1H, d, J=2.2 Hz), 8.34 (1H, t, J=5.9 Hz), 8.40 (1H, d, J=3.0 Hz), 8.85 (1H, d, J=1.9 Hz), 12.98 (1H, brs)

MS (m/z): 412 (M$^+$)

Example 123: N-{3-[4-(5-Methoxypyridin-3-yl)-6-oxo-1,6-dihydropyrimidin-2-yl]-4-(trifluoromethyl)benzyl}isobutyramide By performing operations similar to those of Example 4 using 5-methoxypyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=6.8 Hz), 2.46 (1H, sept, J=6.8 Hz), 3.88 (3H, s), 4.40 (2H, d, J=5.8 Hz), 7.17 (1H, brs), 7.5-7.7 (2H, m), 7.8-8.0 (2H, m), 8.3-8.5 (2H, m), 8.83 (1H, s), 13.04 (1H, brs)

MS (m/z): 446 (M$^+$)

Example 124: N-(4-Chloro-3-{6-oxo-4-[6-propoxypyridin-3-yl]-1,6-dihydropyrimidin-2-yl}benzyl)propionamide By performing operations similar to those of Example 4 using 6-propoxypyridine-3-carbaldehyde, and N-(3-carbamimidoyl-4-chlorobenzyl)propionamide hydrochloride, the title compound was obtained.

$^1$H-NMR (d$_6$-DMSO, δ): 0.9-1.1 (6H, m), 1.6-1.8 (2H, m), 2.16 (2H, q, J=7.8 Hz), 4.2-4.4 (4H, m), 6.89 (1H, d, J=8.8 Hz), 6.95 (1H, brs), 7.43 (1H, dd, J=2.0 Hz, 8.3 Hz), 7.5-7.6 (2H, m), 8.2-8.4 (2H, m), 8.86 (1H, d, J=2.5 Hz), 12.85 (1H, brs)

MS (m/z): 426 (M$^+$)

Example 125: N-(4-Chloro-3-{4-[6-(2,2-difluoroethoxy)pyridin-3-yl]-6-oxo-1,6-dihydropyrimidin-2-yl}benzyl)propionamide By performing operations similar to those of Example 4 using 6-(2,2-difluoroethoxy)pyridine-3-carbaldehyde, and N-(3-carbamimidoyl-4-chlorobenzyl)propionamide hydrochloride, the title compound was obtained.

$^1$H-NMR (d$_6$-DMSO, δ): 1.02 (3H, t, J=7.8 Hz), 2.16 (2H, q, J=7.3 Hz), 4.32 (2H, d, J=5.9 Hz), 4.64 (2H, dt, J=3.4 Hz, 15.1 Hz), 6.41 (1H, tt, J=3.6 Hz, 54.7 Hz), 7.00 (1H, brs), 7.03 (1H, d, J=8.8 Hz), 7.43 (1H, dd, J=1.9 Hz, 8.3 Hz), 7.5-7.6 (2H, m), 8.35 (1H, t, J=5.9 Hz), 8.40 (1H, dd, J=2.5 Hz, 8.8 Hz), 8.90 (1H, d, J=2.0 Hz), 12.89 (1H, brs)

MS (m/z): 448 (M$^+$)

Example 126: N-{4-Chloro-3-[4-(5-methylpyridin-3-yl)-6-oxo-1,6-dihydropyrimidin-2-yl]benzyl}isobutyramide By performing operations similar to those of Example 4 using 5-methylpyridine-3-carbaldehyde, the title compound was obtained.

$^1$H-NMR (d$_6$-DMSO, δ): 1.03 (6H, d, J=6.8 Hz), 2.36 (3H, s), 2.3-2.5 (1H, m), 4.32 (2H, d, J=5.9 Hz), 7.05 (1H, brs), 7.42 (1H, dd, J=1.9 Hz, 8.3 Hz), 7.5-7.6 (2H, m), 8.23 (1H, s), 8.35 (1H, t, J=5.8 Hz), 8.52 (1H, s), 9.03 (1H, d, J=1.4 Hz), 12.95 (1H, brs)

MS (m/z): 396 (M$^+$)

Example 127: N-{3-[4-(5-Methylpyridin-3-yl)-6-oxo-1,6-dihydropyrimidin-2-yl]-4-(trifluoromethyl)benzyl}isobutyramide By performing operations similar to those of Example 4 using 5-methylpyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=6.8 Hz), 2.35 (3H, s), 2.4-2.6 (1H, m), 4.40 (2H, d, J=6.4 Hz), 7.08 (1H, brs), 7.5-7.7 (2H, m), 7.89 (1H, d, J=7.8 Hz), 8.21 (1H, s), 8.40 (1H, t, J=5.9 Hz), 8.51 (1H, s), 9.02 (1H, s), 13.01 (1H, brs)

MS (m/z): 430 (M$^+$)

Example 128: N-{4-Chloro-2-fluoro-3-[4-(5-methylpyridin-3-yl)-6-oxo-1,6-dihydropyrimidin-2-yl]benzyl}isobutyramide By performing operations similar to those of Example 4 using 5-methylpyridine-3-carbaldehyde, and N-(3-carbamimidoyl-4-chloro-2-fluorobenzyl)isobutyramide hydrochloride, the title compound was obtained.

¹H-NMR (d₆-DMSO, δ): 1.05 (6H, d, J=6.8 Hz), 2.36 (3H, s), 2.3-2.6 (1H, m), 4.32 (2H, d, J=5.9 Hz), 7.11 (1H, brs), 7.4-7.6 (2H, m), 8.21 (1H, s), 8.36 (1H, t, J=5.4 Hz), 8.52 (1H, s), 9.01 (1H, d, J=1.2 Hz), 13.17 (1H, brs)

MS (m/z): 414 (M⁺)

Example 129: N-{4-Chloro-3-[4-(5-methoxypyridin-2-yl)-6-oxo-1,6-dihydropyrimidin-2-yl]benzyl}isobutyramide By performing operations similar to those of Example 4 using 5-methoxypyridine-2-carbaldehyde, the title compound was obtained.

¹H-NMR (d₆-DMSO, δ): 1.04 (6H, d, J=6.8 Hz), 2.44 (1H, sept, J=6.8 Hz), 3.90 (3H, s), 4.32 (2H, d, J=5.9 Hz), 7.12 (1H, brs), 7.42 (1H, dd, J=2.4 Hz, 8.3 Hz), 7.50 (1H, dd, J=3.0 Hz, 8.8 Hz), 7.5-7.6 (2H, m), 8.21 (1H, d, J=8.8 Hz), 8.34 (1H, t, J=5.9 Hz), 8.43 (1H, d, J=3.0 Hz), 12.84 (1H, brs)

MS (m/z): 412 (M⁺)

Example 130: N-{4-Chloro-3-[4-(1-isopropyl-1H-pyrazol-4-yl)-6-oxo-1,6-dihydropyrimidin-2-yl]benzyl}isobutyramide By performing operations similar to those of Example 4 using 1-isopropyl-1H-pyrazole-4-carbaldehyde, the title compound was obtained.

¹H-NMR (d₆-DMSO, δ): 1.03 (6H, d, J=6.8 Hz), 1.42 (6H, d, J=6.4 Hz), 2.43 (1H, sept, J=6.8 Hz), 4.30 (2H, d, J=5.8 Hz), 4.52 (1H, sept, J=6.3 Hz), 6.62 (1H, brs), 7.39 (1H, dd, J=1.9 Hz, 8.3 Hz), 7.47 (1H, d, J=1.9 Hz), 7.54 (1H, d, J=8.3 Hz), 8.00 (1H, s), 8.2-8.4 (2H, m), 12.39 (1H, brs)

MS (m/z): 413 (M⁺)

Example 131: N-{4-Chloro-3-[6-oxo-4-(1-propyl-1H-pyrazol-4-yl)-1,6-dihydropyrimidin-2-yl]benzyl}isobutyramide By performing operations similar to those of Example 4 using 1-propyl-1H-pyrazole-4-carbaldehyde, the title compound was obtained.

¹H-NMR (d₆-DMSO, δ): 0.82 (3H, t, J=7.6 Hz), 1.03 (6H, d, J=6.8 Hz), 1.7-1.9 (2H, m), 2.43 (1H, sept, J=6.8 Hz), 4.08 (2H, t, J=6.8 Hz), 4.30 (2H, d, J=6.3 Hz), 6.61 (1H, brs), 7.39 (1H, dd, J=1.9 Hz, 8.3 Hz), 7.48 (1H, d, J=2.5 Hz), 7.54 (1H, d, J=7.8 Hz), 8.01 (1H, s), 8.2-8.4 (2H, m), 12.13 (1H, brs)

MS (m/z): 413 (M⁺)

Example 132: N-(4-Difluoromethoxy-3-{4-[6-(difluoromethoxy)pyridin-3-yl]-6-oxo-1,6-dihydropyrimidin-2-yl}benzyl)isobutyramide By performing operations similar to those of Example 4 using 6-(difluoromethoxy)pyridine-3-carbaldehyde, and N-[3-carbamimidoyl-4-(difluoromethoxy)benzyl]isobutyramide hydrochloride, the title compound was obtained.

¹H-NMR (d₆-DMSO, δ): 1.04 (6H, d, J=6.8 Hz), 2.43 (1H, sept, J=6.8 Hz), 4.32 (2H, d, J=6.4 Hz), 6.9-8.0 (7H, m), 8.34 (1H, t, J=5.9 Hz), 8.56 (1H, dd, J=2.4 Hz, 8.8 Hz), 8.97 (1H, d, J=2.0 Hz), 12.77 (1H, brs)

MS (m/z): 480 (M⁺)

Example 133: N-[4-Chloro-3-(4-{6-[2-(2-methoxyethoxy)ethoxy]pyridin-3-yl}-6-oxo-1,6-dihydropyrimidin-2-yl)benzyl]isobutyramide By performing operations similar to those of Example 4 using 6-[2-(2-methoxyethoxy)ethoxy]pyridine-3-carbaldehyde, the title compound was obtained.

¹H-NMR (d₆-DMSO, δ): 1.03 (6H, d, J=6.8 Hz), 2.43 (1H, sept, J=6.8 Hz), 3.24 (3H, s), 3.4-3.6 (4H, m), 3.7-3.8 (2H, m), 4.31 (2H, d, J=5.8 Hz), 4.4-4.5 (2H, m), 6.92 (1H, d, J=8.8 Hz), 6.96 (1H, brs), 7.41 (1H, dd, J=1.9 Hz, 8.3 Hz), 7.5-7.6 (2H, m), 8.2-8.4 (2H, m), 8.87 (1H, d, J=1.9 Hz), 12.86 (1H, brs)

MS (m/z): 500 (M⁺)

Example 134: N-{4-Chloro-3-[4-(6-{2-[2-(2-ethoxyethoxy)ethoxy]ethoxy}pyridin-3-yl)-6-oxo-1,6-dihydropyrimidin-2-yl]benzyl}isobutyramide By performing operations similar to those of Example 4 using 6-{2-[2-(2-ethoxyethoxy)ethoxy]ethoxy}pyridine-3-carbaldehyde, the title compound was obtained.

¹H-NMR (d₆-DMSO, δ): 1.03 (6H, d, J=6.8 Hz), 1.08 (3H, t, J=6.8 Hz), 2.43 (1H, sept, J=6.8 Hz), 3.3-3.8 (12H, m), 4.31 (2H, d, J=5.8 Hz), 4.4-4.5 (2H, m), 6.92 (1H, d, J=8.8 Hz), 6.96 (1H, brs), 7.42 (1H, dd, J=2.0 Hz, 8.3 Hz), 7.5-7.6 (2H, m), 8.2-8.4 (2H, m), 8.87 (1H, d, J=2.4 Hz), 12.84 (1H, brs)

MS (m/z): 558 (M⁺)

Example 135: N-(4-Chloro-3-{4-[6-(6-methylpyridin-2-ylmethoxy)pyridin-3-yl]-6-oxo-1,6-dihydropyrimidin-2-yl}benzyl)isobutyramide By performing operations similar to those of Example 4 using 6-(6-methylpyridin-2-ylmethoxy)pyridine-3-carbaldehyde, the title compound was obtained.

¹H-NMR (d₆-DMSO, δ): 1.03 (6H, d, J=6.8 Hz), 2.43 (1H, sept, J=6.8 Hz), 2.47 (3H, s), 4.31 (2H, d, J=5.8 Hz), 5.44 (2H, s), 6.97 (1H, brs), 7.04 (1H, d, J=8.8 Hz), 7.18 (1H, d, J=7.8 Hz), 7.24 (1H, d, J=7.3 Hz), 7.41 (1H, dd, J=1.9 Hz, 8.3 Hz), 7.5-7.6 (2H, m), 7.68 (1H, t, J=7.8 Hz), 8.33 (1H, t, J=5.8 Hz), 8.38 (1H, dd, J=2.4 Hz, 8.8 Hz), 8.87 (1H, d, J=2.4 Hz), 12.71 (1H, brs)

MS (m/z): 503 (M⁺)

Example 136: N-(4-Chloro-3-{6-oxo-4-[6-(2-propoxyethoxy)pyridin-3-yl]-1,6-dihydropyrimidin-2-yl}benzyl)propionamide By performing operations similar to those of Example 4 using 6-(2-propoxyethoxy)pyridine-3-carbaldehyde, and N-(3-carbamimidoyl-4-chlorobenzyl)propionamide hydrochloride, the title compound was obtained.

¹H-NMR (d₆-DMSO, δ): 0.86 (3H, t, J=7.3 Hz), 1.02 (3H, t, J=7.6 Hz), 1.4-1.6 (2H, m), 2.16 (2H, q, J=7.8 Hz), 3.40 (2H, t, J=6.8 Hz), 3.6-3.8 (2H, m), 4.32 (2H, d, J=5.9 Hz), 4.4-4.5 (2H, m), 6.93 (1H, d, J=8.8 Hz), 6.96 (1H, brs), 7.43 (1H, dd, J=2.0 Hz, 8.3 Hz), 7.5-7.6 (2H, m), 8.3-8.4 (2H, m), 8.87 (1H, d, J=2.4 Hz), 12.74 (1H, brs)

MS (m/z): 470 (M⁺)

Example 137: N-(4-Chloro-3-{4-[6-(2-ethoxyethoxy)pyridin-3-yl]-6-oxo-1,6-dihydropyrimidin-2-yl}benzyl)butyramide By performing operations similar to those of Example 4 using 6-(2-ethoxyethoxy)pyridine-3-carbaldehyde, and N-(3-carbamimidoyl-4-chlorobenzyl)butyramide hydrochloride, the title compound was obtained.

¹H-NMR (d₆-DMSO, δ): 0.85 (3H, t, J=8.1 Hz), 1.12 (3H, t, J=7.8 Hz), 1.4-1.6 (2H, m), 2.13 (2H, t, J=7.3 Hz), 3.49 (2H, q, J=7.3 Hz), 3.6-3.8 (2H, m), 4.32 (2H, d, J=5.8 Hz), 4.3-4.5 (2H, m), 6.93 (1H, d, J=8.8 Hz), 6.96 (1H, brs), 7.43 (1H, dd, J=2.0 Hz, 8.3 Hz), 7.5-7.7 (2H, m), 8.2-8.5 (2H, m), 8.87 (1H, d, J=2.4 Hz), 12.87 (1H, brs)

MS (m/z): 470 (M⁺)

Example 138: N-(4-Chloro-3-{4-[6-(2-fluoroethoxy)pyridin-3-yl]-6-oxo-1,6-dihydropyrimidin-2-yl}benzyl)butyramide By performing operations similar to those of Example 4 using 6-(2-fluoroethoxy)pyridine-3-carbaldehyde, and N-(3-carbamimidoyl-4-chlorobenzyl)butyramide hydrochloride, the title compound was obtained.

¹H-NMR (d₆-DMSO, δ): 0.85 (3H, t, J=7.3 Hz), 1.4-1.6 (2H, m), 2.13 (2H, t, J=7.1 Hz), 4.32 (2H, d, J=5.8 Hz), 4.5-4.9 (4H, m), 6.97 (1H, d, J=8.3 Hz), 6.97 (1H, brs), 7.43 (1H, dd, J=2.5 Hz, 8.3 Hz), 7.5-7.6 (2H, m), 8.3-8.5 (2H, m), 8.88 (1H, d, J=2.5 Hz), 12.87 (1H, brs)

MS (m/z): 444 (M⁺)

Example 139: N-(4-Chloro-3-{4-[6-(3-fluoropropoxy)pyridin-3-yl]-6-oxo-1,6-dihydropyrimidin-2-yl}benzyl)propionamide By performing operations similar to those of Example 4 using 6-(3-fluoropropoxy)pyridine-3-carbaldehyde, and N-(3-carbamimidoyl-4-chlorobenzyl)propionamide hydrochloride, the title compound was obtained.

¹H-NMR (d₆-DMSO, δ): 1.02 (3H, t, J=7.8 Hz), 2.0-2.3 (4H, m), 4.32 (2H, d, J=6.4 Hz), 4.43 (2H, t, J=6.3 Hz), 4.55 (1H, t, J=6.4 Hz), 4.66 (1H, t, J=5.9 Hz), 6.92 (1H, d, J=8.8 Hz), 6.96 (1H, brs), 7.43 (1H, dd, J=2.0 Hz, 8.3 Hz), 7.5-7.6 (2H, m), 8.3-8.4 (2H, m), 8.88 (1H, d, J=2.5 Hz), 12.87 (1H, brs)

MS (m/z): 444 (M⁺)

Example 140: N-(3-(4-[6-(2-Ethoxyethoxy)pyridin-3-yl]-6-oxo-1,6-dihydropyrimidin-2-yl)-4-(trifluoromethyl)benzyl)isobutyramide By performing operations similar to those of Example 4 using 6-(2-ethoxyethoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=7.2 Hz), 1.12 (3H, t, J=7.2 Hz), 2.46 (1H, sept, J=7.2 Hz), 3.49 (2H, q, J=7.2 Hz), 3.7-3.8 (2H, m), 4.3-4.4 (4H, m), 6.92 (1H, d, J=8.8 Hz), 6.96 (1H, s), 7.5-7.6 (2H, m), 7.88 (1H, d, J=8.0 Hz), 8.31 (1H, d, J=8.8 Hz), 8.39 (1H, t, J=6.0 Hz), 8.84 (1H, s), 12.97 (1H, s)

MS (m/z): 504 (M⁺)

Example 141: N-(3-{6-Oxo-4-[6-(2-propoxyethoxy)pyridin-3-yl]-1,6-dihydropyrimidin-2-yl}-4-(trifluoromethyl)benzyl)isobutyramide By performing operations similar to those of Example 4 using 6-(2-propoxyethoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 0.85 (3H, t, J=7.2 Hz), 1.05 (6H, d, J=7.2 Hz), 1.5-1.6 (2H, m), 2.46 (1H, sept, J=6.8 Hz), 3.40 (2H, t, J=6.8 Hz), 3.6-3.7 (2H, m), 4.4-4.5 (4H, m), 6.92 (1H, d, J=8.4 Hz), 6.97 (1H, s), 7.5-7.6 (2H, m), 7.88 (1H, d, J=8.0 Hz), 8.31 (1H, d, J=8.0 Hz), 8.39 (1H, t, J=6.0 Hz), 8.85 (1H, s), 12.97 (1H, s)

MS (m/z): 518 (M⁺)

Example 142: N-{3-[4-(6-Cyclopropylpyridin-3-yl)-6-oxo-1,6-dihydropyrimidin-2-yl]-4-(trifluoromethyl)benzyl}isobutyramide By performing operations similar to those of Example 4 using 6-cyclopropylpyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.0-1.1 (10H, m), 2.1-2.2 (1H, m), 2.4-2.6 (1H, m), 4.40 (2H, d, J=6.0 Hz), 7.01 (1H, s), 7.39 (1H, d, J=8.0 Hz), 7.5-7.6 (2H, m), 7.88 (1H, d, J=8.0 Hz), 8.23 (1H, d, J=6.8 Hz), 8.39 (1H, t, J=6.0 Hz), 9.04 (1H, s), 13.00 (1H, s)

MS (m/z): 456 (M⁺)

Example 143: N-(3-{4-[6-(2-Butoxyethoxy)pyridin-3-yl]-6-oxo-1,6-dihydropyrimidin-2-yl}-4-(trifluoromethyl)benzyl)isobutyramide By performing operations similar to those of Example 4 using 6-(2-butoxyethoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 0.86 (3H, t, J=7.2 Hz), 1.05 (6H, d, J=6.8 Hz), 1.2-1.3 (2H, m), 1.4-1.5 (2H, m), 2.4-2.6 (1H, m), 3.43 (2H, t, J=6.8 Hz), 3.6-3.7 (2H, m), 4.4-4.5 (4H, m), 6.91 (1H, d, J=8.8 Hz), 6.96 (1H, s), 7.5-7.6 (2H, m), 7.88 (1H, d, J=8.0 Hz), 8.31 (1H, d, J=8.8 Hz), 8.39 (1H, t, J=6.0 Hz), 8.84 (1H, s), 12.96 (1H, s)

MS (m/z): 532 (M⁺)

Example 144: N-(3-{4-[6-(3-Methoxypropoxy)pyridin-3-yl]-6-oxo-1,6-dihydropyrimidin-2-yl}-4-(trifluoromethyl)benzyl)isobutyramide By performing operations similar to those of Example 4 using 6-(3-methoxypropoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=7.2 Hz), 1.96 (2H, quin, J=6.8 Hz), 2.4-2.6 (1H, m), 3.24 (3H, s), 3.46 (2H, t, J=6.4 Hz), 4.36 (2H, t, J=6.8 Hz), 4.40 (2H, d, J=5.6 Hz), 6.89 (1H, d, J=8.8 Hz), 6.96 (1H, s), 7.5-7.6 (2H, m), 7.88 (1H, d, J=8.4 Hz), 8.30 (1H, d, J=8.4 Hz), 8.39 (1H, t, J=6.4 Hz), 8.84 (1H, s), 12.97 (1H, s)

MS (m/z): 504 (M⁺)

Example 145: N-[4-Chloro-3-(6-oxo-4-pyridin-3-yl-1,6-dihydropyrimidin-2-yl)benzyl]isobutyramide By performing operations similar to those of Example 4 using pyridine-3-carbaldehyde, the title compound was obtained.

¹H-NMR (d₆-DMSO, δ): 1.03 (6H, d, J=6.8 Hz), 2.4-2.6 (1H, m), 4.32 (2H, d, J=6.0 Hz), 7.09 (1H, s), 7.42 (1H, dd, J=2.0 Hz, 8.4 Hz), 7.5-7.6 (3H, m), 8.34 (1H, t, J=6.0 Hz), 8.4-8.5 (1H, m), 8.68 (1H, dd, J=1.6 Hz, 4.8 Hz), 9.24 (1H, d, J=2.0 Hz), 12.99 (1H, s)

MS (m/z): 382 (M⁺)

Example 146: N-{3-[4-(6-Methoxypyridin-3-yl)-6-oxo-1,6-dihydropyrimidin-2-yl]-4-methylbenzyl}isobutyramide By performing operations similar to those of Example 4 using 6-methoxypyridine-3-carbaldehyde, and N-(3-carbamimidoyl-4-methylbenzyl)isobutyramide hydrochloride, the title compound was obtained.

$^1$H-NMR (d$_6$-DMSO, δ): 1.03 (6H, d, J=6.8 Hz), 2.3-2.6 (4H, m), 3.92 (3H, s), 4.28 (2H, d, J=6.0 Hz), 6.9-7.0 (2H, m), 7.2-7.3 (2H, m), 7.42 (1H, s), 8.24 (1H, t, J=6.0 Hz), 8.34 (1H, dd, J=2.4 Hz, 8.8 Hz), 8.89 (1H, d, J=2.0 Hz), 12.65 (1H, s)

MS (m/z): 392 (M$^+$)

Example 147: N-(4-Chloro-3-{6-oxo-4-[2-(trifluoromethyl)pyridin-4-yl]-1,6-dihydropyrimidin-2-yl}benzyl)isobutyramide By performing operations similar to those of Example 4 using 2-(trifluoromethyl)pyridine-4-carbaldehyde, the title compound was obtained.

$^1$H-NMR (d$_6$-DMSO, δ): 1.03 (6H, d, J=6.8 Hz), 2.43 (1H, sept, J=6.8 Hz), 4.32 (2H, d, J=6.0 Hz), 7.36 (1H, s), 7.44 (1H, dd, J=2.0 Hz, 8.4 Hz), 7.5-7.6 (2H, m), 8.3-8.4 (2H, m), 8.44 (1H, s), 8.91 (1H, d, J=5.6 Hz), 13.19 (1H, s)

MS (m/z): 450 (M$^+$)

Example 148: N-[4-(Difluoromethyl)-3-{6-oxo-4-[6-(trifluoromethyl)pyridin-3-yl]-1,6-dihydropyrimidin-2-yl}benzyl]isobutyramide By performing operations similar to those of Example 4 using 6-(trifluoromethyl)pyridine-3-carbaldehyde, and N-[3-carbamimidoyl-4-(difluoromethyl)benzyl]isobutyramide hydrochloride, the title compound was obtained.

$^1$H-NMR (d$_6$-DMSO, δ): 1.05 (6H, d, J=6.8 Hz), 2.4-2.6 (1H, m), 4.39 (2H, d, J=6.0 Hz), 7.26 (1H, s), 7.43 (1H, m), 7.58 (1H, d, J=8.0 Hz), 7.68 (1H, t, J=98.4 Hz), 7.80 (1H, d, J=8.0 Hz), 8.05 (1H, d, J=8.4 Hz), 8.34 (1H, t, J=5.6 Hz), 8.72 (1H, d, J=7.2 Hz), 9.44 (1H, a), 13.17 (1H, s)

MS (m/z): 466 (M$^+$)

Example 149: N-(3-{4-[2-(Cyclopropylmethoxy)pyridin-4-yl]-6-oxo-1,6-dihydropyrimidin-2-yl}-4-(trifluoromethyl)benzyl)isobutyramide By performing operations similar to those of Example 4 using 2-(cyclopropylmethoxy)pyridine-4-carbaldehyde, and N-[3-carbamimidoyl-4-(trifluoromethyl)benzyl]isobutyramide hydrochloride, the title compound was obtained.

$^1$H-NMR (d$_6$-DMSO, δ): 0.3-0.4 (2H, m), 0.5-0.6 (2H, m), 1.05 (6H, d, J=6.8 Hz), 1.2-1.3 (1H, m), 2.4-2.6 (1H, m), 4.13 (2H, d, J=6.8 Hz), 4.40 (2H, d, J=6.0 Hz), 7.14 (1H, s), 7.40 (1H, s), 7.5-7.7 (3H, m), 7.89 (1H, d, J=8.0 Hz), 8.23 (1H, d, J=5.6 Hz), 8.39 (1H, t, J=6.4 Hz), 13.13 (1H, s)

MS (m/z): 486 (M$^+$)

Example 150: N-(3-{4-[6-(Cyclopropylmethoxy)pyridazin-3-yl]-6-oxo-1,6-dihydropyrimidin-2-yl}-4-(trifluoromethyl)benzyl)isobutyramide By performing operations similar to those of Example 4 using 6-(cyclopropylmethoxy)pyridazine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 0.4-0.6 (4H, m), 1.05 (6H, d, J=7.2 Hz), 1.3-1.4 (1H, m), 2.45 (1H, sept, J=6.8 Hz), 4.03 (2H, d, J=7.6 Hz), 4.40 (2H, d, J=5.6 Hz), 7.0-7.1 (2H, m), 7.6-7.7 (2H, m), 7.88 (1H, d, J=8.4 Hz), 8.0-8.1 (1H, m), 8.40 (1H, t, J=6.4 Hz), 13.10 (1H, s)

MS (m/z): 487 (M$^+$)

Example 151: 4-(2-{2-Chloro-5-[(3,3,3-trifluoro-2,2-dimethylpropionylamino)methyl]phenyl}-6-oxo-1,6-dihydropyrimidin-4-yl)-N,N-dimethylbenzamide By performing operations similar to those of Example 4 using 4-formyl-N,N-dimethylbenzamide, and N-(3-carbamimidoyl-4-chlorobenzyl)-3,3,3-trifluoro-2,2-dimethylpropionamide hydrochloride, the title compound was obtained.

$^1$H-NMR (d$_6$-DMSO, δ): 1.38 (6H, s), 2.92 (3H, s), 3.00 (3H, s), 4.37 (2H, d, J=6.0 Hz), 7.00 (1H, s), 7.40 (1H, dd, J=2.0 Hz, 8.4 Hz), 7.49 (2H, d, J=8.4 Hz), 7.55 (1H, d, J=2.0 Hz), 7.58 (1H, d, J=8.4 Hz), 8.13 (2H, d, J=8.0 Hz), 8.61 (1H, t, J=6.0 Hz), 12.89 (1H, brs)

MS (m/z): 520 (M$^+$)

Example 152: N-(3-(4-[6-(Difluoromethoxy)pyridin-3-yl]-6-oxo-1,6-dihydropyrimidin-2-yl)-2,4-difluorobenzyl)isobutyramide By performing operations similar to those of Example 4 using 6-(difluoromethoxy)pyridine-3-carbaldehyde, and N-(3-carbamimidoyl-2,4-difluorobenzyl)isobutyramide hydrochloride, the title compound was obtained.

$^1$H-NMR (d$_6$-DMSO, δ): 1.04 (6H, d, J=6.8 Hz), 2.4-2.6 (1H, m), 4.32 (2H, d, J=5.6 Hz), 7.12 (1H, s), 7.20 (1H, d, J=8.8 Hz), 7.29 (1H, t, J=8.8 Hz), 7.4-7.6 (1H, m), 7.77 (1H, t, J=72.8 Hz), 8.33 (1H, t, J=5.6 Hz), 8.52 (1H, dd, J=2.0 Hz, 8.8 Hz), 8.93 (1H, d, J=1.6 Hz), 13.23 (1H, brs)

MS (m/z): 450 (M$^+$)

Example 153: N-[3-(2'-Methoxy-6-oxo-1,6-dihydro-[4,5'-bipyrimidin]-2-yl)-4-(trifluoromethyl)benzyl]isobutyramide By performing operations similar to those of Example 4 using 2-methoxypyrimidine-5-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=6.8 Hz), 2.46 (1H, sept, J=6.8 Hz), 3.99 (3H, s), 4.40 (2H, d, J=6.0 Hz), 7.10 (1H, s), 7.6-7.7 (2H, m), 7.89 (1H, d, J=8.4 Hz), 8.39 (1H, t, J=6.0 Hz), 9.19 (2H, s), 13.05 (1H, brs)

MS (m/z): 447 (M$^+$)

Example 154: N-{4-Chloro-3-[4-(5-chloropyridin-3-yl)-6-oxo-1,6-dihydropyrimidin-2-yl]benzyl}isobutyramide By performing operations similar to those of Example 4 using 5-chloropyridine-3-carbaldehyde, the title compound was obtained.

$^1$H-NMR (d$_6$-DMSO, δ): 1.04 (6H, d, J=7.2 Hz), 2.4-2.6 (1H, m), 4.32 (2H, d, J=6.0 Hz), 7.19 (1H, s), 7.43 (1H, dd, J=2.0 Hz, 8.4 Hz), 7.5-7.6 (2H, m), 8.34 (1H, t, J=5.6 Hz), 8.50 (1H, s), 8.75 (1H, d, J=2.0 Hz), 9.21 (1H, s), 13.08 (1H, brs)

MS (m/z): 416 (M⁺)

Example 155: N-{4-Chloro-3-[4-(6-cyclopropylpyridin-3-yl)-6-oxo-1,6-dihydropyrimidin-2-yl]-2-fluorobenzyl}isobutyramide By performing operations similar to those of Example 4 using 6-cyclopropylpyridine-3-carbaldehyde, and N-(3-carbamimidoyl-4-chloro-2-fluorobenzyl)isobutyramide hydrochloride, the title compound was obtained.

¹H-NMR (d₆-DMSO, δ): 0.9-1.1 (4H, m), 1.04 (6H, d, J=6.8 Hz), 2.1-2.2 (1H, m), 2.4-2.6 (1H, m), 4.32 (2H, d, J=5.6 Hz), 7.04 (1H, s), 7.39 (1H, d, J=8.4 Hz), 7.4-7.5 (2H, m), 8.23 (1H, dd, J=2.0 Hz, 8.4 Hz), 8.35 (1H, t, J=5.6 Hz), 9.03 (1H, s), 13.13 (1H, brs)

MS (m/z): 440 (M⁺)

Example 156: N-[4-Chloro-3-(2'-cyclopropyl-6-oxo-1,6-dihydro-[4,5'-bipyrimidin]-2-yl)benzyl]isobutyramide By performing operations similar to those of Example 4 using 2-cyclopropylpyrimidine-5-carbaldehyde, the title compound was obtained.

¹H-NMR (d₆-DMSO, δ): 1.03 (6H, d, J=7.2 Hz), 1.0-1.2 (4H, m), 2.2-2.3 (1H, m), 2.43 (1H, sept, J=6.8 Hz), 4.31 (2H, d, J=6.4 Hz), 7.10 (1H, s), 7.42 (1H, dd, J=2.0 Hz, 8.4 Hz), 7.5-7.6 (2H, m), 8.33 (1H, t, J=6.0 Hz), 9.21 (2H, s), 13.01 (1H, brs)

MS (m/z): 423 (M⁺)

Example 157: N-(4-Chloro-3-{4-[6-(cyclopropylmethoxy)pyridin-3-yl]-6-oxo-1,6-dihydropyrimidin-2-yl}-2-fluorobenzyl)isobutyramide By performing operations similar to those of Example 4 using 6-(cyclopropylmethoxy)pyridine-3-carbaldehyde, and N-(3-carbamimidoyl-4-chloro-2-fluorobenzyl)isobutyramide hydrochloride, the title compound was obtained.

¹H-NMR (d₆-DMSO, δ): 0.3-0.4 (2H, m), 0.5-0.6 (2H, m), 1.04 (6H, d, J=6.8 Hz), 1.2-1.3 (1H, m), 2.4-2.6 (1H, m), 4.16 (2H, d, J=7.2 Hz), 4.32 (2H, d, J=5.6 Hz), 6.90 (1H, d, J=8.4 Hz), 7.00 (1H, s), 7.4-7.5 (2H, m), 8.30 (1H, dd, J=2.4 Hz, 8.8 Hz), 8.35 (1H, t, J=5.6 Hz), 8.82 (1H, d, J=2.0 Hz), 13.06 (1H, brs)

MS (m/z): 470 (M⁺)

Example 158: N-(4-Chloro-3-{4-[6-(2-ethoxyethoxy)pyridin-3-yl]-6-oxo-1,6-dihydropyrimidin-2-yl}-2-fluorobenzyl)isobutyramide By performing operations similar to those of Example 4 using 6-(2-ethoxyethoxy)pyridine-3-carbaldehyde, and N-(3-carbamimidoyl-4-chloro-2-fluorobenzyl)isobutyramide hydrochloride, the title compound was obtained.

¹H-NMR (d₆-DMSO, δ): 1.04 (6H, d, J=6.8 Hz), 1.10 (3H, t, J=6.8 Hz), 2.45 (1H, sept, J=6.8 Hz), 3.49 (2H, q, J=6.8 Hz), 3.71 (2H, t, J=4.8 Hz), 4.32 (2H, d, J=5.6 Hz), 4.43 (2H, t, J=4.4 Hz), 6.92 (1H, d, J=8.8 Hz), 7.00 (1H, s), 7.4-7.5 (2H, m), 8.3-8.4 (2H, m), 8.84 (1H, d, J=1.6 Hz), 13.10 (1H, brs)

MS (m/z): 488 (M⁺)

Example 159: N-(3-{4-[6-(Cyclopropylmethoxy)pyridin-3-yl]-6-oxo-1,6-dihydropyrimidin-2-yl}-4-(trifluoromethyl)benzyl)isobutyramide By performing operations similar to those of Example 4 using 6-(cyclopropylmethoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 0.3-0.4 (2H, m), 0.5-0.6 (2H, m), 1.05 (6H, d, J=7.2 Hz), 1.2-1.3 (1H, m), 2.45 (1H, sept, J=6.8 Hz), 4.16 (2H, d, J=6.8 Hz), 4.40 (2H, d, J=5.6 Hz), 6.90 (1H, d, J=8.8 Hz), 6.95 (1H, s), 7.5-7.7 (2H, m), 7.88 (1H, d, J=8.4 Hz), 8.30 (1H, d, J=7.2 Hz), 8.39 (1H, t, J=5.6 Hz), 8.83 (1H, s), 12.95 (1H, brs)

MS (m/z): 486 (M⁺)

Example 160: N-(4-Chloro-2-fluoro-3-{6-oxo-4-[6-(2-propoxyethoxy)pyridin-3-yl]-1,6-dihydropyrimidin-2-yl}benzyl)isobutyramide By performing operations similar to those of Example 4 using 6-(2-propoxyethoxy)pyridine-3-carbaldehyde, and N-(3-carbamimidoyl-4-chloro-2-fluorobenzyl)isobutyramide hydrochloride, the title compound was obtained.

¹H-NMR (d₆-DMSO, δ): 0.85 (3H, t, J=7.2 Hz), 1.04 (6H, d, J=6.8 Hz), 1.51 (2H, sext, J=7.2 Hz), 2.45 (1H, sept, J=6.8 Hz), 3.40 (2H, t, J=6.8 Hz), 3.71 (2H, t, J=4.8 Hz), 4.32 (2H, d, J=6.0 Hz), 4.44 (2H, t, J=4.8 Hz), 6.92 (1H, d, J=8.8 Hz), 7.02 (1H, s), 7.4-7.5 (2H, m), 8.31 (1H, dd, J=2.8 Hz, 8.8 Hz), 8.36 (1H, t, J=6.0 Hz), 8.84 (1H, d, J=2.4 Hz), 13.00 (1H, brs)

MS (m/z): 502 (M⁺)

Example 161: N-{4-Chloro-3-[4-(6-ethoxypyridin-3-yl)-6-oxo-1,6-dihydropyrimidin-2-yl]-2-fluorobenzyl}isobutyramide By performing operations similar to those of Example 4 using 6-ethoxypyridine-3-carbaldehyde, and N-(3-carbamimidoyl-4-chloro-2-fluorobenzyl)isobutyramide hydrochloride, the title compound was obtained.

¹H-NMR (d₆-DMSO, δ): 1.04 (6H, d, J=6.8 Hz), 1.33 (3H, t, J=6.8 Hz), 2.45 (1H, sept, J=6.8 Hz), 4.32 (2H, d, J=5.2 Hz), 4.37 (2H, q, J=6.8 Hz), 6.88 (1H, d, J=8.8 Hz), 7.00 (1H, s), 7.4-7.5 (2H, m), 8.30 (1H, dd, J=2.4 Hz, 8.8 Hz), 8.36 (1H, t, J=5.6 Hz), 8.84 (1H, d, J=2.0 Hz), 13.08 (1H, brs)

MS (m/z): 444 (M⁺)

Example 162: N-(4-Chloro-2-fluoro-3-{6-oxo-4-[5-(trifluoromethyl)pyridin-2-yl]-1,6-dihydropyrimidin-2-yl}benzyl)isobutyramide By performing operations similar to those of Example 4 using 5-(trifluoromethyl)pyridine-2-carbaldehyde, and N-(3-carbamimidoyl-4-chloro-2-fluorobenzyl)isobutyramide hydrochloride, the title compound was obtained.

¹H-NMR (d₆-DMSO, δ): 1.05 (6H, d, J=6.8 Hz), 2.4-2.6 (1H, m), 4.33 (2H, d, J=5.6 Hz), 7.34 (1H, s), 7.4-7.6 (2H, m), 8.3-8.5 (3H, m), 9.13 (1H, s), 13.42 (1H, brs)

MS (m/z): 468 (M⁺)

Example 163: N-(3-{4-[6-(2-Ethoxyethoxy)pyridin-3-yl]-6-oxo-1,6-dihydropyrimidin-2-yl}-2,4-difluorobenzyl)isobutyramide By performing operations similar to those of Example 4 using 6-(2-ethoxyethoxy)pyridine-3-carbaldehyde, and N-(3-carbamimidoyl-2,4-difluorobenzyl)isobutyramide hydrochloride, the title compound was obtained.

¹H-NMR (d₆-DMSO, δ): 1.04 (6H, d, J=6.8 Hz), 1.12 (3H, t, J=6.8 Hz), 2.45 (1H, sept, J=6.8 Hz), 3.49 (2H, q, J=6.8 Hz), 3.71 (2H, t, J=4.8 Hz), 4.32 (2H, d, J=5.6 Hz), 4.44 (2H, t, J=4.8 Hz), 6.93 (1H, d, J=8.8 Hz), 7.00 (1H, s), 7.28 (1H, t, J=8.8 Hz), 7.4-7.6 (1H, m), 8.3-8.4 (2H, m), 8.85 (1H, s), 13.11 (1H, brs)

MS (m/z): 472 (M$^+$)

Example 164: N-(3-{4-[6-(Cyclopropylmethoxy)pyridin-3-yl]-6-oxo-1,6-dihydropyrimidin-2-yl}-2,4-difluorobenzyl)isobutyramide By performing operations similar to those of Example 4 using 6-(cyclopropylmethoxy)pyridine-3-carbaldehyde, and N-(3-carbamimidoyl-2,4-difluorobenzyl)isobutyramide hydrochloride, the title compound was obtained.

$^1$H-NMR (d$_6$-DMSO, δ): 0.3-0.4 (2H, m), 0.5-0.6 (2H, m), 1.04 (6H, d, J=6.8 Hz), 1.2-1.3 (1H, m), 2.45 (1H, sept, J=6.8 Hz), 4.16 (2H, d, J=7.6 Hz), 4.32 (2H, d, J=5.6 Hz), 6.91 (1H, d, J=8.8 Hz), 6.98 (1H, s), 7.28 (1H, t, J=8.8 Hz), 7.4-7.6 (1H, m), 8.3-8.4 (2H, m), 8.83 (1H, d, J=1.6 Hz), 13.10 (1H, brs)

MS (m/z): 454 (M$^+$)

Example 165: N-(2-Chloro-3-{4-[6-(difluoromethoxy)pyridin-3-yl]-6-oxo-1,6-dihydropyrimidin-2-yl}-4-fluorobenzyl)isobutyramide By performing operations similar to those of Example 4 using 6-(difluoromethoxy)pyridine-3-carbaldehyde, and N-(3-carbamimidoyl-2-chloro-4-fluorobenzyl)isobutyramide hydrochloride, the title compound was obtained.

$^1$H-NMR (d$_6$-DMSO, δ): 1.07 (6H, d, J=6.8 Hz), 2.4-2.6 (1H, m), 4.34 (2H, d, J=5.2 Hz), 7.13 (1H, s), 7.18 (1H, d, J=8.8 Hz), 7.4-7.6 (2H, m), 7.76 (1H, t, J=72.8 Hz), 8.37 (1H, t, J=6.0 Hz), 8.51 (1H, dd, J=2.4 Hz, 8.4 Hz), 8.92 (1H, d, J=2.4 Hz), 13.22 (1H, brs)

MS (m/z): 466 (M$^+$)

Example 166: N-(2-Chloro-3-{4-[6-(cyclopropylmethoxy)pyridin-3-yl]-6-oxo-1,6-dihydropyrimidin-2-yl}-4-fluorobenzyl)isobutyramide By performing operations similar to those of Example 4 using 6-(cyclopropylmethoxy)pyridine-3-carbaldehyde, and N-(3-carbamimidoyl-2-chloro-4-fluorobenzyl)isobutyramide hydrochloride, the title compound was obtained.

$^1$H-NMR (d$_6$-DMSO, δ): 0.3-0.4 (2H, m), 0.5-0.6 (2H, m), 1.07 (6H, d, J=7.2 Hz), 1.2-1.3 (1H, m), 2.4-2.6 (1H, m), 4.16 (2H, d, J=6.8 Hz), 4.34 (2H, d, J=5.6 Hz), 6.90 (1H, d, J=8.8 Hz), 7.00 (1H, s), 7.4-7.6 (2H, m), 8.30 (1H, dd, J=2.4 Hz, 8.8 Hz), 8.37 (1H, t, J=5.6 Hz), 8.82 (1H, d, J=2.4 Hz), 12.95 (1H, brs)

MS (m/z): 470 (M$^+$)

Example 167: N-(4-Chloro-2-fluoro-3-{6-oxo-4-[6-(2,2,2-trifluoroethoxy)pyridin-3-yl]-1,6-dihydropyrimidin-2-yl}benzyl)isobutyramide By performing operations similar to those of Example 4 using 6-(2,2,2-trifluoroethoxy)pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.4-2.6 (1H, m), 4.32 (2H, d, J=6.0 Hz), 5.07 (2H, q, J=8.8 Hz), 7.0-7.1 (2H, m), 7.4-7.6 (2H, m), 8.36 (1H, t, J=6.0 Hz), 8.41 (1H, d, J=8.0 Hz), 8.88 (1H, s), 13.16 (1H, brs)

MS (m/z): 498 (M$^+$)

Example 168: N-{4-Chloro-3-[4-(5-chloropyridin-3-yl)-6-oxo-1,6-dihydropyrimidin-2-yl]-2-fluorobenzyl}isobutyramide By performing operations similar to those of Example 4 using 5-chloropyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=6.8 Hz), 2.45 (1H, sept, J=6.8 Hz), 4.33 (2H, d, J=6.0 Hz), 7.25 (1H, s), 7.4-7.6 (2H, m), 8.36 (1H, t, J=6.0 Hz), 8.4-8.5 (1H, m), 8.75 (1H, d, J=2.4 Hz), 9.18 (1H, d, J=2.0 Hz), 13.29 (1H, brs)

MS (m/z): 434 (M$^+$)

Example 169: N-(2-Fluoro-3-{6-oxo-4-[6-(trifluoromethyl)pyridin-3-yl]-1,6-dihydropyrimidin-2-yl}-4-(trifluoromethyl)benzyl)isobutyramide 2-[3-Chloro-2-fluoro-6-(trifluoromethyl)phenyl]-6-[6-(trifluoromethyl)pyridin-3-yl]pyrimidin-4(3H)-one (109 mg), potassium N-[(trifluoroborate)methyl]isobutyramide (104 mg), bis(dibenzylideneacetone)palladium(0) (7.2 mg), 2-dicyclohexylphosphino-2',6'-diisopropoxy-1,1'-biphenyl (12 mg), sodium carbonate (53 mg), 1,4-dioxane (4 mL), and water (0.4 mL) were mixed, and reacted at 130° C. for 100 minutes by applying microwaves. After the reaction, the reaction mixture was extracted with ethyl acetate, and the organic layer was dried over magnesium sulfate. The solvent was evaporated, and then the residue was purified by silica gel column chromatography to obtain the title compound (35 mg).

$^1$H-NMR (d$_6$-DMSO, δ): 1.06 (6H, d, J=6.8 Hz), 2.48 (1H, sept, J=6.8 Hz), 4.41 (2H, d, J=5.6 Hz), 7.31 (1H, s), 7.67 (1H, t, J=8.0 Hz), 7.79 (1H, d, J=8.4 Hz), 8.01 (1H, d, J=8.4 Hz), 8.40 (1H, t, J=6.0 Hz), 8.64 (1H, d, J=7.6 Hz), 9.36 (1H, s), 13.38 (1H, brs)

MS (m/z): 502 (M$^+$)

Example 170: N-(2-Chloro-4-fluoro-3-{6-oxo-4-[6-(2,2,2-trifluoroethoxy)pyridin-3-yl]-1,6-dihydropyrimidin-2-yl}benzyl)isobutyramide By performing operations similar to those of Example 4 using 6-(2,2,2-trifluoroethoxy)pyridine-3-carbaldehyde, and N-(3-carbamimidoyl-2-chloro-4-fluorobenzyl)isobutyramide hydrochloride, the title compound was obtained.

$^1$H-NMR (d$_6$-DMSO, δ): 1.07 (6H, d, J=7.2 Hz), 2.4-2.6 (1H, m), 4.34 (2H, d, J=6.0 Hz), 5.06 (2H, q, J=9.2 Hz), 7.0-7.1 (2H, m), 7.4-7.6 (2H, m), 8.38 (1H, t, J=6.0 Hz), 8.41 (1H, dd, J=2.0 Hz, 8.8 Hz), 8.88 (11H, d, J=2.0 Hz), 13.15 (1H, brs)

MS (m/z): 498 (M$^+$)

Example 171: N-{4-Chloro-3-[4-(5-chloropyridin-2-yl)-6-oxo-1,6-dihydropyrimidin-2-yl]-2-fluorobenzyl}isobutyramide By performing operations similar to those of Example 4 using 5-chloropyridine-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=6.8 Hz), 2.45 (1H, sept, J=6.8 Hz), 4.33 (2H, d, J=5.6 Hz), 7.24 (1H, s), 7.4-7.6 (2H, m), 8.06 (1H, dd, J=2.4 Hz, 8.8 Hz), 8.22 (1H, d, J=8.8 Hz), 8.37 (1H, t, J=5.6 Hz), 8.79 (1H, d, J=2.4 Hz), 13.31 (1H, brs)

MS (m/z): 434 (M$^+$)

Example 172: N-(4-Chloro-2-fluoro-3-{6-oxo-4-[6-(3,3,3-trifluoropropoxy)pyridin-3-yl]-1,6-dihydropyrimidin-2-yl}benzyl)isobutyramide By performing operations similar to those of Example 4 using 6-(3,3,3-trifluoropropoxy)pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.45 (1H, sept, J=6.8 Hz), 2.7-2.9 (2H, m), 4.32 (2H, d, J=6.0 Hz), 4.56 (2H, t, J=5.6 Hz), 6.93 (1H, d, J=8.8 Hz), 7.02 (1H, s), 7.4-7.5 (2H, m), 8.3-8.4 (2H, m), 8.87 (1H, d, J=2.0 Hz), 13.12 (1H, brs)

MS (m/z): 512 (M$^+$)

Example 173: N-(2-Chloro-4-fluoro-3-{6-oxo-4-[5-(trifluoromethyl)pyridin-2-yl]-1,6-dihydropyrimidin-2-yl}benzyl)isobutyramide By performing operations similar to those of Example 4 using 5-(trifluoromethyl)pyridine-2-carbaldehyde, and N-(3-carbamimidoyl-2-chloro-4-fluorobenzyl)isobutyramide hydrochloride, the title compound was obtained.

$^1$H-NMR (d$_6$-DMSO, δ): 1.07 (6H, d, J=6.8 Hz), 2.4-2.6 (1H, m), 4.35 (2H, d, J=5.6 Hz), 7.35 (1H, s), 7.4-7.6 (2H, m), 8.34 (1H, dd, J=2.0 Hz, 8.8 Hz), 8.3-8.5 (2H, m), 9.13 (1H, s), 13.38 (1H, brs)

MS (m/z): 468 (M$^+$)

Example 174: N-(3-{4-[6-(Difluoromethoxy)pyridin-3-yl]-6-oxo-1,6-dihydropyrimidin-2-yl}-2-fluoro-4-(trifluoromethyl)benzyl)isobutyramide By performing operations similar to those of Example 169 using 2-[3-chloro-2-fluoro-6-(trifluoromethyl)phenyl]-6-[6-(difluoromethoxy)pyridin-3-yl]pyrimidin-4(3H)-one, the title compound was obtained.

$^1$H-NMR (d$_6$-DMSO, δ): 1.06 (6H, d, J=6.8 Hz), 2.48 (1H, sept, J=6.8 Hz), 4.40 (2H, d, J=5.6 Hz), 7.14 (1H, s), 7.20 (1H, d, J=8.8 Hz), 7.66 (1H, t, J=7.6 Hz), 7.77 (1H, t, J=72.0 Hz), 7.79 (1H, d, J=8.0 Hz), 8.44 (1H, t, J=5.6 Hz), 8.49 (1H, d, J=7.2 Hz), 8.91 (1H, s), 13.29 (1H, brs)

MS (m/z): 500 (M$^+$)

Example 175: N-(4-Chloro-2-fluoro-3-{6-oxo-4-[5-(2-propoxyethoxy)pyridin-2-yl]-1,6-dihydropyrimidin-2-yl}benzyl)isobutyramide By performing operations similar to those of Example 4 using 6-(2-propoxyethoxy)pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 0.86 (3H, t, J=7.6 Hz), 1.05 (6H, d, J=7.2 Hz), 1.4-1.6 (2H, m), 2.46 (1H, sept, J=6.8 Hz), 3.42 (2H, t, J=6.8 Hz), 3.74 (2H, t, J=4.4 Hz), 4.26 (2H, t, J=4.4 Hz), 4.33 (2H, d, J=6.0 Hz), 7.13 (1H, s), 7.4-7.6 (3H, m), 8.15 (1H, d, J=8.8 Hz), 8.36 (1H, t, J=6.0 Hz), 8.44 (1H, d, J=2.8 Hz), 13.13 (1H, brs)

MS (m/z): 502 (M$^+$)

Example 176: N-(3-{4-[6-(2-Ethoxyethoxy)pyridin-3-yl]-6-oxo-1,6-dihydropyrimidin-2-yl}-2-fluoro-4-(trifluoromethyl)benzyl)isobutyramide By performing operations similar to those of Example 169 using 2-[3-chloro-2-fluoro-6-(trifluoromethyl)phenyl]-6-[6-(2-ethoxyethoxy)pyridin-3-yl]pyrimidin-4(3H)-one, the title compound was obtained.

$^1$H-NMR (d$_6$-DMSO, δ): 1.06 (6H, d, J=6.8 Hz), 1.12 (3H, t, J=7.2 Hz), 2.48 (1H, sept, J=6.8 Hz), 3.49 (2H, q, J=6.8 Hz), 3.70 (2H, t, J=4.8 Hz), 4.4-4.5 (4H, m), 6.92 (1H, d, J=8.8 Hz), 7.01 (1H, s), 7.65 (1H, t, J=7.6 Hz), 7.78 (1H, d, J=7.6 Hz), 8.29 (1H, d, J=8.8 Hz), 8.43 (1H, t, J=6.0 Hz), 8.82 (1H, s), 13.17 (1H, brs)

MS (m/z): 522 (M$^+$)

Example 177: N-(4-Chloro-3-{4-[6-(2,2-difluoroethoxy)pyridin-3-yl]-6-oxo-1,6-dihydropyrimidin-2-yl}-2-fluorobenzyl)isobutyramide By performing operations similar to those of Example 4 using 6-(2,2-difluoroethoxy)pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.45 (1H, sept, J=6.8 Hz), 4.32 (2H, d, J=6.0 Hz), 4.60-4.68 (2H, m), 6.2-6.6 (1H, m), 7.02 (1H, d, J=8.0 Hz), 7.05 (1H, s), 7.4-7.5 (2H, m), 8.3-8.4 (2H, m), 8.87 (1H, d, J=2.0 Hz), 13.12 (1H, brs)

MS (m/z): 480 (M$^+$)

Example 178: N-(2-Chloro-3-{4-[6-(2,2-difluoroethoxy)pyridin-3-yl]-6-oxo-1,6-dihydropyrimidin-2-yl}-4-fluorobenzyl)isobutyramide By performing operations similar to those of Example 4 using 6-(2,2-difluoroethoxy)pyridine-3-carbaldehyde, and N-(3-carbamimidoyl-2-chloro-4-fluorobenzyl)isobutyramide hydrochloride, the title compound was obtained.

$^1$H-NMR (d$_6$-DMSO, δ): 1.07 (6H, d, J=7.2 Hz), 2.4-2.6 (1H, m), 4.34 (2H, d, J=6.0 Hz), 4.6-4.7 (2H, m), 6.2-6.6 (1H, m), 7.02 (1H, d, J=8.8 Hz), 7.04 (1H, s), 7.4-7.6 (2H, m), 8.3-8.4 (2H, m), 8.86 (1H, d, J=2.0 Hz), 13.14 (1H, brs)

MS (m/z): 480 (M$^+$)

Example 179: N-(4-Chloro-3-{4-[5-(difluoromethoxy)pyridin-2-yl]-6-oxo-1,6-dihydropyrimidin-2-yl}-2-fluorobenzyl)isobutyramide By performing operations similar to those of Example 4 using 5-(difluoromethoxy)pyridine-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=7.2 Hz), 2.46 (1H, sept, J=6.8 Hz), 4.33 (2H, d, J=6.0 Hz), 7.21 (1H, s), 7.42 (1H, t, J=73.2 Hz), 7.4-7.6 (2H, m), 7.78 (1H, dd, J=2.8 Hz, 8.4 Hz), 8.27 (1H, d, J=8.4 Hz), 8.37 (1H, t, J=6.0 Hz), 8.63 (1H, d, J=2.8 Hz), 13.27 (1H, brs)

MS (m/z): 466 (M$^+$)

Example 180: N-(4-Chloro-3-{4-[5-(2-ethoxyethoxy)pyridin-2-yl]-6-oxo-1,6-dihydropyrimidin-2-yl}-2-fluorobenzyl)isobutyramide By performing operations similar to those of Example 4 using 5-(2-ethoxyethoxy)pyridine-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=7.2 Hz), 1.13 (3H, t, J=7.2 Hz), 2.46 (1H, sept, J=7.2 Hz), 3.51 (2H, q, J=7.2 Hz), 3.73 (2H, t, J=4.4 Hz), 4.25 (2H, t, J=4.4 Hz), 4.33 (2H, d, J=5.6 Hz), 7.14 (1H, s), 7.4-7.6 (3H, m), 8.15

(1H, d, J=8.8 Hz), 8.36 (1H, t, J=6.0 Hz), 8.44 (1H, d, J=2.8 Hz), 13.12 (1H, brs)
MS (m/z): 488 (M$^+$)

Example 181: N-{3-[4-(5-Chloropyridin-3-yl)-6-oxo-1,6-dihydropyrimidin-2-yl]-4-fluorobenzyl}isobutyramide By performing operations similar to those of Example 4 using 5-chloropyridine-3-carbaldehyde, and N-(3-carbamimidoyl-4-fluorobenzyl)isobutyramide hydrochloride, the title compound was obtained.
$^1$H-NMR (d$_6$-DMSO, δ): 1.05 (6H, d, J=7.2 Hz), 2.44 (1H, sept, J=6.8 Hz), 4.33 (2H, d, J=5.6 Hz), 7.19 (1H, s), 7.3-7.4 (1H, m), 7.4-7.6 (1H, m), 7.74 (1H, d, J=6.4 Hz), 8.35 (1H, t, J=5.6 Hz), 8.54 (1H, t, J=2.0 Hz), 8.76 (1H, d, J=2.0 Hz), 9.24 (1H, d, J=1.6 Hz), 12.93 (1H, brs)
MS (m/z): 400 (M$^+$)

Example 182: N-(2-Fluoro-3-{6-oxo-4-[5-(trifluoromethyl)pyridin-2-yl]-1,6-dihydropyrimidin-2-yl}-4-(trifluoromethyl)benzyl)isobutyramide By performing operations similar to those of Example 169 using 2-[3-chloro-2-fluoro-6-(trifluoromethyl)phenyl]-6-[5-(trifluoromethyl)pyridin-2-yl]pyrimidin-4(3H)-one, the title compound was obtained.
$^1$H-NMR (d$_6$-DMSO, δ): 1.06 (6H, d, J=6.8 Hz), 2.4-2.6 (1H, m), 4.41 (2H, d, J=5.6 Hz), 7.35 (1H, s), 7.67 (1H, t, J=7.2 Hz), 7.80 (1H, d, J=8.4 Hz), 8.36 (2H, s), 8.45 (1H, t, J=5.6 Hz), 9.13 (1H, s), 13.49 (1H, brs)
MS (m/z): 502 (M$^+$)

Example 183: N-(4-Chloro-3-{4-[5-(cyclopropylmethoxy)pyridin-2-yl]6-oxo-1,6-dihydropyrimidin-2-yl}-2-fluorobenzyl)isobutyramide By performing operations similar to those of Example 4 using 5-(cyclopropylmethoxy)pyridine-2-carbaldehyde, and N-(3-carbamimidoyl-4-chloro-2-fluorobenzyl)isobutyramide hydrochloride, the title compound was obtained.
$^1$H-NMR (d$_6$-DMSO, δ): 0.3-0.4 (2H, m), 0.5-0.7 (2H, m), 1.05 (6H, d, J=7.6 Hz), 1.1-1.4 (1H, m), 2.46 (1H, sept, J=7.2 Hz), 3.97 (2H, d, J=6.8 Hz), 4.32 (2H, d, J=6.0 Hz), 7.13 (1H, s), 7.45-7.50 (3H,m), 8.14 (1H, d, J=8.4 Hz), 8.36 (1H, t, J=5.6 Hz), 8.42 (1H, d, J=3.2 Hz), 13.12 (1H, brs)
MS (m/z): 470 (M$^+$)

Example 184: N-{4-Chloro-2-fluoro-3-[4-(5-fluoropyridin-3-yl)-6-oxo-1,6-dihydropyrimidin-2-yl]benzyl}isobutyramide By performing operations similar to those of Example 4 using 5-fluoropyridine-3-carbaldehyde, and N-(3-carbamimidoyl-4-chloro-2-fluorobenzyl)isobutyramide hydrochloride, the title compound was obtained.
$^1$H-NMR (d$_6$-DMSO, δ): 1.04 (6H, d, J=6.8 Hz), 2.45 (1H, sept, J=6.8 Hz), 4.33 (2H, d, J=5.6 Hz), 7.24 (1H, s), 7.4-7.6 (2H, m), 8.29 (1H, d, J=9.6 Hz), 8.36 (1H, t, J=5.6 Hz), 8.71 (1H, d, J=2.8 Hz), 9.11 (1H, s), 13.30 (1H, brs)
MS (m/z): 418 (M$^+$)

Example 185: N-(2-Chloro-3-{4-[6-(2-ethoxyethoxy)pyridin-3-yl]-6-oxo-1,6-dihydropyrimidin-2-yl}-4-fluorobenzyl)isobutyramide By performing operations similar to those of Example 4 using 6-(2-ethoxyethoxy)pyridine-3-carbaldehyde, and N-(3-carbamimidoyl-2-chloro-4-fluorobenzyl)isobutyramide hydrochloride, the title compound was obtained.
$^1$H-NMR (d$_6$-DMSO, δ): 1.07 (6H, d, J=7.2 Hz), 1.12 (3H, t, J=6.8 Hz), 2.4-2.6 (1H, m), 3.49 (2H, q, J=6.8 Hz), 3.71 (2H, t, J=4.4 Hz), 4.34 (2H, d, J=6.0 Hz), 4.43 (2H, t, J=4.4 Hz), 6.92 (1H, d, J=8.8 Hz), 7.01 (1H, s), 7.4-7.6 (2H, m), 8.31 (1H, dd, J=2.4 Hz, 8.8 Hz), 8.37 (1H, t, J=6.0 Hz), 8.83 (1H, d, J=2.0 Hz), 13.09 (1H, brs)
MS (m/z): 488 (M$^+$)

Example 186: N-(2-Chloro-3-{4-[5-(cyclopropylmethoxy)pyridin-2-yl]-6-oxo-1,6-dihydropyrimidin-2-yl}-4-fluorobenzyl)isobutyramide By performing operations similar to those of Example 4 using 5-(cyclopropylmethoxy)pyridine-2-carbaldehyde, and N-(3-carbamimidoyl-2-chloro-4-fluorobenzyl)isobutyramide hydrochloride, the title compound was obtained.
$^1$H-NMR (d$_6$-DMSO, δ): 0.3-0.4 (2H, m), 0.5-0.7 (2H, m), 1.07 (6H, d, J=6.8 Hz), 1.2-1.3 (1H, m), 2.4-2.6 (1H, m), 3.97 (2H, d, J=7.6 Hz), 4.35 (2H, d, J=6.0 Hz), 7.14 (1H, s), 7.41-7.51 (3H, m), 8.14 (1H, d, J=8.8 Hz), 8.38 (1H, t, J=5.6 Hz), 8.42 (1H, d, J=2.8 Hz), 13.11 (1H, brs)
MS (m/z): 470 (M$^+$)

Example 187: N-(2-Chloro-4-fluoro-3-{6-oxo-4-[6-(3,3,3-trifluoropropoxy)pyridin-3-yl]-1,6-dihydropyrimidin-2-yl}benzyl)isobutyramide By performing operations similar to those of Example 4 using 6-(3,3,3-trifluoropropoxy)pyridine-3-carbaldehyde, and N-(3-carbamimidoyl-2-chloro-4-fluorobenzyl)isobutyramide hydrochloride, the title compound was obtained.
$^1$H-NMR (d$_6$-DMSO, δ): 1.07 (6H, d, J=6.8 Hz), 2.4-2.6 (1H, m), 2.7-2.9 (2H, m), 4.34 (2H, d, J=5.6 Hz), 4.56 (2H, L, J=6.0 Hz), 6.92 (1H, d, J=8.8 Hz), 7.02 (1H, s), 7.4-7.6 (2H, m), 8.34 (1H, dd, J=2.8 Hz, 8.8 Hz), 8.37 (1H, t, J=6.0 Hz), 8.86 (1H, d, J=1.6 Hz), 13.11 (1H, brs)
MS (m/z): 512 (M$^+$)

Example 188: N-(4-Chloro-3-{6-oxo-4-[6-(tetrahydropyran-4-ylmethoxy)pyridin-3-yl]-1,6-dihydropyrimidin-2-yl}benzyl)isobutyramide By performing operations similar to those of Example 4 using 6-(tetrahydropyran-4-ylmethoxy)pyridine-3-carbaldehyde, the title compound was obtained.
$^1$H-NMR (d$_6$-DMSO, δ): 1.03 (6H, d, J=6.8 Hz), 1.33 (2H, dq, J=4.4 Hz, 12.2 Hz), 1:66 (2H, dd, J=2.0 Hz, 12.7 Hz), 1.9-2.1 (1H, m), 2.43 (1H, sept, J=6.8 Hz), 3.2-3.4 (2H, m), 3.87 (2H, dd, J=3.0 Hz, 11.8 Hz), 4.19 (2H, d, J=6.4 Hz), 4.31 (2H, t, J=5.8 Hz), 6.90 (1H, d, J=8.8 Hz), 6.95 (1H, brs), 7.41 (1H, dd, J=1.9 Hz, 8.3 Hz), 7.5-7.6 (2H, m), 8.2-8.4 (2H, m), 8.86 (1H, d, J=2.5 Hz), 12.83 (1H, brs)
MS (m/z): 496 (M$^+$)

Example 189: N-(3-{6-Oxo-4-[6-(tetrahydropyran-4-ylmethoxy)pyridin-3-yl]-1,6-dihydropyrimidin-2-yl}-4-(trifluoromethyl)benzyl)isobutyramide By performing operations similar to those of Example 4 using 6-(tetrahydropyran-4-ylmethoxy)pyridine-3-carbaldehyde, and N-[3-carbamimidoyl-4-(trifluoromethyl)benzyl]isobutyramide hydrochloride, the title compound was obtained.
$^1$H-NMR (d$_6$-DMSO, δ): 1.05 (6H, d, J=6.8 Hz), 1.32 (2H, dq, J=4.4 Hz, 12.2 Hz), 1.6-1.7 (2H, m), 1.9-2.1 (1H, m), 2.46 (1H, sept, J=6.8 Hz), 3.2-3.4 (2H, m), 3.87 (2H, dd, J=3.4 Hz, 11.2 Hz), 4.18 (2H, d, J=6.3 Hz), 4.40 (2H, d, J=6.3 Hz), 6.90 (1H, d, J=8.8 Hz), 6.97 (1H, brs), 7.5-7.7 (2H, m), 7.88 (1H, d, J=8.3 Hz), 8.31 (1H, d, J=8.8 Hz), 8.39 (1H, t, J=5.9 Hz), 8.84 (1H, d, J=2.5 Hz), 12.94 (1H, brs)

MS (m/z): 530 (M$^+$)

Example 190: N-(4-Chloro-3-{6-oxo-4-[6-(tetrahydropyran-4-ylmethoxy)pyridin-3-yl]-1,6-dihydropyrimidin-2-yl}benzyl)butyramide By performing operations similar to those of Example 4 using 6-(tetrahydropyran-4-ylmethoxy)pyridine-3-carbaldehyde and N-(3-carbamimidoyl-4-chlorobenzyl)butyramide hydrochloride, the title compound was obtained.

$^1$H-NMR (d$_6$-DMSO, δ): 0.85 (3H, t, J=7.3 Hz), 1.33 (2H, dq, J=4.4 Hz, 12.2 Hz), 1.4-1.7 (4H, m), 1.9-2.1 (1H, m), 2.13 (2H, t, J=7.3 Hz), 3.2-3.4 (2H, m), 3.87 (2H, dd, J=3.0 Hz, 11.3 Hz), 4.19 (2H, d, J=6.9 Hz), 4.32 (2H, t, J=5.8 Hz), 6.90 (1H, d, J=8.8 Hz), 6.95 (1H, brs), 7.43 (1H, dd, J=2.0 Hz, 8.3 Hz), 7.5-7.6 (2H, m), 8.33 (1H, dd, J=2.4 Hz, 8.8 Hz), 8.38 (1H, t, J=5.8 Hz), 8.86 (1H, d, J=2.5 Hz), 12.87 (1H, brs)

MS (m/z): 496 (M$^+$)

Example 191: N-{4-Chloro-2-fluoro-3-[6-oxo-4-(4-trifluoromethylthiazol-2-yl]-1,6-dihydropyrimidin-2-yl)benzyl)isobutyramide By performing operations similar to those of Example 4 using 4-trifluoromethylthiazole-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=6.8 Hz), 2.45 (1H, sept, J=6.8 Hz), 4.33 (2H, d, J=5.8 Hz), 7.05 (1H, brs), 7.4-7.6 (2H, m), 8.37 (1H, t, J=5.4 Hz), 8.76 (1H, s), 13.51 (1H, brs)

MS (m/z): 474 (M$^+$)

Example 192: N-{4-Chloro-3-[4-(5-ethynylpyridin-3-yl)-6-oxo-1,6-dihydropyrimidin-2-yl]benzyl}isobutyramide By performing operations similar to those of Example 4 using 5-ethynylpyridine-3-carbaldehyde, the title compound was obtained.

$^1$H-NMR (d$_6$-DMSO, δ): 1.04 (6H, d, J=6.8 Hz), 2.44 (1H, sept, J=6.8 Hz), 4.32 (2H, d, J=5.8 Hz), 4.52 (1H, s), 7.17 (1H, brs), 7.43 (1H, dd, J=1.9 Hz, 8.3 Hz), 7.5-7.7 (2H, m), 8.34 (1H, t, J=5.8 Hz), 8.49 (1H, s), 8.78 (1H, d, J=1.9 Hz), 9.24 (1H, d, J=2.0 Hz), 13.05 (1H, brs)

MS (m/z): 406 (M$^+$)

Example 193: N-(4-Chloro-3-{6-oxo-4-[5-(1-propynyl)pyridin-3-yl]-1,6-dihydropyrimidin-2-yl}benzyl)isobutyramide By performing operations similar to those of Example 4 using 5-(1-propynyl)pyridine-3-carbaldehyde, the title compound was obtained.

$^1$H-NMR (d$_6$-DMSO, δ): 1.04 (6H, d, J=6.8 Hz), 2.10 (3H, s), 2.44 (1H, sept, J=6.8 Hz), 4.32 (2H, d, J=5.8 Hz), 7.14 (1H, brs), 7.43 (1H, dd, J=2.0 Hz, 8.3 Hz), 7.5-7.7 (2H, m), 8.35 (1H, t, J=5.8 Hz), 8.39 (1H, s), 8.68 (1H, d, J=2.0 Hz), 9.17 (1H, d, J=1.5 Hz), 13.02 (1H, brs)

MS (m/z): 420 (M$^+$)

Example 194: N-(3-{4-[6-(3-Methyloxetan-3-ylmethoxy)pyridin-3-yl]-6-oxo-1,6-dihydropyrimidin-2-yl}-4-(trifluoromethyl)benzyl)isobutyramide By performing operations similar to those of Example 4 using 6-(3-methyloxetan-3-ylmethoxy)pyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=6.8 Hz), 1.35 (3H, s), 2.46 (1H, sept, J=6.9 Hz), 4.30 (2H, d, J=5.8 Hz), 4.3-4.5 (4H, m), 4.50 (2H, d, J=5.9 Hz), 6.95 (1H, d, J=9.0 Hz), 6.99 (1H, brs), 7.5-7.7 (2H, m), 7.88 (1H, d, J=8.3 Hz), 8.33 (1H, dd, J=1.9 Hz, 8.8 Hz), 8.39 (1H, t, J=5.4 Hz), 8.86 (1H, d, J=1.5 Hz), 12.90 (1H, brs) ESI(+)-MS: 517 (M$^+$+1)

Example 195: N-{3-[4-(5-Ethynylpyridin-3-yl)-6-oxo-1,6-dihydropyrimidin-2-yl]-4-(trifluoromethyl)benzyl}isobutyramide By performing operations similar to those of Example 4 using 5-ethynylpyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=6.8 Hz), 2.46 (1H, sept, J=6.9 Hz), 4.41 (2H, d, J=5.8 Hz), 4.51 (1H, s), 7.20 (1H, brs), 7.5-7.7 (2H, m), 7.89 (1H, d, J=8.3 Hz), 8.40 (1H, t, J=6.3 Hz), 8.47 (1H, s), 8.77 (1H, d, J=2.0 Hz), 9.22 (1H, d, J=2.0 Hz), 13.12 (1H, brs)

MS (m/z): 440 (M$^+$)

Example 196: N-(4-Chloro-3-{4-[6-(3-methyloxetan-3-ylmethoxy)pyridin-3-yl]-6-oxo-1,6-dihydropyrimidin-2-ylbenzyl}isobutyramide By performing operations similar to those of Example 4 using 6-(3-methyloxetan-3-ylmethoxy)pyridine-3-carbaldehyde, the title compound was obtained.

$^1$H-NMR (d$_6$-DMSO, δ): 1.03 (6H, d, J=6.8 Hz), 1.36 (3H, s), 2.43 (1H, sept, J=6.8 Hz), 4.2-4.4 (4H, m), 4.43 (2H, s), 4.50 (2H, d, J=5.8 Hz), 6.9-7.1 (2H, m), 7.42 (1H, dd, J=2.5 Hz, 8.3 Hz), 7.5-7.6 (2H, m), 8.2-8.4 (2H, m), 8.88 (1H, d, J=2.4 Hz), 12.86 (1H, brs) ESI(+)-MS: 483 (M$^+$+1)

Example 197: N-(3-{6-Oxo-4-[5-(1-propynyl)pyridin-3-yl]-1,6-dihydropyrimidin-2-yl}-4-(trifluoromethyl)benzyl)isobutyramide By performing operations similar to those of Example 4 using 5-(1-propynyl)pyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=6.8 Hz), 2.10 (3H, s), 2.46 (1H, sept, J=6.8 Hz), 4.41 (2H, d, J=5.8 Hz), 7.17 (1H, brs), 7.5-7.7 (2H, m), 7.89 (1H, d, J=7.8 Hz), 8.3-8.5 (2H, m), 8.67 (1H, d, J=1.9 Hz), 9.15 (1H, d, J=2.0 Hz), 13.10 (1H, brs)

MS (m/z): 454 (M$^+$)

Example 198: N-(4-Chloro-3-{6-oxo-4-[5-(trifluoromethyl)pyridin-3-yl]-1,6-dihydropyrimidin-2-yl}benzyl)isobutyramide By performing operations similar to those of Example 4 using 5-(trifluoromethyl)pyridine-3-carbaldehyde, the title compound was obtained.

¹H-NMR (d₆-DMSO, δ): 1.03 (6H, d, J=6.8 Hz), 2.3-2.6 (1H, m), 4.32 (2H, d, J=6.4 Hz), 7.31 (1H, s), 7.44 (1H, dd, J=2.4 Hz, 8.4 Hz), 7.5-7.6 (2H, m), 8.34 (1H, t, J=6.0 Hz), 8.73 (1H, s), 9.10 (1H, d, J=1.2 Hz), 9.54 (1H, d, J=1.2 Hz), 13.11 (1H, s)

MS (m/z): 450 (+)

Example 199: N-(3-{4-[6-(3-Ethoxypropoxy)pyridin-3-yl]-6-oxo-1,6-dihydropyrimidin-2-yl}-4-(trifluoromethyl)benzyl)isobutyramide By performing operations similar to those of Example 4 using 6-(3-ethoxypropoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=7.6 Hz), 1.10 (3H, t, J=6.8 Hz), 1.95 (2H, quin, J=6.4 Hz), 2.4-2.6 (1H, m), 3.42 (2H, q, J=6.8 Hz), 3.50 (2H, t, J=6.4 Hz), 4.36 (2H, t, J=6.8 Hz), 4.40 (2H, d, J=6.0 Hz), 6.89 (1H, d, J=8.4 Hz), 6.96 (1H, s), 7.6-7.7 (2H, m), 7.88 (1H, d, J=8.0 Hz), 8.30 (1H, d, J=8.8 Hz), 8.39 (1H, t, J=6.0 Hz), 8.85 (1H, s), 12.97 (1H, s)

MS (m/z): 518 (M⁺)

Example 200: N-(4-Chloro-3-{4-[6-(2,2-difluoroethoxy)pyridin-3-yl]-6-oxo-1,6-dihydropyrimidin-2-yl}benzyl)isobutyramide By performing operations similar to those of Example 4 using 6-(2,2-difluoroethoxy)pyridine-3-carbaldehyde, the title compound was obtained.

¹H-NMR (d₆-DMSO, δ): 1.03 (6H, d, J=6.8 Hz), 2.4-2.6 (1H, m), 4.31 (2H, d, J=6.0 Hz), 4.63 (2H, dt, J=3.6 Hz, 15.2 Hz), 6.41 (1H, tt, J=3.6 Hz, 54.4 Hz), 6.96 (1H, s), 7.02 (1H, d, J=8.8 Hz), 7.40 (1H, dd, J=2.0 Hz, 8.0 Hz), 7.5-7.6 (2H, m), 8.34 (1H, t, J=6.0 Hz), 8.39 (1H, dd, J=2.4 Hz, 8.8 Hz), 8.89 (1H, d, J=2.0 Hz), 12.86 (1H, s)

MS (m/z): 462 (M⁺)

Example 201: N-(3-{4-[6-(2,2-Difluoroethoxy)pyridin-3-yl]-6-oxo-1,6-dihydropyrimidin-2-yl}-4-(trifluoromethyl)benzyl)isobutyramide By performing operations similar to those of Example 4 using 6-(2,2-difluoroethoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=7.6 Hz), 2.4-2.6 (1H, m), 4.40 (2H, d, J=6.0 Hz), 4.64 (2H, dt, J=3.2 Hz, 15.2 Hz), 6.41 (1H, tt, J=3.2 Hz, 54.8 Hz), 7.02 (2H, d, J=8.8 Hz), 7.5-7.6 (2H, m), 7.88 (1H, d, J=8.4 Hz), 8.3-8.4 (2H, m), 8.87 (1H, d, J=2.0 Hz), 12.96 (1H, s)

MS (m/z): 496 (M⁺)

Example 202: N-(3-{6-Oxo-4-[6-(2,2,2-trifluoroethoxy)pyridin-3-yl]-1,6-dihydropyrimidin-2-yl}-4-(trifluoromethyl)benzyl)isobutyramide By performing operations similar to those of Example 4 using 6-(2,2,2-trifluoroethoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=6.8 Hz), 2.4-2.6 (1H, m), 4.40 (2H, d, J=6.4 Hz), 5.06 (2H, q, J=8.8 Hz), 7.04 (1H, s), 7.09 (1H, d, J=8.8 Hz), 7.5-7.6 (2H, m), 7.88 (1H, d, J=8.4 Hz), 8.3-8.4 (2H, m), 8.89 (1H, d, J=1.2 Hz), 13.01 (1H, s)

MS (m/z): 514 (M⁺)

Example 203: N-(3-({6-Oxo-4-[6-(3,3,3-trifluoropropoxy)pyridin-3-yl]-1,6-dihydropyrimidin-2-yl}-4-(trifluoromethyl)benzyl)isobutyramide By performing operations similar to those of Example 4 using 6-(3,3,3-trifluoropropoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=6.8 Hz), 2.46 (1H, sept, J=6.8 Hz), 2.8-2.9 (2H, m), 4.40 (2H, d, J=6.0 Hz), 4.56 (2H, t, J=6.0 Hz), 6.93 (1H, d, J=8.8 Hz), 6.98 (1H, s), 7.6-7.7 (2H, m), 7.88 (1H, d, J=8.4 Hz), 8.34 (1H, d, J=7.6 Hz), 8.39 (1H, t, J=6.0 Hz), 8.87 (1H, s), 12.99 (1H, s)

MS (m/z): 528 (M⁺)

Example 204: N-(3-{4-[6-(2-Fluoroethoxy)pyridin-3-yl]-6-oxo-1,6-dihydropyrimidin-2-yl}-4-(trifluoromethyl)benzyl)isobutyramide By performing operations similar to those of Example 4 using 6-(2-fluoroethoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=6.8 Hz), 2.4-2.6 (1H, m), 4.40 (2H, d, J=6.0 Hz), 4.5-4.9 (4H, m), 6.9-7.0 (2H, m), 7.5-7.6 (2H, m), 7.88 (1H, d, J=8.4 Hz), 8.34 (1H, d, J=8.8 Hz), 8.39 (1H, t, J=6.0 Hz), 8.86 (1H, s), 12.98 (1H, s)

MS (m/z): 478 (M⁺)

Example 205: N-(3-{4-[6-(3-Fluoropropoxy)pyridin-3-yl]-6-oxo-1,6-dihydropyrimidin-2-yl}-4-(trifluoromethyl)benzyl)isobutyramide By performing operations similar to those of Example 4 using 6-(3-fluoropropoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=7.2 Hz), 2.0-2.2 (2H, m), 2.4-2.6 (1H, m), 4.3-4.7 (6H, m), 6.91 (1H, d, J=8.8 Hz), 6.98 (1H, s), 7.6-7.7 (2H, m), 7.88 (1H, d, J=8.4 Hz), 8.32 (1H, dd, J=2.0 Hz, 8.8 Hz), 8.39 (1H, t, J=6.0 Hz), 8.86 (1H, d, J=2.0 Hz), 12.96 (1H, s)

MS (m/z): 492 (M⁺)

Example 206: N-(3-{4-[2-(Difluoromethoxy)pyridin-4-yl]-6-oxo-1,6-dihydropyrimidin-2-yl}-4-(trifluoromethyl)benzyl)isobutyramide By performing operations similar to those of Example 4 using 2-(difluoromethoxy)pyridine-4-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=6.8 Hz), 2.46 (1H, sept, J=6.8 Hz), 4.40 (2H, d, J=5.6 Hz), 7.25 (1H, s), 7.6-7.7 (3H, m), 7.73 (1H, t, J=72.8 Hz), 7.8-7.9 (2H, m), 8.3-8.4 (2H, m), 13.23 (1H, s)

MS (m/z): 482 (M⁺)

Example 207: N-(3-{6-Oxo-4-[5-(trifluoromethyl)pyridin-2-yl]-1,6-dihydropyrimidin-2-yl}-4-(trifluoromethyl)benzyl)isobutyramide By performing operations similar to those of Example 4 using 5-(trifluoromethyl)pyridine-2-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (61H, d, J=6.81 Hz), 2.4-2.6 (1H, m), 4.41 (2H, d, J=5.6 Hz), 7.33 (1H, s), 7.6-7.7 (2H, m), 7.90 (1H, d, J=8.4 Hz), 8.3-8.4 (3H, m), 9.12 (1H, s), 13.23 (1H, s)

MS (m/z): 484 (M⁺)

Example 208: N-(3-[4-(5-Chloropyridin-2-yl)-6-oxo-1,6-dihydropyrimidin-2-yl]-4-(trifluoromethyl)benzyl)isobutyramide By performing operations similar to those of Example 4 using 5-chloropyridine-2-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=7.2 Hz), 2.4-2.6 (1H, m), 4.40 (2H, d, J=6.0 Hz), 7.21 (1H, s), 7.6-7.7 (2H, m), 7.89 (1H, d, J=7.6 Hz), 8.08 (1H, dd, J=2.8 Hz, 8.8 Hz), 8.19 (1H, d, J=8.0 Hz), 8.40 (1H, t, J=6.0 Hz), 8.78 (1H, d, J=2.4 Hz), 13.17 (1H, s)

MS (m/z): 450 (M⁺)

Example 209: N-(3-{6-Oxo-4-[5-(2-propoxyethoxy)pyridin-2-yl]-1,6-dihydropyrimidin-2-yl}-4-(trifluoromethyl)benzyl)isobutyramide By performing operations similar to those of Example 4 using 5-(propoxyethoxy)pyridine-2-carbaldehyde, and N-[3-carbamimidoyl-4-(trifluoromethyl)benzyl]isobutyramide hydrochloride, the title compound was obtained.

¹H-NMR (d₆-DMSO, δ): 0.86 (3H, t, J=7.2 Hz), 1.05 (6H, d, J=7.21 Hz), 1.52 (2H, sext, J=7.2 Hz), 2.4-2.6 (1H, m), 3.41 (2H, t, J=7.2 Hz), 3.7-3.8 (2H, m), 4.2-4.3 (2H, m), 4.40 (2H, d, J=6.4 Hz), 7.11 (1H, s), 7.52 (1H, dd, J=3.2 Hz, 8.8 Hz), 7.6-7.7 (2H, m), 7.88 (1H, d, J=8.4 Hz), 8.14 (1H, d, J=8.8 Hz), 8.39 (1H, t, J=6.0 Hz), 8.43 (1H, d, J=3.2 Hz), 12.98 (1H, s)

MS (m/z): 518 (M⁺)

Example 210: N-(3-{4-[5-(Difluoromethoxy)pyridin-2-yl]-6-oxo-1,6-dihydropyrimidin-2-yl}-4-(trifluoromethyl)benzyl)isobutyramide By performing operations similar to those of Example 4 using 5-(difluoromethoxy)pyridine-2-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J 6.8 Hz), 2.4-2.6 (1H, m), 4.40 (2H, d, J=6.0 Hz), 7.18 (1H, s), 7.41 (1H, t, J=73.2 Hz), 7.6-7.7 (2H, m), 7.80 (1H, dd, J=3.2 Hz, 8.8 Hz), 7.89 (1H, d, J=8.4 Hz), 8.24 (1H, d, J=8.4 Hz), 8.40 (1H, t, J=6.0 Hz), 8.63 (1H, d, J=2.4 Hz), 13.14 (1H, s)

MS (m/z): 482 (M⁺)

Example 211: N-(4-Chloro-3-{4-[5-(cyclopropylmethoxy)pyridin-2-yl]-6-oxo-1,6-dihydropyrimidin-2-yl}benzyl)isobutyramide By performing operations similar to those of Example 4 using 5-cyclopropylmethoxy)pyridine-2-carbaldehyde, the title compound was obtained.

¹H-NMR (d₆-DMSO, δ): 0.3-0.4 (2H, m), 0.5-0.6 (2H, m), 1.04 (6H, d, J=7.2 Hz), 1.2-1.3 (1H, m), 2.4-2.6 (1H, m), 3.98 (2H, d, J=7.2 Hz), 4.31 (2H, d, J=5.6 Hz), 7.10 (1H, s), 7.41 (1H, dd, J=2.0 Hz, 8.4 Hz), 7.48 (1H, dd, J=2.8 Hz, 8.4 Hz), 7.5-7.6 (2H, m), 8.18 (1H, d, J=8.8 Hz), 8.34 (1H, t, J=5.6 Hz), 8.42 (1H, d, J=2.8 Hz), 12.86 (1H, s)

MS (m/z): 452 (M⁺)

Example 212: N-(3-{4-[5-(Cyclopropylmethoxy)pyridin-2-yl]-6-oxo-1,6-dihydropyrimidin-2-yl}-4-(trifluoromethyl)benzyl)isobutyramide By performing operations similar to those of Example 4 using 5-(cyclopropylmethoxy)pyridine-2-carbaldehyde, and N-[3-carbamimidoyl-4-(trifluoromethyl)benzyl]isobutyramide hydrochloride, the title compound was obtained.

¹H-NMR (d₆-DMSO, δ): 0.3-0.4 (2H, m), 0.5-0.6 (2H, m), 1.05 (6H, d, J=7.2 Hz), 1.2-1.3 (1H, m), 2.4-2.6 (1H, m), 3.97 (2H, d, J=6.8 Hz), 4.40 (2H, d, J=6.0 Hz), 7.11 (1H, s), 7.48 (1H, dd, J=2.8 Hz, 8.4 Hz), 7.6-7.7 (2H, m), 7.88 (1H, d, J=8.4 Hz), 8.13 (1H, d, J=8.4 Hz), 8.3-8.4 (2H, m), 12.97 (1H, s)

MS (m/z): 486 (M⁺)

Example 213: N-(4-Chloro-2-fluoro-3-{6-oxo-4-[6-(trifluoromethyl)pyridin-3-yl]-1,6-dihydropyrimidin-2-yl}benzyl)butyramide By performing operations similar to those of Example 4 using 6-(trifluoromethyl)pyridine-3-carbaldehyde, and N-(3-carbamimidoyl-4-chloro-2-fluorobenzyl)butyramide hydrochloride, the title compound was obtained.

¹H-NMR (d₆-DMSO, δ): 0.87 (3H, t, J=7.2 Hz), 1.55 (2H, sext, J=7.2 Hz), 2.14 (2H, t, J=7.2 Hz), 4.33 (2H, d, J=6.0 Hz), 7.31 (1H, s), 7.4-7.5 (2H, m), 8.02 (1H, d, J=8.4 Hz), 8.40 (1H, t, J=6.0 Hz), 8.67 (1H, d, J=8.0 Hz), 9.39 (1H, s), 13.34 (1H, s)

MS (m/z): 468 (M⁺)

Example 214: N-(4-Chloro-3-{4-[6-(difluoromethoxy)pyridin-3-yl]-6-oxo-1,6-dihydropyrimidin-2-yl}-2-fluorobenzyl)butyramide By performing operations similar to those of Example 4 using 6-(difluoromethoxy)pyridine-3-carbaldehyde, and N-(3-carbamimidoyl-4-chloro-2-fluorobenzyl)butyramide hydrochloride, the title compound was obtained.

¹H-NMR (d₆-DMSO, δ): 0.87 (3H, t, J=7.6 Hz), 1.55 (2H, sext, J=7.6 Hz), 2.14 (2H, t, J=7.6 Hz), 4.33 (2H, d, J=5.2 Hz), 7.13 (1H, s), 7.19 (1H, d, J=8.4 Hz), 7.4-7.5 (2H, m), 7.77 (1H, t, J=76.4 Hz), 8.40 (1H, t, J=5.2 Hz), 8.51 (1H, dd, J=0.8 Hz, 8.8 Hz), 8.92 (1H, s), 13.19 (1H, s)

MS (m/z): 466 (M⁺)

Example 215: N-[3-(2'-Cyclopropylmethoxy-6-oxo-1,6-dihydro-[4,5'-bipyrimidin]-2-yl)-4-(trifluoromethyl)benzyl]isobutyramide By performing operations similar to those of Example 4 using 2-(cyclopropylmethoxy)pyrimidine-5-carbaldehyde, and N-[3-carbamimidoyl-4-(trifluoromethyl)benzyl]isobutyramide hydrochloride, the title compound was obtained.

¹H-NMR (d₆-DMSO, δ): 0.3-0.4 (2H, m), 0.5-0.6 (2H, m), 1.05 (6H, d, J=6.8 Hz), 1.2-1.3 (1H, m), 2.4-2.6 (1H, m), 4.22 (2H, d, J=6.8 Hz), 4.40 (2H, d, J=6.0 Hz), 7.09 (1H, s), 7.5-7.6 (2H, m), 7.89 (1H, d, J=8.4 Hz), 8.39 (1H, t, J=6.0 Hz), 9.1-9.2 (2H, m), 13.07 (1H, s)

MS (m/z): 487 (M$^+$)

Example 216: N-{3-[4-(6-Butoxypyridazin-3-yl)-6-oxo-1,6-dihydropyrimidin-2-yl]-4-(trifluoromethyl)benzyl}isobutyramide By performing operations similar to those of Example 4 using 6-butoxypyridazine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 0.93 (3H, t, J=7.6 Hz), 1.05 (6H, d, J=7.2 Hz), 1.34 (2H, sext, J=7.6 Hz), 1.77 (2H, quin, J=7.2 Hz), 2.4-2.6 (1H, m), 4.17 (2H, t, J=7.6 Hz), 4.39 (2H, d, J=6.0 Hz), 6.96 (1H, s), 7.03 (1H, d, J=10.0 Hz), 7.5-7.7 (2H, m), 7.88 (1H, d, J=8.4 Hz), 7.99 (1H, d, J=9.6 Hz), 8.39 (1H, t, J=6.0 Hz), 13.17 (1H, s)

MS (m/z): 489 (M$^+$)

Example 217: N-{4-Chloro-3-[6-oxo-2'-(trifluoromethyl)-1,6-dihydro-[4,5'-bipyrimidin]-2-yl]benzyl}isobutyramide By performing operations similar to those of Example 4 using 2-(trifluoromethyl)pyrimidine-5-carbaldehyde, the title compound was obtained.

$^1$H-NMR (d$_6$-DMSO, δ): 1.03 (6H, d, J=6.8 Hz), 2.43 (1H, sept, J=6.8 Hz), 4.32 (2H, d, J=6.0 Hz), 7.34 (1H, s), 7.44 (1H, dd, J=2.0 Hz, 8.0 Hz), 7.5-7.6 (2H, m), 8.34 (1H, t, J=6.0 Hz), 9.63 (2H, s), 13.21 (1H, s)

MS (m/z): 451 (M$^+$)

Example 218: N-(4-Chloro-3-{4-[(2-cyclopropylmethoxy)pyridin-4-yl]-6-oxo-1,6-dihydropyrimidin-2-yl}benzyl)isobutyramide By performing operations similar to those of Example 4 using 2-(cyclopropylmethoxy)pyridine-4-carbaldehyde, the title compound was obtained.

$^1$H-NMR (d$_6$-DMSO, δ): 0.3-0.4 (2H, m), 0.5-0.6 (2H, m), 1.04 (6H, d, J=6.8 Hz), 1.2-1.3 (1H, m), 2.4-2.6 (1H, m), 4.14 (2H, d, J=7.2 Hz), 4.32 (2H, d, J=6.4 Hz), 7.11 (1H, s), 7.4-7.5 (2H, m), 7.5-7.6 (3H, m), 8.24 (1H, d, J=5.6 Hz), 8.34 (1H, t, J=5.6 Hz), 13.05 (1H, s)

MS (m/z): 452 (M$^+$)

Example 219: N-{4-Chloro-2-fluoro-3-[4-(5-fluoropyridin-2-yl)-6-oxo-1,6-dihydropyrimidin-2-yl]benzyl}isobutyramide By performing operations similar to those of Example 4 using 5-fluoropyridine-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=7.2 Hz), 2.45 (1H, sept, J=6.8 Hz), 4.33 (2H, d, J=6.0 Hz), 7.21 (1H, s), 7.4-7.6 (2H, m), 7.84 (1H, dt, J=2.8 Hz, 8.8 Hz), 8.2-8.3 (1H, m), 8.37 (1H, t, J=6.0 Hz), 8.74 (1H, d, J=3.2 Hz), 13.28 (1H, brs)

MS (m/z): 418 (M$^+$)

Example 220: N-{2-Fluoro-3-[4-(6-methoxypyridin-3-yl)-6-oxo-1,6-dihydropyrimidin-2-yl]-4-(trifluoromethyl)benzyl}isobutyramide By performing operations similar to those of Example 169 using 2-[3-chloro-2-fluoro-6-(trifluoromethyl)phenyl]-6-(6-methoxypyridin-3-yl)pyrimidin-4(3H)-one, the title compound was obtained.

$^1$H-NMR (d$_6$-DMSO, δ): 1.06 (6H, d, J=6.8 Hz), 2.48 (1H, sept, J=6.8 Hz), 3.91 (3H, s), 4.40 (2H, d, J=6.0 Hz), 6.91 (1H, d, J=8.8 Hz), 7.01 (1H, s), 7.65 (1H, t, J=8.0 Hz), 7.78 (1H, d, J=7.6 Hz), 8.30 (1H, d, J=8.4 Hz), 8.44 (1H, t, J=6.0 Hz), 8.85 (1H, s), 13.17 (1H, brs)

MS (m/z): 464 (M$^+$)

Example 221: N-(4-Chloro-3-{4-[6-(cyclopropylethynyl)pyridin-3-yl]-6-oxo-1,6-dihydropyrimidin-2-yl}-2-fluorobenzyl)isobutyramide By performing operations similar to those of Example 4 using 6-(cyclopropylethynyl)pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 0.8-1.0 (4H, m), 1.04 (6H, d, J=6.8 Hz), 1.6-1.7 (1H, m), 2.45 (1H, sept, J=6.8 Hz), 4.32 (2H, d, J=5.6 Hz), 7.14 (1H, s), 7.4-7.5 (3H, m), 8.3-8.4 (2H, m), 9.13 (1H, d, J=1.6 Hz), 13.22 (1H, brs)

MS (m/z): 464 (M$^+$)

Example 222: N-{2-Chloro-3-[4-(5-chloropyridin-2-yl)-6-oxo-1,6-dihydropyrimidin-2-yl]-4-fluorobenzyl}isobutyramide By performing operations similar to those of Example 4 using 5-chloropyridine-2-carbaldehyde, and N-(3-carbamimidoyl-2-chloro-4-fluorobenzyl)isobutyramide hydrochloride, the title compound was obtained.

$^1$H-NMR (d$_6$-DMSO, δ): 1.07 (6H, d, J=6.8 Hz), 2.4-2.6 (1H, m), 4.35 (2H, d, J=6.0 Hz), 7.25 (1H, s), 7.4-7.5 (2H, m), 8.05 (1H, dd, J=2.4 Hz, 8.4 Hz), 8.21 (1H, d, J=8.4 Hz), 8.38 (1H, t, J=6.0 Hz), 8.79 (1H, d, J=2.4 Hz), 13.29 (1H, brs)

MS (m/z): 434 (M$^+$)

Example 223: N-(4-Chloro-3-[4-(4-cyanophenyl)-6-oxo-1,6-dihydropyrimidin-2-yl]-2-fluorobenzyl)isobutyramide By performing operations similar to those of Example 4 using 4-formylbenzonitrile, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.45 (1H, sept, J=6.8 Hz), 4.32 (2H, d, J=6.0 Hz), 7.17 (1H, s), 7.4-7.5 (2H, m), 7.95 (2H, d, J=8.4 Hz), 8.24 (2H, d, J=8.4 Hz), 8.36 (1H, t, J=6.0 Hz), 13.27 (1H, brs)

MS (m/z): 424 (M$^+$)

Example 224: N-{4-Chloro-2-fluoro-3-[6-oxo-4-(6-phenylpyridin-3-yl)-1,6-dihydropyrimidin-2-yl]benzyl}isobutyramide By performing operations similar to those of Example 4 using 6-phenylpyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=6.8 Hz), 2.46 (1H, sept, J=6.8 Hz), 4.34 (2H, d, J=5.6 Hz), 7.20 (1H, s), 7.4-7.5 (5H, m), 8.09 (1H, d, J=8.4 Hz), 8.1-8.2 (2H, m), 8.37 (1H, t, J=5.6 Hz), 8.48 (1H, dd, J=2.0 Hz, 8.0 Hz), 9.31 (1H, d, J=1.6 Hz), 13.17 (1H, brs)

MS (m/z): 476 (M$^+$)

Example 225: N-(2,4-Difluoro-3-{6-oxo-4-[5-(trifluoromethyl)pyridin-2-yl]-1,6-dihydropyrimidin-2-yl}benzyl)isobutyramide By performing operations similar to those of Example 4 using 5-(trifluoromethyl)pyridine-2-carbaldehyde, and N-(3-carbamimidoyl-2,4-difluorobenzyl)isobutyramide hydrochloride, the title compound was obtained.

$^1$H-NMR (d$_6$-DMSO, δ): 1.05 (6H, d, J=6.8 Hz), 2.45 (1H, sept, J=6.8 Hz), 4.33 (2H, d, J=6.0 Hz), 7.30 (1H, t, J=8.8 Hz), 7.35 (1H, s), 7.53 (1H, q, J=8.0 Hz), 8.3-8.4 (3H, m), 9.13 (1H, s), 13.40 (1H, brs)

MS (m/z): 452 (M$^+$)

Example 226: N-{3-[4-(5-Chloropyridin-3-yl)-6-oxo-1,6-dihydropyrimidin-2-yl]-2,4-difluorobenzyl}isobutyramide By performing operations similar to those of Example 4 using 5-chloropyridine-3-carbaldehyde, and N-(3-carbamimidoyl-2,4-difluorobenzyl)isobutyramide hydrochloride, the title compound was obtained.

$^1$H-NMR (d$_6$-DMSO, δ): 1.04 (6H, d, J=6.8 Hz), 2.45 (1H, sept, J=6.8 Hz), 4.32 (2H, d, J=6.0 Hz), 7.24 (1H, s), 7.29 (1H, t, J=8.8 Hz), 7.4-7.5 (1H, m), 8.33 (1H, t, J=5.6 Hz), 8.49 (1H, s), 8.75 (1H, d, J=2.4 Hz), 9.18 (1H, d, J=1.6 Hz), 13.31 (1H, brs)

MS (m/z): 418 (M$^+$)

Example 227: N-(4-Chloro-3-{4-[6-(difluoromethyl)pyridin-3-yl]-6-oxo-1,6-dihydropyrimidin-2-yl}-2-fluorobenzyl)isobutyramide By performing operations similar to those of Example 4 using 6-(difluoromethyl)pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.45 (1H, sept, J=6.8 Hz), 4.33 (2H, d, J=6.0 Hz), 7.04 (1H, t, J=54.8 Hz), 7.25 (1H, s), 7.4-7.5 (2H, m), 7.81 (1H, d, J=8.4 Hz), 8.39 (1H, t, J=6.0 Hz), 8.60 (1H, d, J=8.0 Hz), 9.31 (1H, s), 13.35 (1H, brs)

MS (m/z): 450 (M$^+$)

Example 228: N-(2-Chloro-3-{4-[6-(cyclopropylethynyl)pyridin-3-yl]-6-oxo-1,6-dihydropyrimidin-2-yl}-4-fluorobenzyl)isobutyramide By performing operations similar to those of Example 4 using 6-(cyclopropylethynyl)pyridine-3-carbaldehyde, and N-(3-carbamimidoyl-2-chloro-4-fluorobenzyl)isobutyramide hydrochloride, the title compound was obtained.

$^1$H-NMR (d$_6$-DMSO, δ): 0.8-1.0 (4H, m), 1.07 (6H, d, J=6.8 Hz), 1.6-1.7 (1H, m), 2.4-2.6 (1H, m), 4.34 (2H, d, J=6.0 Hz), 7.14 (1H, s), 7.4-7.5 (3H, m), 8.3-8.4 (2H, m), 9.13 (1H, d, J=1.6 Hz), 13.21 (1H, brs)

MS (m/z): 464 (M$^+$)

Example 229: N-(4-Chloro-3-{4-[5-(difluoromethyl)pyridin-2-yl]-6-oxo-1,6-dihydropyrimidin-2-yl}-2-fluorobenzyl)isobutyramide By performing operations similar to those of Example 4 using 5-(difluoromethyl)pyridine-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=7.2 Hz), 2.46 (1H, sept, J=6.8 Hz), 4.33 (2H, d, J=6.0 Hz), 7.23 (1H, t, J=55.2 Hz), 7.32 (1H, s), 7.4-7.6 (2H, m), 8.15 (1H, d, J=7.6 Hz), 8.3-8.4 (2H, m), 8.93 (1H, s), 13.33 (1H, brs)

MS (m/z): 450 (M$^+$)

Example 230: N-{3-[4-(5-Chloropyridin-2-yl)-6-oxo-1,6-dihydropyrimidin-2-yl]-2,4-difluorobenzyl}isobutyramide By performing operations similar to those of Example 4 using 5-chloropyridine-2-carbaldehyde, and N-(3-carbamimidoyl-2,4-difluorobenzyl)isobutyramide hydrochloride, the title compound was obtained.

$^1$H-NMR (d$_6$-DMSO, δ): 1.04 (6H, d, J=6.8 Hz), 2.45 (1H, sept, J=6.8 Hz), 4.32 (2H, d, J=6.0 Hz), 7.23 (1H, s), 7.29 (1H, t, J=8.8 Hz), 7.4-7.6 (1H, m), 8.08 (1H, dd, J=2.4 Hz, 8.4 Hz), 8.22 (1H, d, J=8.4 Hz), 8.34 (1H, t, J=6.0 Hz), 8.78 (1H, d, J=2.4 Hz), 13.32 (1H, brs)

MS (m/z): 418 (M$^+$)

Example 231: N-(4-Chloro-2-fluoro-3-{6-oxo-4-[6-(trifluoromethyl)pyridin-2-yl]-1,6-dihydropyrimidin-2-yl}benzyl)isobutyramide By performing operations similar to those of Example 4 using 6-(trifluoromethyl)pyridine-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=7.2 Hz), 2.46 (1H, sept, J=6.8 Hz), 4.33 (2H, d, J=5.6 Hz), 7.26 (1H, s), 7.4-7.5 (2H, m), 8.05 (1H, d, J=7.6 Hz), 8.25 (1H, t, J=8.0 Hz), 8.37 (1H, t, J=5.6 Hz), 8.47 (1H, d, J=8.0 Hz), 13.40 (1H, brs)

MS (m/z): 468 (M$^+$)

Example 232: N-(2-Chloro-4-fluoro-3-{6-oxo-4-[4-(trifluoromethyl)thiazol-2-yl]-1,6-dihydropyrimidin-2-yl}benzyl)isobutyramide By performing operations similar to those of Example 4 using 4-(trifluoromethyl)thiazole-2-carbaldehyde, and N-(3-carbamimidoyl-2-chloro-4-fluorobenzyl)isobutyramide hydrochloride, the title compound was obtained.

$^1$H-NMR (d$_6$-DMSO, δ): 1.07 (6H, d, J=7.2 Hz), 2.4-2.6 (1H, m), 4.35 (2H, d, J=6.0 Hz), 7.05 (1H, s), 7.4-7.6 (2H, m), 8.39 (1H, t, J=6.0 Hz), 8.76 (1H, s), 13.51 (1H, brs)

MS (m/z): 474 (M$^+$)

Example 233: N-(4-Chloro-3-{4-[2-(cyclopropylethynyl)thiazol-5-yl]-6-oxo-1,6-dihydropyrimidin-2-yl}-2-fluorobenzyl)isobutyramide By performing operations similar to those of Example 4 using 2-(cyclopropylethynyl)thiazole-5-carbaldehyde, and N-(3-carbamimidoyl-4-chloro-2-fluorobenzyl)isobutyramide hydrochloride, the title compound was obtained.

$^1$H-NMR (d$_6$-DMSO, δ): 0.8-1.0 (4H, m), 1.04 (6H, d, J=6.8 Hz), 1.6-1.7 (1H, m), 2.45 (1H, sept, J=6.8 Hz), 4.31

(2H, d, J=6.0 Hz), 7.07 (1H, s), 7.4-7.5 (2H, m), 8.36 (1H, t, J=5.6 Hz), 8.59 (1H, s), 13.22 (1H, brs)
MS (m/z): 470 (M⁺)

Example 234: N-(2-Chloro-3-{4-[5-(cyclopropylethynyl)pyridin-2-yl]-6-oxo-1,6-dihydropyrimidin-2-yl}-4-fluorobenzyl)isobutyramide By performing operations similar to those of Example 4 using 5-(cyclopropylethynyl)pyridine-2-carbaldehyde, and N-(3-carbamimidoyl-2-chloro-4-fluorobenzyl)isobutyramide hydrochloride, the title compound was obtained.
¹H-NMR (d₆-DMSO, δ): 0.8-1.0 (4H, m), 1.07 (6H, d, J=7.2 Hz), 1.6-1.7 (1H, m), 2.4-2.6 (1H, m), 4.34 (2H, d, J=6.0 Hz), 7.23 (1H, s), 7.4-7.5 (2H, m), 7.88 (1H, dd, J=2.0 Hz, 8.4 Hz), 8.15 (1H, d, J=8.4 Hz), 8.38 (1H, t, J=6.0 Hz), 8.69 (1H, d, J=2.0 Hz), 13.26 (1H, brs)
MS (m/z): 464 (M⁺)

Example 235: N-(4-Chloro-3-{4-[6-(3-ethyloxetan-3-ylmethoxy)pyridin-3-yl]-6-oxo-1,6-dihydropyrimidin-2-yl}benzyl)isobutyramide By performing operations similar to those of Example 4 using 6-(3-ethyloxetan-3-ylmethoxy)pyridine-3-carbaldehyde, the title compound was obtained.
¹H-NMR (d₆-DMSO, δ): 0.90 (3H, t, J=7.8 Hz), 1.04 (6H, d, J=6.8 Hz), 1.77 (2H, q, J=7.3 Hz), 2.43 (1H, sept, J=6.8 Hz), 4.2-4.6 (8H, m), 6.9-7.0 (2H, m), 7.42 (1H, dd, J=2.0 Hz, 8.3 Hz), 7.5-7.6 (2H, m), 8.2-8.4 (2H, m), 8.89 (1H, d, J=2.2 Hz), 12.85 (1H, brs) ESI(+)-MS: 497 (M⁺+1)

Example 236: N-(3-{4-[6-(3-Ethyloxetan-3-ylmethoxy)pyridin-3-yl]-6-oxo 1,6-dihydropyrimidin-2-yl}-4-(trifluoromethyl)benzyl)isobutyramide By performing operations similar to those of Example 4 using 6-(3-ethyloxetan-3-ylmethoxy)pyridine-3-carbaldehyde, and N-[3-carbamimidoyl-4-(trifluoromethyl)benzyl]isobutyramide hydrochloride, the title compound was obtained.
¹H-NMR (d₆-DMSO, δ): 0.90 (3H, t, J=7.3 Hz), 1.05 (6H, d, J=6.8 Hz), 1.77 (2H, q, J=7.3 Hz), 2.46 (1H, sept, J=6.8 Hz), 4.33 (2H, d, J=5.9 Hz), 4.40 (2H, d, J=5.9 Hz), 4.45 (2H, d, J=5.9 Hz), 4.48 (2H, s), 6.9-7.0 (2H, m), 7.5-7.7 (2H, m), 7.87 (1H, d, J=7.8 Hz), 8.32 (1H, dd, J=2.4 Hz, 8.7 Hz), 8.40 (1H, t, J=5.9 Hz), 8.86 (1H, d, J=2.0 Hz), 12.92 (1H, brs)
ESI(+)-MS: 531 (M⁺+1)

Example 237: N-{4-Chloro-2-fluoro-3-[4-(4-methylthiazol-2-yl)-6-oxo-1,6-dihydropyrimidin-2-yl]benzyl}isobutyramide By performing operations similar to those of Example 4 using 4-methylthiazole-2-carbaldehyde, and N-(3-carbamimidoyl-4-chloro-2-fluorobenzyl)isobutyramide hydrochloride, the title compound was obtained.
¹H-NMR (d₆-DMSO, δ): 1.05 (6H, d, J=6.8 Hz), 2.45 (1H, sept, J=6.8 Hz), 2.47 (3H, s), 4.33 (2H, d, J=5.9 Hz), 6.96 (1H, brs), 7.4-7.6 (2H, m), 7.59 (1H, s), 8.37 (1H, t, J=6.1 Hz), 13.31 (1H, brs)
MS (m/z): 420 (M⁺)

Example 238: N-(4-Chloro-2-fluoro-3-{6-oxo-4-[4-(1-propynyl)thiazol-2-yl]-1,6-dihydropyrimidin-2-yl}benzyl)isobutyramide By performing operations similar to those of Example 4 using 4-(1-propynyl)thiazole-2-carbaldehyde, and N-(3-carbamimidoyl-4-chloro-2-fluorobenzyl)isobutyramide hydrochloride, the title compound was obtained.
¹H-NMR (d₆-DMSO, δ): 1.04 (6H, d, J=6.8 Hz), 2.09 (3H, s), 2.45 (1H, sept, J=6.8 Hz), 4.33 (2H, d, J=5.9 Hz), 6.99 (1H, brs), 7.4-7.6 (2H, m), 8.10 (1H, s), 8.36 (1H, t, J=5.8 Hz), 13.39 (1H, brs)
MS (m/z): 444 (M⁺)

Example 239: N-(4-Chloro-3-{4-[5-(cyclopropylethynyl)thiazol-2-yl]-6-oxo-1,6-dihydropyrimidin-2-yl}-2-fluorobenzyl)isobutyramide By performing operations similar to those of Example 4 using 5-(cyclopropylethynyl)thiazole-2-carbaldehyde, and N-(3-carbamimidoyl-4-chloro-2-fluorobenzyl)isobutyramide hydrochloride, the title compound was obtained.
¹H-NMR (d₆-DMSO, δ): 0.7-1.0 (4H, m), 1.05 (6H, d, J=6.8 Hz), 1.6-1.7 (1H, s), 2.45 (1H, sept, J=6.8 Hz), 4.33 (2H, d, J=5.9 Hz), 6.99 (1H, brs), 7.4-7.6 (2H, m), 8.13 (1H, s), 8.37 (1H, t, J=6.1 Hz), 13.38 (1H, brs)
MS (m/z): 470 (M⁺)

Example 240: N-(4-Chloro-3-{4-[4-(cyclopropylethynyl)thiazol-2-yl]-6-oxo-1,6-dihydropyrimidin-2-yl}-2-fluorobenzyl)isobutyramide By performing operations similar to those of Example 4 using 4-(cyclopropylethynyl)thiazole-2-carbaldehyde, and N-(3-carbamimidoyl-4-chloro-2-fluorobenzyl)isobutyramide hydrochloride, the title compound was obtained.
¹H-NMR (d₆-DMSO, δ): 0.7-1.0 (4H, m), 1.04 (6H, d, J=6.8 Hz), 1.5-1.7 (1H, m), 2.45 (1H, sept, J=6.8 Hz), 4.32 (2H, d, J=5.9 Hz), 6.98 (1H, brs), 7.4-7.6 (2H, m), 8.08 (1H, s), 8.36 (1H, t, J=5.4 Hz), 13.39 (1H, brs)
MS (m/z): 470 (M⁺)

Example 241: N-(3-{4-[5-(Cyclopropylethynyl)thiazol-2-yl]-6-oxo-1,6-dihydropyrimidin-2-yl}-4-(trifluoromethyl)benzyl)isobutyramide By performing operations similar to those of Example 4 using 5-(cyclopropylethynyl)thiazole-2-carbaldehyde, and N-[3-carbamimidoyl-4-(trifluoromethyl)benzyl]isobutyramide hydrochloride, the title compound was obtained.
¹H-NMR (d₆-DMSO, δ): 0.7-1.0 (4H, m), 1.05 (6H, d, J=6.8 Hz), 1.5-1.7 (1H, m), 2.46 (1H, sept, J=6.8 Hz), 4.40 (2H, d, J=5.9 Hz), 6.94 (1H, brs), 7.5-7.7 (2H, m), 7.89 (1H, d, J=8.3 Hz), 8.11 (1H, s), 8.40 (1H, t, J=5.8 Hz), 13.23 (1H, brs)
MS (m/z): 486 (M⁺)

Example 242: N-(3-{4-[6-(Cyclopropylethynyl)pyridin-2-yl]-6-oxo-1,6-dihydropyrimidin-2-yl}-4-(trifluoromethyl)benzyl)isobutyramide By performing operations similar to those of Example 4 using 6-(cyclopropylethynyl)pyridine-2-carbaldehyde, and N-[3-carbamimidoyl-4-(trifluoromethyl)benzyl]isobutyramide hydrochloride, the title compound was obtained.
¹H-NMR (d₆-DMSO, δ): 0.8-1.0 (4H, m), 1.05 (6H, d, J=6.8 Hz), 1.5-1.7 (1H, m), 2.46 (1H, sept, J=6.8 Hz), 4.40 (2H, d, J=6.4 Hz), 7.18 (1H, brs), 7.54 (1H, dd, J=0.9 Hz, 7.8 Hz), 7.5-7.7 (2H, m), 7.8-8.0 (2H, m), 8.10 (1H, d, J=7.4 Hz), 8.40 (1H, t, J=5.8 Hz), 13.11 (1H, brs)
MS (m/z): 480 (M⁺)

Example 243: N-(4-Chloro-3-{4-[5-(cyclopropylethynyl)pyridin-3-yl]-6-oxo-1,6-dihydropyrimidin-2-yl}benzyl)isobutyramide By performing operations similar to those of Example 4 using 5-(cyclopropylethynyl)pyridine-3-carbaldehyde, the title compound was obtained.

$^1$H-NMR (d$_6$-DMSO, δ): 0.7-1.0 (4H, m), 1.04 (6H, d, J=6.8 Hz), 1.5-1.7 (1H, m), 2.44 (1H, sept, J=6.8 Hz), 4.32 (2H, d, J=5.9 Hz), 7.13 (1H, brs), 7.43 (1H, dd, J=2.5 Hz, 8.3 Hz), 7.5-7.7 (2H, m), 8.3-8.4 (2H, m), 8.65 (1H, d, J=1.9 Hz), 9.15 (1H, d, J=2.0 Hz), 13.02 (1H, brs)

MS (m/z): 446 (M$^+$)

Example 244: N-(3-{4-[5-(Cyclopropylethynyl)pyridin-3-yl]-6-oxo-1,6-dihydropyrimidin-2-yl}-4-(trifluoromethyl)benzyl)isobutyramide By performing operations similar to those of Example 4 using 5-(cyclopropylethynyl)pyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 0.7-1.0 (4H, m), 1.05 (6H, d, J=6.8 Hz), 1.5-1.7 (1H, m), 2.46 (1H, sept, J=6.8 Hz), 4.40 (2H, d, J=5.9 Hz), 7.16 (1H, brs), 7.5-7.7 (2H, m), 7.89 (1H, d, J=8.3 Hz), 8.34 (1H, s), 8.40 (1H, t, J=5.8 Hz), 8.64 (1H, d, J=2.0 Hz), 9.13 (1H, d, J=1.5 Hz), 13.11 (1H, brs)

MS (m/z): 480 (M$^+$)

Example 245: N-(3-{4-[6-(3-Morpholin-4-ylpropoxy)pyridin-3-yl]-6-oxo-1,6-dihydropyrimidin-2-yl}-4-(trifluoromethyl)benzyl)isobutyramide By performing operations similar to those of Example 4 using 6-(3-morpholin-4-ylpropoxy)pyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=7.2 Hz), 1.89 (2H, sext, J=6.8 Hz), 2.3-2.6 (7H, m), 3.56 (4H, t, J=4.8 Hz), 4.35 (2H, t, J=6.8 Hz), 4.40 (2H, d, J=5.6 Hz), 6.88 (1H, d, J=8.8 Hz), 6.98 (1H, s), 7.5-7.6 (2H, m), 7.88 (1H, d, J=7.6 Hz), 8.30 (1H, dd, J=2.4 Hz, 8.8 Hz), 8.39 (1H, t, J=6.0 Hz), 8.85 (1H, d, J=2.4 Hz), 12.90 (1H, s)

MS (m/z): 559 (M$^+$)

Example 246: N-(3-{6-Oxo-4-[5-(trifluoromethyl)pyridin-3-yl]-1,6-dihydropyrimidin-2-yl}-4-(trifluoromethyl)benzyl)isobutyramide By performing operations similar to those of Example 4 using 5-(trifluoromethyl)pyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=6.8 Hz), 2.46 (1H, sept, J=6.8 Hz), 4.41 (2H, d, J=5.6 Hz), 7.35 (1H, s), 7.6-7.7 (2H, m), 7.91 (1H, d, J=8.0 Hz), 8.42 (1H, t, J=6.0 Hz), 8.73 (1H, s), 9.10 (1H, s), 9.54 (1H, s), 13.23 (1H, s)

MS (m/z): 484 (M$^+$)

Example 247: N-(4-Chloro-2-fluoro-3-{6-oxo-4-[5-(trifluoromethyl)pyridin-3-yl]-1,6-dihydropyrimidin-2-yl}benzyl)isobutyramide By performing operations similar to those of Example 4 using 5-(trifluoromethyl)pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.43 (1H, sept, J=6.8 Hz), 4.33 (2H, d, J=6.0 Hz), 7.36 (1H, s), 7.4-7.5 (2H, m), 8.36 (1H, t, J=6.0 Hz), 8.70 (1H, s), 9.10 (1H, d, J=1.2 Hz), 9.51 (1H, d, J=1.6 Hz), 13.33 (1H, s)

MS (m/z): 468 (M$^+$)

Example 248: N-[3-(2'-Butyl-6-oxo-1,6-dihydro-[4,5'-bipyrimidin]-2-yl)-4-(trifluoromethyl)benzyl]isobutyramide By performing operations similar to those of Example 4 using 2-butylpyrimidine-5-carbaldehyde, and N-[3-carbamimidoyl-4-(trifluoromethyl)benzyl]isobutyramide hydrochloride, the title compound was obtained.

$^1$H-NMR (d$_6$-DMSO, δ): 0.90 (3H, t, J=7.2 Hz), 1.05 (6H, d, J=6.8 Hz), 1.34 (2H, sext, J=7.6 Hz), 1.76 (2H, quin, J=7.6 Hz), 2.46 (1H, sept, J=6.8 Hz), 2.93 (2H, t, J=7.2 Hz), 4.40 (2H, d, J=6.0 Hz), 7.17 (1H, s), 7.6-7.7 (2H, m), 7.89 (1H, d, J=8.4 Hz), 8.39 (1H, t, J=6.4 Hz), 9.28 (2H, s), 13.15 (1H, s)

MS (m/z): 473 (M$^+$)

Example 249: N-(3-{6-Oxo-4-[5-(trifluoromethyl)pyridin-2-yl]-1,6-dihydropyrimidin-2-yl}-4-(trifluoromethyl)benzyl)butyramide By performing operations similar to those of Example 4 using 5-(trifluoromethyl)pyridine-2-carbaldehyde, and N-[3-carbamimidoyl-4-(trifluoromethyl)benzyl]butyramide hydrochloride, the title compound was obtained.

$^1$H-NMR (d$_6$-DMSO, δ): 0.86 (3H, t, J=7.2 Hz), 1.55 (2H, sext, J=7.2 Hz), 2.15 (2H, t, J=7.2 Hz), 4.42 (2H, d, J=6.0 Hz), 7.31 (1H, s), 7.6-7.7 (2H, m), 7.90 (1H, d, J=7.6 Hz), 8.38 (2H, s), 8.44 (1H, t, J=6.0 Hz), 9.12 (1H, s), 13.26 (1H, s)

MS (m/z): 484 (M$^+$)

Example 250: N-(4-Chloro-2-fluoro-3-{6-oxo-4-[5-(trifluoromethyl)pyridin-2-yl]-1,6-dihydropyrimidin-2-yl}benzyl)butyramide By performing operations similar to those of Example 4 using 5-(trifluoromethyl)pyridine-2-carbaldehyde, and N-(3-carbamimidoyl-4-chloro-2-fluorobenzyl)butyramide hydrochloride, the title compound was obtained.

$^1$H-NMR (d$_6$-DMSO, δ): 0.87 (3H, t, J=7.2 Hz), 1.55 (2H, sext, J=7.2 Hz), 2.14 (2H, t, J=7.2 Hz), 4.34 (2H, d, J=6.0 Hz), 7.36 (1H, s), 7.5-7.6 (2H, m), 8.3-8.5 (3H, m), 9.13 (1H, d, J=1.2 Hz), 13.38 (1H, s)

MS (m/z): 468 (M$^+$)

Example 251: N-{4-Chloro-2-fluoro-3-[6-oxo-4-(6-propylpyridin-3-yl)-1,6-dihydropyrimidin-2-yl]benzyl}isobutyramide By performing operations similar to those of Example 4 using 6-propylpyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 0.91 (3H, t, J=7.2 Hz), 1.04 (6H, d, J=6.8 Hz), 1.07 (2H, sext, J=7.2 Hz), 2.45 (1H, sept, J=6.8 Hz), 2.76 (2H, t, J=7.6 Hz), 4.32 (2H, d, J=6.0 Hz), 7.09 (1H, s), 7.36 (1H, d, J=7.6 Hz), 7.4-7.5 (2H, m), 8.29 (1H, dd, J=2.4 Hz, 8.0 Hz), 8.36 (1H, t, J=6.0 Hz), 9.11 (1H, d, J=2.0 Hz), 13.10 (1H, s)

MS (m/z): 442 (M$^+$)

Example 252: N-{3-[6-Oxo-4-(6-propylpyridin-3-yl)-1,6-dihydropyrimidin-2-yl]-4-(trifluoromethyl)benzyl}isobutyramide By performing operations similar to those of Example 4 using 6-propylpyridine-3-carbaldehyde, and N-[3-carbamimidoyl-4-(trifluoromethyl)benzyl]isobutyramide hydrochloride, the title compound was obtained.

$^1$H-NMR (d$_6$-DMSO, δ): 0.91 (3H, t, J=7.2 Hz), 1.05 (6H, d, J=7.2 Hz), 1.71 (2H, sext, J=7.2 Hz), 2.4-2.6 (1H, m), 2.76 (2H, t, J=7.2 Hz), 4.40 (2H, d, J=6.0 Hz), 7.05 (1H, s), 7.35 (1H, d, J=8.4 Hz), 7.6-7.7 (2H, m), 7.88 (1H, d, J=8.0 Hz), 8.29 (1H, dd, J=2.4 Hz, 8.4 Hz), 8.39 (1H, t, J=6.0 Hz), 9.12 (1H, d, J=1.6 Hz), 13.00 (1H, s)

MS (m/z): 458 (M$^+$)

Example 253: N-{3-[2'-(3,3-Dimethyl-1-butynyl)-6-oxo-1,6-dihydro-[4,5'-bipyrimidin]-2-yl]-4-(trifluoromethyl)benzyl}isobutyramide By performing operations similar to those of Example 4 using 2-(3,3-dimethyl-1-butynyl)pyrimidine-5-carbaldehyde, and N-[3-carbamimidoyl-4-(trifluoromethyl)benzyl]isobutyramide hydrochloride, the title compound was obtained.

$^1$H-NMR (d$_6$-DMSO, δ): 1.05 (6H, d, J=7.2 Hz), 1.33 (9H, s), 2.4-2.6 (1H, m), 4.40 (2H, d, J=6.4 Hz), 7.24 (1H, s), 7.6-7.7 (2H, m), 7.89 (1H, d, J=7.6 Hz), 8.40 (1H, t, J=6.0 Hz), 9.32 (2H, s), 13.19 (1H, s)

MS (m/z): 497 (M$^+$)

Example 254: N-{4-Chloro-3-[2'-(3,3-dimethyl-1-butynyl)-6-oxo-1,6-dihydro-[4,5'-bipyrimidin]-2-yl]-2-fluorobenzyl}isobutyramide By performing operations similar to those of Example 4 using 2-(3,3-dimethyl-1-butynyl)pyrimidine-5-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 1.33 (9H, s), 2.45 (1H, sept, J=6.8 Hz), 4.32 (2H, d, J=5.6 Hz), 7.28 (1H, s), 7.4-7.5 (2H, m), 8.36 (1H, t, J=6.0 Hz), 9.31 (2H, s), 13.31 (1H, s)

MS (m/z): 481 (M$^+$)

Example 255: N-(4-Chloro-3-{4-[5-(cyclopropylethynyl)pyridin-2-yl]-6-oxo-1,6-dihydropyrimidin-2-yl}-2-fluorobenzyl)isobutyramide By performing operations similar to those of Example 4 using 5-(cyclopropylethynyl)pyridine-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 0.8-1.0 (4H, m), 1.04 (6H, d, J=6.8 Hz), 1.6-1.7 (1H, m), 2.45 (1H, sept, J=6.8 Hz), 4.32 (2H, d, J=6.0 Hz), 7.23 (1H, s), 7.4-7.5 (2H, m), 7.89 (1H, dd, J=2.0 Hz, 8.4 Hz), 8.15 (1H, d, J=8.0 Hz), 8.36 (1H, t, J=5.6 Hz), 8.69 (1H, d, J=2.0 Hz), 13.26 (1H, brs)

MS (m/z): 464 (M$^+$)

Example 256: N-{4-Chloro-2-fluoro-3-{6-oxo-4-[6-(1-propynyl)pyridin-3-yl]-1,6-dihydropyrimidin-2-yl}benzyl)isobutyramide By performing operations similar to those of Example 4 using 6-(1-propynyl)pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.11 (3H, s), 2.45 (1H, sept, J=6.8 Hz), 4.32 (2H, d, J=6.0 Hz), 7.14 (1H, s), 7.4-7.6 (3H, m), 8.3-8.4 (2H, m), 9.15 (1H, s), 13.23 (1H, brs)

MS (m/z): 438 (M$^+$)

Example 257: N-(2,4-Difluoro-3-{6-oxo-4-[6-(2-propoxyethoxy)pyridin-3-yl]-1,6-dihydropyrimidin-2-yl}benzyl)isobutyramide By performing operations similar to those of Example 4 using 6-(2-propoxyethoxy)pyridine-3-carbaldehyde, and N-(3-carbamimidoyl-2,4-difluorobenzyl)isobutyramide hydrochloride, the title compound was obtained.

$^1$H-NMR (d$_6$-DMSO, δ): 0.85 (3H, t, J=7.2 Hz), 1.04 (6H, d, J=6.8 Hz), 1.51 (2H, sext, J=7.2 Hz), 2.45 (1H, sept, J=6.8 Hz), 3.40 (2H, t, J=6.8 Hz), 3.71 (2H, t, J=4.4 Hz), 4.32 (2H, d, J=6.0 Hz), 4.44 (2H, t, J=4.4 Hz), 6.92 (1H, d, J=8.8 Hz), 7.00 (1H, s), 7.28 (1H, t, J=8.8 Hz), 7.4-7.6 (1H, m), 8.3-8.4 (2H, m), 8.85 (1H, s), 13.11 (1H, brs)

MS (m/z): 486 (M$^+$)

Example 258: N-{4-Chloro-2-fluoro-3-[4-(6-methoxypyridin-2-yl)-6-oxo-1,6-dihydropyrimidin-2-yl]benzyl}isobutyramide By performing operations similar to those of Example 4 using 6-methoxypyridine-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=7.2 Hz), 2.45 (1H, sept, J=6.8 Hz), 3.98 (3H, s), 4.33 (2H, d, J=6.0 Hz), 6.9-7.0 (1H, m), 7.29 (1H, s), 7.4-7.5 (2H, m), 7.8-7.9 (2H, m), 8.37 (1H, t, J=6.0 Hz), 13.15 (1H, brs)

MS (m/z): 430 (M$^+$)

Example 259: N-{2-Fluoro-3-[4-(5-fluoropyridin-3-yl)-6-oxo-1,6-dihydropyrimidin-2-yl]-4-(trifluoromethyl)benzyl}isobutyramide By performing operations similar to those of Example 169 using 2-[3-chloro-2-fluoro-6-(trifluoromethyl)phenyl]-6-(5-fluoropyridin-3-yl)pyrimidin-4(3H)-one, the title compound was obtained.

$^1$H-NMR (d$_6$-DMSO, δ): 1.06 (6H, d, J=6.8 Hz), 2.48 (1H, sept, J=6.8 Hz), 4.41 (2H, d, J=5.6 Hz), 7.25 (1H, s), 7.66 (1H, t, J=7.2 Hz), 7.80 (1H, d, J=8.0 Hz), 8.27 (1H, d, J=10.4 Hz), 8.44 (1H, t, J=5.6 Hz), 8.71 (1H, d, J=2.4 Hz), 9.10 (1H, s), 13.38 (1H, brs)

MS (m/z): 452 (M$^+$)

Example 260: N-[4-Chloro-2-fluoro-3-(4-{6-[(1-hydroxycyclohexyl)ethynyl]pyridin-3-yl}-6-oxo-1,6-dihydropyrimidin-2-yl)benzyl]isobutyramide By performing operations similar to those of Example 4 using 6-[(1-hydroxycyclohexyl)ethynyl]pyridine-3-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 1.2-1.3 (1H, m), 1.4-1.7 (7H, m), 1.8-1.9 (2H, m), 2.45 (1H, sept, J=6.8 Hz), 4.32 (2H, d, J=6.0 Hz), 5.58 (1H, s), 7.16 (1H, s), 7.4-7.5 (2H, m), 7.57 (1H, d, J=8.0 Hz), 8.3-8.4 (2H, m), 9.19 (1H, s), 13.25 (1H, brs)

MS (m/z): 522 (M+)

Example 261: N-(4-Chloro-2-fluoro-3-{6-oxo-4-[5-(1-propynyl)pyridin-2-yl]-1,6-dihydropyrimidin-2-yl}benzyl)isobutyramide By performing operations similar to those of Example 4 using 5-(1-propynyl)pyridine-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.12 (3H, s), 2.45 (1H, sept, J=6.8 Hz), 4.32 (2H, d, J=6.0 Hz), 7.24 (1H, s), 7.4-7.5 (2H, m), 7.92 (1H, dd, J=2.0 Hz, 8.4 Hz), 8.17 (1H, d, J=8.4 Hz), 8.36 (1H, t, J=5.6 Hz), 8.72 (1H, d, J=2.0 Hz), 13.27 (1H, brs)

MS (m/z): 438 (M+)

Example 262: N-{3-[4-(6-Ethoxypyridin-3-yl)-6-oxo-1,6-dihydropyrimidin-2-yl]-2-fluoro-4-(trifluoromethyl)benzyl}isobutyramide By performing operations similar to those of Example 169 using 2-[3-chloro-2-fluoro-6-(trifluoromethyl)phenyl]-6-(6-ethoxypyridin-3-yl)pyrimidin-4(3H)-one, the title compound was obtained.

$^1$H-NMR (d$_6$-DMSO, δ): 1.06 (6H, d, J=6.8 Hz), 1.33 (3H, t, J=6.8 Hz), 2.48 (1H, sept, J=6.8 Hz), 4.3-4.5 (4H, m), 6.88 (1H, d, J=8.8 Hz), 7.00 (1H, s), 7.65 (1H, t, J=8.0 Hz), 7.78 (1H, d, J=8.4 Hz), 8.28 (1H, d, J=8.4 Hz), 8.43 (1H, t, J=5.6 Hz), 8.83 (1H, s), 13.16 (1H, brs)

MS (m/z): 478 (M+)

Reference Example 94: 6-(2-Isopropoxyethoxy)pyridine-3-carbaldehyde

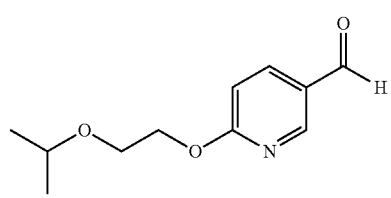

[Formula 107]

A mixture of 6-chloropyridine-3-carbaldehyde (2.83 g), 2-isopropoxyethanol (10 mL), and potassium carbonate (3.32 g) was stirred at 150° C. for 3 hours. The reaction mixture was left to cool, and then poured into saturated aqueous ammonium chloride. The resulting mixture was extracted with t-butyl methyl ether, and the organic layer was washed with brine. The solvent was evaporated, and then the residue was purified by silica gel column chromatography to obtain the title compound (2.27 g).

$^1$H-NMR (CDCl$_3$, δ): 1.20 (6H, d, J=5.8 Hz), 3.49 (1H, sept, J=6.3 Hz), 3.7-3.9 (2H, m), 4.5-4.7 (2H, m), 6.89 (1H, d, J=8.8 Hz), 8.06 (1H, dd, J=2.5 Hz, 8.8 Hz), 8.61 (1H, d, J=1.9 Hz), 9.95 (1H, s)

MS (m/z): 210 (M++1)

Reference Example 95: 6-[2-(2,2,2-Trifluoroethoxy)ethoxy]pyridine-3-carbaldehyde

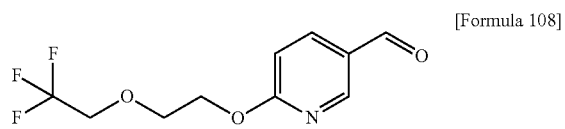 [SMILES: O=Cc1ccc(OCCOCC(F)(F)F)nc1]

[Formula 108]

By performing operations similar to those of Reference Example 94 using 2-(2,2,2-trifluoroethoxy)ethanol, the title compound was obtained.

$^1$H-NMR (CDCl$_3$, δ): 3.94 (2H, q, J=8.3 Hz), 4.01 (2H, t, J=4.4 Hz), 4.5-4.7 (2H, m), 6.90 (1H, d, J=8.3 Hz), 8.09 (11H, dd, J=1.9 Hz, 8.3 Hz), 8.61 (1H, d, J=2.0 Hz), 9.97 (1H, s)

MS (m/z): 249 (MI)

Reference Example 96: Methyl 5-(3,3-dimethyl-1-butynyl)pyrazine-2-carboxylate

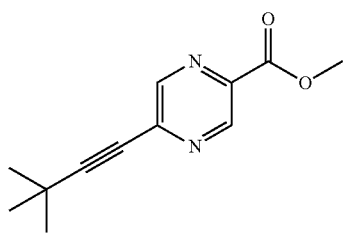

[Formula 109]

To a solution of methyl 5-chloropyrazine-2-carboxylate (1.5 g) in triethylamine (25 mL), 3,3-dimethyl-1-butyne (854 mg), dichlorobis(triphenylphosphine)palladium(II) (309 mg), and copper(I) iodide (42 mg) were added, and the resulting mixture was stirred at 60° C. for 3 hours. After cooling, the solvent was evaporated under reduced pressure. To the obtained residue, ethyl acetate was added, the resulting mixture was washed with 2 N hydrochloric acid, saturated aqueous sodium hydrogencarbonate, and saturated brine, and the organic layer was dried over magnesium sulfate. The organic layer was filtered, and the solvent was evaporated under reduced pressure. Then, the obtained residue was purified by silica gel column chromatography, and dried under reduced pressure to obtain the title compound (1.54 g).

$^1$H-NMR (CDCl$_3$, δ): 1.38 (9H, s), 4.04 (3H, s), 8.67 (1H, d, J=1.2 Hz), 9.21 (1H, d, J=1.2 Hz)

MS (m/z): 218 (M+)

Reference Example 97: [5-(3,3-Dimethyl-1-butynyl)pyrazin-2-yl]methanol

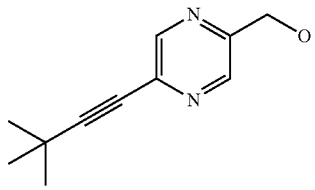

[Formula 110]

To a solution of lithium aluminum hydride (268 mg) in tetrahydrofuran (25 mL), a solution of methyl 5-(3,3-dimethyl-1-butynyl)pyrazine-2-carboxylate (1.54 g) in tetrahydrofuran (10 mL) was slowly added dropwise under a nitrogen atmosphere with ice cooling. The resulting mixture was warmed to room temperature, and stirred for 2 hours. Under ice cooling, saturated aqueous sodium hydrogencarbonate was slowly added to the reaction mixture, and ethyl acetate was added to the resulting mixture. The reaction mixture was filtered through a Celite layer, and then the organic layer was washed with saturated aqueous sodium hydrogencarbonate, and saturated brine, and dried over magnesium sulfate. The organic layer was filtered, the solvent was evaporated under reduced pressure, and the residue was dried under reduced pressure to obtain the title compound (1.21 g).

$^1$H-NMR (CDCl$_3$, δ): 1.17 (9H, s), 3.7-3.8 (1H, m), 4.82 (2H, d, J=8.4 Hz), 8.4-8.6 (2H, m)

MS (m/z): 190 (M$^+$)

Reference Example 98: 5-(3,3-Dimethyl-1-butynyl)pyrazine-2-carbaldehyde

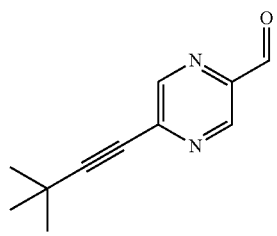

[Formula 111]

By performing operations similar to those of Reference Example 73 using [5-(3,3-dimethyl-1-butynyl)pyrazin-2-yl]methanol, the title compound was obtained.

$^1$H-NMR (CDCl$_3$, δ): 1.19 (9H, s), 8.64 (1H, d, J=0.8 Hz), 9.06 (1H, d, J=1.2 Hz), 10.11 (1H, s)

MS (m/z): 188 (M$^+$)

Reference Example 99: Methyl 5-(cyclopropylethynyl)pyrazine-2-carboxylate

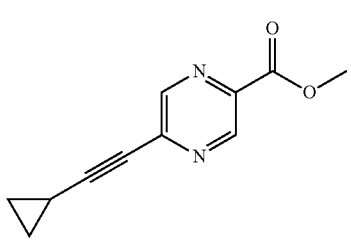

[Formula 112]

By performing operations similar to those of Reference Example 96 using ethynylcyclopropane, the title compound was obtained.

$^1$H-NMR (CDCl$_3$, δ): 0.9-1.1 (4H, m), 1.5-1.6 (1H, in), 4.03 (3H, s), 8.65 (1H, d, J=1.6 Hz), 9.19 (1H, d, J=1.6 Hz)

MS (m/z): 202 (M$^+$)

Reference Example 100: [5-(Cyclopropylethynyl)pyrazin-2-yl]methanol

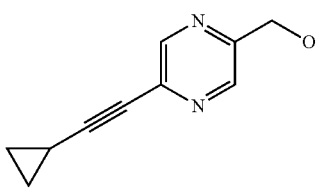

[Formula 113]

By performing operations similar to those of Reference Example 97 using methyl 5-(cyclopropylethynyl)pyrazine-2-carboxylate, the title compound was obtained.

$^1$H-NMR (CDCl$_3$, δ): 0.5-0.7 (2H, m), 0.9-1.0 (2H, m), 1.6-1.7 (1H, m), 3.7-3.8 (1H, m), 4.7-4.8 (2H, m), 8.3-8.6 (2H, m)

MS (m/z): 174 (M$^+$)

Reference Example 101: 5-(Cyclopropylethynyl)pyrazine-2-carbaldehyde

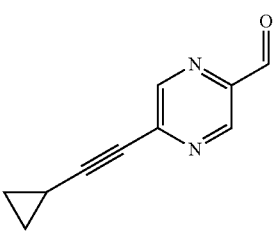

[Formula 114]

By performing operations similar to those of Reference Example 73 using [5-(cyclopropylethynyl)pyrazin-2-yl]methanol, the title compound was obtained.

$^1$H-NMR (CDCl$_3$, δ): 0.7-0.8 (2H, m), 0.9-1.1 (2H, m), 1.7-1.8 (1H, m), 8.53 (1H, d, J=1.6 Hz), 9.01 (1H, d, J=1.2 Hz), 10.08 (1H, s)

MS (m/z): 172 (M$^+$)

Reference Example 102: 2-(4-Methyl-1-pentynyl)pyrimidine-5-carbaldehyde

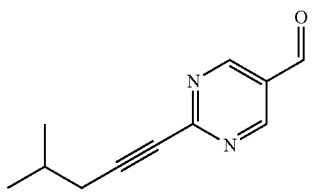

[Formula 115]

To a solution of 2-mercaptopyrimidine-5-carbaldehyde (259 mg) in acetonitrile (12 mL), 4-methyl-1-pentyne (347 μL), palladium acetate (4.5 mg), triphenylphosphine (5.0 mg), and copper(I) 2-thiophenecarboxylate (706 mg) were added, and microwaves were irradiated on the resulting mixture at 110° C. for 23 minutes. The reaction was cooled, then filtered through a Celite layer, and washed with ethyl acetate. The organic layer was washed with water, and saturated brine, and dried over magnesium sulfate. The organic layer was filtered, and the solvent was evaporated under reduced pressure. Then, the obtained residue was purified by silica gel column chromatography, and dried under reduced pressure to obtain the title compound (258 mg).

$^1$H-NMR (CDCl$_3$, δ): 1.09 (6H, d, J=6.0 Hz), 2.03 (1H, sept, J=6.8 Hz), 2.43 (2H, d, J=6.4 Hz), 9.12 (2H, s), 10.13 (1H, s)

MS (m/z): 188 (M$^+$)

Reference Example 103: 2-(1-Propynyl)thiazole-5-carbaldehyde

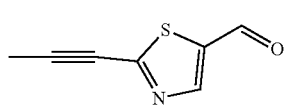

[Formula 116]

By performing operations similar to those of Reference Example 92 using 2-bromothiazole-5-carbaldehyde, the title compound was obtained.

$^1$H-NMR (CDCl$_3$, δ): 2.18 (3H, s), 8.34 (1H, s), 10.00 (1H, s)

MS (m/z): 151 (M$^+$)

Reference Example 104: 2-[3-Chloro-2-fluoro-6-(trifluoromethyl)phenyl]-6-(5-chloropyridin-2-yl)pyrimidin-4(3H)-one

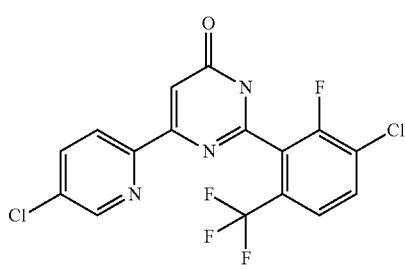

[Formula 117]

By performing operations similar to those of Example 4 using 5-chloropyridine-2-carbaldehyde, and 3-chloro-2-fluoro-6-(trifluoromethyl)benzamidine hydrochloride, the title compound was obtained.

$^1$H-NMR (d$_6$-DMSO, δ): 7.29 (1H, s), 7.87 (1H, d, J=8.8 Hz), 8.0-8.2 (3H, m), 8.79 (1H, d, J=2.4 Hz), 13.40 (1H, brs)

MS (m/z): 403 (M$^+$)

Reference Example 105: 2-[3-Chloro-2-fluoro-6-(trifluoromethyl)phenyl]-6-[5-(1-propynyl)pyridin-2-yl]pyrimidin-4(3H)-one

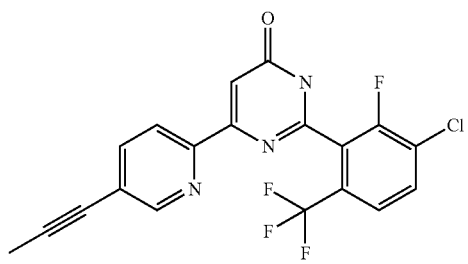

[Formula 118]

By performing operations similar to those of Example 4 using 5-(1-propynyl)pyridine-2-carbaldehyde, and 3-chloro-2-fluoro-6-(trifluoromethyl)benzamidine hydrochloride, the title compound was obtained.

$^1$H-NMR (d$_6$-DMSO, δ): 2.12 (3H, s), 7.29 (1H, s), 7.86 (1H, d, J=8.4 Hz), 7.94 (1H, dd, J=2.0 Hz, 8.0 Hz), 8.0-8.2 (2H, m), 8.73 (1H, d, J=2.0 Hz), 13.37 (1H, brs)

MS (m/z): 407 (M$^+$)

Reference Example 106: 2-[3-Chloro-2-fluoro-6-(trifluoromethyl)phenyl]-6-[6-(cyclopropylethynyl)pyridin-3-yl]pyrimidin-4(3H)-one

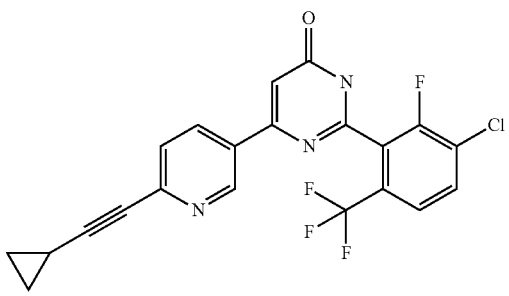

[Formula 119]

By performing operations similar to those of Example 4 using 6-(cyclopropylethynyl)pyridine-3-carbaldehyde, and 3-chloro-2-fluoro-6-(trifluoromethyl)benzamidine hydrochloride, the title compound was obtained.

$^1$H-NMR (d$_6$-DMSO, δ): 0.7-1.0 (4H, m), 1.5-1.7 (1H, m), 7.19 (1H, s), 7.52 (1H, d, J=8.4 Hz), 7.86 (1H, d, J=8.8 Hz), 8.09 (1H, t, J=7.2 Hz), 8.33 (1H, d, J=8.4 Hz), 9.13 (1H, a), 13.32 (1H, brs)

MS (m/z): 433 (M$^+$)

Reference Example 107: 2-[3-Chloro-2-fluoro-6-(trifluoromethyl)phenyl]-6-[6-(2-propoxyethoxy)pyridin-3-yl]pyrimidin-4(3H)-one

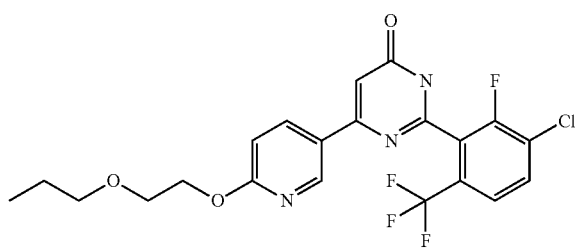

[Formula 120]

By performing operations similar to those of Example 4 using 6-(2-propoxyethoxy)pyridine-3-carbaldehyde, and 3-chloro-2-fluoro-6-(trifluoromethyl)benzamidine hydrochloride, the title compound was obtained.

$^1$H-NMR (d$_6$-DMSO, δ): 0.85 (3H, t, J=7.2 Hz), 1.51 (2H, sext, J=7.2 Hz), 3.40 (2H, t, J=6.8 Hz), 3.71 (2H, t, J=4.8 Hz), 4.44 (2H, t, J=4.8 Hz), 6.93 (1H, d, J=8.8 Hz), 7.06 (1H, a), 7.85 (1H, d, J=8.8 Hz), 8.08 (1H, t, J=8.4 Hz), 8.30 (1H, dd, J=2.0 Hz, 8.8 Hz), 8.84 (1H, s), 13.19 (1H, brs)

MS (m/z): 471 (M$^+$)

Reference Example 108: 2-[3-Chloro-2-fluoro-6-(trifluoromethyl)phenyl]-6-[6-(2-isopropoxyethoxy)pyridin-3-yl]pyrimidin-4(3H)-one

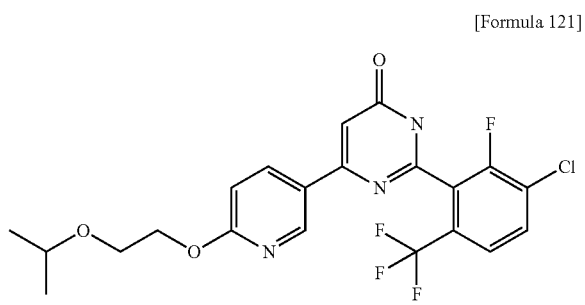 [SMILES: CC(C)OCCOc1ccc(-c2cc(=O)[nH]c(-c3c(C(F)(F)F)ccc(Cl)c3F)n2)cn1]

[Formula 121]

By performing operations similar to those of Example 4 using 6-(2-isopropoxyethoxy)pyridine-3-carbaldehyde, and 3-chloro-2-fluoro-6-(trifluoromethyl)benzamidine hydrochloride, the title compound was obtained.

$^1$H-NMR (d$_6$-DMSO, δ): 1.09 (6H, d, J=6.0 Hz), 3.61 (1H, sept, J=6.0 Hz), 3.70 (2H, t, J=4.8 Hz), 4.41 (2H, t, J=4.8 Hz), 6.93 (1H, d, J=8.8 Hz), 7.07 (1H, s), 7.85 (1H, d, J=8.4 Hz), 8.08 (1H, t, J=8.4 Hz), 8.30 (1H, dd, J=2.0 Hz, 8.8 Hz), 8.84 (1H, d, J=1.6 Hz), 13.18 (1H, brs)

MS (m/z): 471 (M$^+$)

Reference Example 109: 2-[3-Chloro-2-fluoro-6-(trifluoromethyl)phenyl]-6. [12-(cyclopropylethynyl)thiazol-5-yl]pyrimidin-4(3H)-one

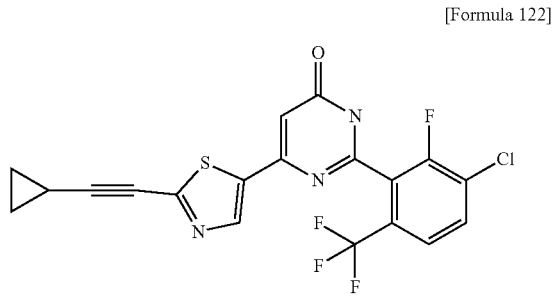 [SMILES: O=c1cc(-c2cnc(C#CC3CC3)s2)nc(-c2c(C(F)(F)F)ccc(Cl)c2F)[nH]1]

[Formula 122]

By performing operations similar to those of Example 4 using 2-(cyclopropylethynyl)thiazole-5-carbaldehyde, and 3-chloro-2-fluoro-6-(trifluoromethyl)benzamidine hydrochloride, the title compound was obtained.

$^1$H-NMR (d$_6$-DMSO, δ): 0.8-1.1 (4H, m), 1.6-1.8 (1H, m), 7.13 (1H, s), 7.85 (1H, d, J=8.0 Hz), 8.09 (1H, t, J=8.0 Hz), 8.60 (1H, s), 13.31 (1H, brs)

MS (m/z): 439 (M$^+$)

Reference Example 110: 2-[3-Chloro-2-fluoro-6-(trifluoromethyl)phenyl]-6-{6-[2-(2,2,2-trifluoroethoxy)ethoxy]pyridin-3-yl}pyrimidin-4(3H)-one

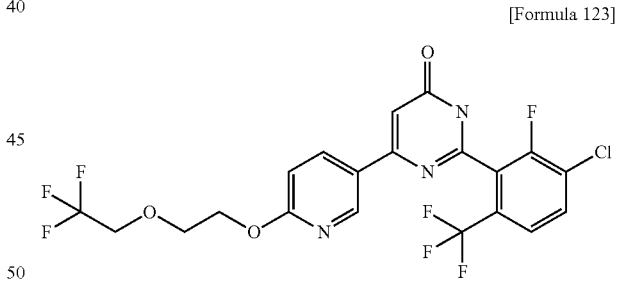

[Formula 123]

By performing operations similar to those of Example 4 using 6-[2-(2,2,2-trifluoroethoxy)ethoxy]pyridine-3-carbaldehyde, and 3-chloro-2-fluoro-6-(trifluoromethyl)benzamidine hydrochloride, the title compound was obtained.

$^1$H-NMR (d$_6$-DMSO, δ): 3.95 (2H, t, J=4.0 Hz), 4.14 (2H, q, J=9.2 Hz), 4.48 (2H, t, J=4.4 Hz), 6.95 (1H, d, J=8.8 Hz), 7.08 (1H, s), 7.85 (1H, d, J=8.8 Hz), 8.08 (1H, t, J=8.4 Hz), 8.31 (1H, dd, J=2.4 Hz, 8.8 Hz), 8.84 (1H, d, J=2.0 Hz), 13.15 (1H, brs)

MS (m/z): 511 (M$^+$)

Reference Example 111: 2,4,6-Trichlorophenyl 5-(2,2,2-trifluoroethyl)pyridine-2-carboxylate

[Formula 124]

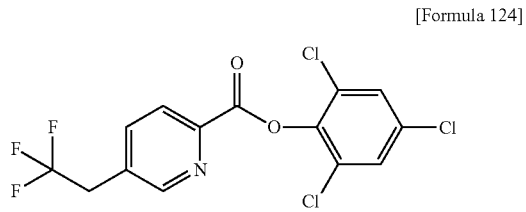 [SMILES: O=C(Oc1c(Cl)cc(Cl)cc1Cl)c1ccc(CC(F)(F)F)cn1]

To a solution of 2-chloro-5-(2,2,2-trifluoroethyl)pyridine (1.93 g), 2,4,6-trichlorophenyl formate (2.67 g), palladium (II) acetate (67 mg), and 4,5-bis(diphenylphosphino)-9,9-dimethylxanthene (343 mg) in toluene (12 mL), a solution of triethylamine (2.8 mL) in toluene (20 mL) was added dropwise at 100° C. under a nitrogen atmosphere, and the resulting mixture was stirred at 100° C. for 1.5 hours. After the reaction, the reaction mixture was filtered through a Celite layer, the solvent was evaporated, and then the residue was purified by silica gel column chromatography to obtain the title compound (1.63 g).

$^1$H-NMR (CDCl$_3$, δ): 3.55 (2H, q, 10.8 Hz), 7.44 (2H, s), 7.92 (1H, dd, J=1.6 Hz, 8.0 Hz), 8.33 (1H, d, J=8.4 Hz), 8.81 (1H, d, J=2.0 Hz)

MS (m/z): 383 (M$^+$)

Reference Example 112: N-Methoxy-N-methyl-5-(2,2,2-trifluoroethyl)pyridine-2-carboxamide

[Formula 125]

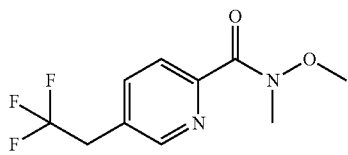

A solution of 2,4,6-trichlorophenyl 5-(2,2,2-trifluoroethyl)pyridine-2-carboxylate (1.61 g), N,O-dimethylhydroxylamine hydrochloride (1.02 g), and tripotassium phosphate (4.45 g) in acetonitrile (40 mL) was refluxed overnight by heating under a nitrogen atmosphere. After the reaction, water was added to the reaction mixture, and the resulting mixture was extracted with ethyl acetate. Then, the organic layer was dried over sodium sulfate, and the solvent was evaporated. The residue was purified by silica gel column chromatography to obtain the title compound (471 mg).

$^1$H-NMR (CDCl$_3$, δ): 3.42 (3H, s), 3.45 (2H, q, 10.8 Hz), 3.76 (3H, s), 7.6-7.8 (2H, m), 8.55 (1H, s)

MS (m/z): 217 (M$^+$−31)

Reference Example 113: 5-(2,2,2-Trifluoroethyl)pyridine-2-carbaldehyde

[Formula 126]

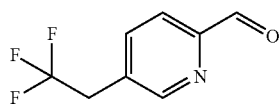

To a solution of bis(cyclopentadienyl)zirconium(IV) chloride hydride (585 mg) in tetrahydrofuran (12 mL), a solution of N-methoxy-N-methyl-5-(2,2,2-trifluoroethyl)pyridine-2-carboxamide (469 mg) in tetrahydrofuran (5 mL) was added, and the resulting mixture was stirred for 30 minutes under a nitrogen atmosphere. After the reaction, silica gel was added to the reaction mixture, the resulting mixture was filtered through a Celite layer, and then purification was performed by silica gel column chromatography to obtain the title compound (142 mg).

$^1$H-NMR (CDCl$_3$, δ): 3.51 (2H, q, 10.8 Hz), 7.85 (1H, d, J=7.2 Hz), 7.99 (1H, d, J=8.0 Hz), 8.73 (1H, d, J=1.2 Hz), 10.10 (1H, s)

MS (m/z): 189 (M$^+$)

Reference Example 114: 2-[3-Chloro-2-fluoro-6-(trifluoromethyl)phenyl]-6-[5-(cyclopropylethynyl)pyridin-2-yl]pyrimidin-4(3H)-one

[Formula 127]

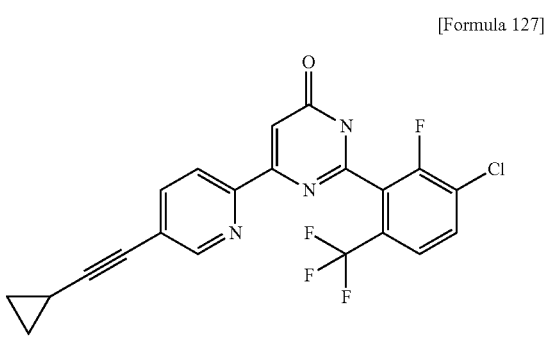 [SMILES: O=c1cc(-c2ccc(C#CC3CC3)cn2)nc(-c2c(C(F)(F)F)ccc(Cl)c2F)[nH]1]

By performing operations similar to those of Example 4 using 5-(cyclopropylethynyl)pyridine-2-carbaldehyde, and 3-chloro-2-fluoro-6-(trifluoromethyl)benzamidine hydrochloride, the title compound was obtained.

$^1$H-NMR (d$_6$-DMSO, δ): 0.7-1.0 (4H, m), 1.5-1.7 (1H, m), 7.28 (1H, s), 7.86 (1H, d, J=8.8 Hz), 7.91 (1H, dd, J=2.0 Hz, 8.4 Hz), 8.0-8.2 (2H, m), 8.69 (1H, d, J=1.2 Hz), 13.35 (1H, brs)

MS (m/z): 433 (M$^+$)

Example 263: N-{3-[4-(Benzothiazol-2-yl)-6-oxo-1,6-dihydropyrimidin-2-yl]-4-chloro-2-fluorobenzyl}isobutyramide By performing operations similar to those of Example 4 using benzothiazole-2-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.05 (6H, d, J=6.8 Hz), 2.48 (1H, sept, J=6.8 Hz), 4.35 (2H, d, J=5.9 Hz), 7.23 (1H, brs), 7.4-7.7 (4H, m), 8.1.8.3 (2H, m), 8.38 (1H, t, J=5.4 Hz), 13.50 (1H, brs)

MS (m/z): 456 (M$^+$)

Example 264: N-(3-{4-[6-(2-Isopropoxyethoxy)pyridin-3-yl]-6-oxo-1,6-dihydropyrimidin-2-yl}-4-(trifluoromethyl)benzyl)isobutyramide By performing operations similar to those of Example 4 using 6-(2-isopropoxyethoxy)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=6.8 Hz), 1.09 (6H, d, J=5.9 Hz), 2.46 (1H, sept, J=6.8 Hz), 3.61 (1H, sept, J=6.4 Hz), 3.6-3.8 (2H, m), 4.3-4.5 (4H, m), 6.92 (1H, d, J=8.8 Hz), 6.98 (1H, brs), 7.5-7.7 (2H, m), 7.88 (1H, d, J=7.8 Hz) 8.31 (1H, dd, J=1.9 Hz, 8.8 Hz), 8.39 (1H, t, J=5.8 Hz), 8.85 (1H, d, J=1.5 Hz), 12.95 (1H, brs)
MS (m/z): 518 (M⁺)

Example 265: N-(4-Chloro-2-fluoro-3-{4-[6-(2-isopropoxyethoxy)pyridin-3-yl]-6-oxo-1,6-dihydropyrimidin-2-yl}benzyl)isobutyramide By performing operations similar to those of Example 4 using 6-(2-isopropoxyethoxy)pyridine-3-carbaldehyde, and N-(3-carbamimidoyl-4-chloro-2-fluorobenzyl)isobutyramide hydrochloride, the title compound was obtained.
¹H-NMR (d₆-DMSO, δ): 1.05 (6H, d, J=6.8 Hz), 1.10 (6H, d, J=5.9 Hz), 2.45 (1H, sept. J=6.8 Hz), 3.61 (1H, sept, J=6.3 Hz), 3.70 (2H, t, J=4.9 Hz), 4.32 (2H, d, J=5.8 Hz), 4.41 (2H, t, J=4.9 Hz), 6.92 (1H, d, J=8.8 Hz), 7.01 (1H, brs), 7.4-7.6 (2H, m), 8.31 (1H, dd, J=2.4 Hz, 8.7 Hz), 8.36 (1H, t, J=5.8 Hz), 8.84 (1H, d, J=2.0 Hz), 13.08 (1H, brs)
MS (m/z): 502 (M⁺)

Example 266: N-(2,4-Difluoro-3-{4-[6-(2-isopropoxyethoxy)pyridin-3-yl]-6-oxo-1,6-dihydropyrimidin-2-yl}benzyl)isobutyramide By performing operations similar to those of Example 4 using 6-(2-isopropoxyethoxy)pyridine-3-carbaldehyde, and N-(3-carbamimidoyl-2,4-difluorobenzyl)isobutyramide hydrochloride, the title compound was obtained.
¹H-NMR (d₆-DMSO, δ): 1.04 (6H, d, J=7.3 Hz), 1.10 (6H, d, J=6.4 Hz), 2.45 (1H, sept, J=6.8 Hz), 3.62 (1H, sept, J=6.3 Hz), 3.70 (2H, t, J=4.9 Hz), 4.32 (2H, d, J=5.9 Hz), 4.41 (2H, t, J=5.4 Hz), 6.92 (1H, d, J=8.8 Hz), 7.01 (1H, brs), 7.28 (1H, t, J=8.8 Hz), 7.50 (1H, dd, J=7.9 Hz), 8.2-8.4 (2H, m), 8.85 (1H, d, J=1.9 Hz), 13.02 (1H, brs)
MS (m/z): 486 (M⁺)

Example 267: N-(2-Chloro-4-fluoro-3-{4-[6-(2-isopropoxyethoxy)pyridin-3-yl]-6-oxo-1,6-dihydropyrimidin-2-yl}benzyl)isobutyramide By performing operations similar to those of Example 4 using 6-(2-isopropoxyethoxy)pyridine-3-carbaldehyde, and N-(3-carbamimidoyl-2-chloro-4-fluorobenzyl)isobutyramide hydrochloride, the title compound was obtained.
¹H-NMR (d₆-DMSO, δ): 1.07 (6H, d, J=6.8 Hz), 1.09 (6H, d, J=6.4 Hz), 2.4-2.6 (1H, m), 3.61 (1H, sept, J=5.9 Hz), 3.70 (2H, t, J=4.9 Hz), 4.34 (2H, d, J=5.8 Hz), 4.41 (2H, t, J=5.4 Hz), 6.91 (1H, d, J=8.8 Hz), 7.01 (1H, brs), 7.3-7.6 (2H, m), 8.31 (1H, dd, J=2.4 Hz, 8.8 Hz), 8.37 (1H, t, J=5.9 Hz), 8.84 (1H, d, J=2.0 Hz), 13.06 (1H, brs)
MS (m/z): 502 (M⁺)

Example 268: N-(3-{6-Oxo-4-[6-(tetrahydropyran-4-ylmethoxy)pyridin-3-yl]-1,6-dihydropyrimidin-2-yl}-4-(trifluoromethyl)benzyl)butyramide By performing operations similar to those of Example 4 using 6-(tetrahydropyran-4-ylmethoxy)pyridine-3-carbaldehyde, and N-[3-carbamimidoyl-4-(trifluoromethyl)benzyl]butyramide hydrochloride, the title compound was obtained.
¹H-NMR (d₆-DMSO, δ): 0.86 (3H, t, J=7.3 Hz), 1.2-1.4 (2H, m), 1.55 (2H, sext, J=7.3 Hz), 1.65 (2H, d, J=2.7 Hz), 1.9-2.1 (1H, m), 2.15 (2H, t, J=7.3 Hz), 3.2-3.5 (2H, m), 3.87 (2H, dd, J=2.9 Hz, 11.2 Hz), 4.18 (2H, d, J=6.3 Hz), 4.41 (2H, d, J=5.4 Hz), 6.90 (1H, d, J=8.8 Hz), 6.98 (1H, s), 7.5-7.7 (2H, m), 7.87 (1H, d, J=8.3 Hz), 8.30 (1H, dd, J=2.0 Hz, 8.3 Hz), 8.43 (1H, t, J=5.8 Hz), 8.84 (1H, d, J=2.0 Hz), 12.54 (1H, brs)
MS (m/z): 530 (M⁺)

Example 269: N-(3-{4-[6-(2-Isopropoxyethoxy)pyridin-3-yl]-6-oxo-1,6-dihydropyrimidin-2-yl}-4-(trifluoromethyl)benzyl)butyramide By performing operations similar to those of Example 4 using 6-(2-isopropoxyethoxy)pyridine-3-carbaldehyde, and N-[3-carbamimidoyl-4-(trifluoromethyl)benzyl]butyramide hydrochloride, the title compound was obtained.
¹H-NMR (d₆-DMSO, δ): 0.86 (3H, t, J=7.3 Hz), 1.09 (6H, d, J=5.9 Hz), 1.55 (2H, sext, J=7.3 Hz), 2.15 (2H, t, J=7.3 Hz), 3.61 (1H, sept, J=5.9 Hz), 3.6-3.8 (2H, m), 4.3-4.5 (4H, m), 6.92 (1H, d, J=8.8 Hz), 6.98 (1H, brs), 7.5-7.7 (2H, m), 7.88 (1H, d, J=8.8 Hz), 8.31 (1H, dd, J=2.4 Hz, 8.8 Hz), 8.43 (1H, t, J=5.8 Hz), 8.85 (1H, d, J=2.7 Hz), 12.81 (1H, brs)
MS (m/z): 518 (M⁺)

Example 270: N-(3-{4-[6-(2-Ethoxyethoxy)pyridin-3-yl]-6-oxo-1,6-dihydropyrimidin-2-yl}-4-(trifluoromethyl)benzyl)butyramide By performing operations similar to those of Example 4 using 6-(2-ethoxyethoxy)pyridine-3-carbaldehyde, and N-[3-carbamimidoyl-4-(trifluoromethyl)benzyl]butyramide hydrochloride, the title compound was obtained.
¹H-NMR (d₆-DMSO, δ): 0.86 (3H, t, J=7.3 Hz), 1.12 (3H, t, J=7.3 Hz), 1.55 (2H, sext, J=7.3 Hz), 2.15 (2H, t, J=7.6 Hz), 3.49 (2H, q, J=6.9 Hz), 3.6-3.8 (2H, m), 4.3-4.5 (4H, m), 6.92 (1H, d, J=8.8 Hz), 6.98 (1H, brs), 7.5-7.7 (2H, m), 7.88 (1H, d, J=8.3 Hz), 8.2-8.4 (1H, m), 8.43 (1H, t, J=5.8 Hz), 8.85 (1H, brs), 12.95 (1H, brs)
MS (m/z): 504 (M⁺)

Example 271: N-(3-{6-Oxo-4-[6-(2-propoxyethoxy)pyridin-3-yl]-1,6-dihydropyrimidin-2-yl}-4-(trifluoromethyl)benzyl)butyramide By performing operations similar to those of Example 4 using 6-(2-propoxyethoxy)pyridine-3-carbaldehyde, and N-[3-carbamimidoyl-4-(trifluoromethyl)benzyl]butyramide hydrochloride, the title compound was obtained.
¹H-NMR (d₆-DMSO, δ): 0.8-0.9 (6H, m), 1.4-1.7 (4H, m), 2.15 (2H, t, J=7.6 Hz), 3.40 (2H, t, J=6.9 Hz), 3.6-3.8 (2H, m), 4.3-4.5 (4H, m), 6.92 (1H, d, J=8.3 Hz), 6.98 (1H, brs), 7.5-7.7 (2H, m), 7.88 (1H, d, J=8.4 Hz), 8.31 (1H, dd, J=1.9 Hz, 8.8 Hz), 8.43 (1H, t, J=6.8 Hz), 8.85 (1H, d, J=1.5 Hz), 12.93 (1H, brs)
MS (m/z): 518 (M⁺)

Example 272: N-{3-[4-(Benzothiazol-2-yl)-6-oxo-1,6-dihydropyrimidin-2-yl]-2,4-difluorobenzyl}isobutyramide By performing operations similar to those of Example 4 using benzothiazole-2-carbaldehyde, and N-(3-carbamimidoyl-2,4-difluorobenzyl)isobutyramide hydrochloride, the title compound was obtained.
¹H-NMR (d₆-DMSO, δ): 1.05 (6H, d, J=6.8 Hz), 2.46 (1H, sept, J=6.8 Hz), 4.34 (2H, d, J=5.3 Hz), 7.23 (1H, brs), 7.32 (1H, t, J=8.8 Hz), 7.5-7.7 (3H, m), 8.1-8.3 (2H, m), 8.35 (1H, t, J=5.6 Hz), 13.48 (1H, brs)
MS (m/z): 440 (M$^+$)

Example 273: N-{3-[4-(Benzothiazol-2-yl)-6-oxo-1,6-dihydropyrimidin-2-yl]-4-(trifluoromethyl)benzyl}isobutyramide By performing operations similar to those of Example 4 using benzothiazole-2-carbaldehyde, and N-[3-carbamimidoyl-4-(trifluoromethyl)benzyl]isobutyramide hydrochloride, the title compound was obtained.
$^1$H-NMR (d$_6$-DMSO, δ): 1.06 (6H, d, J=6.8 Hz), 2.47 (1H, sept, J=6.8 Hz), 4.42 (2H, d, J=5.9 Hz), 7.20 (1H, brs), 7.5-7.8 (4H, m), 7.92 (1H, d, J=8.3 Hz), 8.1-8.3 (2H, m), 8.41 (1H, t, J=5.9 Hz), 13.35 (1H, brs)
MS (m/z): 472 (M$^+$)

Example 274: N-(2-Chloro-4-fluoro-3-{6-oxo-4-[6-(2-propoxyethoxy)pyridin-3-yl]-1,6-dihydropyrimidin-2-yl}benzyl)isobutyramide By performing operations similar to those of Example 4 using 6-(2-propoxyethoxy)pyridine-3-carbaldehyde, and N-(3-carbamimidoyl-2-chloro-4-fluorobenzyl)isobutyramide hydrochloride, the title compound was obtained.
$^1$H-NMR (d$_6$-DMSO, δ): 0.85 (3H, t, J=7.3 Hz), 1.07 (6H, d, J=6.8 Hz), 1.51 (2H, sext, J=7.3 Hz), 2.4-2.6 (1H, m), 3.40 (2H, t, J=6.3 Hz), 3.6-3.8 (2H, m), 4.35 (2H, d, J=5.9 Hz), 4.4-4.5 (2H, m), 6.91 (1H, d, J=8.8 Hz), 7.01 (1H, brs), 7.3-7.6 (2H, m), 8.31 (1H, dd, J=2.4 Hz, 8.8 Hz), 8.37 (1H, t, J=5.9 Hz), 8.84 (1H, d, J=2.4 Hz), 13.10 (1H, brs)
MS (m/z): 502 (M$^+$)

Example 275: N-(3-{6-Oxo-4-[4-(trifluoromethyl)thiazol-2-yl]-1,6-dihydropyrimidin-2-yl}-4-(trifluoromethyl)benzyl)isobutyramide By performing operations similar to those of Example 4 using 4-(trifluoromethyl)thiazole-2-carbaldehyde, and N-[3-carbamimidoyl-4-(trifluoromethyl)benzyl]isobutyramide hydrochloride, the title compound was obtained.
$^1$H-NMR (d$_6$-DMSO, δ): 1.05 (6H, d, J=6.8 Hz), 2.46 (1H, sept, J=6.8 Hz), 4.41 (2H, d, J=6.8 Hz), 7.01 (1H, brs), 7.5-7.7 (2H, m), 7.91 (1H, d, J=8.3 Hz), 8.41 (1H, t, J=5.8 Hz), 8.73 (1H, s), 13.36 (1H, brs)
MS (m/z): 490 (M$^+$)

Example 276: N-{4-Chloro-3-[4-(5-ethynylpyridin-3-yl)-6-oxo-1,6-dihydropyrimidin-2-yl]-2-fluorobenzyl}isobutyramide By performing operations similar to those of Example 4 using 5-ethynylpyridine-3-carbaldehyde, and N-(3-carbamimidoyl-4-chloro-2-fluorobenzyl)isobutyramide hydrochloride, the title compound was obtained.
$^1$H-NMR (d$_6$-DMSO, δ): 1.05 (6H, d, J=6.8 Hz), 2.46 (1H, sept, J=6.8 Hz), 4.33 (2H, d, J=5.9 Hz), 4.52 (1H, s), 7.22 (1H, brs), 7.4-7.6 (2H, m), 8.36 (1H, t, J=5.8 Hz), 8.4-8.5 (1H, m), 8.78 (1H, d, J=2.0 Hz), 9.22 (1H, d, J=2.0 Hz), 13.23 (1H, brs)
MS (m/z): 424 (M$^+$)

Example 277: N-[3-(6-Oxo-4-{6-[2-(2,2,2-trifluoroethoxy)ethoxy]pyridin-3-yl}-1,6-dihydropyrimidin-2-yl)-4-(trifluoromethyl)benzyl]isobutyramide By performing operations similar to those of Example 4 using 6-[2-(2,2,2-trifluoroethoxy)ethoxy]pyridine-3-carbaldehyde, and N-[3-carbamimidoyl-4-(trifluoromethyl)benzyl]isobutyramide hydrochloride, the title compound was obtained.
$^1$H-NMR (d$_6$-DMSO, δ): 1.05 (6H, d, J=6.8 Hz), 2.46 (1H, sept, J=6.8 Hz), 3.95 (2H, t, J=4.7 Hz), 4.14 (2H, q, J=9.3 Hz), 4.40 (2H, d, J=5.9 Hz), 4.4-4.6 (2H, m), 6.94 (1H, d, J=8.8 Hz), 6.99 (1H, brs), 7.5-7.7 (2H, m), 7.88 (1H, d, J=8.3 Hz), 8.33 (1H, dd, J=2.0 Hz, 8.3 Hz), 8.39 (1H, t, J=5.9 Hz), 8.86 (1H, d, J=2.0 Hz), 12.95 (1H, brs)
MS (m/z): 558 (M$^+$)

Example 278: N-[4-Chloro-2-fluoro-3-(6-oxo-4-{6-[2-(2,2,2-trifluoroethoxy)ethoxy]pyridin-3-yl}-1,6-dihydropyrimidin-2-yl)benzyl]isobutyramide By performing operations similar to those of Example 4 using 6-[2-(2,2,2-trifluoroethoxy)ethoxy]pyridine-3-carbaldehyde, and N-(3-carbamimidoyl-4-chloro-2-fluorobenzyl)isobutyramide hydrochloride, the title compound was obtained.
$^1$H-NMR (d$_6$-DMSO, δ): 1.05 (6H, d, J=7.3 Hz), 2.45 (1H, sept, J=6.8 Hz), 3.9-4.0 (2H, m), 4.14 (2H, q, J=9.7 Hz), 4.32 (2H, d, J=5.8 Hz), 4.4-4.6 (2H, m), 6.94 (1H, d, J=8.8 Hz), 7.02 (1H, brs), 7.4-7.6 (2H, m), 8.2-8.4 (2H, m), 8.85 (1H, d, J=1.9 Hz), 13.05 (1H, brs)
MS (m/z): 542 (MI Example 279: N-[2,4-Difluoro-3-(6-oxo-4-{6-[2-(2,2,2-trifluoroethoxy)ethoxy]pyridin-3-yl}-1,6-dihydropyrimidin-2-yl)benzyl]isobutyramide By performing operations similar to those of Example 4 using 6-[2-(2,2,2-trifluoroethoxy)ethoxy]pyridine-3-carbaldehyde, and N-(3-carbamimidoyl-2,4-difluorobenzyl)isobutyramide hydrochloride, the title compound was obtained.
$^1$H-NMR (d$_6$-DMSO, δ): 1.04 (6H, d, J=6.8 Hz), 2.45 (1H, sept, J=6.8 Hz), 3.9-4.0 (2H, m), 4.14 (2H, q, J=9.8 Hz), 4.32 (2H, d, J=5.9 Hz), 4.4-4.6 (2H, m), 6.95 (1H, d, J=8.8 Hz), 7.01 (1H, brs), 7.28 (1H, t, J=8.8 Hz), 7.51 (1H, q, J=8.4 Hz), 8.2-8.4 (2H, m), 8.86 (1H, d, J=2.0 Hz), 13.12 (1H, brs)
MS (m/z): 526 (M$^+$)

Example 280: N-[2-Chloro-4-fluoro-3-(6-oxo-4-{6-[2-(2,2,2-trifluoroethoxy)ethoxy]pyridin-3-yl}-1,6-dihydropyrimidin-2-yl)benzyl]isobutyramide By performing operations similar to those of Example 4 using 6-[2-(2,2,2-trifluoroethoxy)ethoxy]pyridine-3-carbaldehyde, and N-(3-carbamimidoyl-2-chloro-4-fluorobenzyl)isobutyramide hydrochloride, the title compound was obtained.
$^1$H-NMR (d$_6$-DMSO, δ): 1.07 (6H, d, J=6.8 Hz), 2.4-2.6 (1H, m), 3.9-4.0 (2H, m), 4.14 (2H, q, J=9.7 Hz), 4.34 (2H, d, J=5.8 Hz), 4.4-4.6 (2H, m), 6.93 (1H, d, J=8.8 Hz), 7.01 (1H, brs), 7.3-7.6 (2H, m), 8.32 (1H, dd, J=2.4 Hz, 8.8 Hz), 8.37 (1H, t, J=5.9 Hz), 8.84 (1H, d. J=1.9 Hz), 13.10 (1H, brs)
MS (m/z): 542 (MI Example 281: N-(3-{4-[5-(Cyclopropylethynyl)pyridin-2-yl]6-oxo-1,6-dihydropyrimidin-2-yl}-4-(trifluoromethyl)benzyl)butyramide By performing operations similar to those of Example 4 using 5-(cyclopropylethynyl)pyridine-2-carbaldehyde, and N-[3-carbamimidoyl-4-(trifluoromethyl)benzyl]butyramide hydrochloride, the title compound was obtained.

¹H-NMR (d₆-DMSO, δ): 0.7-0.9 (2H, m), 0.86 (3H, t, J=7.2 Hz), 0.9-1.0 (2H, m), 1.5-1.7 (3H, m), 2.15 (2H, t, J=7.2 Hz), 4.41 (2H, d, J=5.6 Hz), 7.21 (1H, s), 7.6-7.7 (2H, m), 7.8-8.0 (2H, m), 8.13 (1H, d, J=8.4 Hz), 8.43 (1H, t, J=5.6 Hz), 8.68 (1H, d, J=1.6 Hz), 13.06 (1H, s)

MS (m/z): 480 (M⁺)

Example 282: N-(4-Chloro-3-{4-[5-(cyclopropylethynyl)pyridin-2-yl]-6-oxo-1,6-dihydropyrimidin-2-yl}-2-fluorobenzyl)butyramide By performing operations similar to those of Example 4 using 5-(cyclopropylethynyl)pyridine-2-carbaldehyde, and N-(3-carbamimidoyl-4-chloro-2-fluorobenzyl)butyramide hydrochloride, the title compound was obtained.

¹H-NMR (d₆-DMSO, δ): 0.7-0.9 (2H, m), 0.87 (3H, t, J=7.2 Hz), 0.9-1.0 (2H, m), 1.4-1.7 (3H, m), 2.14 (2H, t, J=6.8 Hz), 4.33 (2H, d, J=5.6 Hz), 7.24 (1H, s), 7.4-7.6 (2H, m), 7.89 (1H, dd, J=2.8 Hz, 8.4 Hz), 8.15 (1H, d, J=8.4 Hz), 8.40 (1H, t, J=6.0 Hz), 8.69 (1H, d, J=2.0 Hz), 13.20 (1H, s)

MS (m/z): 464 (M⁺)

Example 283: N-(3-{4-[5-(3,3-Dimethyl-1-butynyl)pyrazin-2-yl]-6-oxo-1,6-dihydropyrimidin-2-yl}-4-(trifluoromethyl)benzyl)isobutyramide By performing operations similar to those of Example 4 using 5-(3,3-dimethyl-1 butynyl)pyrazine-2-carbaldehyde, and N-[3-carbamimidoyl-4-(trifluoromethyl)benzyl]isobutyramide hydrochloride, the title compound was obtained.

¹H-NMR (d₆-DMSO, δ): 1.05 (6H, d, J=6.8 Hz), 1.14 (9H, s), 2.4-2.6 (1H, m), 4.41 (2H, d, J=5.6 Hz), 7.17 (1H, s), 7.6-7.7 (2H, m), 7.91 (1H, d, J=8.0 Hz), 8.40 (1H, t, J=5.6 Hz), 8.81 (1H, s), 9.19 (1H, s), 13.18 (1H, s)

MS (m/z): 497 (M⁺)

Example 284: N-(3-{4-[5-(Cyclopropylethynyl)pyrazin-2-yl]-6-oxo-1,6-dihydropyrimidin-2-yl}-4-(trifluoromethyl)benzyl)isobutyramide By performing operations similar to those of Example 4 using 5-(cyclopropylethynyl)pyrazine-2-carbaldehyde, and N-[3-carbamimidoyl-4-(trifluoromethyl)benzyl]isobutyramide hydrochloride, the title compound was obtained.

¹H-NMR (d₆-DMSO, δ): 0.6-0.7 (2H, m), 0.8-1.0 (2H, m), 1.05 (6H, d, J=6.8 Hz), 1.6-1.8 (1H, m), 2.4-2.6 (1H, m), 4.41 (2H, d, J=6.0 Hz), 7.15 (1H, s), 7.6-7.7 (2H, m), 7.90 (1H, d, J=8.0 Hz), 8.40 (1H, t, J=6.0 Hz), 8.73 (1H, s), 9.14 (1H, s), 13.17 (1H, s)

MS (m/z): 481 (M⁺)

Example 285: N-{3-[2'-(4-Methyl-1-pentynyl)-6-oxo-1,6-dihydro-[4,5'-bipyrimidin]-2-yl]-4-(trifluoromethyl)benzyl}isobutyramide By performing operations similar to those of Example 4 using 2-(4-methyl-1-pentynyl)pyrimidine-5-carbaldehyde, and N-[3-carbamimidoyl-4-(trifluoromethyl)benzyl]isobutyramide hydrochloride, the title compound was obtained.

¹H-NMR (d₆-DMSO, δ): 1.02 (6H, d, J=6.8 Hz), 1.05 (6H, d, J=7.2 Hz), 1.91 (1H, sept, J=6.8 Hz), 2.4-2.6 (3H, m), 4.40 (2H, d, J=6.0 Hz), 7.23 (1H, s), 7.6-7.7 (2H, m), 7.89 (1H, d, J=8.0 Hz), 8.40 (1H, t, J=6.0 Hz), 9.32 (2H, s), 13.19 (1H, s)

MS (m/z): 497 (M⁺)

Example 286: N-{3-[6-Oxo-4-(5-propylpyridin-2-yl)-1,6-dihydropyrimidin-2-yl]-4-(trifluoromethyl)benzyl}isobutyramide By performing operations similar to those of Example 4 using 5-propylpyridine-2-carbaldehyde, and N-[3-carbamimidoyl-4-(trifluoromethyl)benzyl]isobutyramide hydrochloride, the title compound was obtained.

¹H-NMR (d₆-DMSO, δ): 0.91 (3H, t, J=7.2 Hz), 1.05 (6H, d, J=7.2 Hz), 1.71 (2H, sext, J=7.2 Hz), 2.46 (1H, sept, J=6.8 Hz), 2.76 (2H, t, J=7.2 Hz), 4.40 (2H, d, J=6.0 Hz), 7.05 (1H, s), 7.35 (1H, d, J=8.4 Hz), 7.5-7.7 (2H, m), 7.88 (1H, d, J=8.0 Hz), 8.29 (1H, dd, J=2.0 Hz, 8.0 Hz), 8.39 (1H, t, J=6.0 Hz), 9.12 (1H, d, J=1.2 Hz), 12.98 (1H, s)

MS (m/z): 458 (M⁺)

Example 287: N-{4-Chloro-2-fluoro-3-[6-oxo-4-(5-propylpyridin-2-yl)-1,6-dihydropyrimidin-2-yl]benzyl}isobutyramide By performing operations similar to those of Example 4 using 5-propylpyridine-2-carbaldehyde, and N-(3-carbamimidoyl-4-chloro-2-fluorobenzyl)isobutyramide hydrochloride, the title compound was obtained.

¹H-NMR (d₆-DMSO, δ): 0.91 (3H, t, J=7.2 Hz), 1.05 (6H, d, J=6.8 Hz), 1.71 (2H, m), 2.3-2.6 (1H, m), 2.76 (2H, t, J=7.6 Hz), 4.32 (2H, d, J=4.8 Hz), 7.09 (1H, s), 7.36 (1H, d, J=8.0 Hz), 7.4-7.6 (2H, m), 8.2-8.5 (2H, m), 9.11 (1H, s), 12.99 (1H, s)

MS (m/z): 442 (M⁺)

Example 288: N-{4-Chloro-3-[2'-(cyclopropylmethoxy)-6-oxo-1,6-dihydro-[4,5'-bipyrimidin]-2-yl]-2-fluorobenzyl}isobutyramide By performing operations similar to those of Example 4 using 2-(cyclopropylmethoxy)pyrimidine-5-carbaldehyde, and N-(3-carbamimidoyl-4-chloro-2-fluorobenzyl)isobutyramide hydrochloride, the title compound was obtained.

¹H-NMR (d₆-DMSO, δ): 0.3-0.4 (2H, m), 0.5-0.7 (2H, m), 1.04 (6H, d, J=6.4 Hz), 1.2-1.4 (1H, m), 2.3-2.6 (1H, m), 4.22 (2H, d, J=7.2 Hz), 4.32 (2H, d, J=4.8 Hz), 7.13 (1H, s), 7.4-7.6 (2H, m), 8.3-8.4 (1H, m), 9.1-9.2 (2H, m), 13.01 (1H, s)

MS (m/z): 471 (M⁺)

Example 289: N-{3-[2'-(Cyclopropylmethoxy)-6-oxo-1,6-dihydro-[4,5'-bipyrimidin]-2-yl]-4-(trifluoromethyl)benzyl}butyramide By performing operations similar to those of Example 4 using 2-(cyclopropylmethoxy)pyrimidine-5-carbaldehyde, and N-[3-carbamimidoyl-4-(trifluoromethyl)benzyl]butyramide hydrochloride, the title compound was obtained.

¹H-NMR (d₆-DMSO, δ): 0.3-0.4 (2H, m), 0.5-0.6 (2H, m), 0.86 (3H, t, J=7.2 Hz), 1.2-1.4 (1H, m), 1.55 (2H, sext, J=7.2 Hz), 2.15 (2H, t, J=7.2 Hz), 4.22 (2H, d, J=7.2 Hz), 4.41 (2H, d, J=5.6 Hz), 7.10 (1H, s), 7.6-7.7 (2H, m), 7.88 (1H, d, J=7.6 Hz), 8.43 (1H, t, J=5.6 Hz), 9.1-9.2 (2H, m), 12.74 (1H, s)

MS (m/z): 487 (M⁺)

Example 290: N-{4-Chloro-3-[2'-(cyclopropylmethoxy)-6-oxo-1,6-dihydro-[4,5'-bipyrimidin]-2-yl]-2-fluorobenzyl}butyramide By performing operations similar to those of Example 4 using 2-(cyclopropylmethoxy)pyrimidine-5-carbaldehyde, and N-(3-carbamimidoyl-4-chloro-2-fluorobenzyl)butyramide hydrochloride, the title compound was obtained.

$^1$H-NMR (d$_6$-DMSO, δ): 0.3-0.4 (2H, m), 0.5-0.6 (2H, m), 0.87 (3H, t, J=7.2 Hz), 1.2-1.4 (1H, m), 1.55 (2H, sext, J=7.2 Hz), 2.14 (2H, t, J=7.2 Hz), 4.22 (2H, d, J=7.2 Hz), 4.33 (2H, d, J=5.6 Hz), 7.12 (1H, s), 7.4-7.6 (2H, m), 8.39 (1H, t, J=4.8 Hz), 9.17 (2H, s), 12.43 (1H, s)

MS (m/z): 471 (M$^+$)

Example 291: N-(3-{4-[5-(Cyclopropylmethoxy)pyrazin-2-yl]-6-oxo-1,6-dihydropyrimidin-2-yl}-4-(trifluoromethyl)benzyl)isobutyramide By performing operations similar to those of Example 4 using 5-(cyclopropylmethoxy)pyrazine-2-carbaldehyde, and N-[3-carbamimidoyl-4-(trifluoromethyl)benzyl]isobutyramide hydrochloride, the title compound was obtained.

$^1$H-NMR (d$_6$-DMSO, δ): 0.3-0.4 (2H, m), 0.5-0.6 (2H, m), 1.05 (6H, d, J=6.8 Hz), 1.2-1.3 (1H, m), 2.4-2.6 (1H, m), 4.21 (2H, d, J=7.6 Hz), 4.40 (2H, d, J=5.6 Hz), 7.06 (1H, s), 7.5-7.7 (2H, m), 7.90 (1H, d, J=8.0 Hz), 8.3-8.5 (2H, m), 8.8-8.9 (1H, m), 13.05 (1H, s)

MS (m/z): 487 (M$^+$)

Example 292: N-(4-Chloro-2-fluoro-3-{6-oxo-4-[2-(1-propynyl)thiazol-5-yl]-1,6-dihydropyrimidin-2-yl}benzyl)isobutyramide By performing operations similar to those of Example 4 using 2-(1-propynyl)thiazole-5-carbaldehyde, and N-(3-carbamimidoyl-4-chloro-2-fluorobenzyl)isobutyramide hydrochloride, the title compound was obtained.

$^1$H-NMR (d$_6$-DMSO, δ): 1.04 (6H, d, J=6.8 Hz), 2.17 (3H, s), 2.45 (1H, sept, J=6.8 Hz), 4.31 (2H, d, J=6.0 Hz), 7.08 (1H, s), 7.4-7.5 (2H, m), 8.36 (1H, t, J=6.0 Hz), 8.61 (1H, s), 13.23 (1H, brs)

MS (m/z): 444 (M$^+$)

Example 293: N-(2-Chloro-3-{4-[2-(cyclopropylethynyl)thiazol-5-yl]-6-oxo-1,6-dihydropyrimidin-2-yl})-4-fluorobenzyl)isobutyramide By performing operations similar to those of Example 4 using 2-(cyclopropylethynyl)thiazole-5-carbaldehyde, and N-(3-carbamimidoyl-2-chloro-4-fluorobenzyl)isobutyramide hydrochloride, the title compound was obtained.

$^1$H-NMR (d$_6$-DMSO, δ): 0.8-1.1 (4H, m), 1.07 (6H, d, J=6.8 Hz), 1.6-1.8 (1H, m), 2.4-2.6 (1H, m), 4.33 (2H, d, J=6.0 Hz), 7.07 (1H, s), 7.4-7.6 (2H, m), 8.37 (1H, t, J=6.0 Hz), 8.59 (1H, s), 13.22 (1H, brs)

MS (m/z): 470 (M$^+$)

Example 294: N-(3-{4-[5-(Cyclopropylethynyl)pyridin-2-yl]-6-oxo-1,6-dihydropyrimidin-2-yl}-2,4-difluorobenzyl)isobutyramide By performing operations similar to those of Example 4 using 5-(cyclopropylethynyl)pyridine-2-carbaldehyde, and N-(3-carbamimidoyl-2,4-difluorobenzyl)isobutyramide hydrochloride, the title compound was obtained.

$^1$H-NMR (d$_6$-DMSO, δ): 0.7-1.0 (4H, m), 1.04 (6H, d, J=6.8 Hz), 1.5-1.7 (1H, m), 2.45 (1H, sept, J=6.8 Hz), 4.32 (2H, d, J=5.6 Hz), 7.23 (1H, s), 7.28 (1H, t, J=8.8 Hz), 7.4-7.6 (1H, m), 7.91 (1H, dd, J=2.4 Hz, 8.4 Hz), 8.17 (1H, d, J=8.0 Hz), 8.33 (1H, t, J=5.6 Hz), 8.69 (1H, d, J=1.2 Hz), 13.26 (1H, brs)

MS (m/z): 448 (M$^+$)

Example 295: N-(3-{4-[6-(Cyclopropylethynyl)pyridin-3-yl]-6-oxo-1,6-dihydropyrimidin-2-yl}-2,4-difluorobenzyl)isobutyramide By performing operations similar to those of Example 4 using 6-(cyclopropylethynyl)pyridine-3-carbaldehyde, and N-(3-carbamimidoyl-2,4-difluorobenzyl)isobutyramide hydrochloride, the title compound was obtained.

$^1$H-NMR (d$_6$-DMSO, δ): 0.8-1.0 (4H, m), 1.04 (6H, d, J=6.8 Hz), 1.5-1.7 (1H, m), 2.44 (1H, sept, J=6.8 Hz), 4.32 (2H, d, J=5.6 Hz), 7.14 (1H, s), 7.28 (1H, t, J=8.8 Hz), 7.4-7.6 (2H, m), 8.3-8.4 (2H, m), 9.14 (1H, d, J=2.0 Hz), 13.22 (1H, brs)

MS (m/z): 448 (M$^+$)

Example 296: N-(2-Fluoro-3-{4-[5-(isobutyrylaminomethyl)pyridin-2-yl]-6-oxo-1,6-dihydropyrimidin-2-yl}-4-(trifluoromethyl)benzyl)isobutyramide By performing operations similar to those of Example 169 using 2-[3-chloro-2-fluoro-6-(trifluoromethyl)phenyl]-6-(5-chloropyridin-2-yl)pyrimidin-4(3H)-one, the title compound was obtained.

$^1$H-NMR (d$_6$-DMSO, δ): 1.03 (6H, d, J=6.8 Hz), 1.06 (6H, d, J=6.8 Hz), 2.3-2.6 (2H, m), 4.34 (2H, d, J=5.6 Hz), 4.41 (2H, d, J=5.6 Hz), 7.24 (1H, s), 7.66 (1H, t, J=8.0 Hz), 7.7-7.9 (2H, m), 8.11 (1H, d, J=7.6 Hz), 8.35 (1H, t, J=5.6 Hz), 8.45 (1H, t, J=6.0 Hz), 8.60 (1H, d, J=1.6 Hz), 13.30 (1H, brs)

MS (m/z): 533 (M$^+$)

Example 297: N-(2-Fluoro-3-{6-oxo-4-[5-(1-propynyl)pyridin-2-yl]-1,6-dihydropyrimidin-2-yl}-4-(trifluoromethyl)benzyl)isobutyramide By performing operations similar to those of Example 169 using 2-[3-chloro-2-fluoro-6-(trifluoromethyl)phenyl]-6-[5-(1-propynyl)pyridin-2-yl]pyrimidin-4(3H)-one, the title compound was obtained.

$^1$H-NMR (d$_6$-DMSO, δ): 1.06 (6H, d, J=6.8 Hz), 2.12 (3H, s), 2.48 (1H, sept, J=6.8 Hz), 4.41 (2H, d, J=5.6 Hz), 7.24 (1H, s), 7.66 (1H, t, J=7.6 Hz), 7.79 (1H, d, J=7.6 Hz), 7.93 (1H, dd, J=2.0 Hz, 8.0 Hz), 8.12 (1H, d, J=8.0 Hz), 8.44 (1H, t, J=5.6 Hz), 8.72 (1H, d, J=2.0 Hz), 13.34 (1H, brs)

MS (m/z): 472 (M$^+$)

Example 298: N-(3-{4-[6-(Cyclopropylethynyl)pyridin-3-yl]-6-oxo-1,6-dihydropyrimidin-2-yl}-2-fluoro-4-(trifluoromethyl)benzyl)isobutyramide By performing operations similar to those of Example 169 using 2-[3-chloro-2-fluoro-6-(trifluoromethyl)phenyl]-6-[6-(cyclopropylethynyl)pyridin-3-yl]pyrimidin-4(3H)-one, the title compound was obtained.

$^1$H-NMR (d$_6$-DMSO, δ): 0.7-1.0 (4H, m), 1.06 (6H, d, J=7.2 Hz), 1.5-1.7 (1H, m), 2.48 (1H, sept, J=6.8 Hz), 4.40 (2H, d, J=6.0 Hz), 7.15 (1H, s), 7.51 (1H, d, J=8.4 Hz), 7.65 (1H, t, J=8.0 Hz), 7.78 (1H, d, J=8.4 Hz), 8.33 (1H, d, J=8.4 Hz), 8.43 (1H, t, J=6.0 Hz), 9.12 (1H, s), 13.29 (1H, brs)

MS (m/z): 498 (M$^+$)

Example 299: N-(3-{4-[6-(Cyclopropylethynyl)pyridin-3-yl]-6-oxo-1,6-dihydropyrimidin-2-yl}-4-(trifluoromethyl)benzyl)isobutyramide By performing operations similar to those of Example 4 using 6-(cyclopropylethynyl)pyridine-3-carbaldehyde, and N-[3-carbamimidoyl-4-(trifluoromethyl)benzyl]isobutyramide hydrochloride, the title compound was obtained.

¹H-NMR (d₆-DMSO, δ): 0.7-1.0 (4H, m), 1.05 (6H, d, J=7.2 Hz), 1.5-1.7 (1H, m), 2.45 (1H, sept, J=6.8 Hz), 4.40 (2H, d, J=6.0 Hz), 7.11 (1H, s), 7.5-7.7 (3H, m), 7.88 (1H, d, J=8.4 Hz), 8.34 (1H, dd, J=2.0 Hz, 8.4 Hz), 8.39 (1H, t, J=6.0 Hz), 9.14 (1H, s), 13.06 (1H, brs)

MS (m/z): 480 (M⁺)

Example 300: N-(2-Fluoro-3-{6-oxo-4-[6-(2-propoxyethoxy)pyridin-3-yl]-1,6-dihydropyrimidin-2-yl}-4-(trifluoromethyl)benzyl)isobutyramide By performing operations similar to those of Example 169 using 2-[3-chloro-2-fluoro-6-(trifluoromethyl)phenyl]-6-.[6-(2-propoxyethoxy)pyridin-3-yl]pyrimidin-4(3H)-one, the title compound was obtained.

¹H-NMR (d₆-DMSO, δ): 0.85 (3H, t, J=7.6 Hz), 1.06 (6H, d, J=6.8 Hz), 1.51 (2H, sext, J=7.6 Hz), 2.48 (1H, sept, J=6.8 Hz), 3.39 (2H, t, J=6.8 Hz), 3.71 (2H, t, J=4.8 Hz), 4.40 (2H, d, J=6.0 Hz), 4.43 (2H, t, J=4.4 Hz), 6.92 (1H, d, J=8.8 Hz), 7.02 (1H, s), 7.65 (1H, t, J=7.6 Hz), 7.79 (1H, d, J=8.0 Hz), 8.30 (1H, d, J=8.4 Hz), 8.46 (1H, t, J=6.0 Hz), 8.83 (1H, s), 13.20 (1H, brs)

MS (m/z): 536 (M⁺)

Example 301: N-(2-Fluoro-3-{4-[6-(2-isopropoxyethoxy)pyridin-3-yl]-6-oxo-1,6-dihydropyrimidin-2-yl}-4-(trifluoromethyl)benzyl)isobutyramide By performing operations similar to those of Example 169 using 2-[3-chloro-2-fluoro-6-(trifluoromethyl)phenyl]-6-[6-(2-isopropoxyethoxy)pyridin-3-yl]pyrimidin-4(3H)-one, the title compound was obtained.

¹H-NMR (d₆-DMSO, δ): 1.0-1.2 (12H, m), 2.48 (1H, sept, J=6.8 Hz), 3.61 (1H, sept. J=6.0 Hz), 3.70 (2H, t, J=4.8 Hz), 4.3-4.5 (4H, m), 6.92 (1H, d, J=8.8 Hz), 7.01 (1H, s), 7.65 (1H, t, J=8.0 Hz), 7.78 (1H, d, J=8.0 Hz), 8.29 (1H, d, J=8.4 Hz), 8.43 (1H, t, J=6.0 Hz), 8.83 (1H, s), 13.17 (1H, brs)

MS (m/z): 536 (M⁺)

Example 302: N-(3-{4-[2-(Cyclopropylethynyl)thiazol-5-yl]-6-oxo-1,6-dihydropyrimidin-2-yl}-2-fluoro-4-(trifluoromethyl)benzyl)isobutyramide By performing operations similar to those of Example 169 using 2-[3-chloro-2-fluoro-6-(trifluoromethyl)phenyl]-6-[2-(cyclopropylethynyl)thiazol-5-yl]pyrimidin-4(3H)-one, the title compound was obtained.

¹H-NMR (d₆-DMSO, δ): 0.8-1.1 (4H, m), 1.06 (6H, d, J=6.8 Hz), 1.6-1.8 (1H, m), 2.47 (1H, sept, J=6.8 Hz), 4.40 (2H, d, J=5.6 Hz), 7.08 (1H, s), 7.65 (1H, t, J=7.6 Hz), 7.77 (1H, d, J=8.0 Hz), 8.43 (1H, t, J=5.6 Hz), 8.59 (1H, s), 13.29 (1H, brs)

MS (m/z): 504 (M⁺)

Example 303: N-[2-Fluoro-3-(6-oxo-4-{6-[2-(2,2,2-trifluoroethoxy)ethoxy]pyridin-3-yl}-1,6-dihydropyrimidin-2-yl)-4-(trifluoromethyl)benzyl]isobutyramide By performing operations similar to those of Example 169 using 2-[3-chloro-2-fluoro-6-(trifluoromethyl)phenyl]-6-{6-[2-(2,2,2-trifluoroethoxy)ethoxy]pyridin-3-yl}pyrimidin-4(3H)-one, the title compound was obtained.

¹H-NMR (d₆-DMSO, δ): 1.06 (6H, d, J=6.8 Hz), 2.48 (1H, sept, J=6.8 Hz), 3.95 (2H, t. J=4.4 Hz), 4.14 (2H, q, J=9.2 Hz), 4.40 (2H, d, J=5.2 Hz), 4.48 (2H, t, J=4.4 Hz), 6.94 (1H, d, J=8.8 Hz), 7.02 (1H, s), 7.65 (1H, t, J=7.6 Hz), 7.78 (1H, d, J=8.0 Hz), 8.31 (1H, d, J=7.6 Hz), 8.43 (1H, t, J=5.6 Hz), 8.83 (1H, s), 13.18 (1H, brs)

MS (m/z): 576 (M⁺)

Example 304: N-(4-Chloro-2-fluoro-3-{6-oxo-4-[5-(2,2,2-trifluoroethyl)pyridin-2-yl]-1,6-dihydropyrimidin-2-yl}benzyl)isobutyramide By performing operations similar to those of Example 4 using 5-(2,2,2-trifluoroethyl)pyridine-2-carbaldehyde, and N-(3-carbamimidoyl-4-chloro-2-fluorobenzyl)isobutyramide hydrochloride, the title compound was obtained.

¹H-NMR (d₆-DMSO, δ): 1.05 (6H, d, J=7.2 Hz), 2.46 (1H, sept, J=6.8 Hz), 3.84 (2H, q, J=11.2 Hz), 4.33 (2H, d, J=6.0 Hz), 7.28 (1H, s), 7.4-7.6 (2H, m), 7.95 (1H, dd, J=2.0 Hz, 8.0 Hz), 8.23 (1H, d, J=7.6 Hz), 8.37 (1H, t, J=6.0 Hz), 8.72 (1H, d, J=1.6 Hz), 13.28 (1H, brs)

MS (m/z): 482 (M⁺)

Example 305: N-(3-{4-[5-(Cyclopropylethynyl)pyridin-2-yl]-6-oxo-1,6-dihydropyrimidin-2-yl}-2-fluoro-4-(trifluoromethyl)benzyl)isobutyramide By performing operations similar to those of Example 169 using 2-[3-chloro-2-fluoro-6-(trifluoromethyl)phenyl]-6-[5-(cyclopropylethynyl)pyridin-2-yl]pyrimidin-4(3H)-one, the title compound was obtained.

¹H-NMR (d₆-DMSO, δ): 0.7-1.0 (4H, m), 1.06 (6H, d, J=6.8 Hz), 1.5-1.7 (1H, m), 2.48 (1H, sept, J=6.8 Hz), 4.40 (2H, d, J=6.0 Hz), 7.23 (1H, s), 7.66 (1H, t, J=8.0 Hz), 7.79 (1H, d, J=8.4 Hz), 7.89 (1H, dd, J=2.0 Hz, 8.0 Hz), 8.10 (1H, d, J=8.0 Hz), 8.44 (1H, t, J=6.0 Hz), 8.69 (1H, d, J=1.2 Hz), 13.33 (1H, brs)

MS (m/z): 498 (M⁺)

Test Example 1: Test for mPGES-1 Inhibitory Activity

Microsomes were prepared from COS-1 cells transiently transfected with a plasmid containing human mPGES-1 cDNA, and used as mPGES-1 enzyme. The mPGES-1 enzyme was diluted with a sodium phosphate buffer (pH 7.2) containing reduced glutathione (2.5 mM) and EDTA (1 mM), DMSO or a DMSO solution of a test compound (final concentration of DMSO was 1%) was added to the enzyme, and the mixture was preincubated at 4° C. for 15 minutes. Then, PGH2 as the substrate was added at a final concentration of 1 μM to start the enzymatic reaction, and after incubation at 4° C. for 4 minutes, a solution of ferric chloride (25 mM) and citric acid (50 mM) was added to terminate the enzymatic reaction. Generated PGE2 was measured by using Prostaglandin E2 Express EIA Kit (Cayman Chemical). IC₅₀ values were determined by using a standard method. The results are shown in Tables 2-1 to 2-5 mentioned below.

TABLE 1-1

| Example No. | Structural formula |
|---|---|
| 1 | |
| 2 | |
| 3 | |
| 4 | |
| 5 | |
| 6 | |
| 7 | |

TABLE 1-1-continued

| Example No. | Structural formula |
|---|---|
| 8 | |
| 9 | |
| 10 | |
| 11 | |
| 12 | |
| 13 | |

TABLE 1-1-continued

| Example No. | Structural formula |
| --- | --- |
| 14 | (structure) |
| 15 | (structure) |
| 16 | (structure) |
| 17 | (structure) |
| 18 | (structure) |

TABLE 1-2

| Example No. | Structural formula |
| --- | --- |
| 19 | (structure) |

TABLE 1-2-continued

| Example No. | Structural formula |
|---|---|
| 20 | 4-(difluoromethoxy)phenyl pyrimidinone-chlorophenyl-CH₂-NH-C(O)-CH(CH₃)₂ |
| 21 | 4-(trifluoromethyl)phenyl pyrimidinone-chlorophenyl-CH₂-NH-C(O)-CH(CH₃)₂ |
| 22 | 3-fluorothiophen-2-yl pyrimidinone-chlorophenyl-CH₂-NH-C(O)-CH(CH₃)₂ |
| 23 | cyclopentyl pyrimidinone-chlorophenyl-CH₂-NH-C(O)-CH(CH₃)₂ |
| 24 | 4-(trifluoromethoxy)phenyl pyrimidinone-chlorophenyl-CH₂-NH-C(O)-CH(CH₃)₂ |
| 25 | 2,4-difluorophenyl pyrimidinone-chlorophenyl-CH₂-NH-C(O)-CH(CH₃)₂ |

TABLE 1-2-continued
| Example No. | Structural formula |
|---|---|
| 26 | 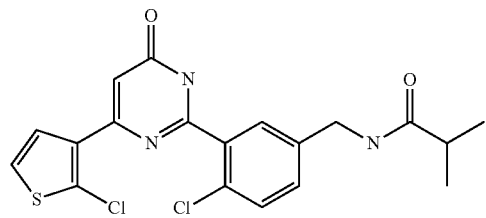 [SMILES: CC(C)C(=O)NCc1ccc(Cl)c(-c2nc(-c3ccsc3Cl)cc(=O)[nH]2)c1] |
| 27 | 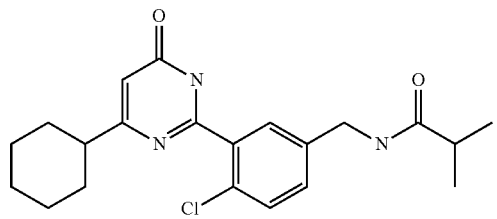 [SMILES: CC(C)C(=O)NCc1ccc(Cl)c(-c2nc(C3CCCCC3)cc(=O)[nH]2)c1] |
| 28 | 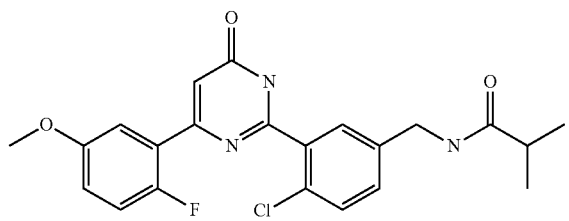 [SMILES: COc1ccc(F)c(-c2cc(=O)[nH]c(-c3cc(CNC(=O)C(C)C)ccc3Cl)n2)c1] |
| 29 | 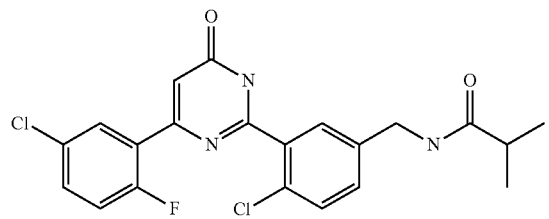 [SMILES: CC(C)C(=O)NCc1ccc(Cl)c(-c2nc(-c3cc(Cl)ccc3F)cc(=O)[nH]2)c1] |
| 30 | 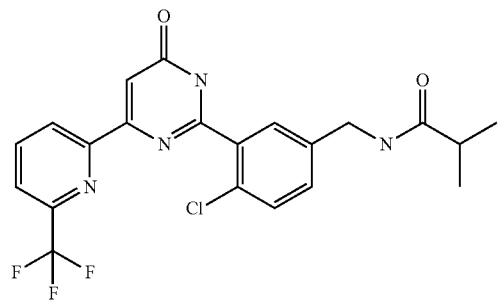 [SMILES: CC(C)C(=O)NCc1ccc(Cl)c(-c2nc(-c3cccc(C(F)(F)F)n3)cc(=O)[nH]2)c1] |
| 31 | 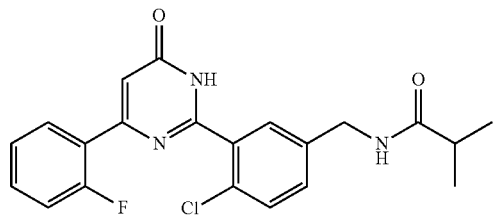 [SMILES: CC(C)C(=O)NCc1ccc(Cl)c(-c2nc(-c3ccccc3F)cc(=O)[nH]2)c1] |

TABLE 1-2-continued

| Example No. | Structural formula |
|---|---|
| 32 | |
| 33 | |
| 34 | |

TABLE 1-3

| Example No. | Structural formula |
|---|---|
| 35 | |
| 36 | |
| 37 | |

TABLE 1-3-continued

| Example No. | Structural formula |
|---|---|
| 38 | (4-chloro-3-(6-(4-(2-methoxyethoxy)phenyl)-4-oxo-1,4-dihydropyrimidin-2-yl)phenyl)methyl isobutyramide |
| 39 | N-(4-chloro-3-(6-(5-methylpyridin-2-yl)-4-oxo-1,4-dihydropyrimidin-2-yl)benzyl)isobutyramide |
| 40 | N-(4-chloro-3-(4-oxo-6-(6-(trifluoromethyl)pyridin-3-yl)-1,4-dihydropyrimidin-2-yl)benzyl)cyclopropanecarboxamide |
| 41 | N-(4-chloro-3-(6-(4-(difluoromethyl)phenyl)-4-oxo-1,4-dihydropyrimidin-2-yl)benzyl)isobutyramide |
| 42 | N-(4-chloro-3-(4-oxo-6-(5-(trifluoromethyl)thiophen-2-yl)-1,4-dihydropyrimidin-2-yl)benzyl)isobutyramide |
| 43 | N-(4-chloro-3-(4-oxo-6-(2-(trifluoromethyl)thiazol-5-yl)-1,4-dihydropyrimidin-2-yl)benzyl)isobutyramide |

TABLE 1-3-continued
| Example No. | Structural formula |
|---|---|
| 44 | 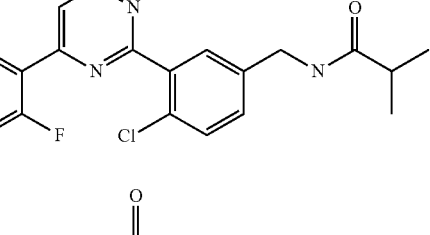 |
| 45 | 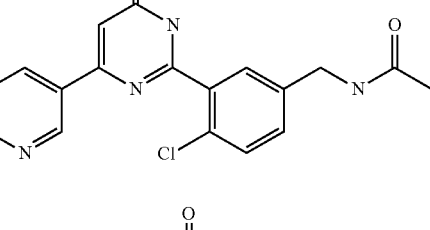 |
| 46 | 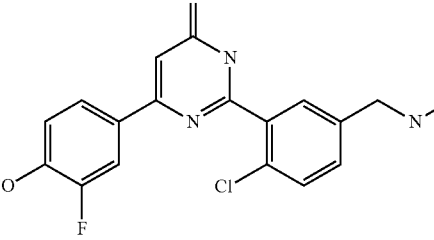 |
| 47 | 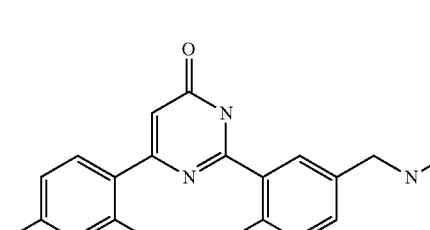 |
| 48 | 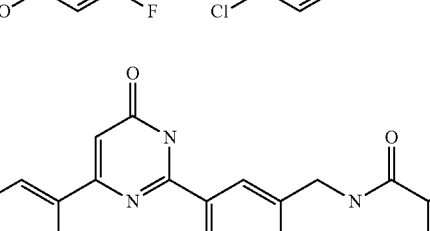 |
| 49 | 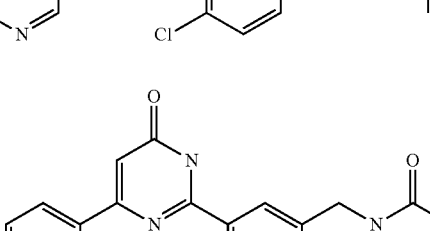 |

TABLE 1-3-continued
| Example No. | Structural formula |
|---|---|
| 50 | 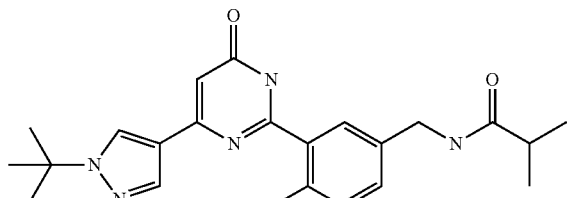 |
| 51 | 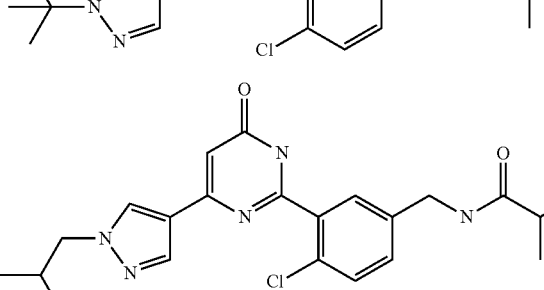 |
| 52 | 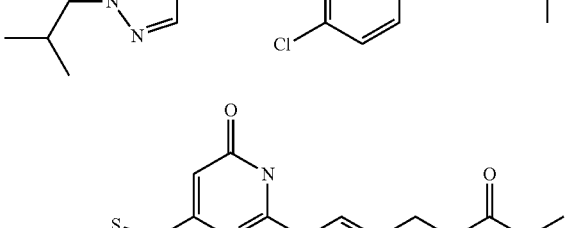 |
TABLE 1-4
| Example No. | Structural formula |
|---|---|
| 53 | 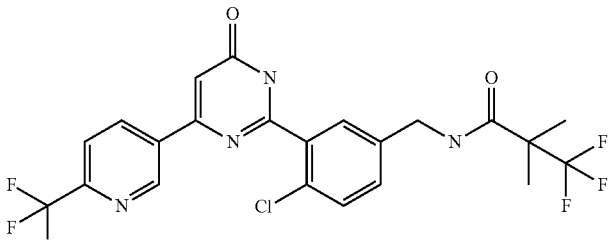 |
| 54 | 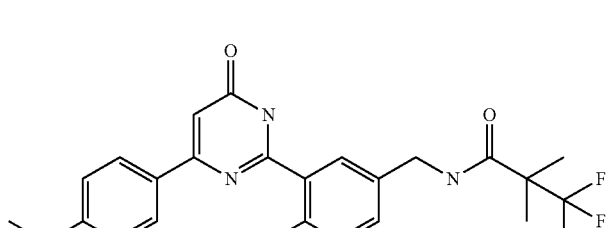 |

TABLE 1-4-continued

| Example No. | Structural formula |
|---|---|
| 55 | |
| 56 | |
| 57 | |
| 58 | |
| 59 | |
| 60 | |

TABLE 1-4-continued
| Example No. | Structural formula |
|---|---|
| 61 | 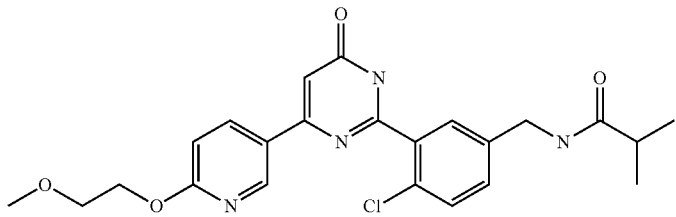 [SMILES: COCCOc1ccc(-c2cc(=O)[nH]c(-c3cc(CNC(=O)C(C)C)ccc3Cl)n2)cn1] |
| 62 | 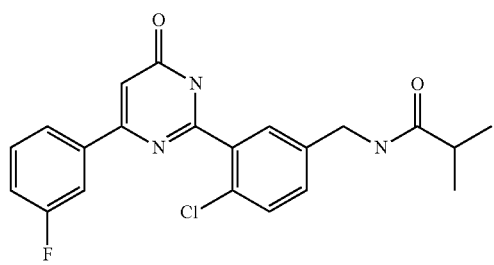 [SMILES: CC(C)C(=O)NCc1ccc(Cl)c(-c2nc(-c3cccc(F)c3)cc(=O)[nH]2)c1] |
| 63 | 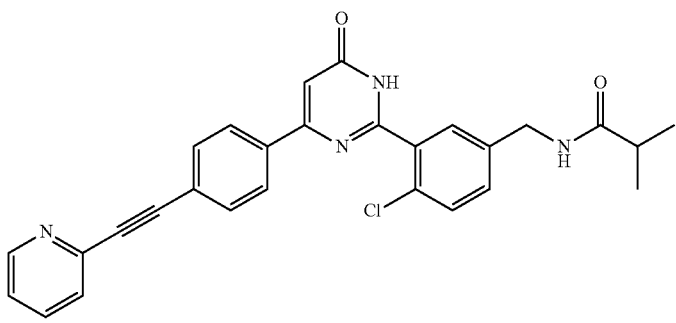 [SMILES: CC(C)C(=O)NCc1ccc(Cl)c(-c2nc(-c3ccc(C#Cc4ccccn4)cc3)cc(=O)[nH]2)c1] |
| 64 | 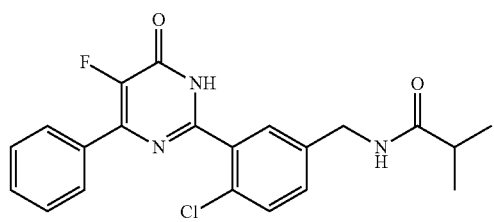 |
| 65 | 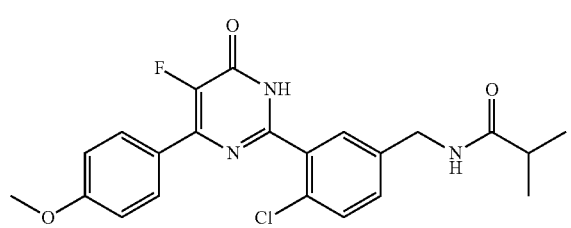 [SMILES: COc1ccc(-c2nc(-c3cc(CNC(=O)C(C)C)ccc3Cl)[nH]c(=O)c2F)cc1] |
| 66 | 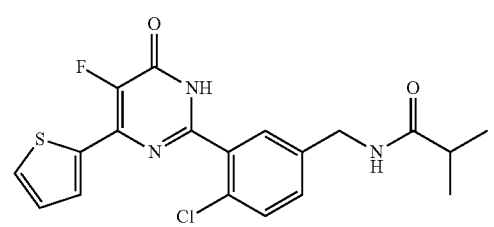 [SMILES: CC(C)C(=O)NCc1ccc(Cl)c(-c2nc(-c3cccs3)c(F)c(=O)[nH]2)c1] |

TABLE 1-4-continued
| Example No. | Structural formula |
|---|---|
| 67 | 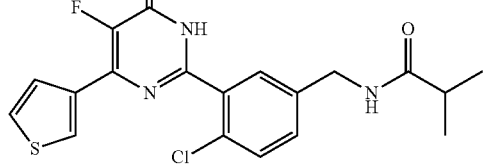 |
| 68 | 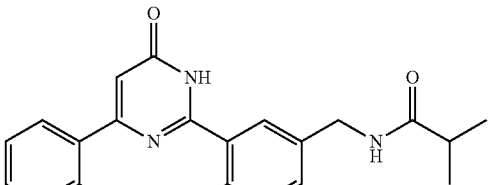 |
| 69 | 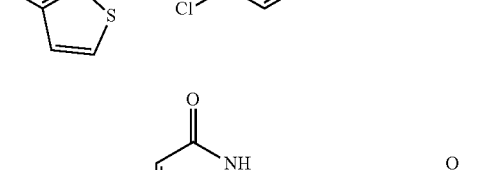 |
| 70 | 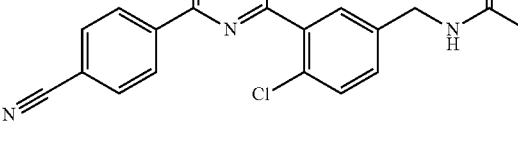 |
TABLE 1-5
| Example No. | Structural formula |
|---|---|
| 71 | 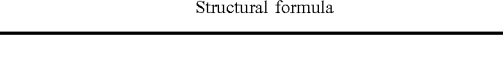 |

TABLE 1-5-continued

| Example No. | Structural formula |
|---|---|
| 72 | |
| 73 | |
| 74 | |
| 75 | |
| 76 | |

TABLE 1-5-continued

| Example No. | Structural formula |
|---|---|
| 77 | (structure) |
| 78 | (structure) |
| 79 | (structure) |
| 80 | (structure) |
| 81 | (structure) |
| 82 | (structure) |

TABLE 1-5-continued

| Example No. | Structural formula |
|---|---|
| 83 | |
| 84 | |
| 85 | |
| 86 | |
| 87 | |
| 88 | |

TABLE 1-6
| Example No. | Structural formula |
|---|---|
| 89 | 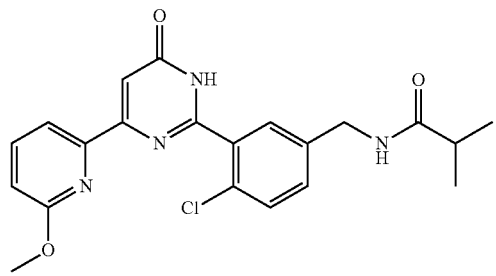 [SMILES: COc1cccc(-c2cc(=O)[nH]c(-c3cc(CNC(=O)C(C)C)ccc3Cl)n2)n1] |
| 90 | 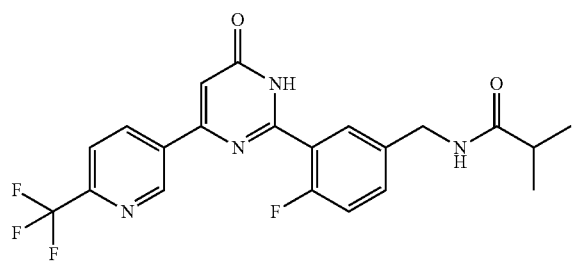 [SMILES: CC(C)C(=O)NCc1ccc(F)c(-c2nc(-c3ccc(C(F)(F)F)nc3)cc(=O)[nH]2)c1] |
| 91 | 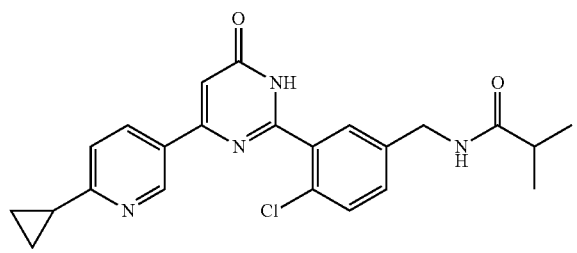 [SMILES: CC(C)C(=O)NCc1ccc(Cl)c(-c2nc(-c3ccc(C4CC4)nc3)cc(=O)[nH]2)c1] |
| 92 | 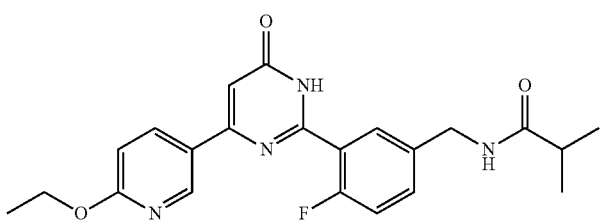 [SMILES: CCOc1ccc(-c2cc(=O)[nH]c(-c3cc(CNC(=O)C(C)C)ccc3F)n2)cn1] |
| 93 | 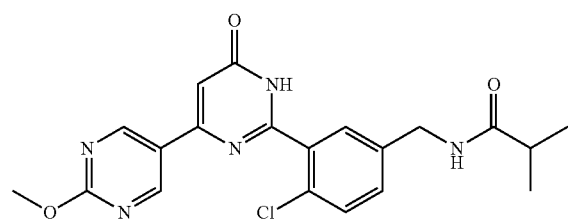 [SMILES: COc1ncc(-c2cc(=O)[nH]c(-c3cc(CNC(=O)C(C)C)ccc3Cl)n2)cn1] |
| 94 | 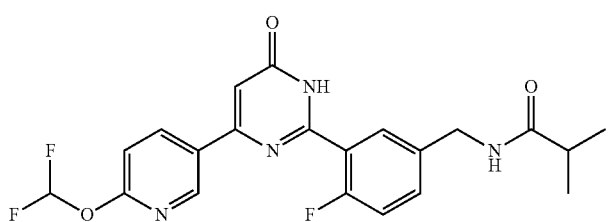 [SMILES: CC(C)C(=O)NCc1ccc(F)c(-c2nc(-c3ccc(OC(F)F)nc3)cc(=O)[nH]2)c1] |

TABLE 1-6-continued
| Example No. | Structural formula |
|---|---|
| 95 | 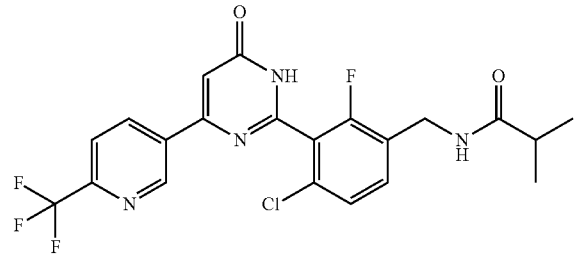 [SMILES: CC(C)C(=O)NCc1ccc(Cl)c(-c2nc(-c3ccc(C(F)(F)F)nc3)cc(=O)[nH]2)c1F] |
| 96 | 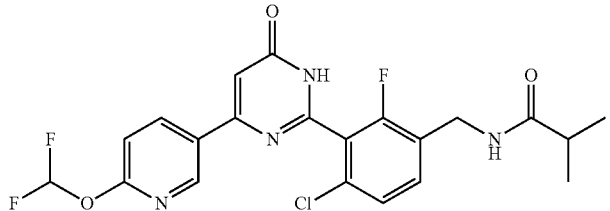 [SMILES: CC(C)C(=O)NCc1ccc(Cl)c(-c2nc(-c3ccc(OC(F)F)nc3)cc(=O)[nH]2)c1F] |
| 97 | 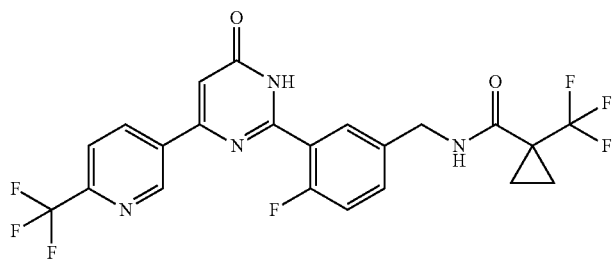 [SMILES: O=C(NCc1ccc(F)c(-c2nc(-c3ccc(C(F)(F)F)nc3)cc(=O)[nH]2)c1)C1(C(F)(F)F)CC1] |
| 98 | 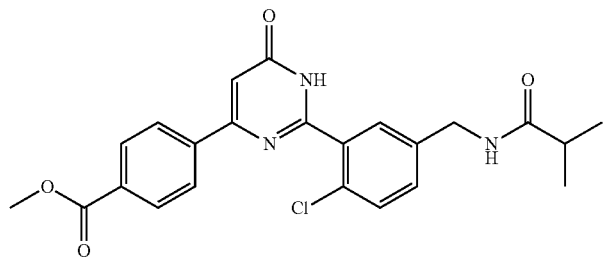 [SMILES: COC(=O)c1ccc(-c2cc(=O)[nH]c(-c3cc(CNC(=O)C(C)C)ccc3Cl)n2)cc1] |
| 99 | 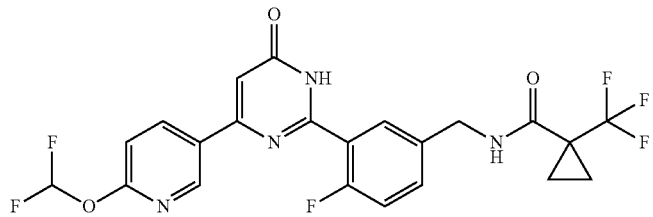 [SMILES: O=C(NCc1ccc(F)c(-c2nc(-c3ccc(OC(F)F)nc3)cc(=O)[nH]2)c1)C1(C(F)(F)F)CC1] |
| 100 | 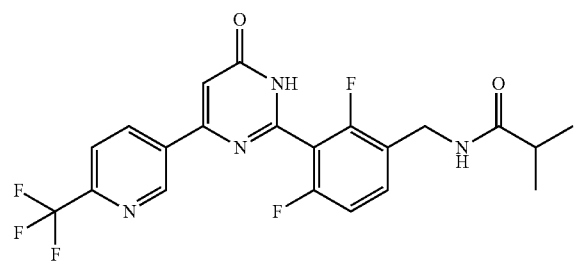 |

TABLE 1-6-continued

| Example No. | Structural formula |
|---|---|
| 101 | |
| 102 | |
| 103 | |
| 104 | |
| 105 | |
| 106 | |

TABLE 1-7

| Example No. | Structural formula |
|---|---|
| 107 | |
| 108 | |
| 109 | |
| 110 | |
| 111 | |

TABLE 1-7-continued

| Example No. | Structural formula |
|---|---|
| 112 | (structure) |
| 113 | (structure) |
| 114 | (structure) |
| 115 | (structure) |
| 116 | (structure) |
| 117 | (structure) |

TABLE 1-7-continued

| Example No. | Structural formula |
|---|---|
| 118 | |
| 119 | |
| 120 | |
| 121 | |
| 122 | |
| 123 | |

183                                                                                                                                    184
TABLE 1-7-continued
| Example No. | Structural formula |
|---|---|
| 124 | 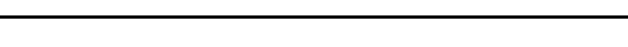 |
TABLE 1-8
| Example No. | Structural formula |
|---|---|
| 125 | |
| 126 | |
| 127 | |
| 128 | 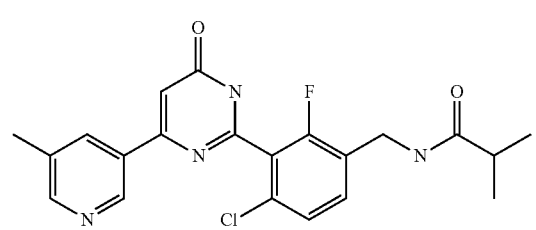 [SMILES: Cc1cncc(-c2cc(=O)[nH]c(-c3c(Cl)ccc(CNC(=O)C(C)C)c3F)n2)c1] |

TABLE 1-8-continued
| Example No. | Structural formula |
|---|---|
| 129 | 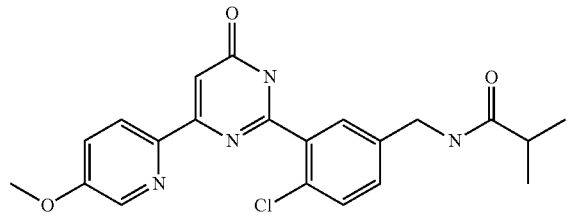 [SMILES: COc1ccc(-c2cc(=O)[nH]c(-c3cc(CNC(=O)C(C)C)ccc3Cl)n2)nc1] |
| 130 | 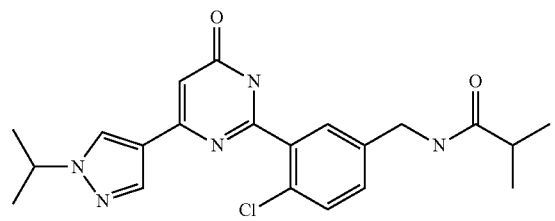 [SMILES: CC(C)C(=O)NCc1ccc(Cl)c(-c2nc(-c3cnn(C(C)C)c3)cc(=O)[nH]2)c1] |
| 131 | 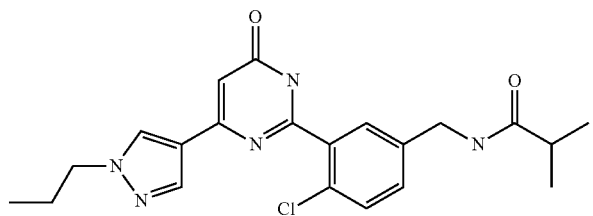 [SMILES: CCCn1cc(-c2cc(=O)[nH]c(-c3cc(CNC(=O)C(C)C)ccc3Cl)n2)cn1] |
| 132 | 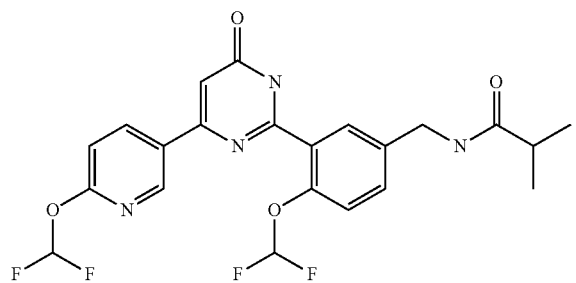 [SMILES: CC(C)C(=O)NCc1ccc(OC(F)F)c(-c2nc(-c3ccc(OC(F)F)nc3)cc(=O)[nH]2)c1] |
| 133 | 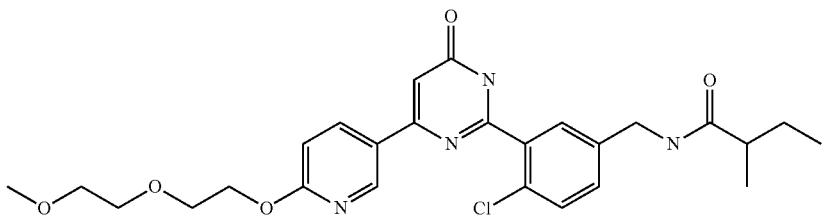 [SMILES: CCC(C)C(=O)NCc1ccc(Cl)c(-c2nc(-c3ccc(OCCOCCOC)nc3)cc(=O)[nH]2)c1] |
| 134 | 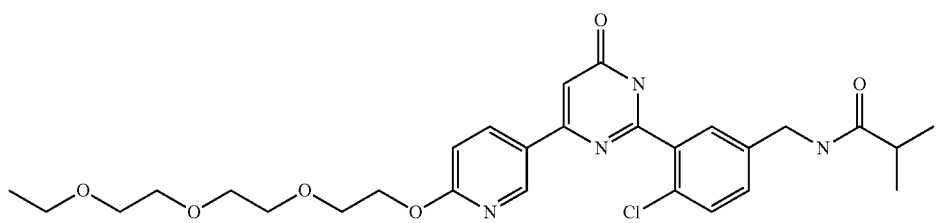 [SMILES: CCOCCOCCOCCOc1ccc(-c2cc(=O)[nH]c(-c3cc(CNC(=O)C(C)C)ccc3Cl)n2)cn1] |

TABLE 1-8-continued

| Example No. | Structural formula |
|---|---|
| 135 | (structure) |
| 136 | (structure) |
| 137 | (structure) |
| 138 | (structure) |
| 139 | (structure) |
| 140 | (structure) |

TABLE 1-8-continued
| Example No. | Structural formula |
|---|---|
| 141 | 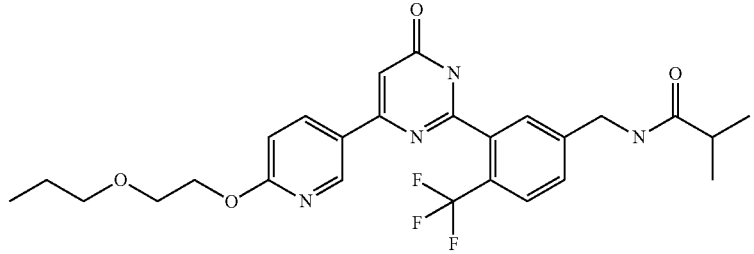 [SMILES: CCCOCCOc1ccc(-c2cc(=O)[nH]c(-c3cc(CNC(=O)C(C)C)ccc3C(F)(F)F)n2)cn1] |
| 142 | 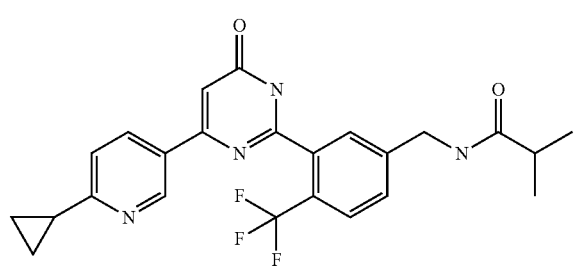 [SMILES: CC(C)C(=O)NCc1ccc(C(F)(F)F)c(-c2nc(-c3ccc(C4CC4)nc3)cc(=O)[nH]2)c1] |
TABLE 1-9
| Example No. | Structural formula |
|---|---|
| 143 | 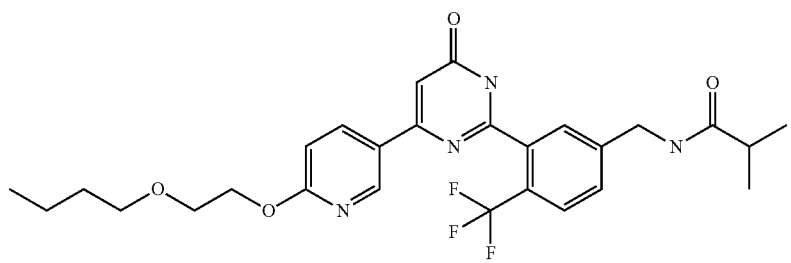 [SMILES: CCCCOCCOc1ccc(-c2cc(=O)[nH]c(-c3cc(CNC(=O)C(C)C)ccc3C(F)(F)F)n2)cn1] |
| 144 | 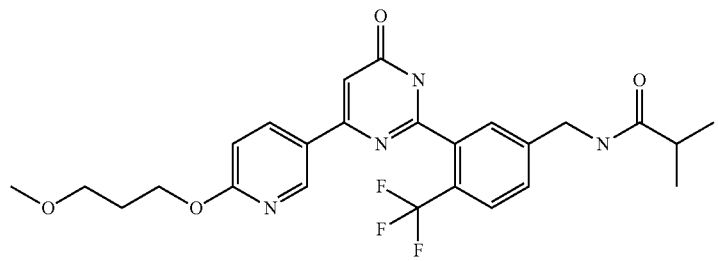 [SMILES: COCCCOc1ccc(-c2cc(=O)[nH]c(-c3cc(CNC(=O)C(C)C)ccc3C(F)(F)F)n2)cn1] |
| 145 | 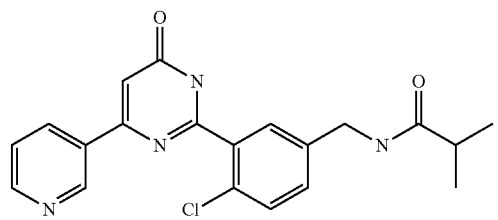 [SMILES: CC(C)C(=O)NCc1ccc(Cl)c(-c2nc(-c3cccnc3)cc(=O)[nH]2)c1] |

TABLE 1-9-continued
| Example No. | Structural formula |
|---|---|
| 146 | 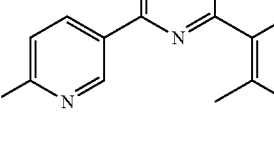 |
| 147 | 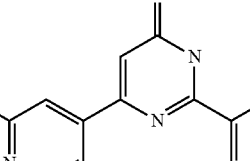 |
| 148 | 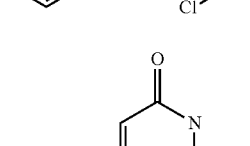 |
| 149 | 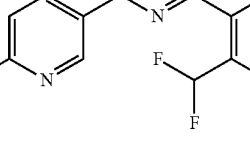 |
| 150 | 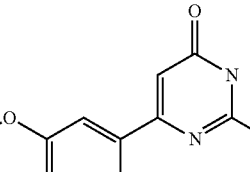 |
| 151 | 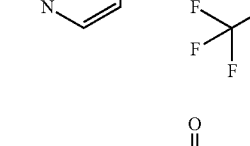 |

TABLE 1-9-continued

| Example No. | Structural formula |
|---|---|
| 152 | (structure) |
| 153 | (structure) |
| 154 | (structure) |
| 155 | (structure) |
| 156 | (structure) |
| 157 | (structure) |

TABLE 1-9-continued
| Example No. | Structural formula |
|---|---|
| 158 | 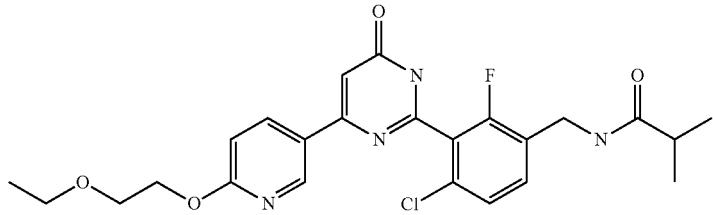 [SMILES: CCOCCOc1ccc(-c2cc(=O)[nH]c(-c3c(Cl)ccc(CNC(=O)C(C)C)c3F)n2)cn1] |
| 159 | 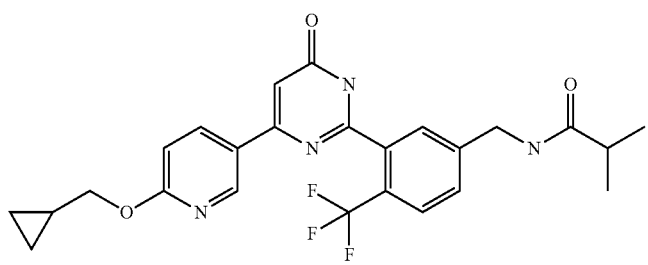 [SMILES: CC(C)C(=O)NCc1ccc(C(F)(F)F)c(-c2nc(-c3ccc(OCC4CC4)nc3)cc(=O)[nH]2)c1] |
| 160 | 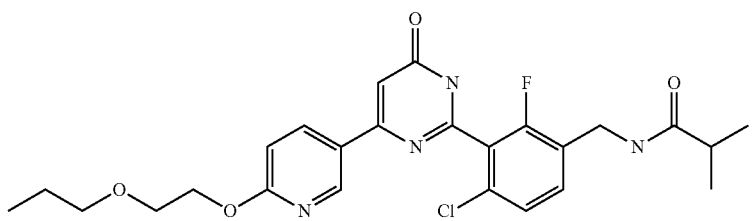 [SMILES: CCCOCCOc1ccc(-c2cc(=O)[nH]c(-c3c(Cl)ccc(CNC(=O)C(C)C)c3F)n2)cn1] |
TABLE 1-10
| Example No. | Structural formula |
|---|---|
| 161 | 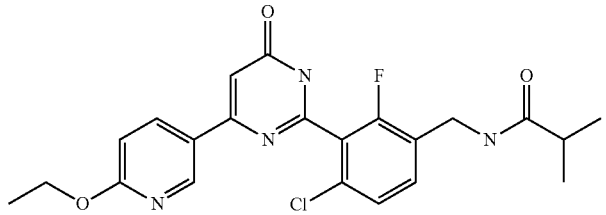 [SMILES: CCOc1ccc(-c2cc(=O)[nH]c(-c3c(Cl)ccc(CNC(=O)C(C)C)c3F)n2)cn1] |
| 162 | 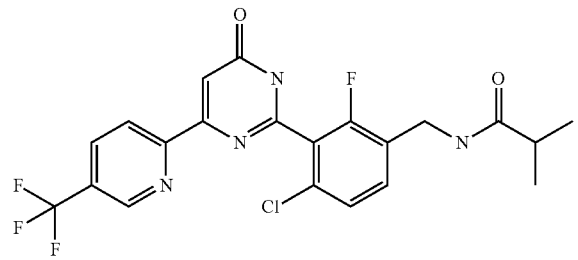 [SMILES: CC(C)C(=O)NCc1ccc(Cl)c(-c2nc(-c3ccc(C(F)(F)F)cn3)cc(=O)[nH]2)c1F] |

TABLE 1-10-continued
| Example No. | Structural formula |
|---|---|
| 163 | 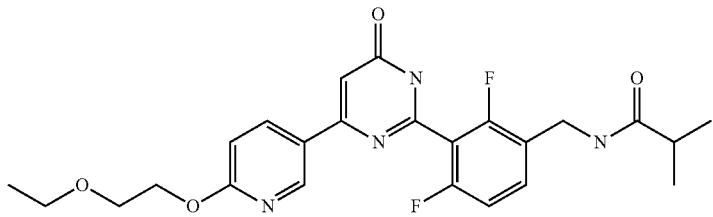 [SMILES: CCOCCOc1ccc(-c2cc(=O)[nH]c(-c3c(F)ccc(CNC(=O)C(C)C)c3F)n2)cn1] |
| 164 | 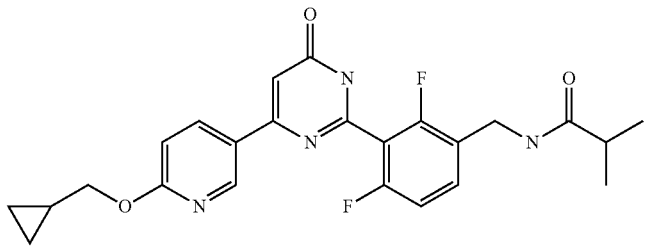 [SMILES: CC(C)C(=O)NCc1ccc(F)c(-c2nc(-c3ccc(OCC4CC4)nc3)cc(=O)[nH]2)c1F] |
| 165 | 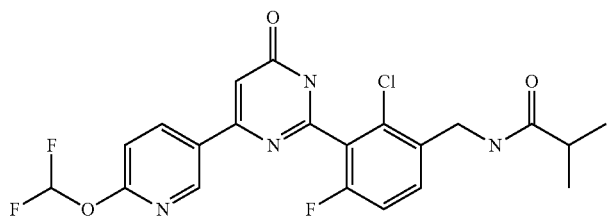 [SMILES: CC(C)C(=O)NCc1ccc(F)c(-c2nc(-c3ccc(OC(F)F)nc3)cc(=O)[nH]2)c1Cl] |
| 166 | 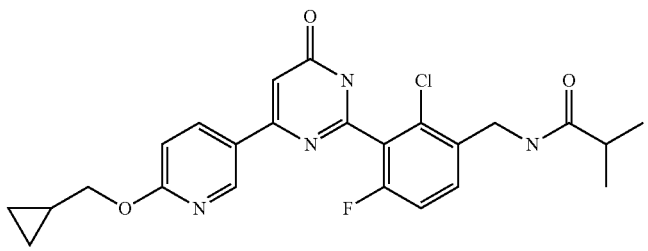 [SMILES: CC(C)C(=O)NCc1ccc(F)c(-c2nc(-c3ccc(OCC4CC4)nc3)cc(=O)[nH]2)c1Cl] |
| 167 | 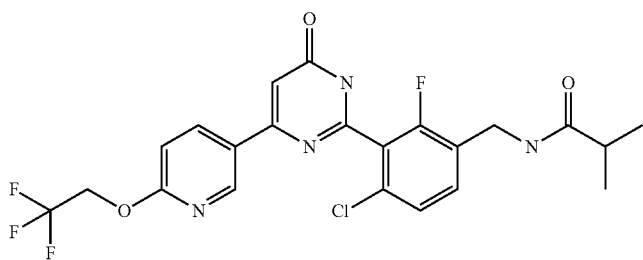 [SMILES: CC(C)C(=O)NCc1ccc(Cl)c(-c2nc(-c3ccc(OCC(F)(F)F)nc3)cc(=O)[nH]2)c1F] |
| 168 | 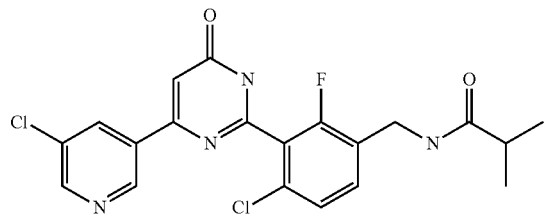 |

TABLE 1-10-continued

| Example No. | Structural formula |
|---|---|
| 169 | (structure) |
| 170 | (structure) |
| 171 | (structure) |
| 172 | (structure) |
| 173 | (structure) |
| 174 | (structure) |

TABLE 1-10-continued
| Example No. | Structural formula |
|---|---|
| 175 | 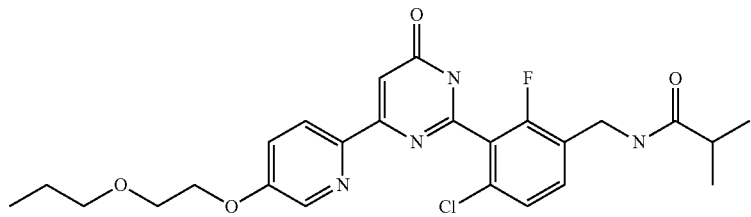 |
| 176 | 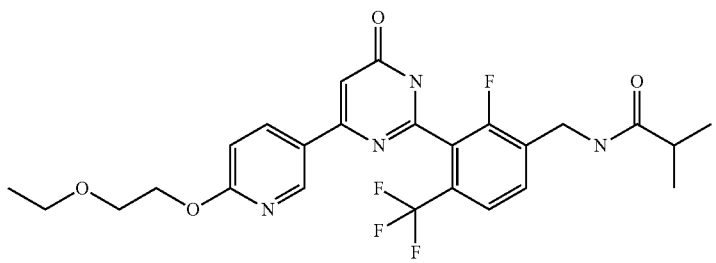 [SMILES: CCOCCOc1ccc(-c2cc(=O)[nH]c(-c3c(C(F)(F)F)ccc(CNC(=O)C(C)C)c3F)n2)cn1] |
| 177 | 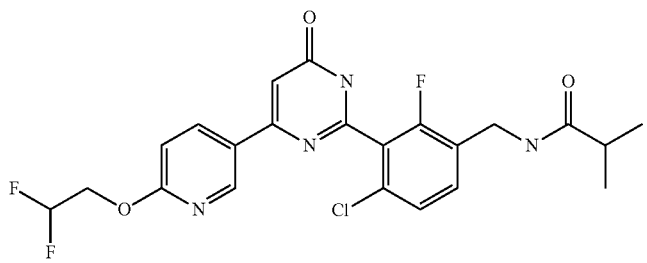 [SMILES: CC(C)C(=O)NCc1ccc(Cl)c(-c2nc(-c3ccc(OCC(F)F)nc3)cc(=O)[nH]2)c1F] |
| 178 | 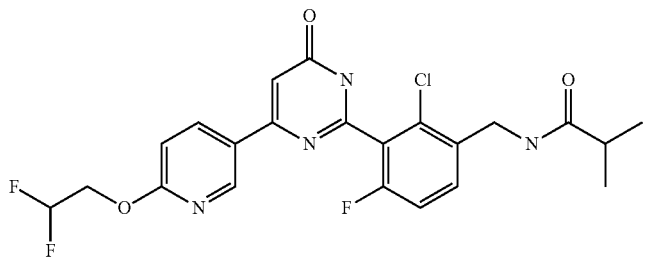 [SMILES: CC(C)C(=O)NCc1ccc(F)c(-c2nc(-c3ccc(OCC(F)F)nc3)cc(=O)[nH]2)c1Cl] |
TABLE 1-11
| Example No. | Structural formula |
|---|---|
| 179 | 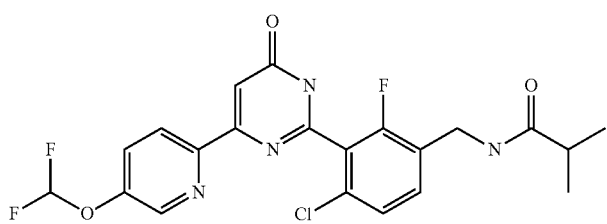 [SMILES: CC(C)C(=O)NCc1ccc(Cl)c(-c2nc(-c3ccc(OC(F)F)cn3)cc(=O)[nH]2)c1F] |

TABLE 1-11-continued

| Example No. | Structural formula |
|---|---|
| 180 | |
| 181 | |
| 182 | |
| 183 | |
| 184 | |
| 185 | |

TABLE 1-11-continued
| Example No. | Structural formula |
|---|---|
| 186 | 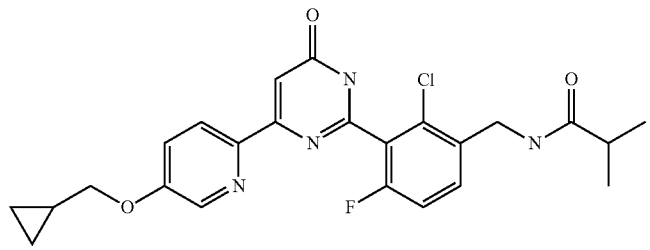 [SMILES: CC(C)C(=O)NCc1ccc(F)c(-c2nc(-c3ccc(OCC4CC4)cn3)cc(=O)[nH]2)c1Cl] |
| 187 | 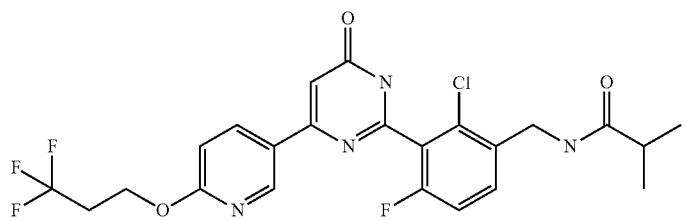 [SMILES: CC(C)C(=O)NCc1ccc(F)c(-c2nc(-c3ccc(OCCC(F)(F)F)nc3)cc(=O)[nH]2)c1Cl] |
| 188 | 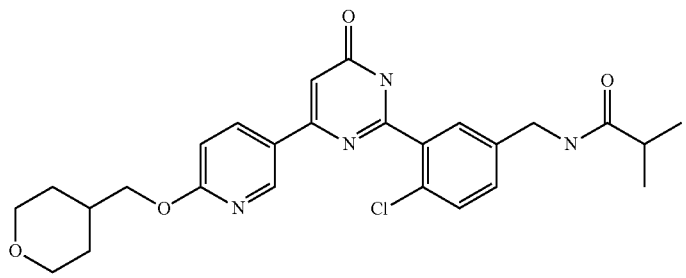 [SMILES: CC(C)C(=O)NCc1ccc(Cl)c(-c2nc(-c3ccc(OCC4CCOCC4)nc3)cc(=O)[nH]2)c1] |
| 189 | 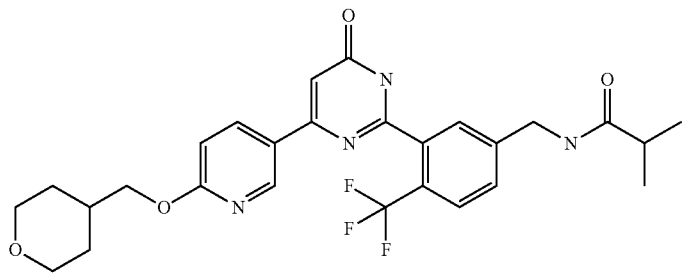 [SMILES: CC(C)C(=O)NCc1ccc(C(F)(F)F)c(-c2nc(-c3ccc(OCC4CCOCC4)nc3)cc(=O)[nH]2)c1] |
| 190 | 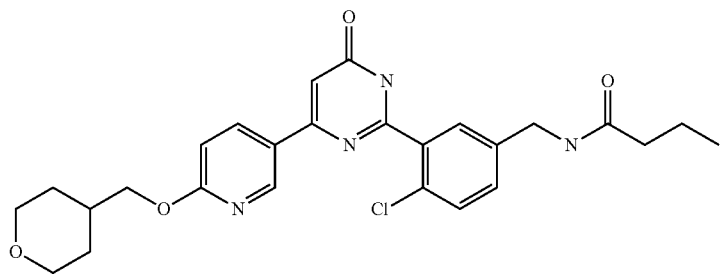 [SMILES: CCCC(=O)NCc1ccc(Cl)c(-c2nc(-c3ccc(OCC4CCOCC4)nc3)cc(=O)[nH]2)c1] |

TABLE 1-11-continued
| Example No. | Structural formula |
|---|---|
| 191 | 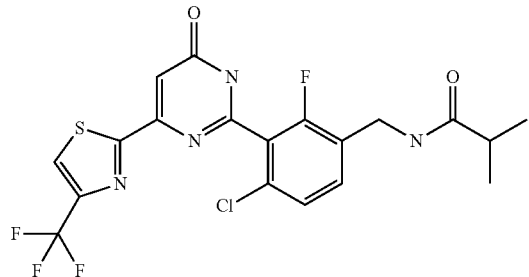 [SMILES: CC(C)C(=O)NCc1ccc(Cl)c(-c2nc(-c3nc(C(F)(F)F)cs3)cc(=O)[nH]2)c1F] |
| 192 | 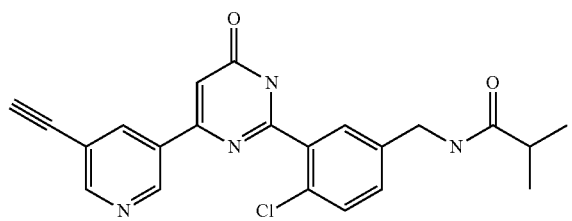 [SMILES: C#Cc1cncc(-c2cc(=O)[nH]c(-c3cc(CNC(=O)C(C)C)ccc3Cl)n2)c1] |
| 193 | 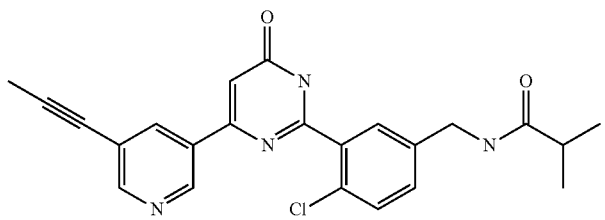 [SMILES: CC#Cc1cncc(-c2cc(=O)[nH]c(-c3cc(CNC(=O)C(C)C)ccc3Cl)n2)c1] |
| 194 | 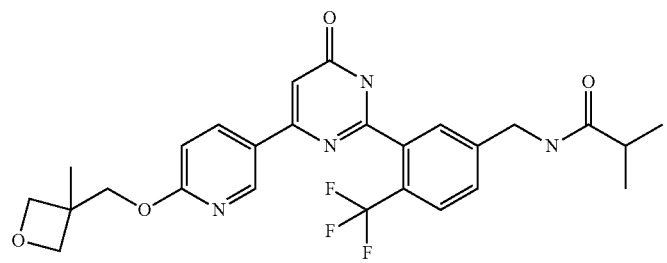 [SMILES: CC(C)C(=O)NCc1ccc(C(F)(F)F)c(-c2nc(-c3ccc(OCC4(C)COC4)nc3)cc(=O)[nH]2)c1] |
| 195 | 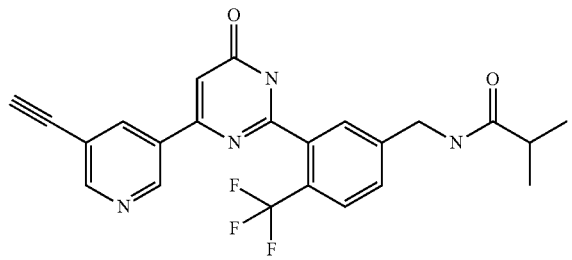 [SMILES: C#Cc1cncc(-c2cc(=O)[nH]c(-c3cc(CNC(=O)C(C)C)ccc3C(F)(F)F)n2)c1] |

TABLE 1-11-continued
| Example No. | Structural formula |
|---|---|
| 196 | 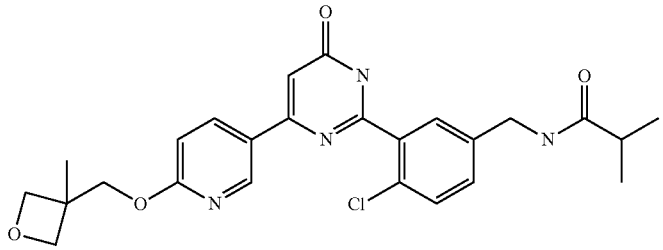 [SMILES: CC(C)C(=O)NCc1ccc(Cl)c(-c2nc(-c3ccc(OCC4(C)COC4)nc3)cc(=O)[nH]2)c1] |
TABLE 1-12
| Example No. | Structural formula |
|---|---|
| 197 | 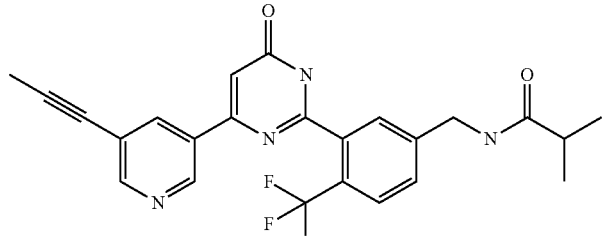 |
| 198 | 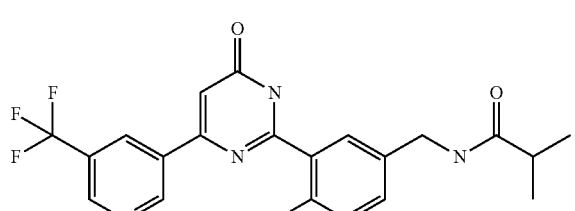 |
| 199 | 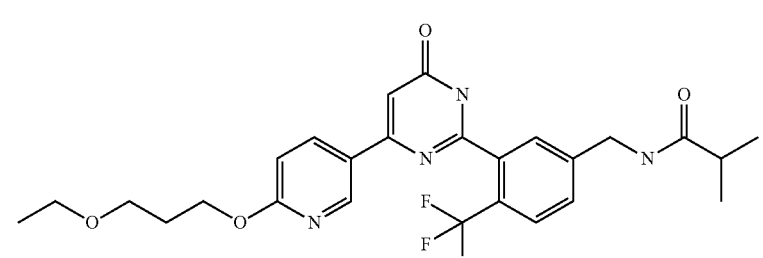 |
| 200 | 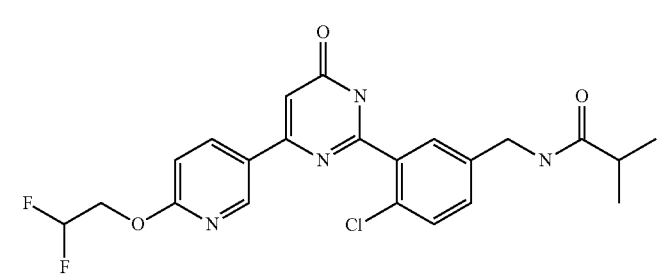 [SMILES: CC(C)C(=O)NCc1ccc(Cl)c(-c2nc(-c3ccc(OCC(F)F)nc3)cc(=O)[nH]2)c1] |

TABLE 1-12-continued

| Example No. | Structural formula |
|---|---|
| 201 | |
| 202 | |
| 203 | |
| 204 | |
| 205 | |

TABLE 1-12-continued
| Example No. | Structural formula |
|---|---|
| 206 | 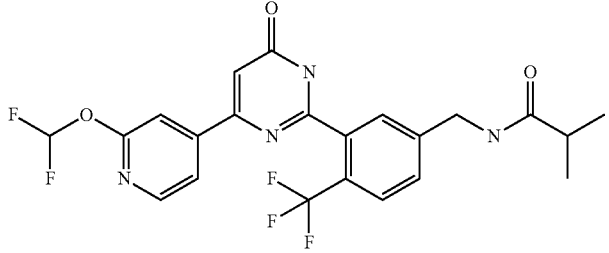 [SMILES: CC(C)C(=O)NCc1ccc(C(F)(F)F)c(-c2nc(-c3ccnc(OC(F)F)c3)cc(=O)[nH]2)c1] |
| 207 | 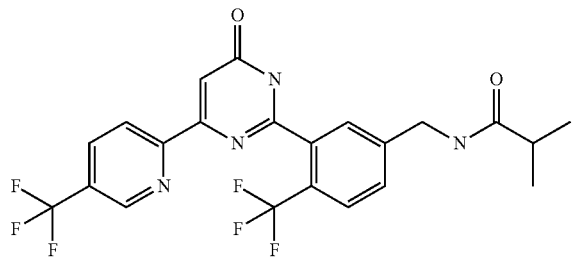 [SMILES: CC(C)C(=O)NCc1ccc(C(F)(F)F)c(-c2nc(-c3ccc(C(F)(F)F)cn3)cc(=O)[nH]2)c1] |
| 208 | 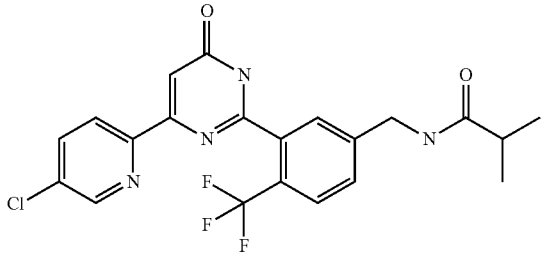 [SMILES: CC(C)C(=O)NCc1ccc(C(F)(F)F)c(-c2nc(-c3ccc(Cl)cn3)cc(=O)[nH]2)c1] |
| 209 | 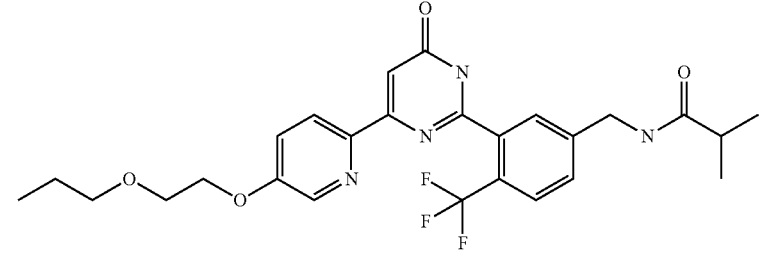 [SMILES: CCCOCCOc1ccc(-c2cc(=O)[nH]c(-c3cc(CNC(=O)C(C)C)ccc3C(F)(F)F)n2)nc1] |
| 210 | 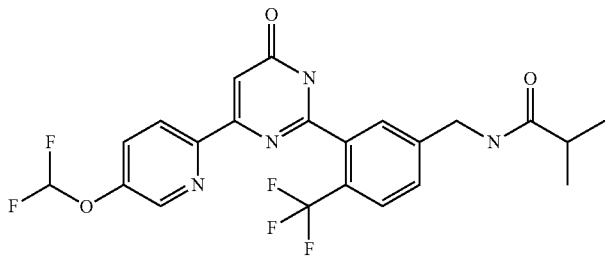 [SMILES: CC(C)C(=O)NCc1ccc(C(F)(F)F)c(-c2nc(-c3ccc(OC(F)F)cn3)cc(=O)[nH]2)c1] |

TABLE 1-12-continued

| Example No. | Structural formula |
|---|---|
| 211 | |
| 212 | |
| 213 | |
| 214 | |

TABLE 1-13

| Example No. | Structural formula |
|---|---|
| 215 | |

TABLE 1-13-continued
| Example No. | Structural formula |
|---|---|
| 216 | 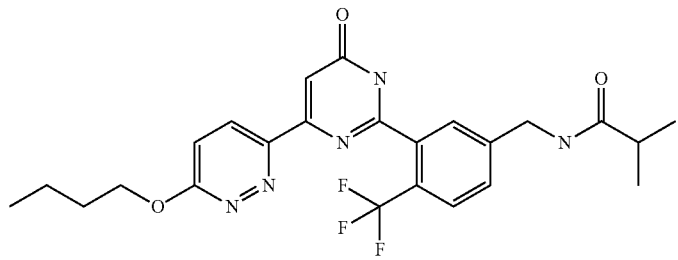 [SMILES: CCCCOc1ccc(-c2cc(=O)[nH]c(-c3cc(CNC(=O)C(C)C)ccc3C(F)(F)F)n2)nn1] |
| 217 | 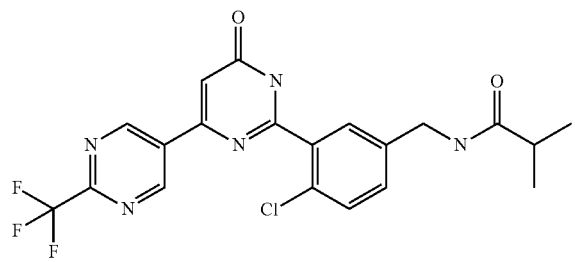 [SMILES: CC(C)C(=O)NCc1ccc(Cl)c(-c2nc(-c3cnc(C(F)(F)F)nc3)cc(=O)[nH]2)c1] |
| 218 | 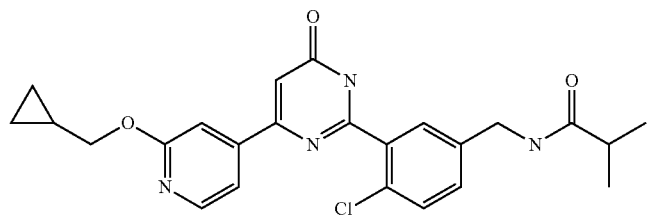 [SMILES: CC(C)C(=O)NCc1ccc(Cl)c(-c2nc(-c3ccnc(OCC4CC4)c3)cc(=O)[nH]2)c1] |
| 219 | 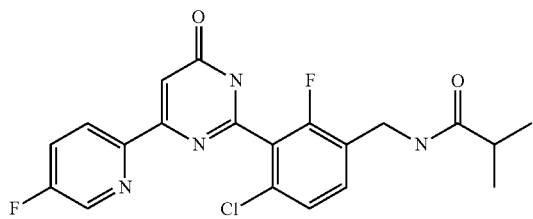 [SMILES: CC(C)C(=O)NCc1ccc(Cl)c(-c2nc(-c3ccc(F)cn3)cc(=O)[nH]2)c1F] |
| 220 | 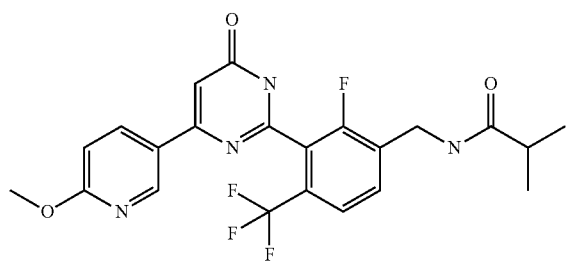 [SMILES: COc1ccc(-c2cc(=O)[nH]c(-c3c(C(F)(F)F)ccc(CNC(=O)C(C)C)c3F)n2)cn1] |

219
220
TABLE 1-13-continued
| Example No. | Structural formula |
|---|---|
| 221 | 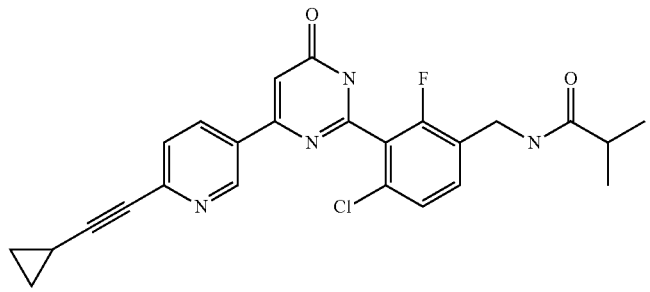 [SMILES: CC(C)C(=O)NCc1ccc(Cl)c(-c2nc(-c3ccc(C#CC4CC4)nc3)cc(=O)[nH]2)c1F] |
| 222 | 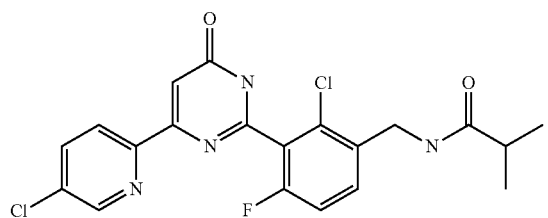 |
| 223 | 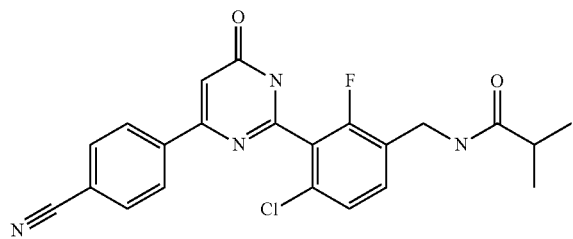 [SMILES: CC(C)C(=O)NCc1ccc(Cl)c(-c2nc(-c3ccc(C#N)cc3)cc(=O)[nH]2)c1F] |
| 224 | 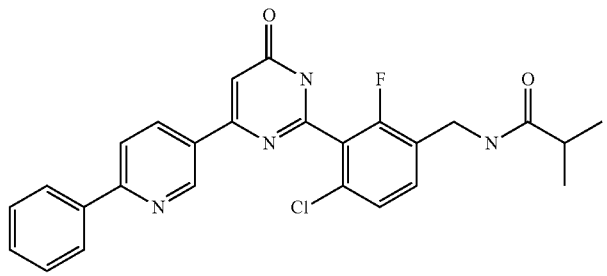 [SMILES: CC(C)C(=O)NCc1ccc(Cl)c(-c2nc(-c3ccc(-c4ccccc4)nc3)cc(=O)[nH]2)c1F] |
| 225 | 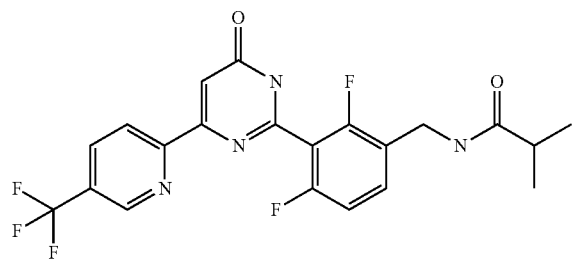 |

TABLE 1-13-continued
| Example No. | Structural formula |
|---|---|
| 226 | 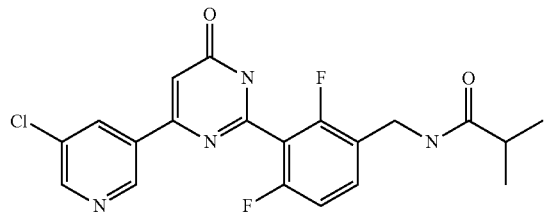 [SMILES: CC(C)C(=O)NCc1ccc(F)c(-c2nc(-c3cncc(Cl)c3)cc(=O)[nH]2)c1F] |
| 227 | 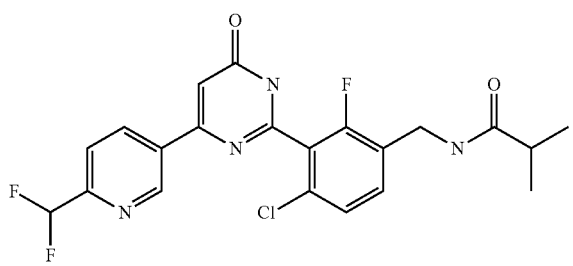 [SMILES: CC(C)C(=O)NCc1ccc(Cl)c(-c2nc(-c3ccc(C(F)F)nc3)cc(=O)[nH]2)c1F] |
| 228 | 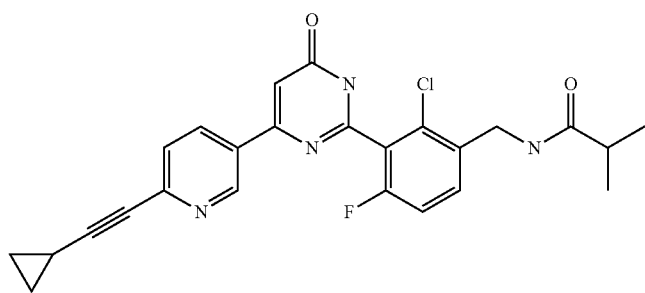 |
| 229 | 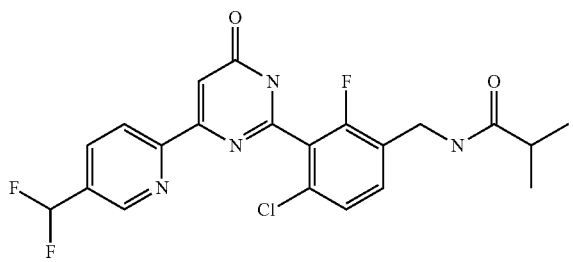 [SMILES: CC(C)C(=O)NCc1ccc(Cl)c(-c2nc(-c3ccc(C(F)F)cn3)cc(=O)[nH]2)c1F] |
| 230 | 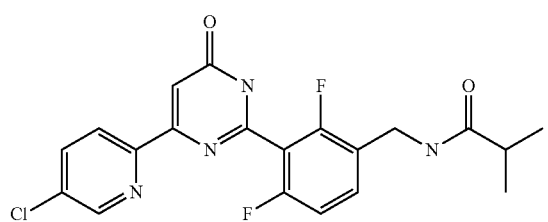 |

TABLE 1-13-continued
| Example No. | Structural formula |
|---|---|
| 231 | 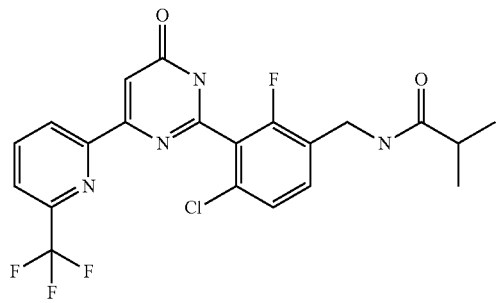 [SMILES: CC(C)C(=O)NCc1ccc(Cl)c(-c2nc(-c3cccc(C(F)(F)F)n3)cc(=O)[nH]2)c1F] |
| 232 | 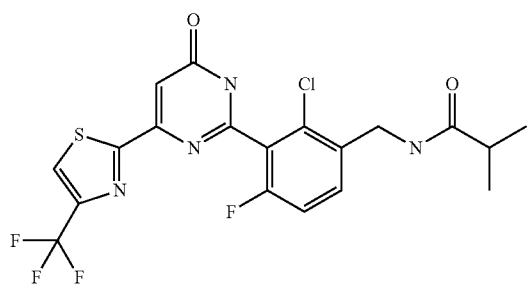 [SMILES: CC(C)C(=O)NCc1ccc(F)c(-c2nc(-c3nc(C(F)(F)F)cs3)cc(=O)[nH]2)c1Cl] |
TABLE 1-14
| Example No. | Structural formula |
|---|---|
| 233 | 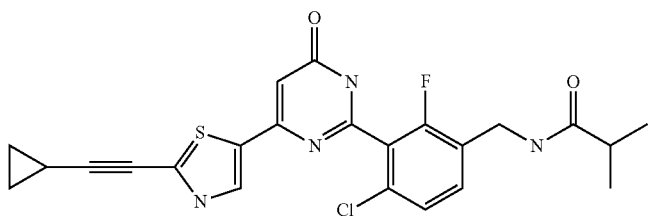 |
| 234 | 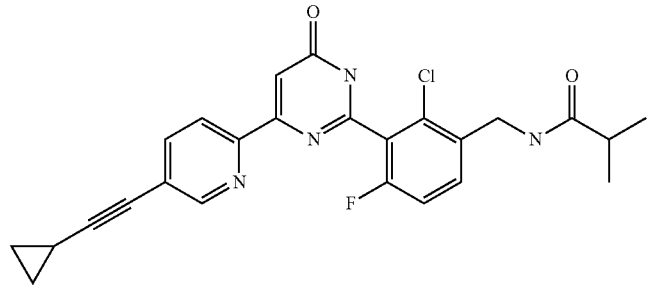 [SMILES: CC(C)C(=O)NCc1ccc(F)c(-c2nc(-c3ccc(C#CC4CC4)cn3)cc(=O)[nH]2)c1Cl] |

TABLE 1-14-continued
| Example No. | Structural formula |
| --- | --- |
| 235 | 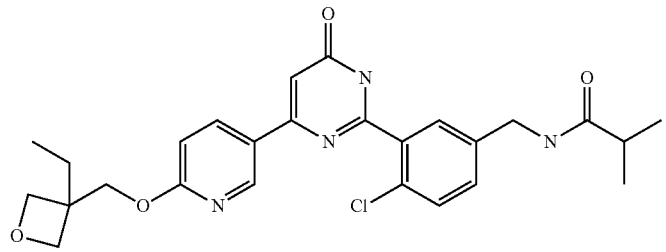 [SMILES: CCC1(COc2ccc(-c3cc(=O)[nH]c(-c4cc(CNC(=O)C(C)C)ccc4Cl)n3)cn2)COC1] |
| 236 | 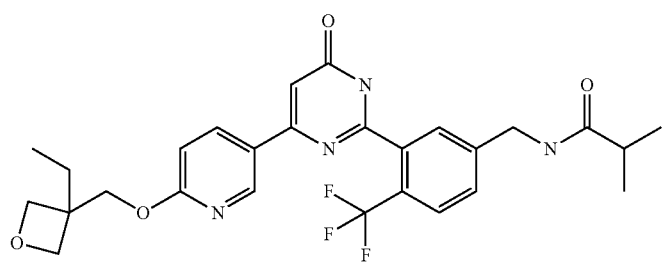 [SMILES: CCC1(COc2ccc(-c3cc(=O)[nH]c(-c4cc(CNC(=O)C(C)C)ccc4C(F)(F)F)n3)cn2)COC1] |
| 237 | 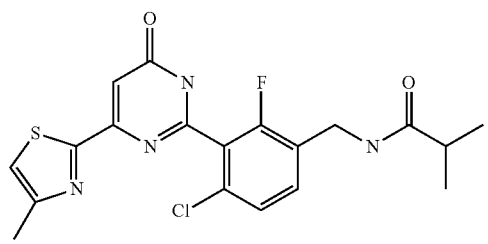 [SMILES: Cc1csc(-c2cc(=O)[nH]c(-c3c(Cl)ccc(CNC(=O)C(C)C)c3F)n2)n1] |
| 238 | 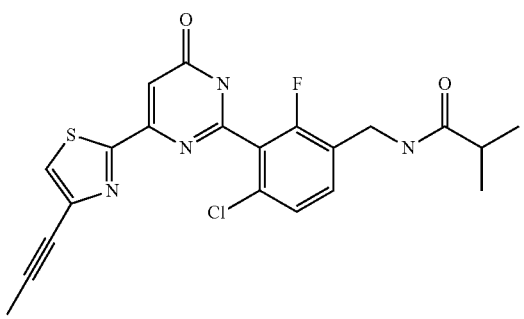 [SMILES: CC#Cc1csc(-c2cc(=O)[nH]c(-c3c(Cl)ccc(CNC(=O)C(C)C)c3F)n2)n1] |
| 239 | 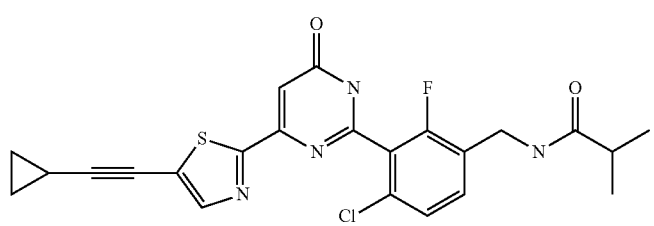 [SMILES: CC(C)C(=O)NCc1ccc(Cl)c(-c2nc(-c3ncc(C#CC4CC4)s3)cc(=O)[nH]2)c1F] |

TABLE 1-14-continued
| Example No. | Structural formula |
|---|---|
| 240 | 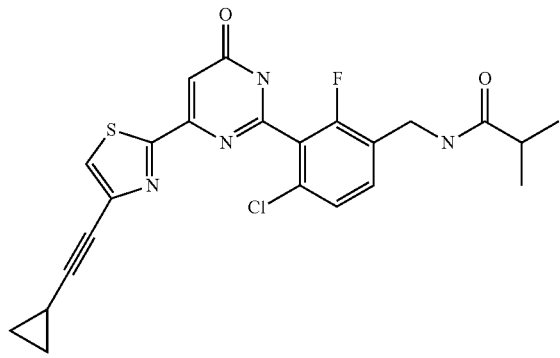 [SMILES: CC(C)C(=O)NCc1ccc(Cl)c(-c2nc(-c3nc(C#CC4CC4)cs3)cc(=O)[nH]2)c1F] |
| 241 | 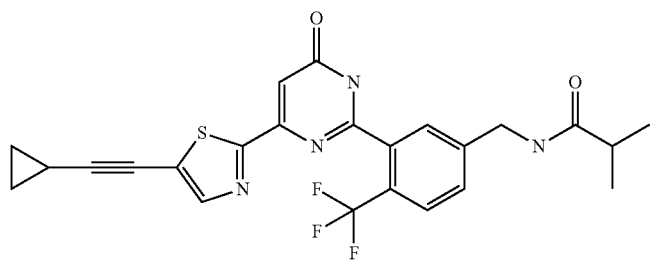 [SMILES: CC(C)C(=O)NCc1ccc(C(F)(F)F)c(-c2nc(-c3ncc(C#CC4CC4)s3)cc(=O)[nH]2)c1] |
| 242 | 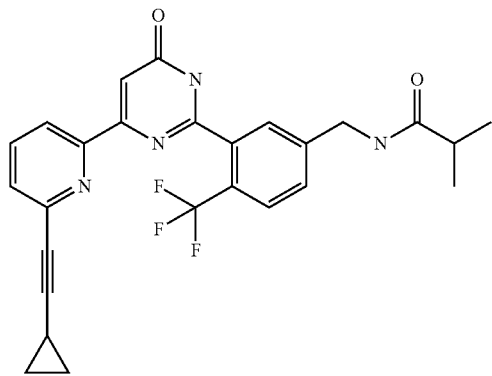 [SMILES: CC(C)C(=O)NCc1ccc(C(F)(F)F)c(-c2nc(-c3cccc(C#CC4CC4)n3)cc(=O)[nH]2)c1] |
| 243 | 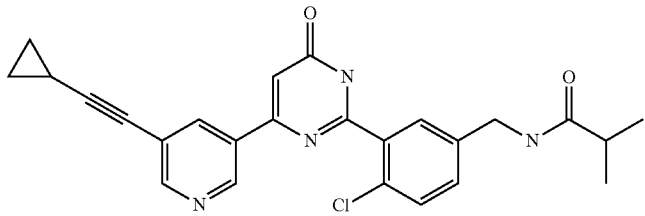 [SMILES: CC(C)C(=O)NCc1ccc(Cl)c(-c2nc(-c3cncc(C#CC4CC4)c3)cc(=O)[nH]2)c1] |
| 244 | 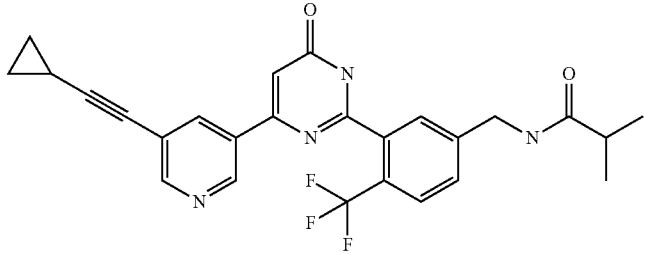 [SMILES: CC(C)C(=O)NCc1ccc(C(F)(F)F)c(-c2nc(-c3cncc(C#CC4CC4)c3)cc(=O)[nH]2)c1] |

TABLE 1-14-continued

| Example No. | Structural formula |
|---|---|
| 245 | |
| 246 | |
| 247 | |
| 248 | |
| 249 | |

TABLE 1-14-continued

| Example No. | Structural formula |
|---|---|
| 250 | (structure) |

TABLE 1-15

| Example No. | Structural formula |
|---|---|
| 251 | (structure) |
| 252 | (structure) |
| 253 | (structure) |
| 254 | (structure) |

TABLE 1-15-continued
| Example No. | Structural formula |
|---|---|
| 255 | 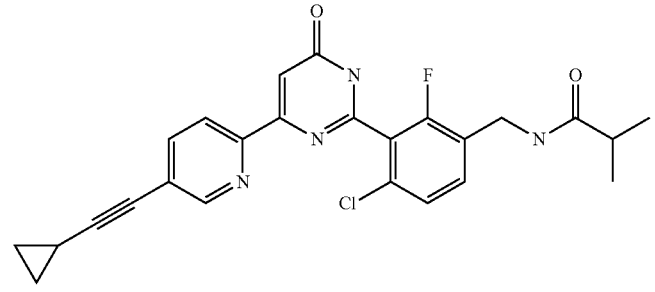 [SMILES: CC(C)C(=O)NCc1ccc(Cl)c(-c2nc(-c3ccc(C#CC4CC4)cn3)cc(=O)[nH]2)c1F] |
| 256 | 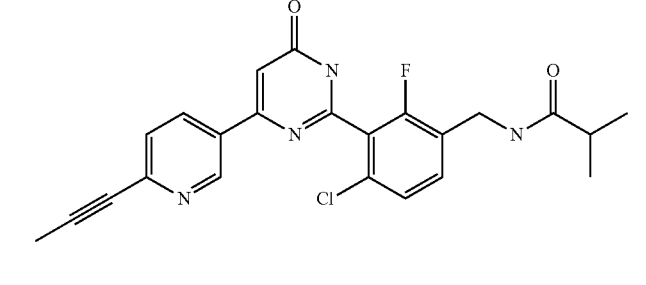 [SMILES: CC#Cc1ccc(-c2cc(=O)[nH]c(-c3c(Cl)ccc(CNC(=O)C(C)C)c3F)n2)cn1] |
| 257 | 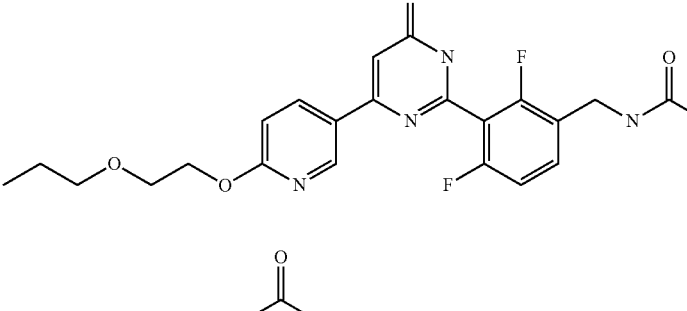 |
| 258 | 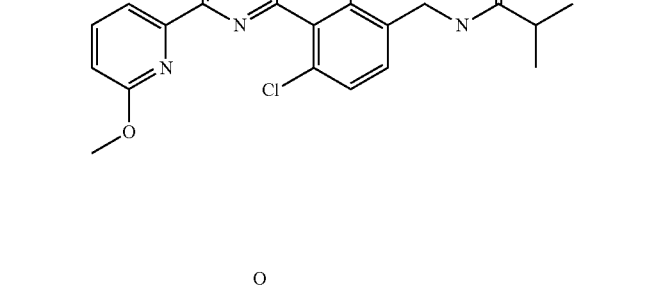 |
| 259 | 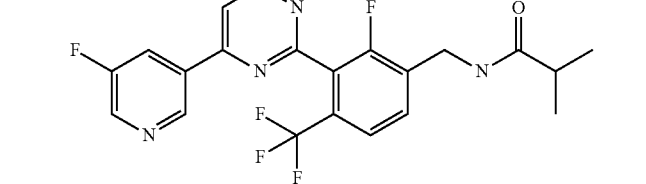 |

TABLE 1-15-continued
| Example No. | Structural formula |
|---|---|
| 260 | 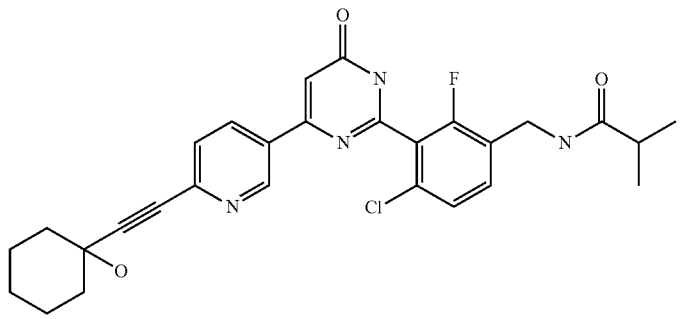 [SMILES: CC(C)C(=O)NCc1ccc(Cl)c(-c2nc(-c3ccc(C#CC4(O)CCCCC4)nc3)cc(=O)[nH]2)c1F] |
| 261 | 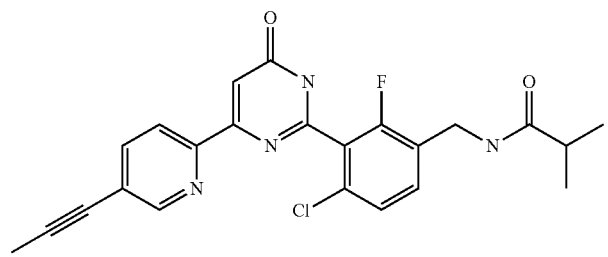 [SMILES: CC#Cc1ccc(-c2cc(=O)[nH]c(-c3c(Cl)ccc(CNC(=O)C(C)C)c3F)n2)nc1] |
| 262 | 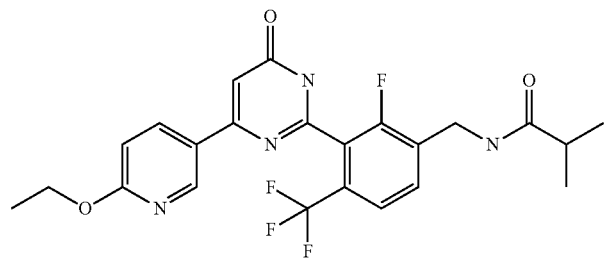 [SMILES: CCOc1ccc(-c2cc(=O)[nH]c(-c3c(C(F)(F)F)ccc(CNC(=O)C(C)C)c3F)n2)cn1] |
| 263 | 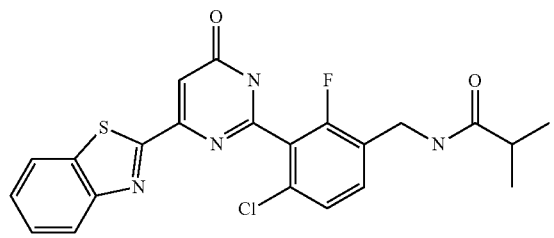 [SMILES: CC(C)C(=O)NCc1ccc(Cl)c(-c2nc(-c3nc4ccccc4s3)cc(=O)[nH]2)c1F] |
| 264 | 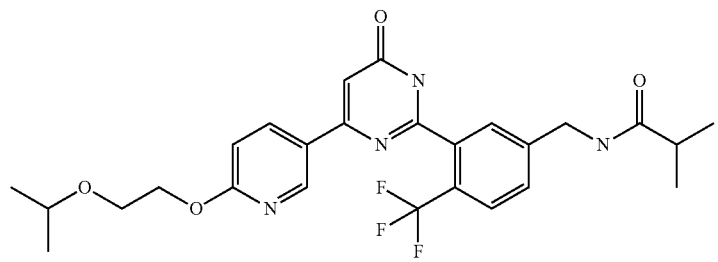 [SMILES: CC(C)OCCOc1ccc(-c2cc(=O)[nH]c(-c3cc(CNC(=O)C(C)C)ccc3C(F)(F)F)n2)cn1] |

TABLE 1-15-continued
| Example No. | Structural formula |
|---|---|
| 265 | |
| 266 | |
| 267 | |
| 268 | |
TABLE 1-16
| Example No. | Structural formula |
|---|---|
| 269 | |
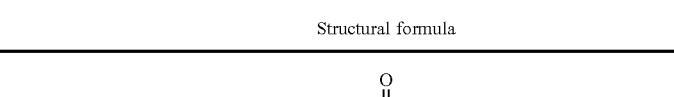

TABLE 1-16-continued
| Example No. | Structural formula |
| --- | --- |
| 270 | 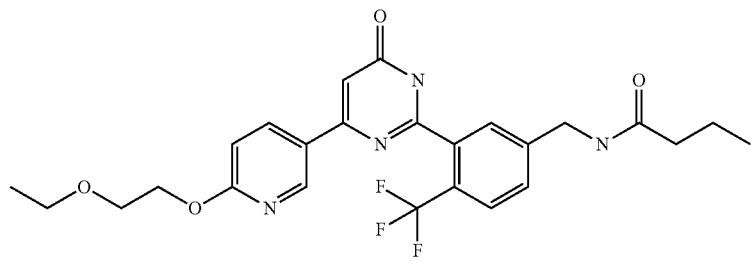 [SMILES: CCCC(=O)NCc1ccc(C(F)(F)F)c(-c2nc(-c3ccc(OCCOCC)nc3)cc(=O)[nH]2)c1] |
| 271 | 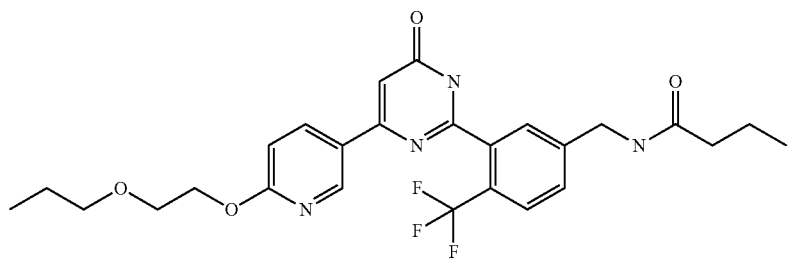 [SMILES: CCCOCCOc1ccc(-c2cc(=O)[nH]c(-c3cc(CNC(=O)CCC)ccc3C(F)(F)F)n2)cn1] |
| 272 | 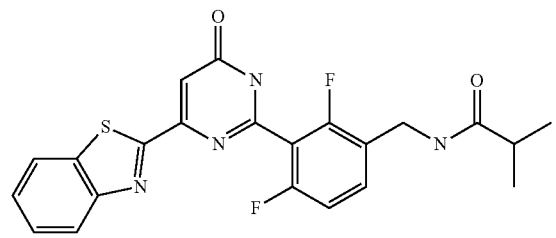 |
| 273 | 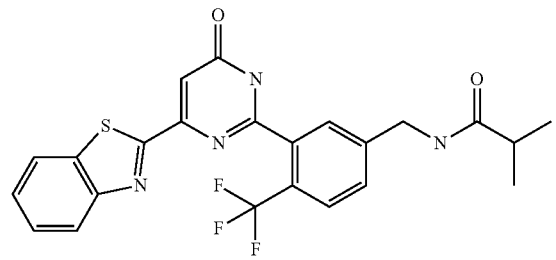 [SMILES: CC(C)C(=O)NCc1ccc(C(F)(F)F)c(-c2nc(-c3nc4ccccc4s3)cc(=O)[nH]2)c1] |
| 274 | 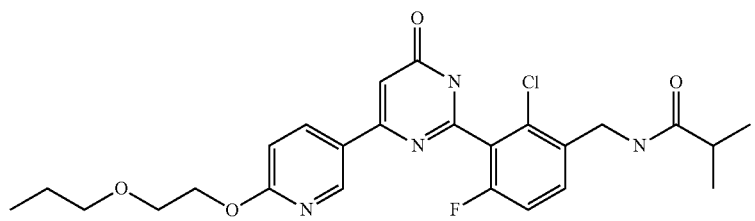 [SMILES: CCCOCCOc1ccc(-c2cc(=O)[nH]c(-c3c(F)ccc(CNC(=O)C(C)C)c3Cl)n2)cn1] |

TABLE 1-16-continued
| Example No. | Structural formula |
|---|---|
| 275 | 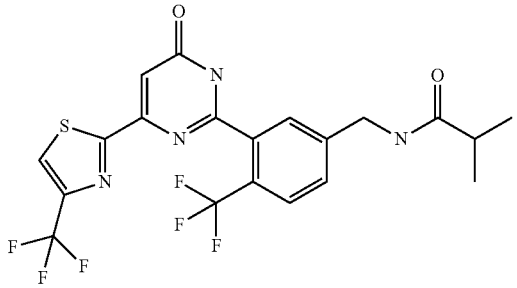 [SMILES: CC(C)C(=O)NCc1ccc(C(F)(F)F)c(-c2nc(-c3nc(C(F)(F)F)cs3)cc(=O)[nH]2)c1] |
| 276 | 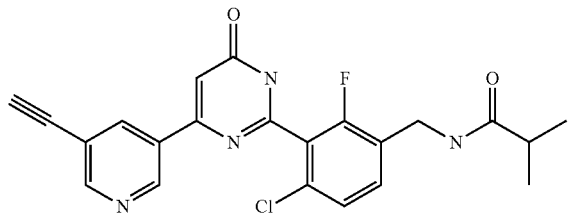 [SMILES: C#Cc1cncc(-c2cc(=O)[nH]c(-c3c(Cl)ccc(CNC(=O)C(C)C)c3F)n2)c1] |
| 277 | 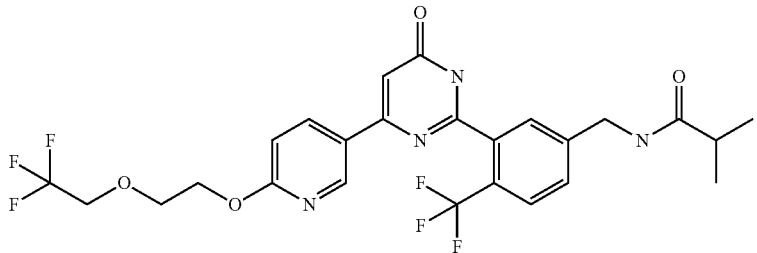 [SMILES: CC(C)C(=O)NCc1ccc(C(F)(F)F)c(-c2nc(-c3ccc(OCCOCC(F)(F)F)nc3)cc(=O)[nH]2)c1] |
| 278 | 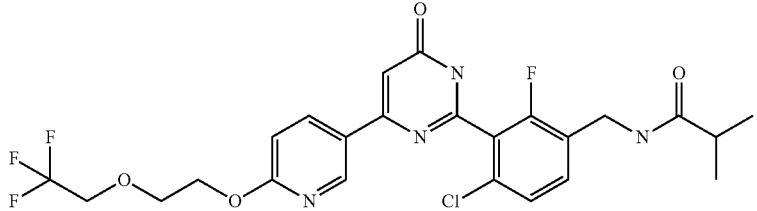 |
| 279 | 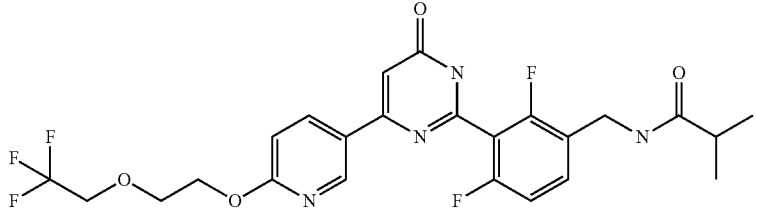 |
| 280 | 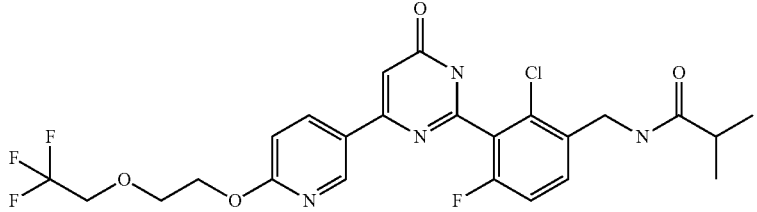 [SMILES: CC(C)C(=O)NCc1ccc(Cl)c(-c2nc(-c3ccc(OCCOCC(F)(F)F)nc3)cc(=O)[nH]2)c1F] |

TABLE 1-16-continued
| Example No. | Structural formula |
|---|---|
| 281 | 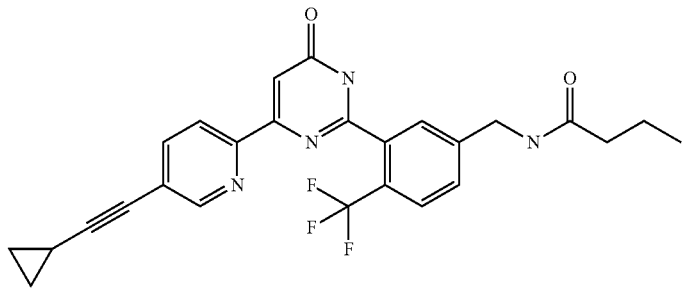 [SMILES: CCCC(=O)NCc1ccc(C(F)(F)F)c(-c2nc(-c3ccc(C#CC4CC4)cn3)cc(=O)[nH]2)c1] |
| 282 | 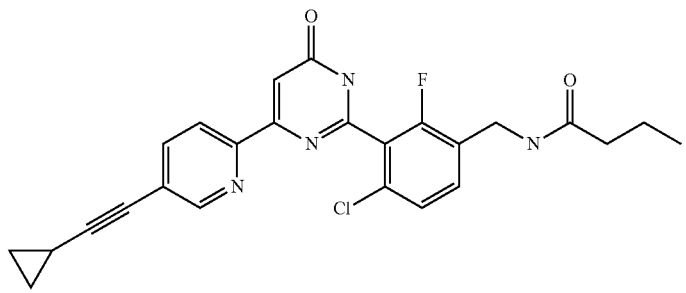 [SMILES: CCCC(=O)NCc1ccc(Cl)c(-c2nc(-c3ccc(C#CC4CC4)cn3)cc(=O)[nH]2)c1F] |
| 283 | 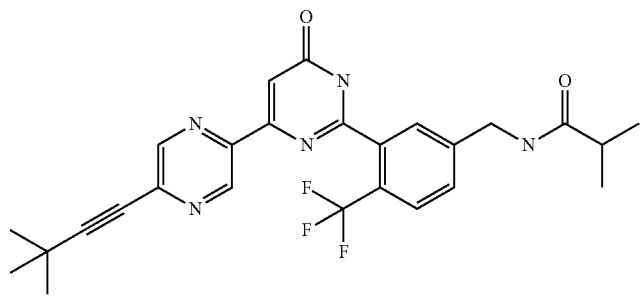 [SMILES: CC(C)C(=O)NCc1ccc(C(F)(F)F)c(-c2nc(-c3cnc(C#CC(C)(C)C)cn3)cc(=O)[nH]2)c1] |
| 284 | 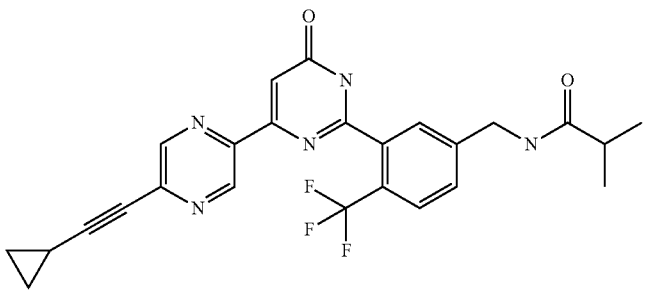 [SMILES: CC(C)C(=O)NCc1ccc(C(F)(F)F)c(-c2nc(-c3cnc(C#CC4CC4)cn3)cc(=O)[nH]2)c1] |
| 285 | 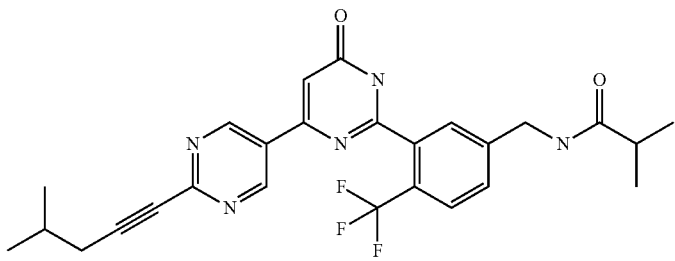 [SMILES: CC(C)CC#Cc1ncc(-c2cc(=O)[nH]c(-c3cc(CNC(=O)C(C)C)ccc3C(F)(F)F)n2)cn1] |

TABLE 1-16-continued
| Example No. | Structural formula |
|---|---|
| 286 | 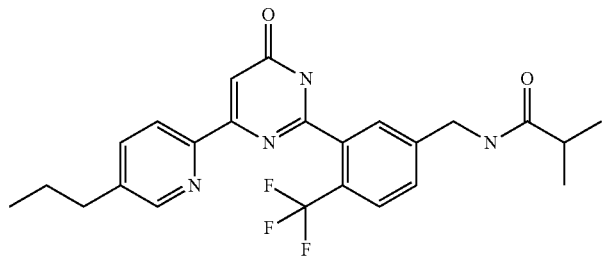 [SMILES: CCCc1ccc(-c2cc(=O)[nH]c(-c3cc(CNC(=O)C(C)C)ccc3C(F)(F)F)n2)nc1] |
TABLE 1-17
| Example No. | Structural formula |
|---|---|
| 287 | 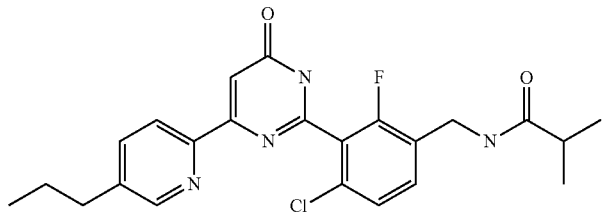 [SMILES: CCCc1ccc(-c2cc(=O)[nH]c(-c3c(Cl)ccc(CNC(=O)C(C)C)c3F)n2)nc1] |
| 288 | 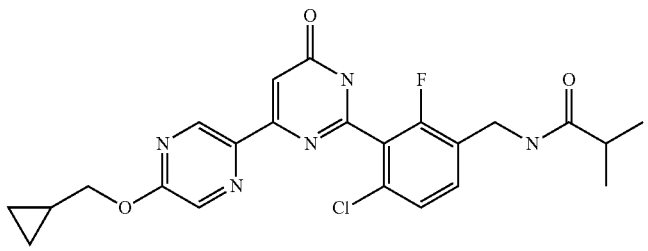 [SMILES: CC(C)C(=O)NCc1ccc(Cl)c(-c2nc(-c3cnc(OCC4CC4)cn3)cc(=O)[nH]2)c1F] |
| 289 | 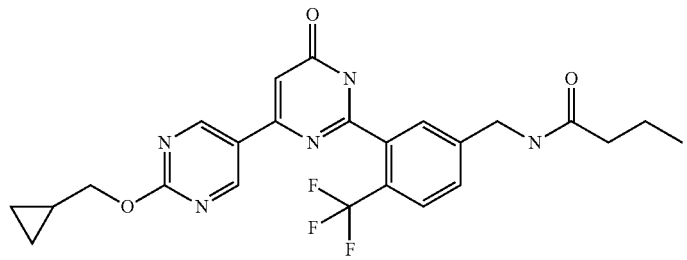 [SMILES: CCCC(=O)NCc1ccc(C(F)(F)F)c(-c2nc(-c3cnc(OCC4CC4)nc3)cc(=O)[nH]2)c1] |
| 290 | 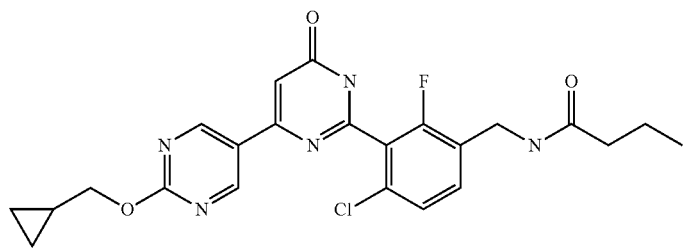 [SMILES: CCCC(=O)NCc1ccc(Cl)c(-c2nc(-c3cnc(OCC4CC4)nc3)cc(=O)[nH]2)c1F] |

TABLE 1-17-continued
| Example No. | Structural formula |
|---|---|
| 291 | 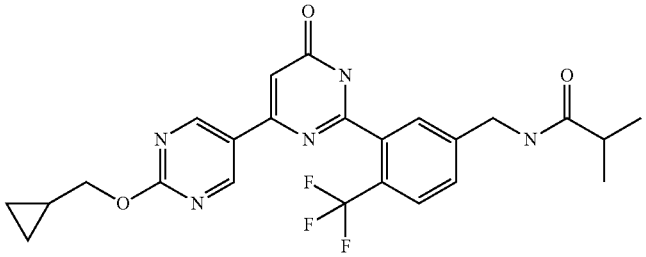 |
| 292 | 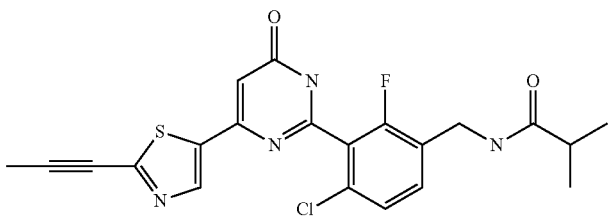 [SMILES: CC#Cc1ncc(-c2cc(=O)[nH]c(-c3c(Cl)ccc(CNC(=O)C(C)C)c3F)n2)s1] |
| 293 | 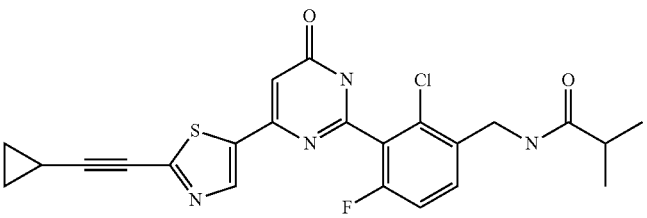 [SMILES: CC(C)C(=O)NCc1ccc(F)c(-c2nc(-c3cnc(C#CC4CC4)s3)cc(=O)[nH]2)c1Cl] |
| 294 | 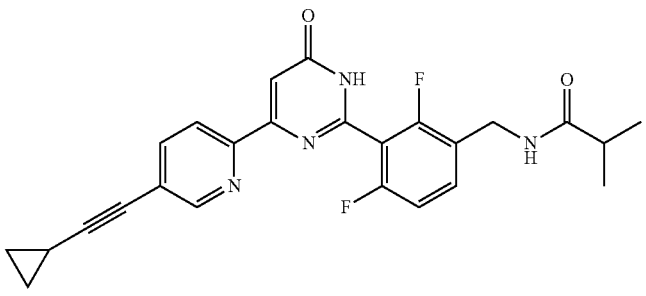 [SMILES: CC(C)C(=O)NCc1ccc(F)c(-c2nc(-c3ccc(C#CC4CC4)cn3)cc(=O)[nH]2)c1F] |
| 295 | 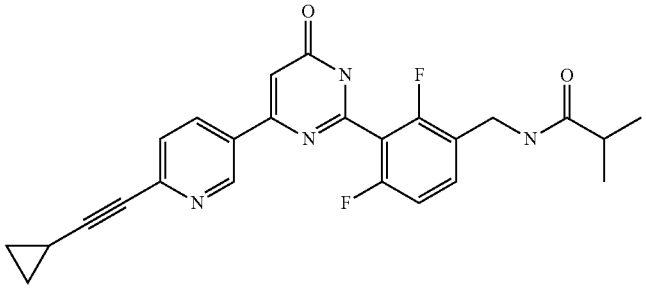 |

TABLE 1-17-continued
| Example No. | Structural formula |
| --- | --- |
| 296 | 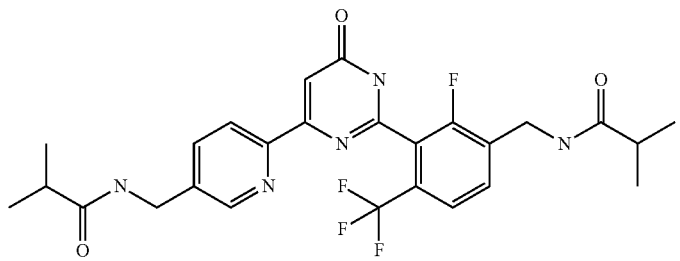 [SMILES: CC(C)C(=O)NCc1ccc(-c2cc(=O)[nH]c(-c3c(C(F)(F)F)ccc(CNC(=O)C(C)C)c3F)n2)nc1] |
| 297 | 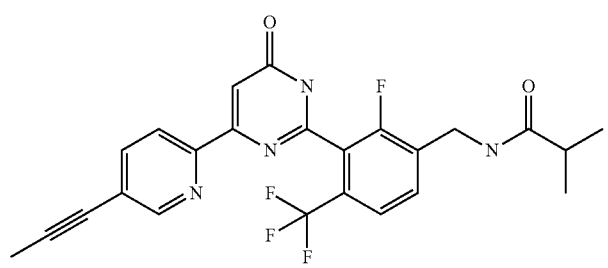 [SMILES: CC#Cc1ccc(-c2cc(=O)[nH]c(-c3c(C(F)(F)F)ccc(CNC(=O)C(C)C)c3F)n2)nc1] |
| 298 | 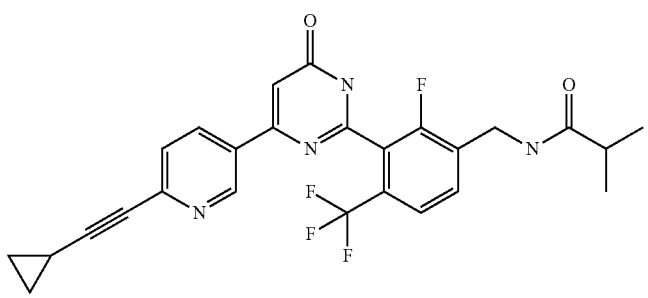 [SMILES: CC(C)C(=O)NCc1ccc(C(F)(F)F)c(-c2nc(-c3ccc(C#CC4CC4)nc3)cc(=O)[nH]2)c1F] |
| 299 | 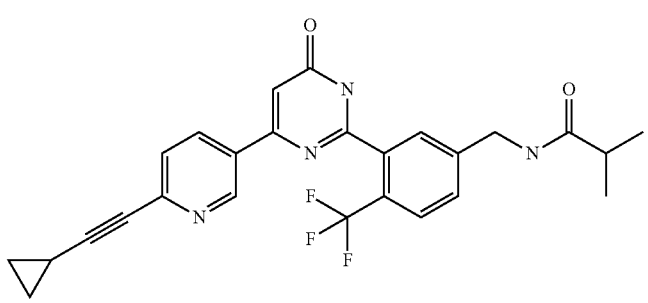 [SMILES: CC(C)C(=O)NCc1ccc(C(F)(F)F)c(-c2nc(-c3ccc(C#CC4CC4)nc3)cc(=O)[nH]2)c1] |
| 300 | 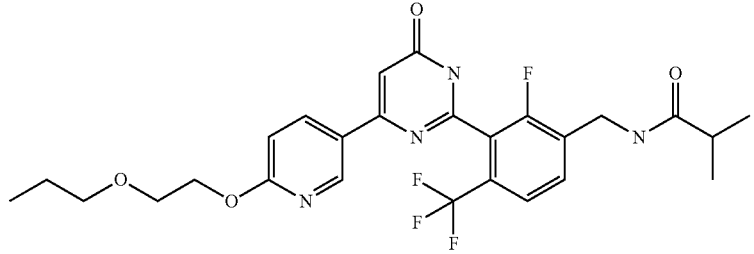 [SMILES: CCCOCCOc1ccc(-c2cc(=O)[nH]c(-c3c(C(F)(F)F)ccc(CNC(=O)C(C)C)c3F)n2)cn1] |

TABLE 1-17-continued

| Example No. | Structural formula |
|---|---|
| 301 | |
| 302 | |
| 303 | |
| 304 | |

TABLE 1-18

| Example No. | Structural formula |
|---|---|
| 305 | |

TABLE 2-1

| Example No. | human mPGES1 IC$_{50}$ (nM) |
|---|---|
| 1 | 0.02 |
| 2 | 0.01 |
| 3 | 0.48 |
| 4 | 12 |
| 5 | 2.8 |
| 6 | 1.6 |
| 7 | 0.48 |
| 8 | 28 |
| 9 | 13 |
| 10 | 62 |
| 11 | 7.9 |
| 12 | 0.18 |
| 13 | 7.4 |
| 14 | 7.2 |
| 16 | 2.3 |
| 17 | 0.86 |
| 18 | 3.7 |
| 19 | 8.5 |
| 21 | 0.88 |
| 22 | 0.11 |
| 23 | 8.1 |
| 24 | 0.31 |
| 25 | 1.4 |
| 26 | 9 |
| 27 | 1.1 |
| 28 | 57 |
| 29 | 160 |
| 30 | 90 |
| 31 | 11 |
| 33 | 7.6 |

TABLE 2-2

| Example No. | human mPGES1 IC$_{50}$ (nM) |
|---|---|
| 20 | 0.06 |
| 35 | 25 |
| 36 | 24 |
| 37 | 1 |
| 38 | 59 |
| 39 | 5.2 |
| 40 | 5.4 |
| 41 | 2.5 |
| 42 | 1.5 |
| 43 | 0.13 |
| 44 | 19 |
| 45 | 0.76 |
| 46 | 8.8 |
| 47 | 7.4 |
| 48 | 2.3 |
| 49 | 2.7 |
| 50 | 7.3 |
| 51 | 5.4 |
| 52 | 7.1 |
| 53 | 2.7 |
| 54 | 3.2 |
| 55 | 1.3 |
| 56 | 19 |
| 57 | 11 |
| 58 | 33 |
| 59 | 1.4 |
| 60 | 2.7 |
| 61 | 41 |
| 62 | 27 |
| 63 | 1.0 |
| 64 | 1.6 |
| 65 | 1.1 |
| 66 | 1.8 |
| 67 | 47 |
| 68 | 25 |
| 69 | 1.1 |
| 70 | 3.5 |
| 71 | 1.6 |

TABLE 2-2-continued

| Example No. | human mPGES1 IC$_{50}$ (nM) |
|---|---|
| 72 | 1.3 |
| 74 | 0.11 |
| 75 | 1.4 |
| 76 | 17 |
| 77 | 16 |
| 78 | <1.0 |
| 79 | 19 |
| 80 | 3.9 |
| 81 | 41 |
| 82 | 7.3 |
| 83 | 25 |
| 84 | 18 |
| 85 | 13 |
| 86 | 3.3 |
| 87 | 29 |
| 88 | 10 |
| 89 | 2.3 |
| 90 | 4.1 |
| 91 | 6.4 |
| 92 | 26 |
| 93 | 16 |
| 94 | 9.1 |
| 95 | 7.8 |
| 96 | 1.5 |
| 97 | 38 |
| 98 | 13 |
| 99 | 25 |
| 100 | 28 |
| 101 | 12 |
| 102 | 4.1 |
| 103 | 37 |

TABLE 2-3

| Example No. | human mPGES1 IC$_{50}$ (nM) |
|---|---|
| 104 | 9.4 |
| 105 | <1 |
| 106 | 3.7 |
| 107 | 76 |
| 108 | 2.8 |
| 109 | 6.2 |
| 110 | 3.4 |
| 111 | 1.4 |
| 112 | 55 |
| 113 | 23 |
| 114 | 13 |
| 115 | 23 |
| 116 | 4.5 |
| 117 | 15 |
| 118 | 10 |
| 119 | 6.4 |
| 120 | 15 |
| 122 | 7.5 |
| 123 | 5.2 |
| 124 | 15 |
| 125 | 100 |
| 126 | 4.5 |
| 127 | <1 |
| 128 | 2.1 |
| 129 | 31 |
| 130 | 47 |
| 131 | 7.0 |
| 132 | 18 |
| 133 | 87 |
| 134 | 89 |
| 135 | 8.8 |
| 136 | 66 |
| 137 | 92 |
| 138 | 15 |
| 139 | 23 |
| 140 | 3.3 |
| 141 | 4.1 |

TABLE 2-3-continued

| Example No. | human mPGES1 IC$_{50}$ (nM) |
|---|---|
| 142 | 110 |
| 143 | 8.7 |
| 144 | 7.3 |
| 145 | 3.9 |
| 147 | 18 |
| 148 | 7.3 |
| 149 | 7.3 |
| 150 | 12 |
| 151 | 130 |
| 152 | 27 |
| 153 | 30 |
| 154 | 6.4 |
| 155 | 52 |
| 156 | 75 |
| 157 | 0.78 |
| 158 | 4.7 |
| 159 | 2.1 |
| 180 | 2.5 |
| 161 | 23 |
| 162 | <1 |
| 163 | 6.9 |
| 164 | 2.4 |
| 165 | 18 |
| 166 | 6.4 |
| 167 | 3.1 |
| 168 | 7.7 |
| 169 | 1.1 |
| 170 | 1.7 |
| 171 | 2.0 |
| 172 | 6.1 |
| 173 | 38 |
| 174 | 6.0 |
| 175 | 18 |
| 176 | 1.3 |
| 177 | 33 |

TABLE 2-4

| Example No. | human mPGES1 IC$_{50}$ (nM) |
|---|---|
| 178 | <1 |
| 179 | 32 |
| 180 | 67 |
| 181 | 69 |
| 182 | 1.2 |
| 183 | 6.2 |
| 184 | 20 |
| 185 | 52 |
| 186 | 32 |
| 187 | 5.9 |
| 188 | 1.9 |
| 189 | 4.3 |
| 190 | 32 |
| 191 | <1 |
| 192 | <1 |
| 193 | <1 |
| 194 | 3.1 |
| 195 | 2.1 |
| 196 | 8.3 |
| 197 | 4.2 |
| 198 | 3.6 |
| 199 | 6.5 |
| 200 | 4.6 |
| 201 | 3.2 |
| 202 | <1 |
| 203 | <1 |
| 204 | 3.7 |
| 205 | 9.9 |
| 206 | 8.9 |
| 207 | 1.9 |
| 208 | 4.8 |
| 209 | 7.5 |
| 210 | 1.4 |

TABLE 2-4-continued

| Example No. | human mPGES1 IC$_{50}$ (nM) |
|---|---|
| 211 | 31 |
| 212 | 37 |
| 213 | 4.7 |
| 214 | 4.1 |
| 215 | <1 |
| 216 | 22 |
| 217 | 37 |
| 218 | 6.3 |
| 219 | 7.1 |
| 220 | 1.1 |
| 221 | <1 |
| 222 | 30 |
| 223 | <1 |
| 224 | 8.0 |
| 225 | 1.5 |
| 226 | 19 |
| 227 | 1.7 |
| 228 | 3.1 |
| 229 | 5.8 |
| 230 | 29 |
| 231 | 25 |
| 232 | 1.6 |
| 233 | <1 |
| 234 | 12 |
| 235 | 1.0 |
| 236 | 2.2 |
| 237 | <1 |
| 238 | <1 |
| 239 | 1.5 |
| 240 | <1 |
| 241 | 15 |
| 242 | 45 |
| 243 | 2.9 |
| 244 | 3.7 |
| 245 | 68 |
| 246 | 1.4 |
| 247 | 2.0 |
| 248 | 2.3 |
| 249 | 5.2 |

TABLE 2-5

| Example No. | human mPGES1 IC$_{50}$ (nM) |
|---|---|
| 250 | 5.8 |
| 251 | 39 |
| 252 | 26 |
| 253 | 3.6 |
| 254 | 3.9 |
| 255 | <1 |
| 256 | 1.0 |
| 257 | 11 |
| 258 | 15 |
| 259 | 4.7 |
| 260 | 4.5 |
| 261 | 3.4 |
| 262 | 2.2 |
| 263 | <1 |
| 264 | 1.2 |
| 265 | 1.5 |
| 266 | <1 |
| 267 | 6.2 |
| 268 | 13 |
| 269 | 23 |
| 270 | 27 |
| 271 | 23 |
| 272 | 2.9 |
| 273 | 2.4 |
| 274 | 36 |
| 275 | 1.9 |
| 276 | 3.2 |
| 277 | 2.0 |
| 278 | <1 |

TABLE 2-5-continued

| Example No. | human mPGES1 IC$_{50}$ (nM) |
|---|---|
| 279 | 1.6 |
| 280 | 8.7 |
| 281 | <1 |
| 282 | <1 |
| 283 | 1.9 |
| 284 | 3.1 |
| 285 | <1 |
| 286 | 3.4 |
| 287 | 1.2 |
| 288 | <1 |
| 289 | 2.5 |
| 290 | <1 |
| 291 | 4.8 |
| 292 | <1 |
| 293 | 2.4 |
| 294 | <1 |
| 295 | <1 |
| 296 | 62 |
| 297 | 2.8 |
| 298 | 2.6 |
| 299 | 3.7 |
| 300 | <1 |
| 301 | 1.2 |
| 302 | <1 |
| 303 | <1 |
| 304 | 4.7 |
| 305 | 5.0 |

What is claimed is:

1. A compound represented by the following general formula (1):

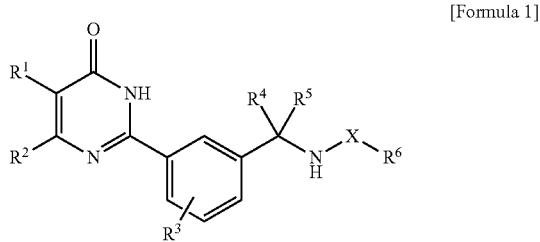

[Formula 1]

wherein, X represents carbonyl group, or sulfonyl group; $R^1$ represents hydrogen atom, a halogen atom, an alkyl group, an alkanoyl group, cyano group, or carboxyl group; $R^2$ represents an alkyl group, a cyclic carbon group which may have a substituent, or a heterocyclic group which may have a substituent; $R^3$ represents hydrogen atom, or 1 to 3 substituents substituting on the benzene ring (these substituents are selected from the group consisting of a halogen atom, an alkyl group (this alkyl group may be substituted with a halogen atom), and an alkoxy group (this alkoxy group may be substituted with a halogen atom)); $R^4$ and $R^5$ independently represent hydrogen atom, a halogen atom, or an alkyl group; and $R^6$ represents an alkyl group (this alkyl group may be substituted with hydroxy group, a halogen atom, or an alkoxy group), or an alkoxy group, or a salt thereof.

2. The compound represented by the general formula (1), or a salt thereof according to claim 1, wherein X is carbonyl group.

3. The compound represented by the general formula (1), or a salt thereof according to claim 1, wherein $R^6$ is a branched $C_{1-6}$ alkyl group (this alkyl group may be substituted with a $C_{1-6}$ alkoxy group).

4. The compound represented by the general formula (1), or a salt thereof according to claim 1, wherein both $R^4$ and $R^5$ are hydrogen atoms.

5. The compound represented by the general formula (1), or a salt thereof according to claim 1, wherein $R^3$ consists of one or two halogen atoms, or alkyl groups which may be substituted with a halogen atom.

6. The compound represented by the general formula (1), or a salt thereof according to claim 1, wherein $R^1$ is hydrogen atom, an alkyl group, or cyano group.

7. The compound represented by the general formula (1), or a salt thereof according to claim 1, wherein $R^2$ is a saturated or partially saturated 3- to 7-membered monocyclic cyclic hydrocarbon group which may have a substituent, a phenyl group which may have a substituent, a saturated or partially saturated 3- to 7-membered monocyclic heterocyclic group which may have a substituent (this heterocyclic group contains 1 to 3 ring-constituting heteroatoms), or a monocyclic aromatic heterocyclic group which may have a substituent (this heterocyclic group contains 1 to 3 ring-constituting heteroatoms).

8. The compound represented by the general formula (1), or a salt thereof according to claim 1, wherein $R^2$ is a phenyl group which may have a substituent, or a pyridyl group which may have a substituent.

9. The compound represented by the general formula (1), or a salt thereof according to claim 1, which is:
N-(4-chloro-3-{4-[6-(difluoromethoxy)pyridin-3-yl]-6-oxo-1,6-dihydropyrimidin-2-yl-2-fluorobenzyl)isobutyramide,
N-(3-{4-[6-(2-ethoxyethoxy)pyridin-3-yl]-6-oxo-1,6-dihydropyrimidin-2-yl}-4-(trifluoromethyl)benzyl) isobutyramide,
N-(3-{6-oxo-4-[6-(2-propoxyethoxy)pyridin-3-yl]-1,6-dihydropyrimidin-2-yl-4-(trifluoromethyl)benzyl) isobutyramide,
N-(4-chloro-3-{4-[6-(cyclopropylmethoxy)pyridin-3-yl]-6-oxo-1,6-dihydropyrimidin-2-yl}-2-fluorobenzyl) isobutyramide,
N-(4-chloro-2-fluoro-3-{6-oxo-4-[5-(trifluoromethyl) pyridin-2-yl]-1,6-dihydropyrimidin-2-yl}benzyl) isobutyramide,
N-(3-{4-[6-(cyclopropylmethoxy)pyridin-3-yl]-6-oxo-1,6-dihydropyrimidin-2-yl-2,4-difluorobenzyl)isobutyramide,
N-(4-chloro-2-fluoro-3-{6-oxo-4-[6-(2,2,2-trifluoroethoxy)pyridin-3-yl]-1,6-dihydropyrimidin-2-yl}benzyl) isobutyramide,
N-{4-chloro-3-[4-(5-chloropyridin-2-yl)-6-oxo-1,6-dihydropyrimidin-2-yl]-2-fluorobenzyl}isobutyramide,
N-(4-chloro-2-fluoro-3-{6-oxo-4-[6-(3,3,3-trifluoropropoxy)pyridin-3-yl]-1,6-dihydropyrimidin-2-yl}benzyl)isobutyramide,
N-(2-chloro-4-fluoro-3-{6-oxo-4-[5-(trifluoromethyl) pyridin-2-yl]-1,6-dihydropyrimidin-2-yl}benzyl) isobutyramide,
N-(3-{4-[6-(difluoromethoxy)pyridin-3-yl]-6-oxo-1,6-dihydropyrimidin-2-yl)-2-fluoro-4-(trifluoromethyl)benzyl)isobutyramide,
N-(3-{4-[6-(2-ethoxyethoxy)pyridin-3-yl]-6-oxo-1,6-dihydropyrimidin-2-yl}-2-fluoro-4-(trifluoromethyl) benzyl)isobutyramide,
N-(2-fluoro-3-6-oxo-4-[5-(trifluoromethyl)pyridin-2-yl]-1,6-dihydropyrimidin-2-yl}-4-(trifluoromethyl)benzyl) isobutyramide, N-(3-{6-oxo-4-[6-(tetrahydropyran-4-ylmethoxy)pyridin-3-yl]-1,6-dihydropyrimidin-2-yl}-4-(trifluoromethyl)benzyl)isobutyramide, N-(3-{4-[6-(3-ethoxypropoxy)pyridin-3-yl]-6-oxo-1,6-dihydropyrimidin-2-yl}-4-(trifluoromethyl)benzyl) isobutyramide, N-{2-fluoro-3-[4-(6-methoxypyridin-3-yl)-6-oxo-1,6-dihydropyrimidin-2-yl]-4-(trifluoromethyl) benzyl}isobutyramide, or N-(4-chloro-3-{4-[6-(cyclopropylethynyl)pyridin-3-yl]-6-oxo-1,6-dihydropyrimidin-2-yl}-2-fluorobenzyl) isobutyramide.

10. An mPGES-1 inhibiting composition comprising the compound represented by the aforementioned general formula (1), or a salt thereof according to claim 1.

11. A PGE2 biosynthesis inhibiting composition comprising the compound represented by the aforementioned general formula (1), or a salt thereof according to claim 1.

12. A medicament containing the compound represented by the aforementioned general formula (1), or a physiologically acceptable salt thereof according to claim 1.

13. The medicament according to claim 12, which is for use in therapeutic treatment of inflammation, pain, rheumatism, osteoarthritis, pyrexia, Alzheimer's disease, multiple sclerosis, arteriosclerosis, ocular hypertension, ischemic retinopathy, systemic scleroderma, malignant tumor, overactive bladder, bladder outlet obstruction associated with benign prostatic hyperplasia, nocturia, urinary incontinence, neurogenic bladder, interstitial cystitis, bladder pain syndrome, urinary calculus, benign prostatic hyperplasia, or a disease for which suppression of the PGE2 production exhibits efficacy.

* * * * *

UNITED STATES PATENT AND TRADEMARK OFFICE
CERTIFICATE OF CORRECTION

PATENT NO. : 10,710,967 B2  
APPLICATION NO. : 15/770002  
DATED : July 14, 2020  
INVENTOR(S) : M. Okada et al.

Page 1 of 1

It is certified that error appears in the above-identified patent and that said Letters Patent is hereby corrected as shown below:

In the Claims

Column 258, Line 30 (Claim 9) please change "2-yl-2" to -- 2-yl}-2 --  
Column 258, Line 37 (Claim 9) please change "2-yl-4" to -- 2-yl}-4 --  
Column 258, Line 46 (Claim 9) please change "2-yl-2" to -- 2-yl}-2 --  
Column 258, Line 60 (Claim 9) please change "2-yl)" to -- 2-yl} --  
Column 258, Line 65 (Claim 9) please change "3-6" to -- 3-{-6 --

Signed and Sealed this  
Second Day of February, 2021

Drew Hirshfeld  
*Performing the Functions and Duties of the*  
*Under Secretary of Commerce for Intellectual Property and*  
*Director of the United States Patent and Trademark Office*